(12) United States Patent
Choi

(10) Patent No.: US 9,834,535 B2
(45) Date of Patent: Dec. 5, 2017

(54) SULFAMATE DERIVATIVE COMPOUNDS FOR USE IN TREATING OR ALLEVIATING PAIN

(71) Applicant: Bio-Pharm Solutions Co., Ltd., Suwon-si, Gyeonggi-do (KR)

(72) Inventor: Yong Moon Choi, Seoul (KR)

(73) Assignee: Bio-Pharm Solutions Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/103,699

(22) PCT Filed: Dec. 12, 2014

(86) PCT No.: PCT/KR2014/012261
§ 371 (c)(1),
(2) Date: Jun. 10, 2016

(87) PCT Pub. No.: WO2015/088273
PCT Pub. Date: Jun. 18, 2015

(65) Prior Publication Data
US 2016/0318894 A1    Nov. 3, 2016

Related U.S. Application Data

(60) Provisional application No. 61/915,046, filed on Dec. 12, 2013, provisional application No. 61/915,047, filed on Dec. 12, 2013.

(51) Int. Cl.
| | |
|---|---|
| *C07D 317/24* | (2006.01) |
| *A61K 31/18* | (2006.01) |
| *A61K 31/357* | (2006.01) |
| *C07D 317/36* | (2006.01) |
| *A61K 31/381* | (2006.01) |
| *A61K 31/427* | (2006.01) |
| *A61K 31/443* | (2006.01) |
| *A61K 31/506* | (2006.01) |
| *C07D 317/72* | (2006.01) |
| *C07D 405/04* | (2006.01) |
| *C07D 409/04* | (2006.01) |
| *C07D 417/04* | (2006.01) |

(52) U.S. Cl.
CPC ............ *C07D 317/24* (2013.01); *A61K 31/18* (2013.01); *A61K 31/357* (2013.01); *A61K 31/381* (2013.01); *A61K 31/427* (2013.01); *A61K 31/443* (2013.01); *A61K 31/506* (2013.01); *C07D 317/36* (2013.01); *C07D 317/72* (2013.01); *C07D 405/04* (2013.01); *C07D 409/04* (2013.01); *C07D 417/04* (2013.01)

(58) Field of Classification Search
CPC .... A61K 31/18; A61K 31/357; A61K 31/381; A61K 31/427; A61K 31/443; C07D 417/04; C07D 317/36
See application file for complete search history.

(56) References Cited

U.S. PATENT DOCUMENTS

| | | |
|---|---|---|
| 4,582,916 A | 4/1986 | Maryanoff et al. |
| 4,591,601 A | 5/1986 | Maryanoff et al. |
| 4,792,569 A | 12/1988 | Maryanoff et al. |
| 5,998,380 A | 12/1999 | Ehrenberg et al. |
| 8,084,490 B2 | 12/2011 | Mccomsey et al. |
| 2010/0063138 A1 | 3/2010 | Mccomsey et al. |
| 2013/0252924 A1 | 9/2013 | Penninger et al. |

FOREIGN PATENT DOCUMENTS

| | | |
|---|---|---|
| WO | 2008054291 A1 | 5/2008 |
| WO | 2013187727 A1 | 12/2013 |

*Primary Examiner* — Savitha Rao
*Assistant Examiner* — Angela Brown-Pettigrew
(74) *Attorney, Agent, or Firm* — McDonnell Boehnen Hulbert & Berghoff LLP

(57) ABSTRACT

The present invention relates to sulfamate derivative compounds and a composition for treating and/or alleviating pain containing the sulfamate derivative compounds or a pharmaceutically acceptable salt thereof as an active ingredient. More specifically, the present invention relates to a pharmaceutical composition for treating or alleviating pain containing a sulfamate derivative compound and/or a pharmaceutically acceptable salt thereof as an active ingredient. Furthermore, the present invention relates to a method for treatment or alleviation of pain comprising administering a sulfamate derivative compound in a pharmaceutically effective amount to a subject in need of treatment or alleviation of pain; and a use of the sulfamate derivative compound or the pharmaceutically acceptable salt thereof in treating and/or alleviating pain, are provided.

9 Claims, 2 Drawing Sheets

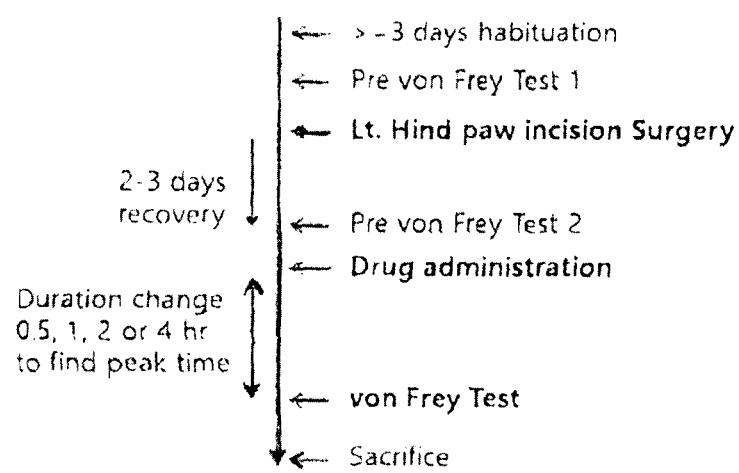
Figure 1. Experimental Timeline

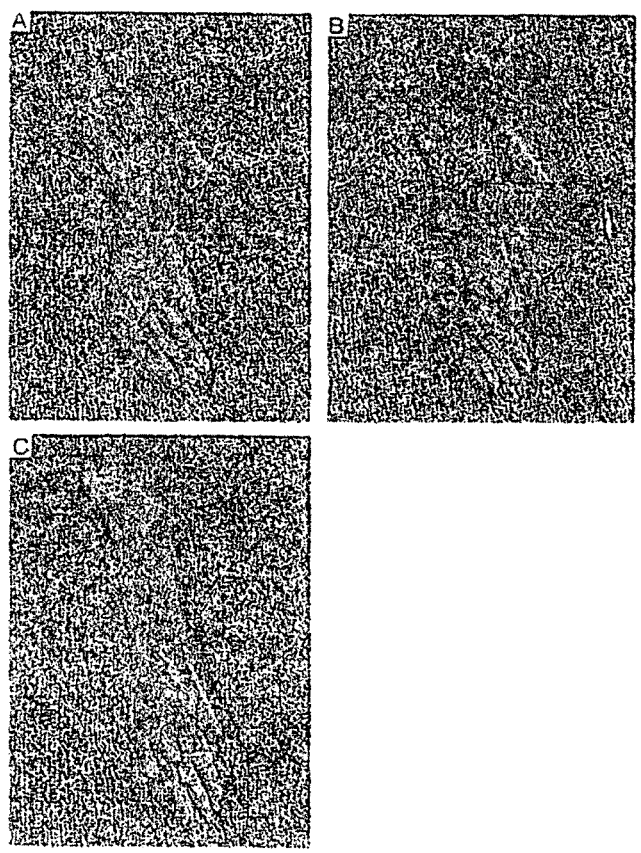
Figure 2. Photographs of the different stages of surgery of the rat paw(foot)

SULFAMATE DERIVATIVE COMPOUNDS FOR USE IN TREATING OR ALLEVIATING PAIN

This application is the U.S. national phase under 35 U.S.C. §371 of international application PCT/KR2014/012261, filed Dec. 12, 2014, which claims priority to U.S. Provisional Application Nos. 61/915,046 and 61/915,047, both filed on Dec. 12, 2013.

TECHNICAL FIELD

The present invention relates to sulfamate derivative compounds and a composition for treating and/or alleviating pain containing the sulfamate derivative compounds or a pharmaceutically acceptable salt thereof as an active ingredient. More specifically, the present invention relates to a pharmaceutical composition for treating or alleviating pain containing a sulfamate derivative compound and/or a pharmaceutically acceptable salt thereof as an active ingredient. Furthermore, the present invention relates to a method for treatment or alleviation of pain comprising administering a sulfamate derivative compound in a pharmaceutically effective amount to a subject in need of treatment or alleviation of pain.

BACKGROUND ART

Pain is one of the most common reasons for a patient to seek medical care and in consequence, pain results in a tremendous number of lost work days per year.

Pain is an unpleasant feeling often caused by intense or damaging stimuli, such as stubbing a toe, burning a finger, putting alcohol on a cut, and bumping the funny bone. The International Association for the Study of Pain's widely used definition states: "Pain is an unpleasant sensory and emotional experience associated with actual or potential tissue damage, or described in terms of such damage". Pain motivates the individual to withdraw from damaging situations, to protect a damaged body part while it heals, and to avoid similar experiences in the future. Most pain resolves promptly once the painful stimulus is removed and the body has healed, but sometimes pain persists despite removal of the stimulus and apparent healing of the body; and sometimes pain arises in the absence of any detectable stimulus, damage or disease.

Pain is the most common reason for physician consultation. It is a major symptom in many medical conditions, and can significantly interfere with a person's quality of life and general functioning. Psychological factors such as social support, hypnotic suggestion, excitement, or distraction can significantly modulate pain's intensity or unpleasantness.

In 1994, responding to the need for a more useful system for describing chronic pain, the International Association for the Study of Pain (IASP) classified pain according to specific characteristics: (1) region of the body involved (e.g., abdomen, lower limbs), (2) system whose dysfunction may be causing the pain (e.g., nervous, gastrointestinal), (3) duration and pattern of occurrence, (4) intensity and time since onset, and (5) etiology.

This system has been criticized by Clifford J. Woolf and others as inadequate for guiding research and treatment. According to Woolf, there are three classes of pain: nociceptive pain (see hereunder), inflammatory pain which is associated with tissue damage and the infiltration of immune cells, and pathological pain which is a disease state caused by damage to the nervous system or by its abnormal function (dysfunctional pain, irritable bowel syndrome, tension type headache, etc.).

In nociceptive pain, the stimulation of the sensory nerve endings called nociceptors causes the sensation of pain. Such pain often occurs after injury or surgery. The pain signals are transmitted by the nociceptors to the brain. Often the pain is localised, constant and has an aching or throbbing quality. Once the damage to the tissue heals the pain usually resolves. Treatment with opioids may resolve nociceptive pain. Psychogenic pain is a pain disorder that is associated with psychological factors. Some types of mental or emotional problems can cause pain. They can also increase or prolong pain. Stomach pain is one of the most common types of psychogenic pain. People with this pain disorder actually have real pain. The diagnosis is made when all physical causes of pain are ruled out.

Neuropathic pain is caused by abnormalities in the nerves, spinal cord or brain and is a chronic type of non-malignant pain with an estimated prevalence of over 1% of the population. Optimizing pain relief in these patients is crucial in helping a patient regain control of his or her life. The most common cause of neuropathic pain is injury or dysfunction of nerves. Injury or dysfunction of peripheral nerves or nerves descending from the spinal cord results disinhibition of nerve impulses at the spinal cord which in consequence results in pain. Neuropathic pain can also be centrally mediated, rather than peripheral, in conditions such as spinal cord injury and multiple sclerosis.

Neuropathic pain can therefore be divided into two further classes; peripheral neuropathic pain and central neuropathic pain depending on whether the peripheral or central nervous system is affected.

Inadequate treatment of pain is widespread throughout surgical wards, intensive care units, accident and emergency departments, in general practice, in the management of all forms of chronic pain and in end of life care. This neglect is extended to all ages, from neonates to the frail elderly. African and Hispanic Americans are more likely than others to suffer needlessly in the hands of a physician; and women's pain is more likely to be undertreated than men's.

Therefore, it is needed to develop therapeutic measures for treating or alleviating pain.

BRIEF DESCRIPTION OF THE DRAWINGS

FIG. 1 shows the overall experimental timeline.
FIG. 2 shows photographs of the different stages of surgery of the rat paw (foot).

DISCLOSURE

Technical Problem

Inadequate treatment of pain is widespread throughout surgical wards, intensive care units, accident and emergency departments, in general practice, in the management of all forms of chronic pain and in end of life care. This neglect is extended to all ages, from neonates to the frail elderly. African and Hispanic Americans are more likely than others to suffer needlessly in the hands of a physician; and women's pain is more likely to be undertreated than men's.

Technical Solution

The present invention relates to sulfamate derivative compounds and a composition for treating and/or alleviating pain containing the sulfamate derivative compounds or a pharmaceutically acceptable salt thereof as an active ingredient.

Advantageous Effects

It is an object of this invention to provide a novel sulfamate derivative compounds or a pharmaceutically acceptable salt thereof.

Another object of this invention to provide a pharmaceutical composition for treating or alleviating pain containing the sulfamate derivative compound and/or the pharmaceutically acceptable salt thereof as an active ingredient.

A further object of this invention to provide a method for treatment or alleviation of pain comprising administering a sulfamate derivative compound in a pharmaceutically effective amount to a subject in need of treatment or alleviation of pain.

BEST MODE

The present inventor has clone intensive studies to develop a novel anti-pain drug with excellent activity and low toxicity which may be an effective treatment for pain. As a result, the present inventors have discovered that the sulfamate derivative compounds represented by the below formula 1 or 1' provide highly enhanced anti-pain activity with significantly decreased side effects.

Accordingly, it is an object of this invention to provide a novel sulfamate derivative compounds or a pharmaceutically acceptable salt thereof.

Another object of this invention to provide a pharmaceutical composition for treating or alleviating pain containing the sulfamate derivative compound and/or the pharmaceutically acceptable salt thereof as an active ingredient.

A further object of this invention to provide a method for treatment or alleviation of pain comprising administering a sulfamate derivative compound in a pharmaceutically effective amount to a subject in need of treatment or alleviation of pain.

MODE FOR INVENTION

In one aspect of this invention, there is provided a compound represented by the following formula 1 or a pharmaceutically acceptable salt thereof:

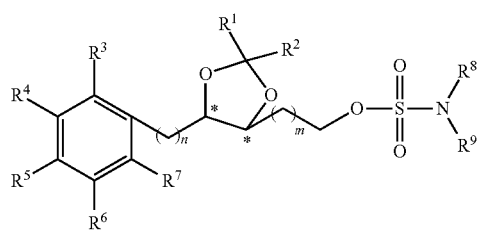

(1)

wherein $R^1$ and $R^2$ are each independently selected from the group consisting of hydrogen, $C_1$-$C_5$ alkyl group, $C_2$-$C_5$ alkenyl and $C_6$-$C_{10}$ aryl group, $R_1$ and $R_2$ together with the carbon atom to which they attach form a $C_3$-$C_{12}$ cycloalkyl group, or $R^1$ and $R^2$ are bond and they together with the oxygen atom to which they attach form a carbonyl group; $R^3$, $R^4$, $R^5$, $R^6$ and $R^7$ are each independently selected from the group consisting of hydrogen, hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen; $R^8$ and $R^9$ are each independently hydrogen or $C_1$-$C_3$ alkyl group; n and m are each independently an integer of 0-4.

According to a concrete embodiment, $R^1$ and $R^2$ are each independently selected from the group consisting of hydrogen, $C_1$-$C_3$ alkyl and phenyl or $R^1$ and $R^2$ together with the carbon atom to which they attach form a $C_3$-$C_6$ cycloalkyl group.

According to a concrete embodiment, $R^8$ and $R^9$ are each independently hydrogen or methyl.

In a preferred embodiment according to the invention, m and n are each independently an integer of 0-2.

In a more preferred embodiment according to the invention, m and n are each independently an integer of 0-1.

In another aspect of this invention, there is provided a compound represented by the following formula 1' or a pharmaceutically acceptable salt thereof:

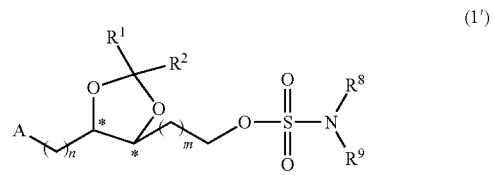

(1')

wherein $R^1$ and $R^2$ are each independently selected from the group consisting of hydrogen, $C_1$-$C_5$ alkyl, $C_2$-$C_5$ alkenyl and $C_6$-$C_{10}$ aryl, $R^1$ and $R^2$ together with the carbon atom to which they attach form a $C_3$-$C_{12}$ cycloalkyl group, or $R^1$ and $R^2$ are bond and they together with the oxygen atom to which they attach form a carbonyl group; A is a heterocyclic moiety optionally substituted by one or more substituents selected from the group consisting of hydrogen, hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen; $R^8$ and $R^9$ are each independently hydrogen or $C_1$-$C_3$ alkyl; and l and m are each independently an integer of 0~4.

According to a concrete embodiment, $R^1$ and $R^2$ are each independently selected from the group consisting of hydrogen, $C_1$-$C_3$ alkyl and phenyl or $R^1$ and $R^2$ together with the carbon atom to which they attach form a $C_3$-$C_6$ cycloalkyl group.

In a preferred embodiment according to the invention, A is a heterocyclic moiety representing a $C_3$-$C_{10}$ heterocyclic group.

According to a concrete embodiment, $R^8$ and $R^9$ are each independently hydrogen or methyl.

In a preferred embodiment according to the invention, n and m are each independently an integer of 0-2.

In a more preferred embodiment according to the invention, n and m are each independently an integer of 0-1.

Particular examples of the substituents represented by A in Chemical Formula 1' include the following:

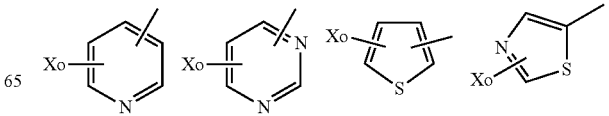

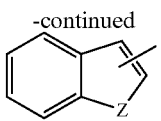

wherein X is each independently selected from the group consisting of halogen, nitro, amine and $C_1$-$C_5$ alkyl; o is an integer of 0-4; and Z is selected from S, O or NH.

In a preferred embodiment according to the invention, o is an integer of 0-2.

In a more preferred embodiment according to the invention, o is an integer of 0-1.

The term "alkyl" as used herein, refers to a linear or branched chain of a saturated hydrocarbon group, e.g., methyl, ethyl, propyl, butyl, isobutyl, tert-butyl and pentyl. "$C_1$-$C_5$ alkyl group" as used herein, refers to an alkyl group with a carbon number of 1-5.

The term "alkenyl", as used herein, unless otherwise indicated, includes alkyl moieties having at least one carbon-carbon double bond wherein alkyl is as defined above.

The term "alkoxy", as used herein, unless otherwise indicated, includes O-alkyl groups wherein alkyl is as defined above.

The term "alkyl thio", as used herein, unless otherwise indicated, includes S-alkyl groups wherein alkyl is as defined above.

The term "alkoxycarbonyl", as used herein, unless otherwise indicated, includes —C(O)O-alkyl groups wherein alkyl is as defined above.

The term. "acyl", as used herein, unless otherwise indicated, includes —C(O)-alkyl groups wherein alkyl is as defined above.

The term "aryl" or "aryl group" as used herein, refers to a totally or partially unsaturated monocyclic or polycyclic carbon rings having aromaticity. The aryl group of the present invention is preferably monoaryl or biaryl, such as phenyl or naphthyl. The aryl radical may be optionally substituted by one or more substituents such as hydroxy, mercapto, halo, alkyl, phenyl, alkoxy, haloalkyl, nitro, cyano, dialkylamino, aminoalkyl, acyl and alkoxycarbonyl, as defined herein.

The term "cycloalkyl" or "cycloalkyl group" as used herein, refers to a monocyclic or polycyclic saturated ring comprising carbon and hydrogen atoms.

The term "heterocyclic" or "heterocyclic group", as used herein, unless otherwise indicated, means aromatic and non-aromatic heterocyclic groups (including saturated heterocyclic groups) containing one or more heteroatoms each, selected from O, S and N, wherein each ring of a heterocyclic group has from 4 to 10 atoms. Non-aromatic heterocyclic groups may include rings having only 4 atoms, but aromatic heterocyclic rings must have at least 5 atoms. Heterocyclic groups of this invention unless otherwise indicated may contain one ring or more than one ring, i.e. they may be monocyclic or polycyclic, for example bicyclic (which may comprise non-aromatic and/or aromatic rings).

According to more concrete embodiment, the compound is selected from the group consisting of:

(1) (5-(2-chlorophenyl)-2,2-dimethyl-1,3-dioxolan-4-yl) methylsulfamate;
(2) (5-(2-chlorophenyl)-2-methyl-1,3-dioxolan-4-yl) methyl sulfamate;
(3) (5-(2-chlorophenyl)-2,2-diethyl-1,3-dioxolan-4-yl) methyl sulfamate;
(4) (3-(2-chlorophenyl)-1,4-dioxaspiro[4,4]nonan-2-yl) methyl sulfamate;
(5) (3-(2-chlorophenyl)-1,4-dioxaspiro[4,5]decan-2-yl) methyl sulfamate;
(6) (5-(2-chlorophenyl)-2-phenyl-1,3-dioxolan-4-yl)methyl sulfamate;
(7) (5-(2-fluorophenyl)-2,2-dimethyl-1,3-dioxolan-4-yl) methyl sulfamate;
(8) (5-(2-fluorophenyl)-2-methyl-1,3-dioxolan-4-yl) methyl sulfamate;
(9) (5-(2-fluorophenyl)-2,2-diethyl-1,3-dioxolan-4-yl) methyl sulfamate;
(10) (3-(2-fluorophenyl)-1,4-dioxaspiro[4,4]nonan-2-yl) methyl sulfamate;
(11) (3-(2-fluorophenyl)-1,4-dioxaspiro[4,5]decan-2-yl) methyl sulfamate;
(12) (5-(2-fluorophenyl)-2-phenyl-1,3-dioxolan-4-yl)methyl sulfamate;
(13) (5-(2-iodophenyl)-2,2-dimethyl-1,3-dioxolan-4-yl) methyl sulfamate;
(14) (5-(2-iodophenyl)-2-methyl-1,3-dioxolan-4-yl) methyl sulfamate;
(15) (5-(2-iodophenyl)-2,2-diethyl-1,3-dioxolan-4-yl) methyl sulfamate;
(16) (3-(2-iodophenyl)-1,4-dioxaspiro[4,4]nonan-2-yl) methyl sulfamate;
(17) (3-(2-iodophenyl)-1,4-dioxaspiro[4,5]decan-2-yl) methyl sulfamate;
(18) (5-(2-iodophenyl)-2-phenyl-1,3-dioxolan-4-yl)methyl sulfamate;
(19) (5-(2,4-dichlorophenyl)-2,2-dimethyl-1,3-dioxolan-4-yl)methyl sulfamate;
(20) (5-(2,4-dichlorophenyl)-2-methyl-1,3-dioxolan-4-yl) methyl sulfamate;
(21) (5-(2,4-dichlorophenyl)-2,2-diethyl-1,3-dioxolan-4-yl) methyl sulfamate;
(22) (3-(2,4-dichlorophenyl)-1,4-dioxaspiro[4,4]nonan-2-yl)methyl sulfamate;
(23) (3-(2,4-dichlorophenyl)-1,4-dioxaspiro[4,5]decan-2-yl) methyl sulfamate;
(24) (5-(2,4-dichlorophenyl)-2-phenyl-1,3-dioxolan-4-yl) methyl sulfamate;
(25) (5-(2,6-dichlorophenyl)-2,2-dimethyl-1,3-dioxolan-4-yl)methylsulfamate;
(26) (5-(2,6-dichlorophenyl)-2-methyl-1,3-dioxolan-4-yl) methyl sulfamate;
(27) (5-(2,6-dichlorophenyl)-2,2-diethyl-1,3-dioxolan-4-yl) methyl sulfamate;
(28) (3-(2,6-dichlorophenyl)-1,4-dioxaspiro[4,4]nonan-2-yl)methyl sulfamate;
(29) (3-(2,6-dichlorophenyl)-1,4-dioxaspiro[4,5]decan-2-yl) methyl sulfamate;
(30) (5-(2,6-dichlorophenyl)-2-phenyl-1,3-dioxolan-4-yl) methyl sulfamate;
(31) (5-(2-aminophenyl)-2,2-dimethyl-1,3-dioxolan-4-yl) methyl sulfamate;
(32) (5-(2-aminophenyl)-2-methyl-1,3-dioxolan-4-yl) methyl sulfamate;
(33) (5-(2-aminophenyl)-2,2-diethyl-1,3-dioxolan-4-yl) methyl, sulfamate;
(34) (3-(2-aminophenyl)-1,4-dioxaspiro[4,4]nonan-2-yl) methyl sulfamate;
(35) (3-(2-aminophenyl)-1,4-dioxaspiro[4,5]decan-2-yl) methyl sulfamate;
(36) (5-(2-aminophenyl)-2-phenyl-1,3-dioxolan-4-yl) methyl sulfamate;
(37) (5-(2-nitrophenyl)-2,2-dimethyl-1,3-dioxolan-4-yl) methyl sulfamate;

(38) (5-(2-nitrophenyl)-2-methyl-1,3-dioxolan-4-yl) methyl sulfamate;
(39) (5-(2-nitrophenyl)-2,2-diethyl-1,3-dioxolan-4-yl) methyl sulfamate;
(40) (3-(2-nitrophenyl)-1,4-dioxaspiro[4,4]nonan-2-yl) methyl sulfamate;
(41) (3-(2-nitrophenyl)-1,4-dioxaspiro[4,5]decan-2-yl) methyl sulfamate;
(42) (5-(2-nitrophenyl)-2-phenyl-1,3-dioxolan-4-yl)methyl sulfamate;
(43) (5-(2-nitrophenyl)-2-oxo-1,3-dioxolan-4-yl)methyl sulfamate;
(44) (5-(2-methylphenyl)-2,2-dimethyl-1,3-dioxolan-4-yl) methyl sulfamate;
(45) (5-(2-methylphenyl)-2-methyl-1,3-dioxolan-4-yl) methyl sulfamate;
(46) (5-(2-methylphenyl)-2,2-diethyl-1,3-dioxolan-4-yl) methyl sulfamate;
(47) (3-(2-methylphenyl)-1,4-dioxaspiro[4,4]nonan-2-yl) methyl sulfamate;
(48) (3-(2-methylphenyl)-1,4-dioxaspiro[4,5]decan-2-yl) methyl sulfamate;
(49) (5-(2-methylphenyl)-2-phenyl-1,3-dioxolan-4-yl) methyl sultanate;
(50) (5-(2-methylaminophenyl)-2,2-dimethyl-1,3-dioxolan-4-yl)methyl methyl sulfamate;
(51) (5-phenyl-2,2-dimethyl-1,3-dioxolan-4-yl)methyl sulfamate;
(52) (5-phenyl-2,2-diethyl-1,3-dioxolan-4-yl)methyl sulfamate;
(53) (3-phenyl-1,4-dioxaspiro[4,4]nonan-2-yl)methyl sulfamate;
(54) (3-phenyl-1,4-dioxaspiro[4,5]decan-2-yl)methyl sulfamate;
(55) 2-(5-benzyl-2,2-dimethyl-1,3-dioxolan-4-yl)ethyl sulfamate;
(56) 2-(5-benzyl-2,2-diethyl-1,3-dioxolan-4-yl)ethyl sulfamate;
(57) 2-(3-benzyl-1,4-dioxaspiro[4,4]nonan-2-yl)ethyl sulfamate;
(58) 2-(3-benzyl-1,4-dioxaspiro[4,5]decane-2-yl)ethyl sulfamate;
(59) (5-benzyl-2,2-dimethyl-1,3-dioxolan-4-yl)methyl sulfamate;
(60) (5-benzyl-2,2-diethyl-1,3-dioxolan-4-yl)methyl sulfamate;
(61) (3-benzyl-1,4-dioxaspiro[4,4]nonan-2-yl)methyl sulfamate;
(62) (3-benzyl-1,4-dioxaspiro[4,5]decan-2-yl)methyl sulfamate;
(63) 2-(5-phenyl-2,2-dimethyl-1,3-dioxolan-4-yl)ethyl sulfamate;
(64) 2-(5-phenyl-2,2-diethyl-1,3-dioxolan-4-yl)ethyl sulfamate;
(65) 2-(3-phenyl-1,4-dioxaspiro[4,4]nonan-2-yl)ethyl sulfamate;
(66) 2-(3-phenyl-1,4-dioxaspiro[4,5]decan-2-yl)ethyl sulfamate;
(67) 2-(5-(2-chlorobenzyl)-2,2-dimethyl-1,3-dioxolan-4-yl) ethyl sulfamate;
(68) 2-(5-(2-chlorobenzyl)-2,2-diethyl-1,3-dioxolan-4-yl) ethyl sulfamate;
(69) 2-(3-(2-chlorobenzyl)-1,4-dioxaspiro[4,4]nonan-2-yl) ethyl sulfamate;
(70) 2-(3-(2-chlorobenzyl)-1,4-dioxaspiro[4,5]decan-2-yl) ethyl sulfamate;
(71) (5-(2-chlorobenzyl)-2,2-dimethyl-1,3-dioxolan-4-yl) methyl sulfamate;
(72) (5-(2-chlorobenzyl)-2,2-diethyl-1,3-dioxolan-4-yl) methyl sulfamate;
(73) (3-(2-chlorobenzyl)-1,4-dioxaspiro[4,4]nonan-2-yl) methyl sulfamate;
(74) (3-(2-chlorobenzyl)-1,4-dioxaspiro[4,5]decan-2-yl) methyl sulfamate;
(75) 2-(5-(2-chlorophenyl)-2,2-dimethyl-1,3-dioxolan-4-yl) ethyl sulfamate;
(76) 2-(5-(2-chlorophenyl)-2,2-diethyl-1,3-dioxolan-4-yl) ethyl sulfamate;
(77) 2-(3-(2-chlorophenyl)-1,4-dioxaspiro[4,4]nonan-2-yl) ethyl sulfamate;
(78) 2-(3-(2-chlorophenyl)-1,4-dioxaspiro[4,5]decan-2-yl) ethyl sulfamate;
(79) (5-(2,4-dichlorothiazol-5-yl)-2,2-dimethyl-1,3-dioxolan-4-yl)methyl sulfamate;
(80) (5-(2-chlorothiazol-5-yl)-2,2-dimethyl-1,3-dioxolan-4-yl)methylsulfamate; 1
(81) (2,2-dimethyl-5-(4-methylthiazol-5-yl)-1,3-dioxolan-4-yl)methylsulfamate;
(82) (2,2-dimethyl-5-(2-chloro-4-methylthiazol-5-yl)-1,3-dioxolan-4-yl)methylsulfamate;
(83) (2,2-dimethyl-5-(thiophen-3-yl)-1,3-dioxolan-4-yl) methylsulfamate;
(84) (2,2-dimethyl-5-(5-chlorothiophen-2-yl)-1,3-dioxolan-4-yl)methylsulfamate;
(85) (5-(3-chloropyridin-4-yl)-2,2-dimethyl-1,3-dioxolan-4-yl)methylsulfamate;
(86) (5-(4-chloropyridin-3-yl)-2,2-dimethyl-1,3-dioxolan-4-yl)methylsulfamate;
(87) (2,2-dimethyl-5-(pyrimidin-5-yl)-1,3-dioxolan-4-yl) methylsulfamate and
(88) (2,2-dimethyl-5-(2-chloropyrimidin-5-yl)-1,3-dioxolan-4-yl)methylsulfamate.

According to a concrete embodiment, the compound is in the form of a racemate, an enantiomer, a diastereomer, a mixture of enantiomers or a mixture of diastereomers.

As seen in the Examples, the present inventors have synthesized the compounds of various stereochemistries, and investigated their relief pain activity by multilateral experiments.

The term "enantiomer" as used herein, refers to one of two stereoisomers that are mirror images of each other which are non-superposable due to existence of one or more chiral carbons. According to a concrete embodiment, the enantiomer of the present invention is one in which chiral carbons of $C_4$ and $C_5$ are diverse in stereo-configuration.

The term "diastereomer" as used herein, refers to stereoisomers that are not enantiomers, which occurs when two or more stereoisomers of a compound have different configurations at one or more (but not all) of the equivalent chiral centers thus are not mirror images of each other.

The term "racemate" as used herein, refers to one that has equal amounts of two enantiomers of different stereo-configuration, and lack in optical activity.

It would be obvious to the skilled artisan from the Examples below that the compounds of this invention are not limited to those with specific stereochemistry.

According to a concrete embodiment, the pharmaceutically acceptable salt is produced by reacting the compound with an inorganic acid, an organic acid, an amino acid, sulfonic acid, an alkali metal or ammonium ion.

The pharmaceutically acceptable salts of the present invention are those which can be manufactured by using a method known in the art, for example, but not limited to, salts with inorganic acids such as hydrochloric acid, bromic acid, sulfuric acid, sodium hydrogen sulfate, phosphate, nitrate and carbonate; and salts with organic acids such as formic acid, acetic acid, propionic acid, oxalic acid, succinic acid, benzoic acid, citric acid, maleic acid, malonic acid, tartaric acid, gluconic acid, lactic acid, gestisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine, and proline; salts with sulfonic acid such as methane sulfonate, ethanesulfonate, benzene sulfonate and toluene sulfonate; metal salts by reaction with an alkali metal such as sodium and potassium; or salts with ammonium ion.

In another aspect of this invention, there is provided a method for management Pain comprising administering pharmaceutically effective amount of the compound of the present invention or the pharmaceutically acceptable salt thereof to a subject in need thereof.

The term "pharmaceutically effective amount" as used herein, refers to an amount enough to show and accomplish efficacies and activities for preventing, alleviating, treating a disease associated with pain.

The pharmaceutical composition of this invention includes a pharmaceutically acceptable carrier besides the active ingredient compound. The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995).

The pharmaceutical composition according to the present invention may be administered orally or parenterally, and concretely, administered parenterally. For parenteral administration, it may be administered intravenously, subcutaneously, intramuscularly, intraperitoneally, transdermally or intra-articularly. More concretely, it is administered intramuscularly or intraperitoneally.

The compound or the pharmaceutically acceptable salt thereof according to the pain is one or more selected from the group consisting of nociceptive pain, psychogenic pain, inflammatory pain, and pathological pain. More concretely, the pain is one or more selected from the group consisting of neuropathic pain, cancer pain, postoperative pain, trigeminal neuralgia pain, idiopathic pain, diabetic neuropathic pain, and migraine.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, pharmaceutical composition of the present invention may be administered with a daily dosage of 0.001-10000 mg/kg (body weight).

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but are not limited to, a solution, a suspension or an emulsion in oil or aqueous medium, an elixir, a powder, a granule, a tablet and a capsule, and may further comprise a dispersion agent or a stabilizer.

The sulfamate derivative compound of the present invention may be prepared by the following reaction scheme.

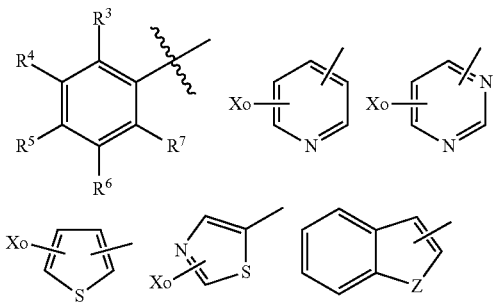

[Reaction scheme 1] Synthesis of alcohol compound

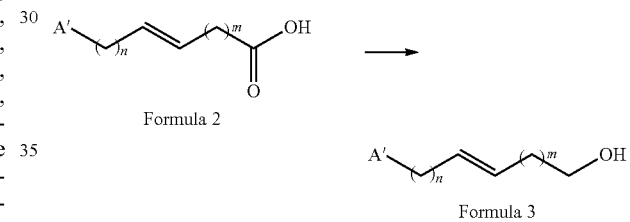

An alcohol compound of formula 3 is synthesized by a reduction reaction using a reducing agent, including but not limited to, LiAlH$_4$ (Lithium aluminum hydride), NaBH$_4$ (Sodium borohydride), Zn(BH$_4$)$_2$ (Zincborohydride), NaH (Sodium hydride), KH (Potassium hydride), AlH$_3$ (Aluminum hydride), and NaOMe (Sodiummethoxyde) in a basic condition from the Carboxylic acid compound of formula 2.

[Reaction scheme 2] Synthesis of protected alcohol compound

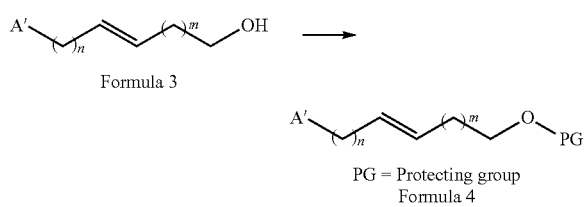

PG = Protecting group
Formula 4

OH of an alcohol compound of formula 3 is protected by a protecting group, including but not limited to, TMS (Trimethyl silyl), TES (Triethyl silyl), TIPS (Triisopropyl TBDMS (tert-butyldimethyl silyl), TBDPS (tert-butyldiphenyl silyl), Piv (Pivaloyl), MOM (Methoxymethyl), Acetyl, Benzoyl, and Tityl (Triphenylmethyl) in a basic condition for using in a next reaction.

[Reaction scheme 3] Synthesis of diol compound

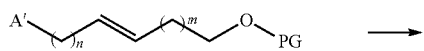

PG = Protecting group
Formula 4

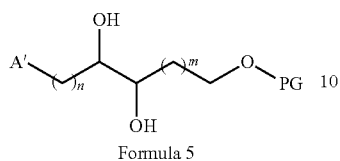

Formula 5

The asymmetric dihydroxylation catalyst may be one or more selected from the group consisting of a chiral ligand (e.g., $(DHQD)_2PHAL$, $(DHQ)_2PHAL$, etc.), an osmium catalyst (e.g., $OsO_4$, $K_2OsO_2(OH)_4$, etc.), $K_2CO_3$, $K_3Fe(CN)_6$, N-methylmorpholine oxide (NMO), methane sulfone amide ($CH_3SO_2NH_2$), and the like. For example, the asymmetric dihydroxylation catalyst may include, but is not limited to, AD-mix-α ($K_2OsO_2(OH)_4$(cat), $K_2CO_3$, $K_3Fe(CN)_6$, $(DHQ)_2PHAL$(cat)) and methane sulfone amide ($CH_3SO_2NH_2$), or $OsO_4$ and N-methylmorpholine oxide (NMO).

[Reaction scheme 4] Synthesis of dioxolan-alcohol compound

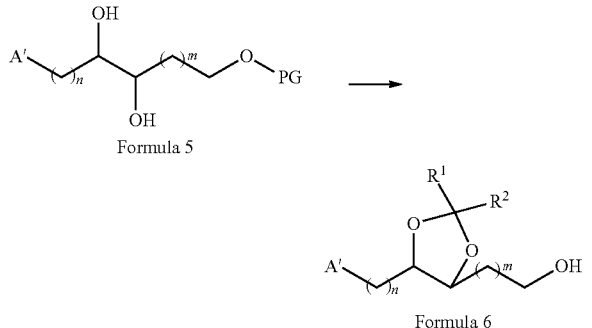

Formula 6

A diol compound of formula 5 is reacted with a ketone compound (such as acetone, 3-pentanone, cyclopentanone, or cyclohexanone), an alkoxy compound (such as dimethoxypropan, diethoxyethane, or methoxy propene), or an aldehyde compound (such as benzaldyde, cyclopentanecarboxaldehyde, or cyclohexaecarboxaldehyde) in an acidic condition, for example, a solution dissolved with an acid such as p-TsOH (p-toluenesulfonic acid), $H_2SO_4$(Sulfuric acid), $HNO_3$(Nitric acid), followed by removing a protecting group to afford the Dioxolan-alcohol compound of formula 6. But while we have described sever al examples of the ketone compound, the alkoxy compound, the aldehyde compound and the ac id for the above reaction, it is not limited thereto and may be appropriately selected depending on the intended purpose.

[Reaction scheme 5] Synthesis of ester compound

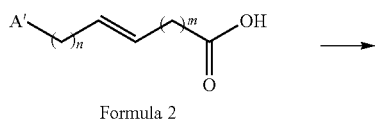

Formula 2

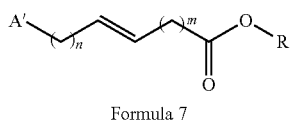

Formula 7

An ester compound of formula 7 having R selected from the group consisting of linear or branched $C_1$-$C_{10}$ alkyl, or cyclic $C_3$-$C_{10}$ alkyl, allyl and benzyl is synthesized by an esterification reaction in an acidic condition from the carboxylic acid compound of formula 2.

[Reaction scheme 6] Synthesis of ester-diol compound

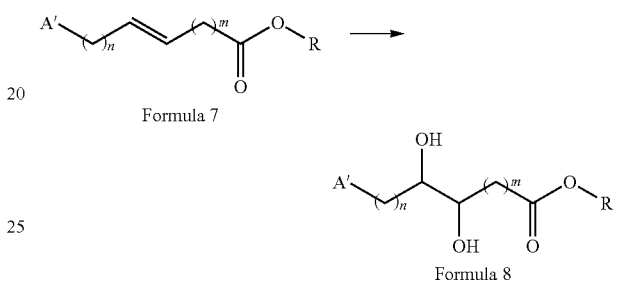

Formula 8

The asymmetric dihydroxylation catalyst may be one or more selected from the group consisting of a chiral ligand (e.g., $(DHQD)_2PHAL$, $(DHQ)_2PHAL$, etc.),) an osmium catalyst (e.g., $OsO_4$, $K_2OsO_2(OH)_4$, etc.), $K_2CO_3$, $K_3Fe(CN)_6$, N-methylmorpholine oxide (NMO), methane sulfone amide ($CH_3SO_2NH_2$), and the like. For example, the asymmetric dihydroxylation catalyst may include, but is not limited to, AD-mix-α ($K_2OsO_2(OH)_4$(cat), $K_2CO_3$, $K_3Fe(CN)_6$, $(DHQ)_2PHAL$ (cat)) and methane sulfone amide ($CH_3SO_2NH_2$) or $OsO_4$ and N-methylmorpholine oxide (NMO).

[Reaction scheme 7] Synthesis of dioxolan-ester compound

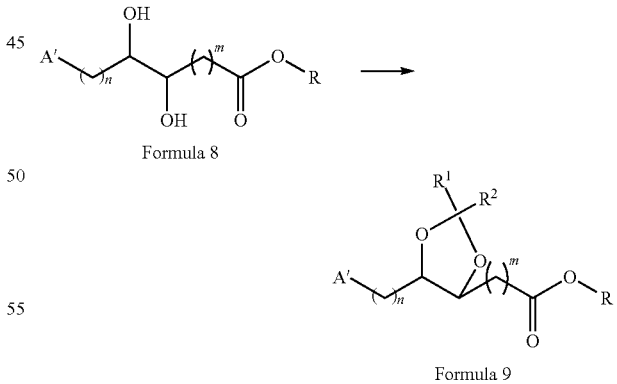

Formula 9

A diol compound of formula 8 is reacted with a ketone compound (such as acetone, 3-pentanone, cyclopentanone, or cyclohexanone), an alkoxy compound (such as dimethoxypropan, diethoxyethane, 3-methoxypente-2-ene, 1-methoxycyclopent-1-ene, 1-methoxycyclohex-1-ene or methoxy propene), or an aldehyde compound (such as benzaldyde, cyclopentanecarboxaldehyde, or cyclohexaecarboxaldehyde) in an acidic condition, for example, a solution dissolved with an acid such as p-TsOH (p-toluenesulfonic acid), H₂SO₄(Sulfuric acid), HNO₃(Nitric acid) to afford the Dioxolan-alcohol compound of formula 9. But while we have described several examples of the ketone compound, the alkoxy compound, the aldehyde compound and the acid for the above reaction, it is not limited thereto and may be appropriately selected depending on the intended purpose.

[Reaction scheme 8] Synthesis of dioxolan-alcohol compound

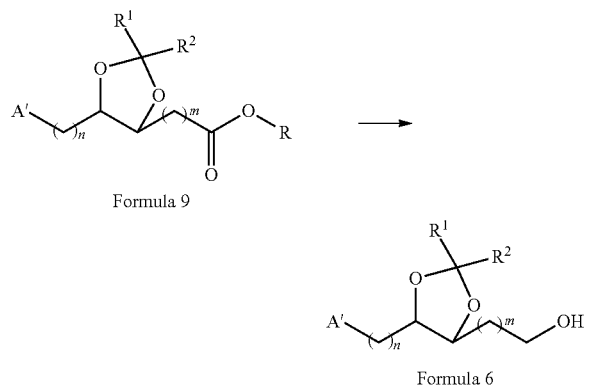

A dioxolan-alcohol compound of formula 6 is synthesized by a reduction reaction using a reducing agent, including but not limited to, LiAlH₄ (Lithium aluminum hydride), NaBH₄ (Sodium borohydride), Zn(BH₄)₂ (Zincborohydride), NaH (Sodium hydride), KH (Potassium hydride), AlH₃ (Aluminum hydride), and NaOMe (Sodiummethoxyde) in a basic condition from the dioxolan-ester compound of formula 9.

[Reaction scheme 9] Synthesis of Sulfamate compound

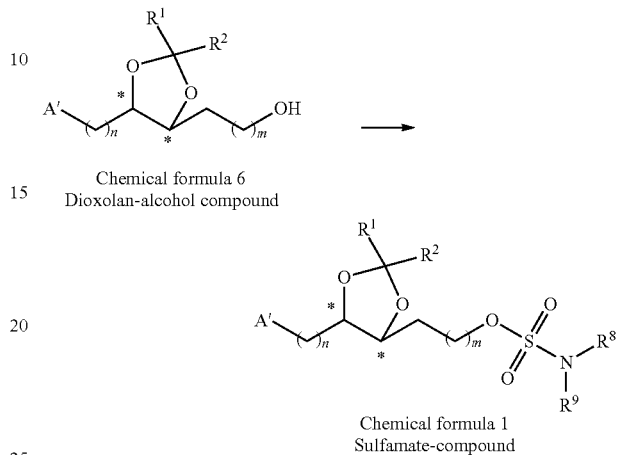

A dioxolan-alcohol compound of formula 6 is reacted with sulfamide or sulfamoyl chloride in a basic condition using a base, including but not limited to, pyridine, piperidine, and piperazine to produce the sulfamate compound of formula 1 or 1'.

[Reaction scheme 10] Synthesis of dioxolan-alcohol compound

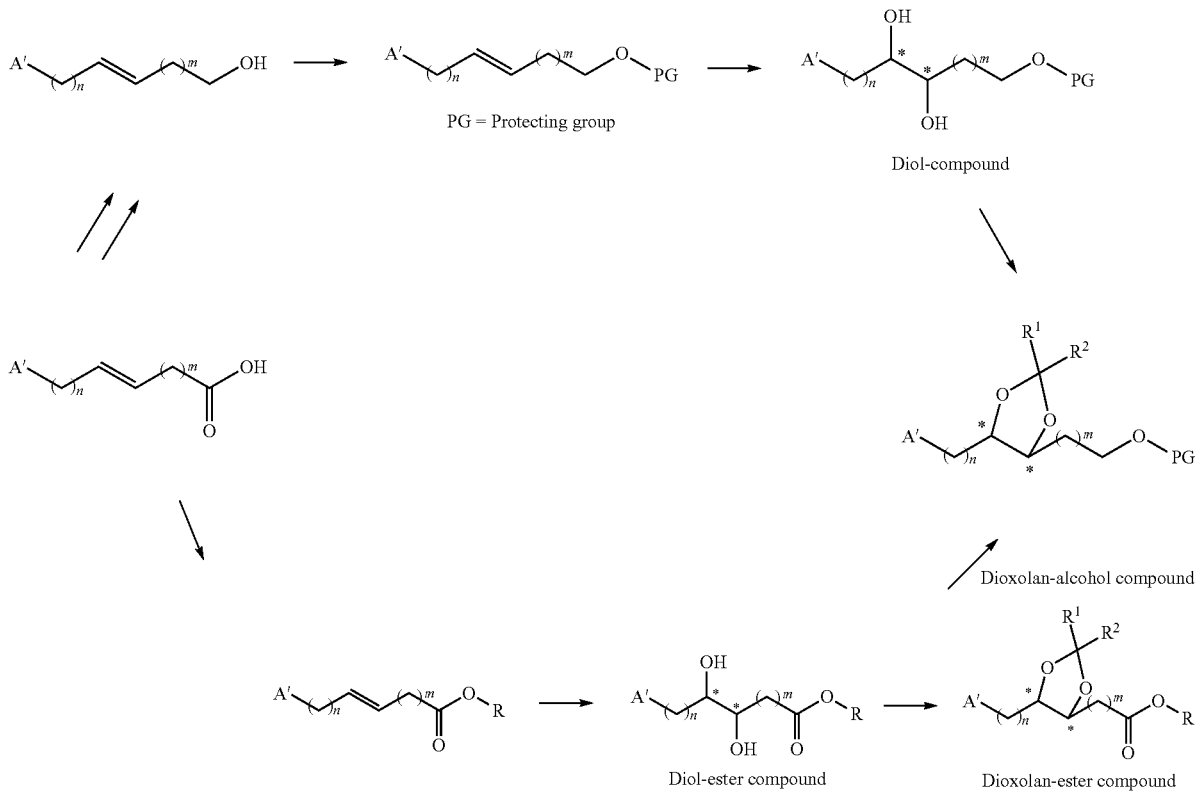

A dioxolan-alcohol compound used in the synthesis of a sulfamate compound is synthesized by dihydroxylation, condensation and a deprotection reaction.

EXAMPLES

Preparation Example 1: (E)-3-(2-chlorophenyl)prop-2-en-1-ol

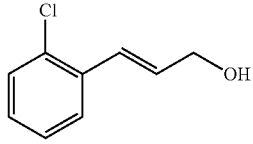 [SMILES: OC/C=C/c1ccccc1Cl]

To a 100 ml round-bottomed flask, 2-Chlorocinnamic acid (5 g, 7.3 mmol) and THF (20 ml) were added and the reaction mixture was cooled to 0° C. Triethylamine (4.2 ml, 30.1 mmol) and Ethyl chloroformate (2.88 ml, 30.1 mmol) were added. The reaction mixture was precipitated as a white solid during stirring. After 2 hr, the reaction mixture was filtered with THF (white solid+yellow solution).

The yellow solution was added dropwise to Sodium borohydride (2.68 g, 142.3 mmol) in $H_2O$ at 0° C. and stirred for 2 hrs, quenched with 1N HCl solution. The reaction mixture was extracted by EtOAc and washed with $H_2O$. The combined organic extracts were dried over anhydrous magnesium sulfate ($MgSO_4$), filtered and concentrated under vacuum. The crude compound was purified by a silica gel column to produce the title compound (2.96 g, 60~70%).

$^1$H NMR (400 MHz, $CDCl_3$) δ 1.67 (s, 1H), 4.39 (t, J=4.0, 2H), 6.37 (dt J=5.6, 16.0, 1H), 7.03 (d, J=16.0, 1H), 7.18~7.38 (m, 4H),

Preparation Example 2: (E)-1-chloro-2-(3-(methoxymethoxy)prop-1-enyl)benzene

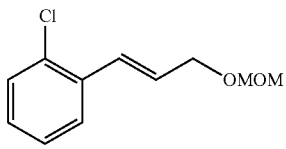

To a 250 ml round-bottomed flask, (E)-3-(2-chlorophenyl)prop-2-en-1-ol (2.96 g, 17.5 mmol, Preparation example 1) and Dichloromethane (17.5 ml) were added and the reaction mixture was cooled to 0° C. Diisopropylethylamine (6.1 ml, 35.1 mmol) was added and stirred at 0° C. Methyl chloromethyl ether (2.77 ml, 35.1 mmol) was added dropwise and stirred for overnight. The reaction mixture was quenched with 1N NaOH solution, extracted by dichloromethane. The combined organic extracts were dried over anhydrous magnesium sulfate ($MgSO_4$), filtered and concentrated under vacuum. The crude compound was purified by a silica gel column to produce the title compound (3.43 g, 85~95%).

$^1$H NMR (400 MHz, $CDCl_3$) δ 3.44 (s, 3H), 4.30 (dd, J=8.0, 1.6, 1H), 4.73 (s, 2H), 6.30 (1H, dt. J=6.0, 16), 7.04 (d, J=16.0, 1H), 7.20~7.57 (m, 4H)

Preparation Example 3: (1R,2R)-1-(2-chlorophenyl)-3-(methoxymethoxy)propane-1,2-diol

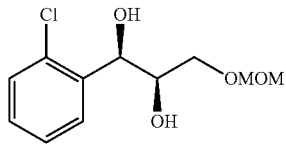

A 250 ml round-bottomed flask, equipped with a magnetic stirrer, was fitted with 80 ml of tert-butyl alcohol, 80 ml of water, and $K_3Fe(CN)_6$ (15.93 g, 48.3 mmol), $K_2CO_3$ (6.7 g, 48.3 mmol), $(DHQD)_2$-PHAL (0.12 g, 0.16 mmol), $K_2OsO_2(OH)_4$, (11.8 mg, 0.03 mmol), and Methanesulfonamide (1.53 g, 16.1 mmol). Stirring at 0° C. (E)-1-chloro-2-(3-(methoxymethoxy)prop-1-enyl)benzene (3.43 g, 16.1 mmol, Preparation example 2) was added at once, and the mixture was stirred vigorously at 0° C. overnight. While the mixture was stirred at 0° C., solid sodium sulfite ($Na_2SO_3$, 24.4 g, 193.5 mmol) was added and the mixture was allowed to warm to room temperature. Ethyl acetate was added to the reaction mixture, and after the separation of the layers, the aqueous phase was further extracted with the organic solvent. The combined organic layers were washed with 2 N KOH. The combined organic extracts were dried over anhydrous magnesium sulfate ($MgSO_4$), filtered and concentrated under vacuum. The crude compound was purified by a silica gel column to produce the title compound (3.31 g, 75~90%).

$^1$H NMR (400 MHz, $CDCl_3$) δ 3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 1H)

Preparation Example 4: (1S,2S)-1-(2-chlorophenyl)-3-(methoxymethoxy)propane-1,2-diol

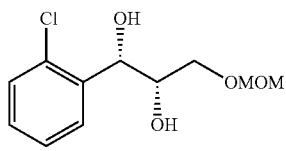

The substantially same method as described in Preparation Example 3 was conducted, except that $(DHQ)_2$-PHAL was used instead of $(DHQD)_2$-PHAL, to obtain the title compound. 3.1 g (75~90%).

$^1$H NMR (400 MHz, $CDCl_3$) δ 3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 5: 1-(2-chlorophenyl)-3-(methoxymethoxy)propane-1,2-diol

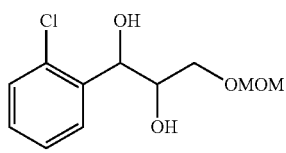

(E)-1-chloro-2-(3-(methoxymethoxy)prop-1-enyl)benzene (9.1 g, Preparation Example 2) was dissolved in 45 mL of a mixture of acetone/t-BuOH/H₂O (5:1:1 V/V). At room temperature, N-methylmorpholine-N-oxide (7.51 g) and OsO₄ (0.54 g) were added thereto and stirred for 2-3 hours. When the reaction was completed, the obtained product was washed with water and methylenechloride (MC). Then, the organic layer was dehydrated with anhydrous magnesium sulfate (MgSO₄). filtrated, and concentrated under reduced pressure. The crude compound was purified by a silica gel column to produce the title compound (7.42 g, 70~90%).

¹H NMR (400 MHz, CDCl₃) δ 3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 6: ((4R,5R)-5-(2-chlorophenyl)-2,2-dimethyl-1,3-dioxolan-4-yl)methanol

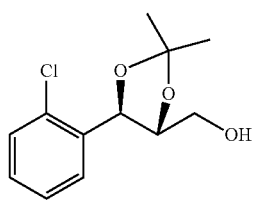 [SMILES: CC1(C)O[C@H](c2ccccc2Cl)[C@@H](CO)O1]

To (1R,2R)-1-(2-chlorophenyl)-3-(methoxymethoxy)propane-1,2-diol (3.31 g, 13.4 mmol, Preparation example 3), Dichloromethane was added and cooled to 0° C. 2,2-Dimethoxypropane (3.3 ml, 26.8 mmol) and p-toluenesulfonic acid (2 g, 10.7 mmol) was added and stirred at room temperature for 5 hrs. The reaction mixture was quenched with H2O, extracted with DCM, and washed with H2O. The organic layer was dried over anhydrous magnesium sulfate (MgSO₄), filtered and concentrated. The crude compound was purified by a silica gel column to produce the title compound (1.05 g, 30~40%).

¹H NMR (400 MHz, CDCl₃) δ 1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 7: ((4S,5S)-5-(2-chlorophenyl)-2,2-dimethyl-1,3-dioxolan-4-yl)methanol

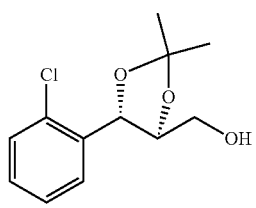 [SMILES: CC1(C)O[C@@H](CO)[C@H](c2ccccc2Cl)O1]

The substantially same method as described in Preparation Example 6 was conducted, except that (1S,2S)-1-(2-chlorophenyl)-3-(methoxymethoxy)propane-1,2-diol (Preparation example 4) was used instead of (1R,2R)-1-(2-chlorophenyl)-3-(methoxymethoxy)propane-1,2-diol (Preparation example 3), to obtain the title compound (1.1 g, 30~40%).

¹H NMR (400 MHz, CDCl₃) δ 1.57 (s, 3H), 1.64 (s, 3H), 1.98 (m, 1H), 3.76~3.83 (m, 1H), 3.88~3.90 (m, 2H), 5.41 (d, J=8.4, 1H), 7.25~7.66 (m, 4H)

Preparation Example 8: (5-(2-chlorophenyl)-2,2-dimethyl-4,3-dioxolan-4-yl)methanol

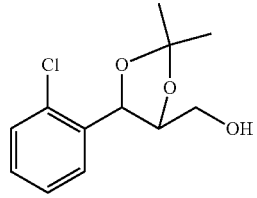 [SMILES: CC1(C)OC(CO)C(c2ccccc2Cl)O1]

The substantially same method as described in Preparation Example 6 was conducted, except that 1-(2-chlorophenyl)-3-(methoxymethoxy)propane-1,2-diol (Preparation example 5) was used instead of (1R,2R)-1-(2-chlorophenyl)-3-(methoxymethoxy)propane-1,2-diol (Preparation example 3), to obtain the title compound (2.1 g, 30~40%).

¹H NMR (400 MHz, CDCl₃) δ 1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 9: (E)-3-(2-fluorophenyl)-acrylic acid

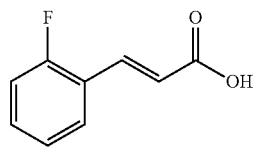

Piperidine (247 mg, 2.90 mmol) was added to a stirred solution of malonic acid (3.1 g, 29.00 mmol) and 2-fluoroaldehyde (3 g, 24.17 mmol) in pyridine at room temperature under N₂ condition. The solution was cooled to room temperature, then quenched with HCl solution. The residue was treated with EA and H₂O. The organic layer was separated and the aqueous layer was extracted further with EA. The combined extracts were washed with brine. The organic layer was dried over Na₂SO₄, filtered and concentrated. The crude compound was purified by a silica gel column to produce the title compound (3.66 g, 70~90%).

¹H NMR (400 MHz, CDCl₃) δ 6.60 (d, J=16.0, 1H), 7.24~7.50 (m, 3H), 7.66 (d, J=16.0, 1H), 7.84 (t, J=8.0, 1H)

Preparation Example 10: (E)-3-(2-fluorophenyl)-prop-2-en-1-ol

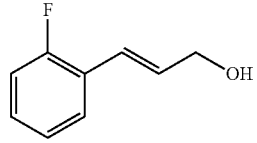

The substantially same method as described in Preparation Example 1 was conducted, except that (E)-3-(2-fluorophenyl)-acrylic acid (Preparation example 9) was used instead of 2-Chlorocinnamic acid, to obtain the title compound (1.6 g, 30~40%).

$^1$H NMR (400 MHz, CDCl$_3$) δ 1.67 (s, 1H), 4.39 (t, J=4.0, 2H), 6.34~6.41 (m, 1H) 7.00~7.38 (m, 4H)

Preparation Example 11: (E)-1-Fluoro-2-(3-(methoxymethoxy)prop-1-enyl)benzene

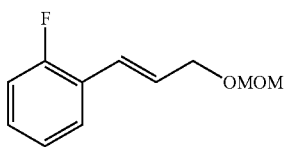

The substantially same method as described in Preparation Example 2 was conducted, except that (E)-3-(2-fluorophenyl)-prop-2-en-1-ol (Preparation example 10) was used instead of (E)-3-(2-chlorophenyl)-prop-2-en-1-ol (Preparation example 1), to obtain the title compound (2.23 g, 85~95%).

$^1$H NMR (400 MHz, CDCl$_3$) δ 3.44 (s, 3H), 4.30 (dd, J=1.6, 8.0, 1H), 4.73 (s, 2H), 6.27~6.37 (m, 1H), 7.02~7.57 (m, 4H)

Preparation Example 12: (1R,2R)-1-(2-fluorophenyl)-3-(methoxymethoxy)propane-1,2-diol

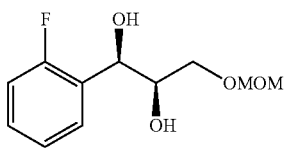

The substantially same method as described in Preparation Example 3 was conducted, except that (E)-1-Fluoro-2-(3-(methoxymethoxy)prop-1-enyl)benzene (Preparation example 11) was used instead of (E)-1-chloro-2-(3-(methoxymethoxy) prop-1-enyl)benzene (Preparation example 2), to obtain the title compound (2.13 g, 75~90%).

$^1$H NMR (400 MHz, CDCl$_3$) δ 3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 13: ((4R,5R)-5-(2-fluorophenyl)-2,2-dimethyl-1,3-dioxolan-4-yl)methanol

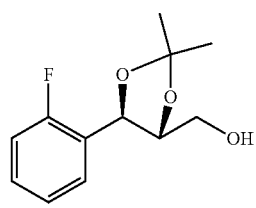 [SMILES: CC1(C)O[C@H](c2ccccc2F)[C@@H](CO)O1]

The substantially same method as described in Preparation Example 6 was conducted, except that (1R, 2R)-1-(2-fluorophenyl)-3-(methoxymethoxy)propane-1,2-diol (Preparation example 12) was used instead of (1R, 2R)-1-(2-chlorophenyl)-3-(methoxymethoxy)propane-1,2-diol (Preparation example 3), to obtain the title compound (1.73 g, 30~40%).

$^1$H NMR (400 MHz, CDCl$_3$) δ 1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 14: (1S,2S)-1-(2-fluorophenyl)-3-(methoxymethoxy)propane-1,2-diol

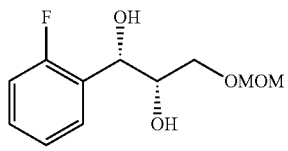

The substantially same method as described in Preparation Example 4 was conducted, except that (E)-1-Fluoro-2-(3-(methoxymethoxy)prop-1-enyl)benzene (Preparation example 11) was used instead of (E)-1-chloro-2-(3-(methoxymethoxy)prop-1-enyl)benzene (Preparation example 2), to obtain the title compound (2.13 g, 75~90%).

$^1$H NMR (400 MHz, CDCl$_3$) δ 3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 15: ((4S,5S)-5-(2-fluorophenyl)-2,2-dimethyl-1,3-dioxolan-4-yl)methanol

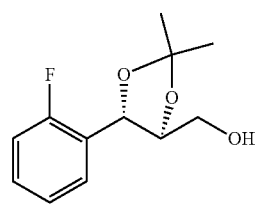

The substantially same method as described in Preparation Example 6 was conducted, except that (1S, 2S)-1-(2-fluorophenyl)-3-(methoxymethoxy)propane-1,2-diol (Preparation example 14) was used instead of (1R, 2R)-1-(2-chlorophenyl)-3-(methoxymethoxy)propane-1,2-diol (Preparation example 3), to obtain the title compound (1.73 g, 30~40%).

$^1$H NMR (400 MHz, CDCl$_3$) δ 1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 16: 2-Iodobenzenealdehyde

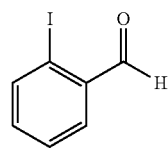

In a flask, 2-iodobenzyl alcohol (4 g, 17.09=01) was dissolved in dichloromethane (MC, 85 ml), and then, manganese oxide (MnO$_2$, 14.86 g, 170.92 mmol) was added thereto. The obtained reaction product was stirred under reflux. When the reaction was completed, the obtained reaction product was cooled to room temperature, and then, filtered and concentrated using celite, to obtain the title compound (3.6 g, yield 75~90%).

¹H NMR (400 MHz, CDCl₃) δ 7.30~7.99 (m, 4H), 10.10 (s, 1H)

Preparation Example 17: (E)-3-(2-iodophenyl)-acrylic acid

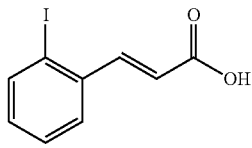 [SMILES: O=C(O)/C=C/c1ccccc1I]

The substantially same method as described in Preparation Example 9 was conducted, except that 2-Iodobenzenealdehyde (Preparation example 16) was used instead of 2-Fluoroaldehyde, to obtain the title compound (2.06 g, 70~90%)

¹H NMR (400 MHz, CDCl₃) δ 6.60 (d, J=16.0, 1H), 7.24~7.50 (m, 3H), 7.66 (d, J=16.0, 1H), 7.84 (t, J=8.0, 1H)

Preparation Example 18: (E)-3-(2-iodophenyl)-prop-2-en-1-ol

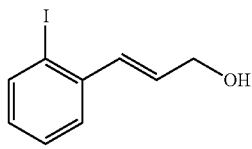 [SMILES: OC/C=C/c1ccccc1I]

The substantially same method as described in Preparation Example 1 was conducted, except that (E)-3-(2-iodophenyl)-acrylic acid (Preparation example 17) was used instead of 2-Chlorocinnamic acid, to obtain the title compound (1.08 g, 30~40%).

¹H NMR (400 MHz, CDCl₃) δ 1.67 (s, 1H), 4.39 (t, J=4.0, 2H), 6.34~6.41 (m, 1H), 7.00~7.38 (m, 4H)

Preparation Example 19: (E)-1-Iodo-2-(3-(methoxymethoxy)prop-1-enyl)benzene

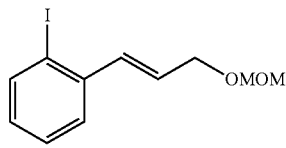

The substantially same method as described in Preparation Example 2 was conducted, except that (E)-3-(2-iodophenyl)-prop-2-en-1-ol (Preparation example 18) was used instead of (E)-3-(2-chlorophenyl)-prop-2-en-1-ol (Preparation example 1), to obtain the title compound (1.37 g, 85~95%).

¹H NMR (400 MHz, CDCl₃) δ 3.44 (s, 3H), 4.30 (dd, J=8.0, 1.6, 1H), 4.73 (s, 2H), 6.27~6.34 (m, 1H), 7.02~7.57 (m, 4H)

Preparation Example 20: (1R, 2R)-1-(2-iodophenyl)-3-(methoxymethoxy)propane-1,2-diol

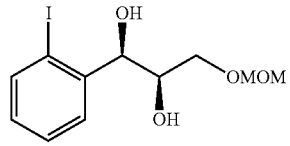

The substantially same method as described in Preparation Example 3 was conducted, except that (E)-1-Iodo-2-(3-(methoxymethoxy)prop-1-enyl)benzene (Preparation example 19) was used instead of (E)-1-chloro-2-(3-(methoxymethoxy)prop-1-enyl)benzene (Preparation example 2), to obtain the title compound (1.32 g, 75~90%).

¹H NMR (400 MHz, CDCl₃) δ 3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 21: ((4R, 5R)-5-(2-iodophenyl)-2,2-dimethyl-1,3-dioxolan-4-yl)methanol

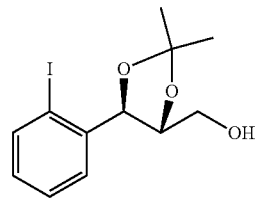 [SMILES: CC1(C)O[C@H](c2ccccc2I)[C@@H](CO)O1]

The substantially same method as described in Preparation Example 6 was conducted, except that (1R, 2R)-1-(2-iodophenyl)-3-(methoxymethoxy)propane-1,2-diol (Preparation example 20) was used instead of (1R,2R)-1-(2-chlorophenyl)-3-(methoxymethoxy)propane-1,2-diol (Preparation example 3), to obtain the title compound (1.33 g, 30~40%).

¹H NMR (400 MHz, CDCl₃) δ 1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 22: (1S,2S)-1-(2-iodophenyl)-3-(methoxymethoxy)propane-1,2-diol

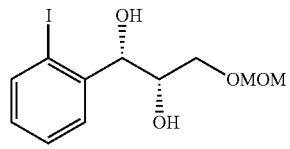

The substantially same method as described in Preparation Example 4 was conducted, except that (E)-1-Iodo-2-(3-(methoxymethoxy)prop-1-enyl)benzene (Preparation example 19) was used instead of (E)-1-chloro-2-(3-(methoxymethoxy)prop-1-enyl)benzene (Preparation example 2), to obtain the title compound (1.32 g, 75~90%).

¹H NMR (400 MHz, CDCl₃) δ 3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 23: ((4S,5S)-5-(2-iodophenyl)-2,2-dimethyl-1,3-dioxolan-4-yl)methanol

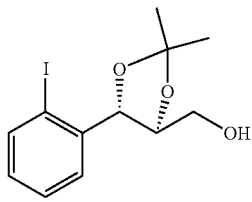 [SMILES: CC1(C)O[C@@H](CO)[C@H](c2ccccc2I)O1]

The substantially same method as described in Preparation Example 6 was conducted, except that (1S,2S)-1-(2-iodophenyl)-3-(methoxymethoxy)propane-1,2-diol (Preparation example 22) was used instead of (1R,2R)-1-(2-chlorophenyl)-3-(methoxymethoxy)propane-1,2-diol (Preparation example 3), to obtain the title compound (1.33 g, 30~40%).

$^1$H NMR (400 MHz, CDCl$_3$) δ 1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 24: (E)-Methyl-3-(2-chlorophenyl)acrylate

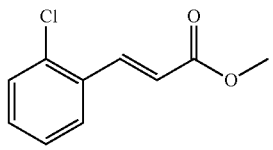

To a 250 ml round-bottomed flask, 2-Chlorocinnamic acid (25 g, 136.9 mmol) and MeOH (56 ml) were added. POCl$_3$ (1.27 ml, 13.6 mmol) was added dropwise. The reaction mixture was stirred under reflux for 3~4 h. The reaction mixture was cooled to room temperature, quenched with 1N NaOH solution. The mixture was extracted by EtOAc and washed with H$_2$O. The aqueous layer was further extracted with EtOAc. The combined organic layer was dried over anhydrous magnesium sulfate (MgSO$_4$), filtered and concentrated under vacuum (26.98 g, 85~97%)

$^1$H NMR (400 MHz, CDCl$_3$) δ 3.84 (s, 3H), 6.45 (d, J=16.0, 1H), 7.28~7.65 (m, 4H), 8.12 (d, J=16.0, 1H)

Preparation Example 25: (2R,3S)-methyl-3-(2-chlorophenyl)-2,3-dihydroxypropanoate

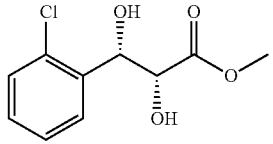

A 1000 ml round-bottomed flask, equipped with a magnetic stirrer, was filled with 362 ml of tert-butyl alcohol, 362 ml of water, K$_3$Fe(CN)$_6$ (135.53 g, 411.63 mmol), K$_2$CO$_3$ (56.89 g, 411.63 mmol), (DHQ)$_2$PHAL (1.06 g, 1.37 mmol), K$_2$OsO$_2$(OH)$_4$, (0.1 g, 0.27 mmol), and Methanesulfonamide (13.05 g, 137.21 mmol) and stirred at 0° C. (E)-Methyl-3-(2-chlorophenyl)acrylate (26.98 g, Preparation example 24) was added at once, and the mixture was stirred vigorously at 0° C. overnight. While the mixture was stirred at 0° C., solid sodium sulfite (Na$_2$SO$_3$, 24.4 g, 193.5 mmol), EtOAc and water was added and the mixture was allowed to warm to room temperature and stirred. After the separation of the layer, the aqueous layer was added to EtoAc, and the aqueous layer was separated. The combined organic layers were washed with 0.3M H$_2$SO$_4$/Na$_2$SO$_4$ solution (H$_2$SO$_4$ 76 ml, H$_2$O 2 L, Na$_2$SO$_4$ 360 g) twice. After separation of the organic layer, the organic layer was washed with H2O. After separating of the layer, the organic layer were dried over anhydrous MgSO$_4$, filtered and concentrated under vacuum. The crude compound was purified by a silica gel column to produce the title compound (24.42 g, 70~90%)

$^1$H NMR (400 MHz, CDCl$_3$) δ 7.62~7.26 (4H, m), 5.51 (1H, dd, J=7.2, 2.4), 4.50 (1H, dd, J=5.6, 2.4), 3.86 (3H, s), 3.13 (1H, d, J=6.0), 2.79 (1H, d, J=7.2)

Preparation Example 26: (4R,5S)-methyl-5-(2-chlorophenyl)-2,2-dimethyl-1,3-dioxolane-4-carboxylate

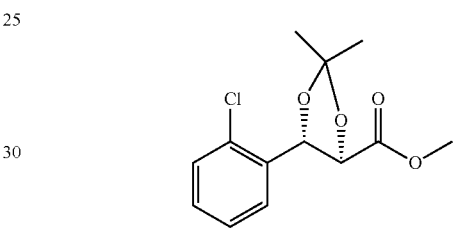

Dichloromethane (DMC) was added to (2R,3S)-methyl-3-(2-chlorophenyl)-2,3-dihydroxypropanoate (24.4 g, Preparation example 25) and cooled to 0° C. 2,2-Dimethoxypropane (26 ml, 211.77 mmol) and p-toluenesulfonic acid (2 g, 10.58 mmol) was added and stirred at room temperature. The reaction mixture was quenched with H$_2$O, extracted with DCM, washed with H$_2$O, dried over anhydrous magnesium sulfate, filtered and concentrated. The crude compound was purified by a silica gel column to produce the title compound (23.6 g, 70~95%).

$^1$H NMR (400 MHz, CDCl$_3$) δ 1.63 (s, 3H), 1.65 (s, 3H), 3.78 (s, 3H), 4.30 (d, J=7.6, 1H), 5.62 (d, J=7.6, 1H), 7.28~7.64 (m, 4H)

Preparation Example 27: ((4S,5S)-5-(2-chlorophenyl)-2,2-dimethyl-1,3-dioxolane-4-yl)methanol

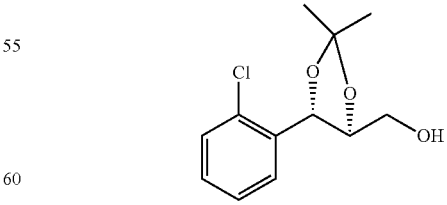

A solution of To a solution LAH(LiAlH$_4$ 3.31 g, 87.25 mmol) in THF was added dropwise to a solution of (4R, 5S)-methyl 5-(2-chlorophenyl)-2,2-dimethyl-1,3-dioxolane-4-carboxylate (23.6 g, Preparation 26) in THF at 0° C., and the mixture stirred at room temp. The reaction mixture was quenched with H₂O at 0° C., celite filtered with EtOAc, washed with EtOAc, dried over anhydrous magnesium sulfate (MgSO₄), filtered and concentrated. The crude compound was purified by a silica gel column to produce the title compound (21.13 g 70~95%)

¹H NMR (400 MHz, CDCl₃) δ 1.57 (s, 3H), 1.64 (s, 3H), 1.98 (m, 1H), 3.76~3.83 (m, 1H), 3.88~3.90 (m, 2H), 5.41 (d, J=8.4, 1H), 7.25~7.66 (m, 4H)

Preparation Example 28:
(E)-Methyl-3-(2,4-dichlorophenyl)acrylate

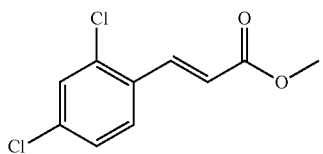

The substantially same method as described in Preparation Example 24 was conducted, except that 2,4-dichlorocinnamic acid was used instead of 2-chlorocinnamic acid, to obtain the title compound (9.7 g, 70~90%)

¹H NMR (400 MHz, CDCl₃): δ 3.84 (s, 3H), 6.44 (d, J=16, 1H), 7.28~7.33 (m, 1H), 7.41 (d, J=2.0, 1H), 7.55 (d, J=8.4, 1H), 8.04 (d, J=16, 1H).

Preparation Example 29: (2R,3S)-methyl-3-(2,4-dichlorophenyl)-2,3-dihydroxypropanoate

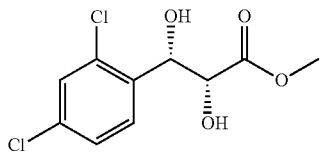 [SMILES: COC(=O)[C@H](O)[C@@H](O)c1ccc(Cl)cc1Cl]

The substantially same method as described in Preparation Example 25 was conducted, except that (E)-Methyl-3-(2,4-dichlorophenyl)acrylate (Preparation example 28) was used instead of (E)-Methyl-3-(2-chlorophenyl)acrylate (Preparation example 24), to obtain the title compound (3.8 g, 60~80%)

¹H NMR (400 MHz, CDCl₃): δ 3.11 (s, 1H), 3.88 (s, 3H), 4.42 (d, J=2.4, 1H), 5.43 (d, J=2.0, 1H), 7.28~7.33 (m, 1H), 7.41 (d, J=2.0, 1H), 7.55 (d, J=8.4, 1H).

Preparation Example 30: (4R,5S)-methyl-5-(2,4-dichlorophenyl)-2,2-dimethyl-1.3-dioxolane-4-carboxylate

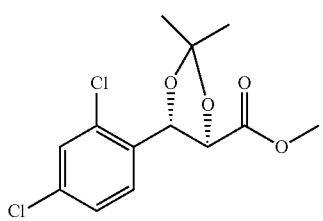 [SMILES: COC(=O)[C@@H]1OC(C)(C)O[C@H]1c1ccc(Cl)cc1Cl]

The substantially same method as described in Preparation Example 26 was conducted, except that (2R,3S)-methyl-3-(2,4-dichlorophenyl)-2,3-dihydroxypropanoate (Preparation example 29) was used instead of (2S,3R)-methyl-3-(2-chlorophenyl)-2,3-dihydroxypropanoate (Preparation example 25), to obtain the title compound (3.5 g, 60~80%)

¹H NMR (400 MHz, CDCl₃): δ 1.59 (s, 3H), 1.63 (d, J=8.8, 3H), 3.78 (s, 3H), 4.25 (d, J=7.6, 1H), 5.56 (d, J=8.0, 1H), 7.28~7.33 (m, 1H), 7.41 (d, J=2.0, 1H), 7.56 (d, J=8.4, 1H).

Preparation Example 31: ((4S,5S)-5-(2,4-dichlorophenyl)-2,2-dimethyl-1.3-dioxolane-4-yl)methanol

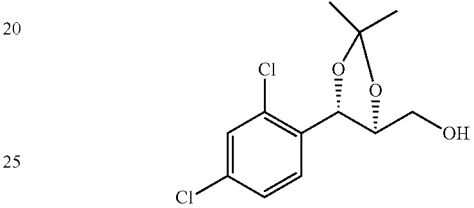

The substantially same method as described in Preparation Example 27 was conducted, except that (4R,5S)-methyl-5-(2,4-dichlorophenyl)-2,2-dimethyl-1.3-dioxolane-4-carboxylate (Preparation example 30) was used instead of (4S,5R)-methyl-5-(2-chlorophenyl)-2,2-dimethyl-1.3-dioxolane-4-carboxylate (Preparation example 26), to obtain the title compound (3.2 g, 70~95%)

¹H NMR (400 MHz, CDCl₃): δ 1.56 (s, 3H), 1.62 (d, J=4.8, 6H), 1.97 (dd, J=7.6, J=7.2, 1H), 3.75~3.80 (m, 1H), 3.82~3.86 (m, 1H), 3.89~3.94 (m, 1H), 5.36 (d, J=8.4, 1H), 7.28~7.33 (m, 1H), 7.41 (d, J=2.0, 1H), 7.56 (d, J=8.4, 1H).

Preparation Example 32:
(E)-Ethyl-3-(2,6-dichlorophenyl)acrylate

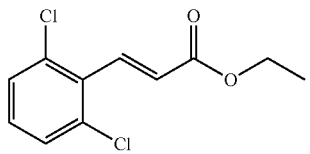

To a stirred solution of 2,6-dichlorobenzaldehyde (5.0 g, 28.56 mmol) in THF was added triethyl phosphono acetate (6.4 g, 28.56 mmol) at 0° C. The reaction mixture was added t-BuOK (3.2 g, 28.56 mmol) at room temperature.

The mixture was stirred for 10 h then the resulting mixture was quenched with 1N HCl, diluted with ether, washed with water, dried over MgSO₄, filtered, and concentrated under reduced pressure. The crude product was purified by SiO₂ gel column chromatography (4.3 g 40~60%)

¹H NMR (400 MHz, CDCl₃): δ 1.36 (t, J=3.6, 3H), 4.31 (q, J=3.7, 2H), 6.61 (d, J=16, 1H), 7.21 (t, J=4.2, 1H), 7.38 (d, J=5.2, 1H), 7.81 (d, J=16, 1H).

Preparation Example 33: (2R,3S)-ethyl-3-(2,6-dichlorophenyl)-2,3-dihydroxypropanoate

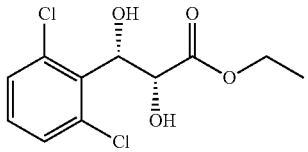 [SMILES: CCOC(=O)[C@H](O)[C@@H](O)c1c(Cl)cccc1Cl]

The substantially same method as described in Preparation Example 25 was conducted, except that (E)-ethyl-3-(2,6-dichlorophenyl)acrylate (Preparation example 32) was used instead of (E)-Methyl-3-(2-chlorophenyl)acrylate (Preparation example 24), to obtain the title-compound (3.9 g, 60~80%)

$^1$H NMR (400 MHz, CDCl$_3$): δ 1.21 (t, J=7.2, 3H), 3.22 (s, 1H), 3.69 (s, 1H), 4.20~4.28 (m, 1H), 4.70 (d, J=5.2, 1H), 5.62 (d, J=5.6, 1H), 7.19~7.36 (m, 3H).

Preparation Example 34: (4R,5S)-ethyl-5-(2,4-dichlorophenyl)-2,2-dimethyl-1.3-dioxolane-4-carboxylate

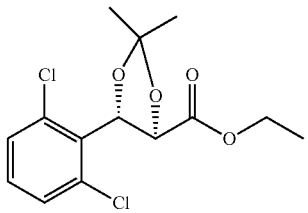 [SMILES: CCOC(=O)[C@@H]1OC(C)(C)O[C@H]1c1c(Cl)cccc1Cl]

The substantially same method as described in Preparation Example 26 was conducted, except that (2R,3S)-ethyl-3-(2,6-dichlorophenyl)-2,3-dihydroxypropanoate (Preparation example 29) was used instead of (2R,3S)-methyl-3-(2-chlorophenyl)-2,3-dihydroxypropanoate (Preparation example 25), to obtain the title compound (4.1 g, 60~90%)

$^1$H NMR (400 MHz, CDCl$_3$): δ 1.26 (t, J=7.2, 3H), 1.58 (s, 3H), 1.70 (s, 3H), 3.77 (s, 3H), 4.24 (q, J=7.2, 1H), 4.95 (q, J=4.4, 1H), 5.95 (q, J=3.0, 1H), 7.20~7.39 (m, 3H).

Preparation Example 35: ((4S,5S)-5-(2,6-dichlorophenyl)-2,2-dimethyl-1.3-dioxolane-4-yl)methanol

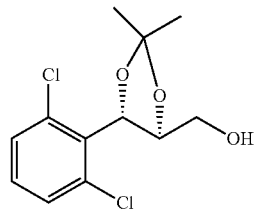 [SMILES: CC1(C)O[C@@H](CO)[C@H](c2c(Cl)cccc2Cl)O1]

The substantially same method as described in Preparation Example 27 was conducted, except that (4R,5S)-ethyl-5-(2,6-dichlorophenyl)-2,2-dimethyl-1.3-dioxolane-4-carboxylate (Preparation example 33) was used instead of (4R,5S)-methyl-5-(2-chlorophenyl)-2,2-dimethyl-1.3-dioxolane-4-carboxylate (Preparation example 26), to obtain the title compound (3.5 g, 70~95%)

$^1$H NMR (400 MHz, CDCl$_3$): δ 1.55 (s, 3H), 1.68 (s, 3H), 3.66 (q, J=5.5, 1H), 3.85 (q, J=5.1, 1H), 4.56~4.61 (m, 1H), 5.78 (d, J=9.2, 1H), 7.19~7.37 (m, 3H).

Preparation Example 36: (2S,3R)-methyl-3-(2,4-dichlorophenyl)-2,3-dihydroxypropanoate

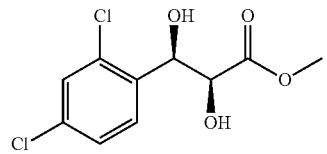 [SMILES: COC(=O)[C@@H](O)[C@H](O)c1ccc(Cl)cc1Cl]

The substantially same method as described in Preparation Example 3 was conducted, except that (E)-Methyl-3-(2,4-dichlorophenyl)acrylate (Preparation example 28) was used instead of (E)-1-chloro-2-(3-(methoxymethoxy)prop-1-enyl)benzene (Preparation example 2), to obtain the title compound (2.4 g, 75~90%).

$^1$H NMR (400 MHz, CDCl$_3$): δ 3.11 (s, 1H), 3.88 (s, 3H), 4.42 (d, J=2.4, 1H), 5.43 (d, J=2.0, 1H), 7.28~7.33 (m, 1H), 7.41 (d, J=2.0, 1H), 7.55 (d, J=8.4, 1H).

Preparation Example 37: (4S, 5R)-methyl-5-(2,4-dichlorophenyl)-2,2-dimethyl-1.3-dioxolane-4-carboxylate

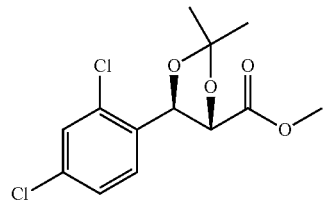 [SMILES: COC(=O)[C@H]1OC(C)(C)O[C@@H]1c1ccc(Cl)cc1Cl]

The substantially same method as described in Preparation Example 26 was conducted, except that (2S,3R)-methyl-3-(2,4-dichlorophenyl)-2,3-dihydroxypropanoate (Preparation example 36) was used instead of (2R,3S)-methyl-3-(2-chlorophenyl)-2,3-dihydroxypropanoate (Preparation example 25), to obtain the title compound (3.2 g, 60~80%)

$^1$H NMR (400 MHz, CDCl$_3$): δ 1.59 (s, 3H), 1.63 (d, J=8.8, 3H), 3.78 (s, 3H), 4.25 (d, J=7.6, 1H), 5.56 (d, J=8.0, 1H), 7.28~7.33 (m, 1H), 7.41 (d, J=2.0, 1H), 7.56 (d, J=8.4, 1H).

Preparation Example 38: ((4R,5R)-5-(2,4-dichlorophenyl)-2,2-dimethyl-1.3-dioxolane-4-yl)methanol

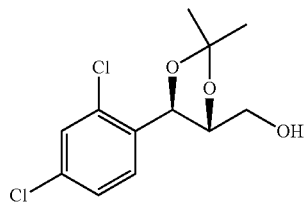 [SMILES: CC1(C)O[C@H](c2ccc(Cl)cc2Cl)[C@@H](CO)O1]

The substantially same method as described in Preparation Example 27 was conducted, except that (4S,5R)-methyl-5-(2,4-dichlorophenyl)-2,2-dimethyl-1.3-dioxolane-4-carboxylate (Preparation example 37) was used instead of (4S,5R)-methyl-5-(2-chlorophenyl)-2,2-dimethyl-1.3-dioxolane-4-carboxylate (Preparation example 26), to obtain the title compound (3.5 g, 70~95%)

¹H NMR (400 MHz, CDCl₃): δ 1.56 (s, 3H), 1.62 (d, J=4.8, 6H), 1.97 (dd, J=7.6, J=7.2, 1H), 3.75~3.80 (m, 1H), 3.82~3.86 (m, 1H), 3.89~3.94 (m, 1H), 5.36 (d, J=8.4, 1H), 7.28~7.33 (m, 1H), 7.41 (d, J=2.0, 1H), 7.56 (d, J=8.4, 1H).

Preparation Example 39: (2S,3R)-ethyl-3-(2,6-dichlorophenyl)-2,3-dihydroxypropanoate

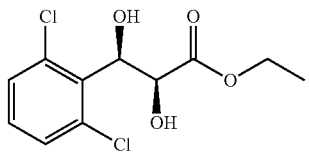 [SMILES: CCOC(=O)[C@@H](O)[C@H](O)c1c(Cl)cccc1Cl]

The substantially same method as described in Preparation Example 3 was conducted, except that (E)-ethyl-3-(2,6-dichlorophenyl)acrylate (Preparation example 32) was used instead of (E)-1-chloro-2-(3-(methoxymethoxy)prop-1-enyl)benzene (Preparation example 2), to obtain the title compound (2.8 g, 75~90%).

¹H NMR (400 MHz, CDCl₃): δ 3.11 (s, 1H), 3.88 (s, 3H), 4.42 (d, J=2.4, 1H), 5.43 (d, J=2.0, 1H), 7.28~7.33 (m, 1H), 7.41 (d, J=2.0, 1H), 7.55 (d, J=8.4, 1H). ¹H NMR (400 MHz, CDCl₃): δ=1.21 (t, J=7.2, 3H), 3.22 (s, 1H), 3.69 (s, 1H), 4.20~4.28 (m, 1H), 4.70 (d, J=5.2, 1H), 5.62 (d, J=5.6, 1H), 7.19~7.36 (m, 3H).

Preparation Example 40: (4S,5R)-ethyl-5-(2,4-dichlorophenyl)-2,2-dimethyl-1.3-dioxolane-4-carboxylate

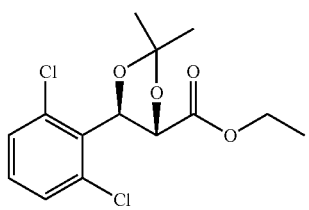 [SMILES: CCOC(=O)[C@H]1OC(C)(C)O[C@@H]1c1c(Cl)cccc1Cl]

The substantially same method as described in Preparation Example 26 was conducted, except that (2S,3R)-ethyl-3-(2,6-dichlorophenyl)-2,3-dihydroxypropanoate (Preparation example 39) was used instead of (2R,3S)-methyl-3-(2-chlorophenyl)-2,3-dihydroxypropanoate (Preparation example 25), to obtain the title compound (4.1 g, 60~90%)

¹H NMR (400 MHz, CDCl₃): δ 1.26 (t, J=7.2, 3H), 1.58 (s, 3H), 1.70 (s, 3H), 3.77 (s, 3H), 4.24 (q, J=7.2, 1H), 4.95 (q, J=4.4, 1H), 5.95 (q, J=3.0, 1H), 7.20~7.39 (m, 3H).

Preparation Example 41: ((4R,5R)-5-(2,6-dichlorophenyl)-2,2-dimethyl-1.3-dioxolane-4-yl)methanol

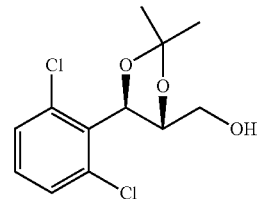 [SMILES: CC1(C)O[C@H](c2c(Cl)cccc2Cl)[C@@H](CO)O1]

The substantially same method as described in Preparation Example 27 was conducted, except that (4S,5R)-ethyl-5-(2,6-dichlorophenyl)-2,2-dimethyl-1.3-dioxolane-4-carboxylate (Preparation example 40) was used instead of (4R,5S)-methyl-5-(2-chlorophenyl)-2,2-dimethyl-1.3-dioxolane-4-carboxylate (Preparation example 26), to obtain the title compound (5.2 g, 70~95%)

¹H NMR (400 MHz, CDCl₃): δ 1.55 (s, 3H), 1.68 (s, 3H), 3.66 (q, J=5.5, 1H), 3.85 (q, J=5.1, 1H), 4.56~4.61 (m, 1H), 5.78 (d, J=9.2, 1H), 7.19~7.37 (m, 3H).

Preparation Example 42: (E)-3-(2-nitrophenyl)-acrylic acid

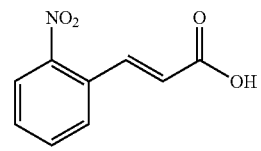 [SMILES: O=C(O)/C=C/c1ccccc1[N+](=O)[O-]]

The substantially same method as described in Preparation Example 9 was conducted, except that 2-nitrobenzenealdehyde was used instead of 2-Fluoroaldehyde, to obtain the title compound (2.06 g, 70~90%)

¹H NMR (400 MHz, DMSO) δ 6.52 (d, J=15.6, 1H), 7.65 (t, J=8.1, 1H), 7.75 (t, J=7.4, 1H), 7.83 (d, J=15.8, 1H), 7.92 (dd, J=7.6, 1.1, 1H), 8.05 (dd, J=8.1, 1.2, 1H)

Preparation Example 43: (E)-Methyl-3-(2-nitrophenyl)acrylate

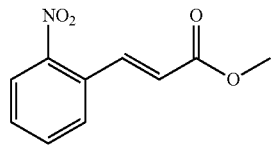

The substantially same method as described in Preparation Example 24 was conducted, except that (E)-3-(2-nitrophenyl)-acrylic acid (Preparation example 42) was used instead of 2-chlorocinnamic acid, to obtain the title compound (15.8 g, 70~90%)

¹H NMR (400 MHz, CDCl₃) δ 3.80 (s, 3H), 6.34 (d, J=15.9 Hz, 1H), 7.49-7.68 (m, 4H), 8.01 (d, J=7.9 Hz, 1H), 8.08 (d, J=15.9, 1H).

Preparation Example 44: (2S,3R)-methyl-3-(2-nitrophenyl)-2,3-dihydroxypropanoate

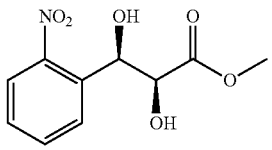 [SMILES: COC(=O)[C@@H](O)[C@H](O)c1ccccc1[N+](=O)[O-]]

The substantially same method as described in Preparation Example 3 was conducted, except that (E)-Methyl-3-(2-nitrophenyl)acrylate (Preparation example 43) was used instead of (E)-1-chloro-2-(3-(methoxymethoxy)prop-1-enyl)benzene (Preparation example 2), to obtain the title compound (12.5 g, 75~90%).

$^1$H NMR (400 MHz, CDCl$_3$): δ=4.31 (s, 3H), 5.44 (m, 4H), 5.89 (s, 1H), 7.53~7.90 (m, 4H).

Preparation Example 45: (4S, 5R)-methyl-5-(2-nitrophenyl)-2,2-dimethyl-1,3-dioxolane-4-carboxylate

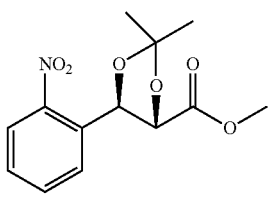 [SMILES: COC(=O)[C@H]1OC(C)(C)O[C@@H]1c1ccccc1[N+](=O)[O-]]

The substantially same method as described in Preparation Example 26 was conducted, except that (2S,3R)-methyl-3-(2-nitrophenyl)-2,3-dihydroxypropanoate (Preparation example 44) was used instead of (2R,3S)-methyl-3-(2-chlorophenyl)-2,3-dihydroxypropanoate (Preparation example 25), to obtain the title compound (11 g, 60~80%)

$^1$H NMR (400 MHz, CDCl$_3$): δ 1.38 (s, 3H), 1.40 (s, 3H), 3.75 (s, 3H), 4.49 (d, J=7.4, 1H), 5.25 (d, J=7.4, 1H), 7.48~7.77 (m, 3H, 8.08 (m, 1H)

Preparation Example 46: ((4R,5R)-5-(2-nitrophenyl)-2,2-dimethyl-1.3-dioxolane-4-yl)methanol

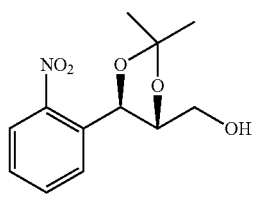 [SMILES: CC1(C)O[C@H](c2ccccc2[N+](=O)[O-])[C@@H](CO)O1]

The substantially same method as described in Preparation. Example 27 was conducted, except that (4S,5R)-methyl-5-(2-nitrophenyl)-2,2-dimethyl-1.3-dioxolane-4-carboxylate (Preparation example 45) was used instead of (4S,5R)-methyl-5-(2-chlorophenyl)-2,2-dimethyl-1,3-dioxolane-4-carboxylate (Preparation example 26), to obtain the title compound (13.1 g, 70~95%)

$^1$H NMR (400 MHz, CDCl$_3$): δ 1.38 (s, 3H), 1.40 (s, 3H), 3.89 (d, J=4.1, 2H), 4.26 (dt, J=7.0, 4.1, 1H), 5.26 (d, J=7.0, 1H), 7.55~7.86 (m, 3H), 8.08 (m, 1H).

Preparation Example 47: ((4R,5R)-5-(2-aminophenyl)-2,2-dimethyl-1.3-dioxolane-4-yl)methanol

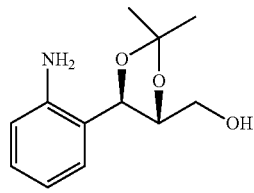 [SMILES: CC1(C)O[C@H](c2ccccc2N)[C@@H](CO)O1]

To a stirred solution of ((4R,5R)-5-(2-nitrophenyl)-2,2-dimethyl-1.3-dioxolane-4-yl)methanol (Preparation example 46, 14 g) in EtOAc was added Pd(OH)$_2$ (20 wt %, 2.8 g) under hydrogen gas (balloon). The mixture was stirred for 6 h then the resulting mixture was filtered through celite and concentrated under reduced pressure. The crude product was purified by SiO$_2$ gel column chromatography to give title compound (7.5 g 65~85%)

$^1$H NMR (400 MHz, CDCl$_3$): δ 1.39 (s, 3H), 1.40 (s, 3H), 3.88 (d, J=4.27, 2H), 3.99 (dt, J=7.02, J=4.30, 1H), 4.74 (d, J=7.02, 1H), 6.65~6.72 (m, 2H), 6.98 (m, 1H), 7.25 (m, 1H).

Preparation Example 48: (2R,3S)-methyl-3-(2-nitrophenyl)-2,3-dihydroxypropanoate

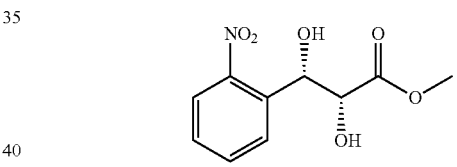

The substantially same method as described in Preparation Example 25 was conducted, except that (E)-methyl-3-(2-nitrophenyl)acrylate (Preparation example 43) was used instead of (E)-Methyl-3-(2-chlorophenyl)acrylate (Preparation example 24), to obtain the title compound (21.7 g, 60~80%)

$^1$H NMR (400 MHz, CDCl$_3$): δ 4.31 (s, 3H), 5.44 (m, 4H), 5.89 (s, 1H), 7.53~7.90 (m, 4H)

Preparation Example 49: (4R,5S)-methyl-5-(2-nitrophenyl)-2,2-dimethyl-1.3-dioxolane-4-carboxylate

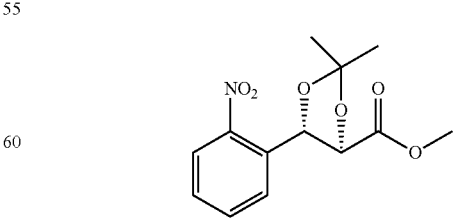

The substantially same method as described in Preparation Example 26 was conducted, except that (2R,3S)-methyl-3-(2-nitrophenyl)-2,3-dihydroxypropanoate (Preparation example 48) was used instead of (2S,3R)-methyl-3-(2-chlorophenyl)-2,3-dihydroxypropanoate (Preparation example 25), to obtain the title compound (21 g, 60~90%)

¹H NMR (400 MHz, CDCl₃): δ 1.38 (s, 3H), 1.40 (s, 3H), 3.75 (s, 3H), 4.49 (d, J=7.4, 1H), 5.25 (d, J=7.4, 1H), 7.48~7.77 (m, 3H), 8.08 (m, 1H)

Preparation Example 50: ((4S,5S)-5-(2-nitrophenyl)-2,2-dimethyl-1.3-dioxolane-4-yl)methanol

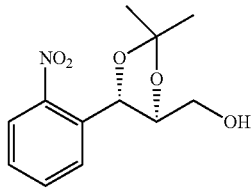 [SMILES: CC1(C)O[C@@H](CO)[C@H](c2ccccc2[N+](=O)[O-])O1]

The substantially same method as described in Preparation Example 27 was conducted, except that (4R,5S)-methyl-5-(2-nitrophenyl)-2,2-dimethyl-1.3-dioxolane-4-carboxylate (Preparation example 48) was used instead of (4R,5S)-methyl-5-(2-chlorophenyl)-2,2-dimethyl-1.3-dioxolane-4-carboxylate (Preparation example 26), to obtain the title compound (14 g, 70~95%)

¹H NMR (400 MHz, CDCl₃): δ δ 1.38 (s, 3H), 1.40 (s, 3H), 3.89 (d, J=4.1, 2H), 4.26 (dt, J=7.0, 4.1, 1H), 5.26 (d, J=7.0, 1H), 7.55~7.86 (m, 3H), 8.08 (m, 1H).

Preparation Example 51: ((4S,5S)-5-(2-aminophenyl)-2,2-dimethyl-1.3-dioxolane-4-yl)methanol

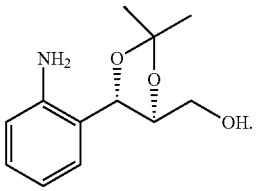 [SMILES: CC1(C)O[C@@H](CO)[C@H](c2ccccc2N)O1]

The substantially same method as described in Preparation Example 47 was conducted, except that (4S,5S)-methyl-5-(2-nitrophenyl)-2,2-dimethyl-1.3-dioxolane-4-carboxylate (Preparation example 50) was used instead of (4R,5R)-5-(2-nitrophenyl)-2,2-dimethyl-1.3-dioxolane-4-yl)methanol (Preparation example 46), to obtain the title compound (11 g, 70~95%)

¹H NMR (400 MHz, CDCl₃): δ δ 1.38 (s, 3H), 1.40 (s, 3H), 3.89 (d, J=4.1, 2H), 4.26 (dt, J=7.0, 4.1, 1H), 5.26 (d, J=7.0, 1H), 7.55~7.86 (m, 3H), 8.08 (m, 1H).

Preparation Example 52: (E)-3-o-tolyacrylic acid

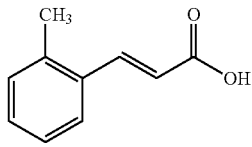

The substantially same method as described in Preparation Example 9 was conducted, except that 2-methylbenzenealdehyde was used instead of 2-Fluoroaldehyde, to obtain the title compound (1.5 g, 70~90%)

¹H NMR (400 MHz, CDCl₃): δ 2.48 (s, 3H), 6.16 (d, J=15.1, 1H), 7.00~7.10 (m, 1H), 7.21~7.26 (m, 3H), 8.04 (d, J=15.1, 1H), 11.0 (s, 1H).

Preparation Example 53: (E)-Methyl-3-o-tolyacrylate

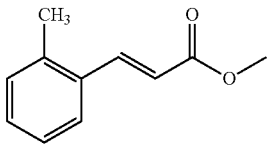

The substantially same method as described in Preparation Example 24 was conducted, except that (E)-3-o-tolyacrylic acid (Preparation example 52) was used instead of 2-chlorocinnamic acid, to obtain the title compound (1.5 g, 70~90%)

¹H NMR (400 MHz, CDCl₃): δ 2.48 (s, 3H), 3.77 (s, 3H), 6.14 (d, J=15.1, 1H), 7.00~7.10 (m, 1H), 7.21~7.26 (m, 3H), 8.07 (d, J=15.1, 1H).

Preparation Example 54: (2S,3R)-methyl-3-(2-methylphenyl)-2,3-dihydroxypropanoate

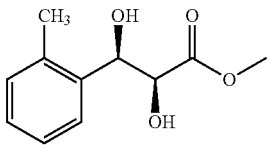

The substantially same method as described in Preparation Example 3 was conducted, except that (E)-Methyl-3-o-tolyacrylate (Preparation example 53) was used instead of (E)-1-chloro-2-(3-(methoxymethoxy)prop-1-enyl)benzene (Preparation example 2), to obtain the title compound (1.3 g, 75~90%).

¹H NMR (400 MHz, CDCl₃): δ 2.34 (s, 3H), 2.80 (s, 1H), 3.65 (s, 1H), 3.68 (s, 3H), 4.52 (d, J=7.0, 1H), 5.22 (d, J=7.0, 1H), 7.19~7.39 (m, 4H).

Preparation Example 55: (4S, 5R)-methyl-5-(2-methylphenyl)-2,2-dimethyl-1.3-dioxolane-4-carboxylate

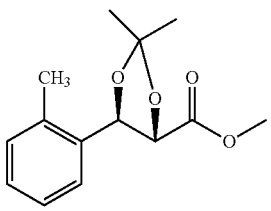 [SMILES: COC(=O)[C@H]1OC(C)(C)O[C@@H]1c1ccccc1C]

The substantially same method as described in Preparation Example 26 was conducted, except that (2S,3R)-methyl-3-(2-methylphenyl)-2,3-dihydroxypropanoate (Preparation example 54) was used instead of (2R,3S)-methyl-3-(2-chlorophenyl)-2,3-dihydroxypropanoate (Preparation example 25), to obtain the title compound (1.7 g, 60~80%)

$^1$H NMR (400 MHz, CDCl$_3$): δ 1.27 (s, 6H), 2.34 (s, 3H), 3.68 (s, 3H), 5.11 (d, J=7.0, 1H), 5.81 (d, J=7.0, 1H), 7.19~7.26 (m, 3H), 7.37~7.39 (m, 1H).

Preparation Example 56: ((4R,5R)-5-(2-methylphenyl)-2,2-dimethyl-1.3-dioxolane-4-yl)methanol

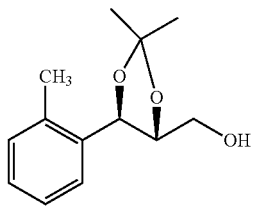 [SMILES: Cc1ccccc1[C@H]1OC(C)(C)O[C@@H]1CO]

The substantially same method as described in Preparation Example 27 was conducted, except that (4S,5R)-methyl-5-(2-methylphenyl)-2,2-dimethyl-1.3-dioxolane-4-carboxylate (Preparation example 55) was used instead of (4R,5S)-methyl-5-(2-chlorophenyl)-2,2-dimethyl-1.3-dioxolane-4-carboxylate (Preparation example 26), to obtain the title compound (1.3 g, 70~95%)

$^1$H NMR (400 MHz, CDCl$_3$): δ 1.27 (s, 6H), 2.34 (s, 3H); 3.52~3.60 (m, 2H), 3.65 (s, 1H), 4.36 (dd, J=7.0, J=7.0, 1H), 5.17 (d, J=7.0, 1H), 7.19~7.26 (m, 3H), 7.37~7.39 (m, 1H).

Preparation Example 57: (2R,3S)-methyl-3-(2-methylphenyl)-2,3-dihydroxypropanoate

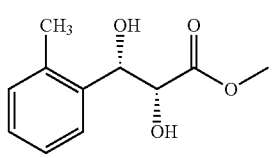

The substantially same method as described in Preparation Example 25 was conducted, except that (E)-methyl-3-o-tolyacrylate (Preparation example 53) was used instead of (E)-Methyl-3-(2-chlorophenyl)acrylate (Preparation example 24), to obtain the title compound (1.7 g, 60~80%)

$^1$H NMR (400 MHz, CDCl$_3$): δ 2.34 (s, 3H), 2.80 (s, 1H), 3.65 (s, 1H), 3.68 (s, 3H), 4.52 (d, J=7.0, 1H), 5.22 (d, J=7.0, 1H), 7.19~7.39 (m, 4H).

Preparation Example 58: (4R,5S)-methyl-5-(2-methylphenyl)-2,2-dimethyl-1.3-dioxolane-4-carboxylate

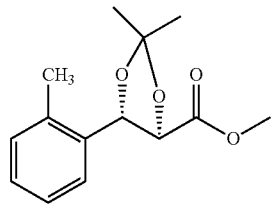 [SMILES: COC(=O)[C@@H]1OC(C)(C)O[C@H]1c1ccccc1C]

The substantially same method as described in Preparation Example 26 was conducted, except that (2R,3S)-methyl-3-(2-methylphenyl)-2,3-dihydroxypropanoate (Preparation example 57) was used instead of (2R,3S)-methyl-3-(2-chlorophenyl)-2,3-dihydroxypropanoate (Preparation example 25), to obtain the title compound (1.9 g, 60~90%)

$^1$H NMR (400 MHz, CDCl$_3$): δ 1.27 (s, 6H), 2.34 (s, 3H), 3.68 (s, 3H), 5.11 (d, J=7.0, 1H), 5.81 (d, J=7.0, 1H), 7.19~7.26 (m, 3H), 7.37~7.39 (m, 1H).

Preparation Example 59: ((4S,5S)-5-(2-methylphenyl)-2,2-dimethyl-1.3-dioxolane-4-yl)methanol

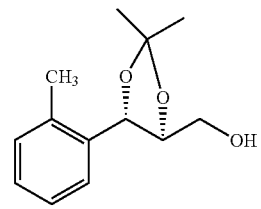 [SMILES: Cc1ccccc1[C@@H]1OC(C)(C)O[C@H]1CO]

The substantially same method as described in Preparation Example 27 was conducted, except that (4R,5S)-methyl-5-(2-methylphenyl)-2,2-dimethyl-1.3-dioxolane-4-carboxylate (Preparation example 58) was used instead of (4R,5S)-methyl-5-(2-chlorophenyl)-2,2-dimethyl-1.3-dioxolane-4-carboxylate (Preparation example 26), to obtain the title compound (1.5 g, 70~95%)

$^1$H NMR (400 MHz, CDCl$_3$): δ 1.27 (s, 6H), 2.34 (s, 3H), 3.52~3.60 (m, 2H); 3.65 (s, 1H), 4.36 (dd, j=7.0, J=7.0, 1H), 5.17 (d, J=7.0, 1H), 7.19~7.26 (m, 3H), 7.37~7.39 (m, 1H).

Preparation Example 60: ((4S,5R)-methyl-5-(2-chlorophenyl)-2-mehtyl-1.3-dioxolane-4-carboxylate

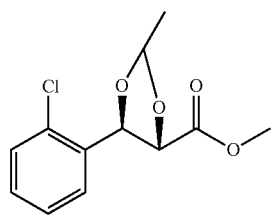

Dichloromethane (MC) was added to (2S,3R)-methyl-3-(2-chlorophenyl)-2,3-dihydroxypropanoate (Preparation example 433) at room temperature. 1,1-Diethoxyethane (8 ml) and p-toluenesulfonic acid (0.27 g) was added and stirred at room temperature. The reaction mixture was quenched with H₂O, extracted with MC, washed with H₂O, dried over anhydrous magnesium sulfate (MgSO₄), filtered and concentrated. The crude compound was purified by a silica gel column to produce the title compound (3.6 g, 70~95%).

¹H NMR (400 MHz, CDCl₃) δ 1.36 (d, J=6.4, 3H), 3.78 (s, 3H), 4.30 (d, J=7.6, 1H), 5.07 (m, 1H), 5.62 (d, J=7.6, 1H), 7.28~7.64 (m, 4H)

Preparation Example 61: ((4R,5R)-5-(2-chlorophenyl)-2-mehtyl-1.3-dioxolane-4-yl)methanol

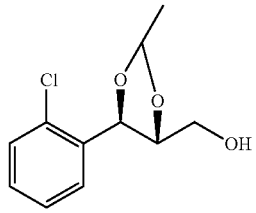

The substantially same method as described in Preparation Example 27 was conducted, except that (4S,5R)-methyl-5-(2-chlorophenyl)-2-mehtyl-1.3-dioxolane-4-carboxylate (Preparation example 60) was used instead of (4R,5S)-methyl-5-(2-chlorophenyl)-2,2-dimethyl-1.3-dioxolane-4-carboxylate (Preparation example 26), to obtain the title compound (3.1 g, 70~95%)

¹H NMR (400 MHz, CDCl₃): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.19~7.26 (m, 3H), 7.37~7.39 (m, 1H).

Preparation Example 62: ((4R,5S)-methyl-5-(2-chlorophenyl)-2-mehtyl-1.3-dioxolane-4-carboxylate

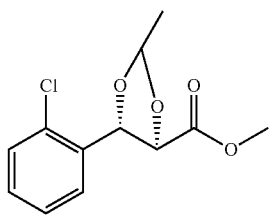

The substantially same method as described in Preparation Example 60 was conducted, except that (2R,3S)-methyl-3-(2-chlorophenyl)-2.3-dihydroxypropanote (Preparation example 25) was used instead of (2S,3R)-methyl-3-(2-chlorophenyl)-2.3-dihydroxypropanote (Preparation example 54), to obtain the title compound (2.1 g, 70~95%).

¹H NMR (400 MHz, CDCl₃) δ 1.36 (d, J=6.4, 3H), 3.78 (s, 3H), 4.30 (d, J=7.6, 1H), 5.07 (m, 1H), 5.62 (d, J=7.6, 1H), 7.28~7.64 (m, 4H)

Preparation Example 63: ((4S,5S)-5-(2-chlorophenyl)-2-mehtyl-1.3-dioxolane-4-yl)methanol

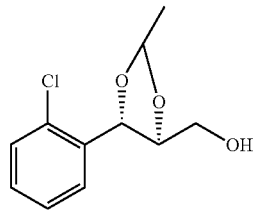

The substantially same method as described in Preparation Example 27 was conducted, except that (4R,5S)-methyl-5-(2-chlorophenyl)-2-mehtyl-1.3-dioxolane-4-carboxylate (Preparation example 62) was used instead of (4R,5S)-methyl-5-(2-chlorophenyl)-2,2-dimethyl-1.3-dioxolane-4-carboxylate (Preparation example 26), to obtain the title compound (3.1 g, 70~95%)

¹H NMR (400 MHz, CDCl₃): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.19~7.26 (m, 3H), 7.37~7.39 (m, 1H).

Preparation Example 64: (4S, 5R)-methyl-5-(2-chlorophenyl)-2,2-diethyl-1.3-dioxolane-4-carboxylate

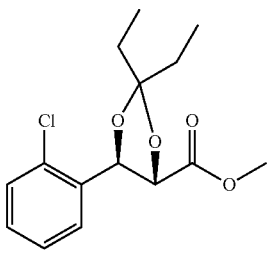 [SMILES: CCC1(CC)O[C@H](C(=O)OC)[C@@H](c2ccccc2Cl)O1]

3-pentanone was added to (2S,3R)-methyl-3-(2-chlorophenyl)-2,3-dihydroxypropanoate (Preparation example 433) at room temperature. Sulfuric acid (H₂SO₄) was added and stirred at room temperature. The reaction mixture was quenched with H₂O, extracted with EA, washed with H₂O, dried over anhydrous sodium sulfate (Na₂SO₄), filtered and concentrated. The crude compound was purified by a silica gel column to produce the title compound (1.6 g, 60~85%).

¹H NMR (400 MHz, CDCl₃) δ 0.96 (m, 6H), 1.59 (m, 4H), 3.67 (s, 3H), 5.11 (d, J=7.6, 1H), 5.81 (d, J=7.6, 1H), 7.22~7.60 (m, 4H)

Preparation Example 65: ((4R,5R)-5-(2-chlorophenyl)-2,2-diethyl-1.3-dioxolane-4-yl)methanol

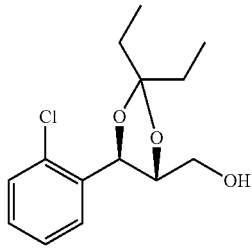 [SMILES: CCC1(CC)O[C@H](c2ccccc2Cl)[C@@H](CO)O1]

The substantially same method as described in Preparation Example 27 was conducted, except that (4S,5R)-methyl-5-(2-chlorophenyl)-2,2-diethyl-1.3-dioxolane-4-carboxylate (Preparation example 64) was used instead of (4R,5S)-methyl-5-(2-chlorophenyl)-2,2-dimethyl-1.3-dioxolane-4-carboxylate (Preparation example 26), to obtain the title compound (2.0 g, 70~95%)

$^1$H NMR (400 MHz, CDCl$_3$): δ 0.96 (m, 6H), 1.59 (m, 4H), 3.66 (d, J=8.0, 2H), 5.09 (d, J=7.6, 1H), 5.88 (d, J=7.6, 1H), 7.26~7.62 (m, 4H).

Preparation Example 66: (4R, 5S)-methyl-5-(2-chlorophenyl)-2,2-diethyl-1.3-dioxolane-4-carboxylate

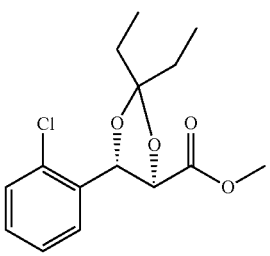 [SMILES: CCC1(CC)O[C@@H](C(=O)OC)[C@H](c2ccccc2Cl)O1]

The substantially same method as described in Preparation Example 64 was conducted, except that (2R,3S)-methyl-3-(2-chlorophenyl)-2.3-dihydroxypropanote (Preparation example 25) was used instead of (2S,3R)-methyl-3-(2-chlorophenyl)-2.3-dihydroxypropanote (Preparation example 54), to obtain the title compound (1.4 g, 70~95%).

$^1$H NMR (400 MHz, CDCl$_3$) δ 0.96 (m, 6H), 1.59 (m, 4H), 3.67 (s, 3H), 5.11 (d, J=7.6, 1H), 5.81 (d, J=7.6, 1H), 7.22~7.60 (m, 4H)

Preparation Example 67: ((4S,5S)-5-(2-chlorophenyl)-2,2-diethyl-1.3-dioxolane-4-yl)methanol

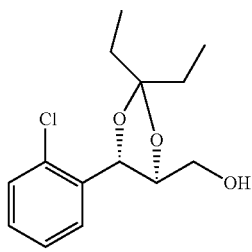 [SMILES: CCC1(CC)O[C@@H](CO)[C@H](c2ccccc2Cl)O1]

The substantially same method as described in Preparation Example 65 was conducted, except that (4R,5S)-methyl-5-(2-chlorophenyl)-2,2-diethyl-1.3-dioxolane-4-carboxylate (Preparation example 66) was used instead of (4R,5S)-methyl-5-(2-chlorophenyl)-2,2-diethyl-1.3-dioxolane-4-carboxylate (Preparation example 64), to obtain the title compound (2.2 g, 70~95%)

$^1$H NMR (400 MHz, CDCl$_3$): δ 0.96 (m, 6H), 1.59 (m, 4H), 3.66 (d, J=8.0, 2H), 5.09 (d, J=7.6, 1H), 5.88 (d, J=7.6, 1H), 7.26~7.62 (m, 4H).

Preparation Example 68: (2S, 3R)-methyl-3-(2-chlorophenyl)-1,4-dioxaspiro[4,4]nonane-2-carboxylate

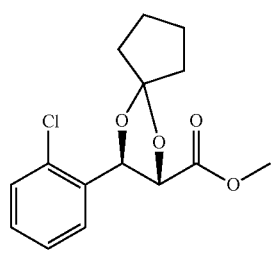 [SMILES: COC(=O)[C@H]1OC2(CCCC2)O[C@@H]1c1ccccc1Cl]

The substantially same method as described in Preparation Example 64 was conducted, except that cyclopentanone was used instead of 3-pentanone, to obtain the title compound (2.2 g, 70~95%).

$^1$H NMR (400 MHz, DMSO) δ 1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.39~7.61 (m, 4H)

Preparation Example 69: ((2R,3R)-3-(2-chlorophenyl)-1,4-dioxaspiro[4,4]nonane-2-yl)methanol

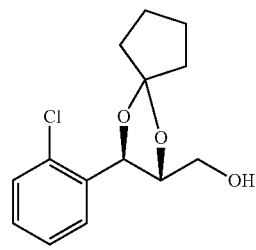 [SMILES: OC[C@H]1OC2(CCCC2)O[C@@H]1c1ccccc1Cl]

The substantially same method as described in Preparation Example 65 was conducted, except that (2S, 3R)-methyl-3-(2-chlorophenyl)-1,4-dioxaspiro[4,4]nonane-2-carboxylate (Preparation example 68) was used instead of (4S,5R)-methyl-5-(2-chlorophenyl)-2,2-diethyl-1.3-dioxolane-4-carboxylate (Preparation example 64), to obtain the title compound (1.7 g, 70~95%)

$^1$H NMR (400 MHz, DMSO): δ 1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.34~7.58 (m, 4H)

Preparation Example 70: (2R, 3S)-methyl-3-(2-chlorophenyl)-1,4-dioxaspiro[4,4]nonane-2-carboxylate

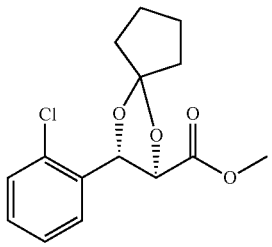 [SMILES: COC(=O)[C@@H]1OC2(CCCC2)O[C@H]1c1ccccc1Cl]

The substantially same method as described in Preparation Example 68 was conducted, except that (2R,3S)-methyl-3-(2-chlorophenyl)-2,3-dihydroxypropanoate (Preparation example 25) was used instead of (2S,3R)-methyl-3-(2-chlorophenyl)-2,3-dihydroxypropanoate (Preparation example 433), to obtain the title compound (1.5 g, 70~95%).
$^1$H NMR (400 MHz, DMSO) δ 1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.39~7.61 (m, 4H)

Preparation Example 71: ((2R,3R)-3-(2-chlorophenyl)-1,4-dioxaspiro[4,4]nonane-2-yl)methanol

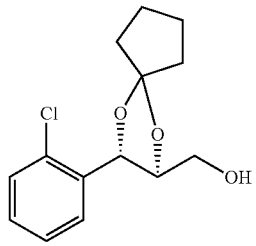 [SMILES: OC[C@@H]1OC2(CCCC2)O[C@H]1c1ccccc1Cl]

The substantially same method as described in Preparation Example 69 was conducted, except that (2R, 3S)-methyl-3-(2-chlorophenyl)-1,4-dioxaspiro[4,4]nonane-2-carboxylate (Preparation example 70) was used instead of (2S, 3R)-methyl-3-(2-chlorophenyl)-1,4-dioxaspiro[4,4]nonane-2-carboxylate (Preparation example 68), to obtain the title compound (1.8 g, 70~95%)
$^1$H NMR (400 MHz, DMSO): δ 1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.34~7.58 (m, 4H)

Preparation Example 72: (2S, 3R)-methyl-3-(2-chlorophenyl)-1,4-dioxaspiro[4,5]decane-2-carboxylate

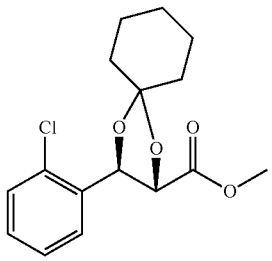 [SMILES: COC(=O)[C@H]1OC2(CCCCC2)O[C@@H]1c1ccccc1Cl]

The substantially same method as described in Preparation Example 64 was conducted, except that cyclohexanone was used instead of 3-pentanone, to obtain the title compound (1.2 g, 70~95%).
$^1$H NMR (400 MHz, DMSO) δ 1.61~1.69 (m, 10H), 3.79 (s, 3H), 4.33 (d, J=8.0, 1H), 5.85 (d, J=8.0, 1H), 7.35~7.63 (m, 4H)

Preparation Example 73: ((2R,3R)-3-(2-chlorophenyl)-1,4-dioxaspiro[4,5]decane-2-yl)methanol

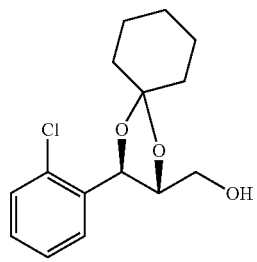 [SMILES: OC[C@H]1OC2(CCCCC2)O[C@@H]1c1ccccc1Cl]

The substantially same method as described in Preparation Example 65 was conducted, except that (2S, 3R)-methyl-3-(2-chlorophenyl)-1,4-dioxaspiro[4,5]decane-2-carboxylate (Preparation example 72) was used instead of (4S,5R)-methyl-5-(2-chlorophenyl)-2,2-diethyl-1,3-dioxolane-4-carboxylate (Preparation example 64), to obtain the title compound (1.8 g, 70~95%)
$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.48~7.87 (m, 4H)

Preparation Example 74: (2R, 3S)-methyl-3-(2-chlorophenyl)-1,4-dioxaspiro[4,5]decane-2-carboxylate

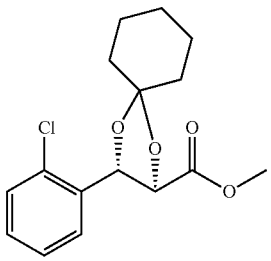 [SMILES: COC(=O)[C@@H]1OC2(CCCCC2)O[C@H]1c1ccccc1Cl]

The substantially same method as described in Preparation Example 72 was conducted, except that (2R,3S)-methyl-3-(2-chlorophenyl)-2,3-dihydroxypropanoate (Preparation example 25) was used instead of (2S,3R)-methyl-3-(2-chlorophenyl)-2,3-dihydroxypropanoate (Preparation example 433), to obtain the title compound (2.1 g, 70~95%).
$^1$H NMR (400 MHz, DMSO) δ 1.61~1.69 (m, 10H), 3.79 (s, 3H), 4.33 (d, J=8.0, 1H), 5.85 (d, J=8.0, 1 H), 7.35~7.63 (m, 4H)

Preparation Example 75: ((2S,3S)-3-(2-chlorophenyl)-1,4-dioxaspiro[4,5]decane-2-yl)methanol

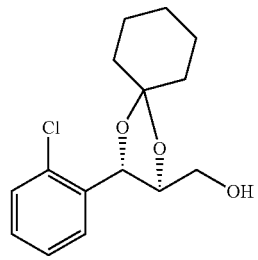 [SMILES: OC[C@@H]1OC2(CCCCC2)O[C@H]1c1ccccc1Cl]

The substantially same method as described in Preparation Example 65 was conducted, except that (2R, 3S)-methyl-3-(2-chlorophenyl)-1,4-dioxaspiro[4,5]decane-2-carboxylate (Preparation example 74) was used instead of (4S,5R)-methyl-5-(2-chlorophenyl)-2,2-diethyl-1.3-dioxolane-4-carboxylate (Preparation example 64), to obtain the title compound (1.6 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.48~7.87 (m, 4H)

Preparation Example 76: (4S, 5R)-methyl-5-(2-chlorophenyl)-2-phenyl-1,3-dioxolane-4-carboxylate

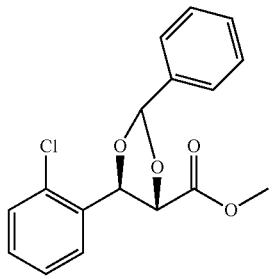

The substantially same method as described in Preparation Example 64 was conducted, except that benzaldehyde was used instead of 3-pentanone, to obtain the title compound (1.1 g, 50~70%).

$^1$H NMR (400 MHz, DMSO) δ 1.61~1.69 (m, 10H), 3.79 (s, 3H), 4.33 (d, J=8.0, 1H), 5.85 (d, J=8.0, 1H), 7.35~7.63 (m, 4H)

Preparation Example 77: ((4R,5R)-5-(2-chlorophenyl)-2-phenyl-1,3-dioxolane-4-yl)methanol

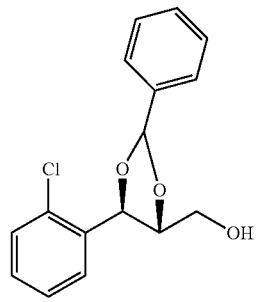

The substantially same method as described in Preparation Example 65 was conducted, except that (2S, 3R)-methyl-3-(2-chlorophenyl)-2-phenyl-1,3-dioxolane-4-carboxylate (Preparation example 76) was used instead of (4S,5R)-methyl-5-(2-chlorophenyl)-2,2-diethyl-1.3-dioxolane-4-carboxylate (Preparation example 64), to obtain the title compound (0.7 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.48~7.87 (m, 4H)

Preparation Example 78: (4R, 5S)-methyl-5-(2-chlorophenyl)-2-phenyl-1,3-dioxolane-4-carboxylate

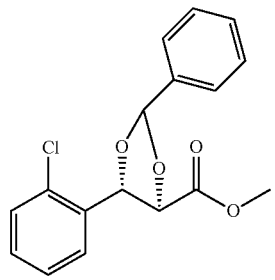

The substantially same method as described in Preparation Example 66 was conducted, except that benzaldehyde was used instead of 3-pentanone, to obtain the title compound (1.9 g, 50~70%).

$^1$H NMR (400 MHz, DMSO) δ 1.61~1.69 (m, 10H), 3.79 (s, 3H), 4.33 (d, J=8.0, 1H), 5.85 (d, J=8.0, 1H), 7.35~7.63 (m, 4H)

Preparation Example 79: ((4R,5S)-5-(2-chlorophenyl)-2-phenyl-1,3-dioxolane-4-yl)methanol

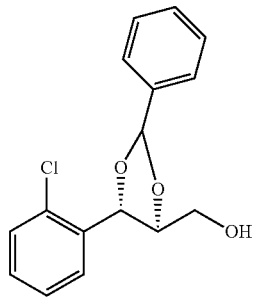

The substantially same method as described in Preparation Example 65 was conducted, except that (2R, 3S)-methyl-3-(2-chlorophenyl)-2-phenyl-1,3-dioxolane-4-carboxylate (Preparation example 78) was used instead of (4S,5R)-methyl-5-(2-chlorophenyl)-2,2-diethyl-1.3-dioxolane-4-carboxylate (Preparation example 64), to obtain the title compound (1.3 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.48~7.87 (m, 4H)

Preparation Example 80: (E)-Methyl-3-(2-fluorophenyl)acrylate

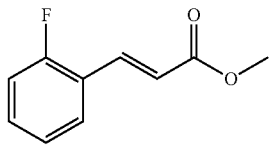

The substantially same method as described in Preparation Example 24 was conducted, except that (E)-3 (2-fluorophenyl)-acrylic acid (Preparation example 9) was used instead of 2-chlorocinnamic acid, to obtain the title compound. (6.98 g, 70~90%)

$^1$H NMR (400 MHz, CDCl$_3$) δ 3.84 (s, 3H), 6.45 (d, J=16.0, 1H), 7.24~7.62 (m, 4H), 8.12 (d, J=16.0, 1H)

Preparation Example 81: (2S,3R)-methyl-3-(2-fluorophenyl)-2,3-dihydroxypropanoate

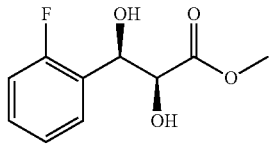

The substantially same method as described in Preparation Example 3 was conducted, except that (E)-Methyl-3-(2-fluorophenyl)acrylate (Preparation example 80) was used instead of (E)-1-chloro-2-(3-(methoxymethoxy)prop-1-enyl) benzene (Preparation example 2), to obtain the title compound (7.5 g, 75~90%).

$^1$H NMR (400 MHz, CDCl$_3$): δ=4.31 (s, 3H), 5.44 (m, 4H), 5.89 (s, 1H), 7.32~7.70 (m, 4H).

Preparation Example 82: (2R,3S)-methyl-3-(2-fluorophenyl)-2,3-dihydroxypropanoate

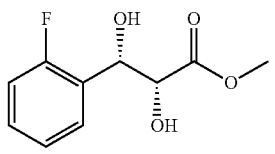

The substantially same method as described in Preparation Example 25 was conducted, except that (E)-methyl-3-(2-fluorophenyl)acrylate (Preparation example 80) was used instead of (E)-Methyl-3-(2-chlorophenyl)acrylate (Preparation example 24), to obtain the title compound (7.2 g, 60~80%)

$^1$H NMR (400 MHz, CDCl$_3$): δ=4.31 (s, 3H), 5.44 (m, 4H), 5.89 (s, 1H), 7.32~7.70 (m, 4H).

Preparation Example 83: ((4S,5R)-methyl-5-(2-fluorophenyl)-2-mehtyl-1.3-dioxolane-4-carboxylate

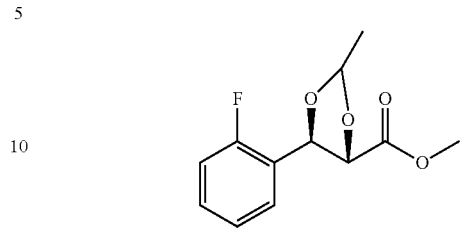

The substantially same method as described in Preparation Example 60 was conducted, except that (2S,3R)-methyl-3-(2-fluorophenyl)-2,3-dihydroxypropanoate (Preparation example 81) was used instead of ((2S,3R)-methyl-3-(2-chlorophenyl)-2,3-dihydroxypropanoate (Preparation example 433), to obtain the title compound (3.1 g, 70~95%).

$^1$H NMR (400 MHz, CDCl$_3$) δ 1.36 (d, J=6.4, 3H), 3.78 (s, 3H), 4.30 (d, J=7.6, 1H), 5.07 (m, 1H), 5.62 (d, J=7.6, 1H), 7.29~7.67 (m, 4H)

Preparation Example 84: ((4R,5R)-5-(2-fluorophenyl)-2-mehtyl-1.3-dioxolane-4-yl)methanol

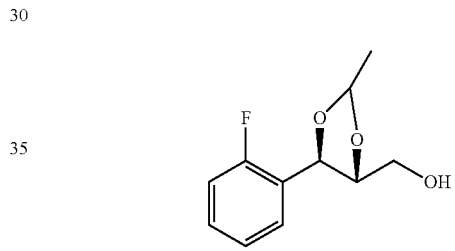

The substantially same method as described in Preparation Example 27 was conducted, except that (4S,5R)-methyl-5-(2-fluorophenyl)-2-mehtyl-1.3-dioxolane-4-carboxylate (Preparation example 83) was used instead of (4R,5S)-methyl-5-(2-chlorophenyl)-2,2-dimethyl-1.3-dioxolane-4-carboxylate (Preparation example 26), to obtain the title compound (3.3 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.19~7.39 (m, 4H).

Preparation Example 85: ((4R,5S)-methyl-5-(2-fluorophenyl)-2-mehtyl-1.3-dioxolane-4-carboxylate

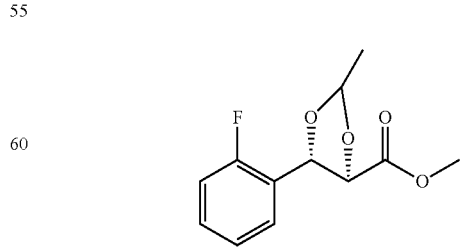

The substantially same method as described in Preparation Example 60 was conducted, except that (2R,3S)- methyl-3-(2-fluorophenyl)-2.3-dihydroxypropanote (Preparation example 82) was used instead of (2S,3R)-methyl-3-(2-chlorophenyl)-2.3-dihydroxypropanote (Preparation example 433), to obtain the title compound (2.9 g, 70~95%).

¹H NMR (400 MHz, CDCl₃) δ 1.36 (d, J=6.4, 3H), 3.78 (s, 3H), 4.30 (d, J=7.6, 1H) 5.07 (m, 1H), 5.62 (d, J=7.6, 1H), 7.29~7.69 (m, 4H)

Preparation Example 86: ((4S,5S)-5-(2-fluorophenyl)-2-mehtyl-1.3-dioxolane-4-yl)methanol

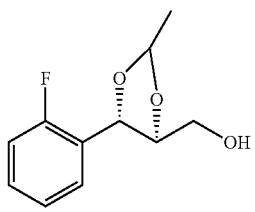

The substantially same method as described in Preparation Example 27 was conducted, except that (4R,5S)-methyl-5-(2-fluorophenyl)-2-mehtyl-1.3-dioxolane-4-carboxylate (Preparation example 85) was used instead of (4R,5S)-methyl-5-(2-chlorophenyl)-2,2-dimethyl-1.3-dioxolane-4-carboxylate (Preparation example 26), to obtain the title compound (3.8 g, 70~95%)

¹H NMR (400 MHz, CDCl₃): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.19~7.4.2 (m, 4H).

Preparation Example 87: (4S, 5R)-methyl-5-(2-fluorophenyl)-2,2-diethyl-1.3-dioxolane-4-carboxylate

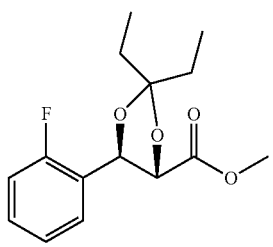 [SMILES: CCC1(CC)O[C@H](C(=O)OC)[C@@H](c2ccccc2F)O1]

The substantially same method as described in Preparation Example 64 was conducted, except that (2S,3R)-methyl-3-(2-fluorophenyl)-2,3-dihydroxypropanoate (Preparation example 81) was used instead of (2S,3R)-methyl-3-(2-chlorophenyl)-2,3-dihydroxypropanoate (Preparation example 433), to obtain the title compound (2.1 g, 60~85%).

¹H NMR (400 MHz, CDCl₃) δ 0.96 (m, 6H), 1.59 (m, 4H), 3.67 (s, 3H), 5.11 (d, J=7.6, 1H), 5.81 (d, J=7.6, 1H), 7.20~7.61 (m, 4H)

Preparation Example 88: ((4R,5R)-5-(2-fluorophenyl)-2,2-diethyl-1.3-dioxolane-4-yl)methanol

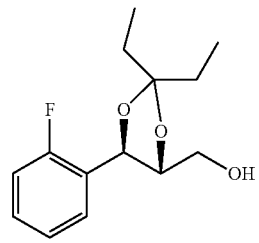 [SMILES: CCC1(CC)O[C@H](c2ccccc2F)[C@@H](CO)O1]

The substantially same method as described in Preparation Example 27 was conducted, except that (4S,5R)-methyl-5-(2-fluorophenyl)-2,2-diethyl-1.3-dioxolane-4-carboxylate (Preparation example 87) was used instead of (4R,5S)-methyl-5-(2-chlorophenyl)-2,2-dimethyl-1.3-dioxolane-4-carboxylate (Preparation example 26), to obtain the title compound (2.2 g, 70~95%)

¹H NMR (400 MHz, CDCl₃): δ 0.96 (m, 6H), 1.59 (m, 4H), 3.66 (d, J=8.0, 2H), 5.09 (d, J=7.6, 1H), 5.88 (d, J=7.6, 1H), 7.23~7.60 (m, 4H).

Preparation Example 89: (4R, 5S)-methyl-5-(2-fluorophenyl)-2,2-diethyl-1.3-dioxolane-4-carboxylate

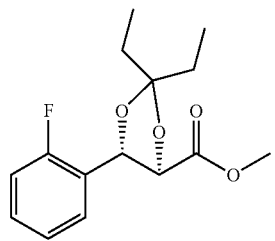 [SMILES: CCC1(CC)O[C@@H](C(=O)OC)[C@H](c2ccccc2F)O1]

The substantially same method as described in Preparation Example 87 was conducted, except that (2R,3S)-methyl-3-(2-fluorophenyl)-2,3-dihydroxypropanoate (Preparation example 82) was used instead of (2S,3R)-methyl-3-(2-fluorophenyl)-2.3-dihydroxypropanote (Preparation example 81), to obtain the title compound (2.3 g, 70~95%).

¹H NMR (400 MHz, CDCl₃) δ 0.96 (m, 6H), 1.59 (m, 4H), 3.67 (s, 3H), 5.11 (d, J=7.6, 1H), 5.81 (d, J=7.6, 1H), 7.20~7.61 (m, 4H)

Preparation Example 90: ((4S,5S)-5-(2-fluorophenyl)-2,2-diethyl-1.3-dioxolane-4-yl)methanol

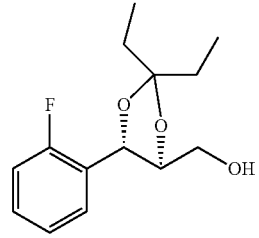

The substantially same method as described in Preparation Example 88 was conducted, except that (4R,5S)- methyl-5-(2-fluorophenyl)-2,2-diethyl-1.3-dioxolane-4-carboxylate (Preparation example 89) was used instead of (4S,5R)-methyl-5-(2-fluorophenyl)-2,2-diethyl-1.3-dioxolane-4-carboxylate (Preparation example 87), to obtain the title compound (2.2 g, 70~95%)

$^1$H NMR (400 MHz, CDCl$_3$): δ 0.96 (m, 6H), 1.59 (m, 4H), 3.66 (d, J=8.0, 2H), 5.09 (d, J=7.6, 1H), 5.88 (d, J=7.6, 1H), 7.23~7.62 (m, 4H).

Preparation Example 91: (2S, 3R)-methyl-3-(2-fluorophenyl)-1,4-dioxaspiro[4,4]nonane-2-carboxylate

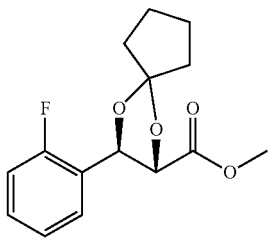 [SMILES: COC(=O)[C@H]1OC2(CCCC2)O[C@@H]1c1ccccc1F]

The substantially same method as described in Preparation Example 87 was conducted, except that cyclopentanone was used instead of 3-pentanone, to obtain the title compound (2.1 g, 70~95%).

$^1$H NMR (400 MHz, DMSO) δ 1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.33~7.62 (m, 4H)

Preparation Example 92: ((2R,3R)-3-(2-fluorophenyl)-1,4-dioxaspiro[4,4]nonane-2-yl)methanol

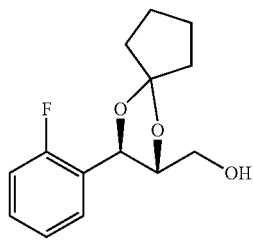 [SMILES: OC[C@H]1OC2(CCCC2)O[C@@H]1c1ccccc1F]

The substantially same method as described in Preparation Example 65 was conducted, except that (2S, 3R)-methyl-3-(2-fluorophenyl)-1,4-dioxaspiro[4,4]nonane-2-carboxylate (Preparation example 91) was used instead of (4S,5R)-methyl-5-(2-chlorophenyl)-2,2-diethyl-1.3-dioxolane-4-carboxylate (Preparation example 64), to obtain the title compound (1.9 g, 70~95%)

$^1$H NMR (400 MHz, DMSO): δ 1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.32~7.57 (m, 4H)

Preparation Example 93: (2R, 3S)-methyl-3-(2-fluorophenyl)-1,4-dioxaspiro[4,4]nonane-2-carboxylate

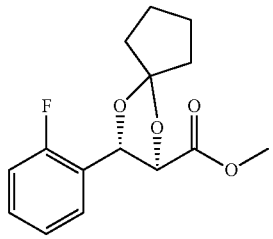 [SMILES: COC(=O)[C@@H]1OC2(CCCC2)O[C@H]1c1ccccc1F]

The substantially same method as described in Preparation Example 91 was conducted, except that (2R,3S)-methyl-3-(2-fluorophenyl)-2,3-dihydroxypropanoate (Preparation example 82) was used instead of (2S,3R)-methyl-3-(2-fluorophenyl)-2.3-dihydroxypropanote (Preparation example 81), to obtain the title compound (1.5 g, 70~95%).

$^1$H NMR (400 MHz, DMSO) δ 1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.39~7.61 (m, 4H)

Preparation Example 94: ((2R,3R)-3-(2-fluorophenyl)-1,4-dioxaspiro[4,4]nonane-2-yl)methanol

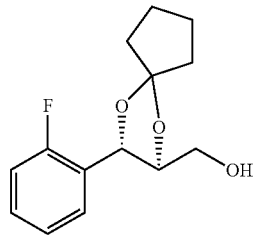 [SMILES: OC[C@@H]1OC2(CCCC2)O[C@H]1c1ccccc1F]

The substantially same method as described in Preparation Example 88 was conducted, except that (2R,3S)-methyl-3-(2-fluorophenyl)-1,4-dioxaspiro[4,4]nonane-2-carboxylate (Preparation example 93) was used instead of (4S,5R)-methyl-5-(2-fluorophenyl)-2,2-diethyl-1.3-dioxolane-4-carboxylate (Preparation example 87), to obtain the title compound (1.2 g, 70~95%)

$^1$H NMR (400 MHz, DMSO): δ 1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.38~7.63 (m, 4H)

Preparation Example 95: (2S, 3R)-methyl-3-(2-fluorophenyl)-1,4-dioxaspiro[4,5]decane-2-carboxylate

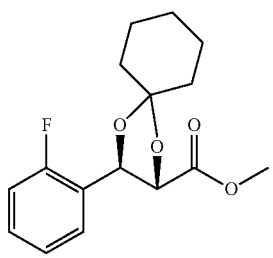 [SMILES: COC(=O)[C@H]1OC2(CCCCC2)O[C@@H]1c1ccccc1F]

The substantially same method as described in Preparation Example 91 was conducted, except that cyclohexanone was used instead of cyclopentanone, to obtain the title compound (1.7 g, 70~95%).

¹H NMR (400 MHz, DMSO) δ 1.61~1.69 (m, 10H), 3.79 (s, 3H), 4.33 (d, J=8.0, 1H), 5.85 (d, J=8.0, 1H), 7.37~7.63 (m, 4H)

Preparation Example 96: ((2R,3R)-3-(2-fluorophenyl)-1,4-dioxaspiro[4,5]decane-2-yl)methanol

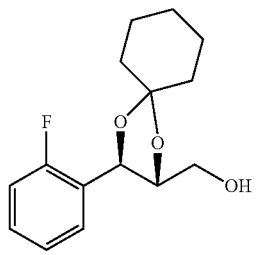 [SMILES: OC[C@H]1OC2(CCCCC2)O[C@@H]1c1ccccc1F]

The substantially same method as described in Preparation Example 73 was conducted, except that (2S, 3R)-methyl-3-(2-fluorophenyl)-1,4-dioxaspiro[4,5]decane-2-carboxylate (Preparation example 95) was used instead of (2S,3R)-methyl-3-(2-chlorophenyl)-1,4-dioxaspiro[4,5]decane-2-carboxylate (Preparation example 72), to obtain the title compound (1.4 g, 70~95%)

¹H NMR (400 MHz, DMSO): δ 1.63~1.75 (m, 10H), 3.52~3.81 (m, 2H), 3.95 (t, J=8.0, 1H), 5.43 (d, J=7.6, 1H), 7.42~7.89 (m, 4H)

Preparation Example 97: (2R, 3S)-methyl-3-(2-fluorophenyl)-1,4-dioxaspiro[4,5]decane-2-carboxylate

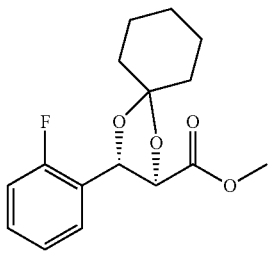 [SMILES: COC(=O)[C@@H]1OC2(CCCCC2)O[C@H]1c1ccccc1F]

The substantially same method as described in Preparation Example 95 was conducted, except that (2R,3S)-methyl-3-(2-fluorophenyl)-2,3-dihydroxypropanoate (Preparation example 82) was used instead of (2S,3R)-methyl-3-(2-fluorophenyl)-2,3-dihydroxypropanote (Preparation example 81), to obtain the title compound (1.8 g, 70~95%).

¹H NMR (400 MHz, DMSO) δ 1.61~1.69 (m, 10H), 3.79 (s, 3H), 4.33 (d, J=8.0, 1H), 5.85 (d, J=8.0, 1H), 7.32~7.64 (m, 4H)

Preparation Example 98: ((2S,3S)-3-(2-fluorophenyl)-1,4-dioxaspiro[4,5]decane-2-yl)methanol

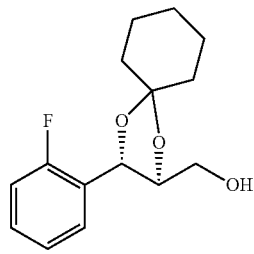

The substantially same method as described in Preparation Example 96 was conducted, except that (2R, 3S)-methyl-3-(2-fluorophenyl)-1,4-dioxaspiro[4,5]decane-2-carboxylate (Preparation example 97) was used instead of (2S, 3R)-methyl-3-(2-fluorophenyl)-1,4-dioxaspiro[4,5]decane-2-carboxylate (Preparation example 95), to obtain the title compound (1.5 g, 70~95%)

¹H NMR (400 MHz, DMSO): δ 1.63~1.75 (m, 10H), 3.52~3.81 (m, 2H), 3.95 (t, J=8.0, 1H), 5.43 (d, J=7.6, 1H), 7.33~7.67 (m, 4H)

Preparation Example 99: (4S, 5R)-methyl-5-(2-fluorophenyl)-2-phenyl-1,3-dioxolane-4-carboxylate

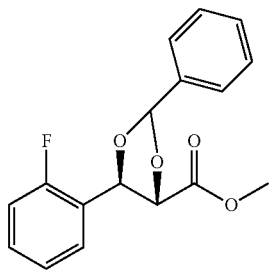

The substantially same method as described in Preparation Example 87 was conducted, except that benzaldehyde was used instead of 3-pentanone, to obtain the title compound (1.6 g, 50~70%).

¹H NMR (400 MHz, DMSO) δ 1.61~1.69 (m, 10H), 3.79 (s, 3H), 4.33 (d, J=8.0, 1H), 5.85 (d, J=8.0, 1H), 7.33~7.64 (m, 4H)

Preparation Example 100: ((4R,5R)-5-(2-fluorophenyl)-2-phenyl-1,3-dioxolane-4-yl)methanol

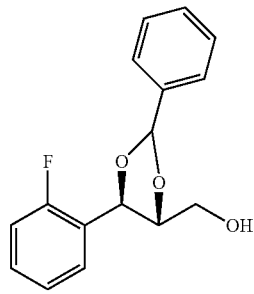

The substantially same method as described in Preparation example 65 was conducted, except that (2S, 3R)-methyl-3-(2-fluorophenyl)-2-phenyl-1,3-dioxolane-4-carboxylate (Preparation example 99) was used instead of (4S,5R)-methyl-5-(2-chlorophenyl)-2,2-diethyl-1.3-dioxolane-4-carboxylate (Preparation example 64), to obtain the title compound (1.3 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.43~7.85 (m, 4H)

Preparation Example 101: (4R, 5S)-methyl-5-(2-fluorophenyl)-2-phenyl-1,3-dioxolane-4-carboxylate

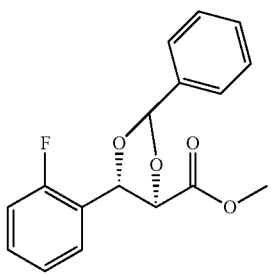

The substantially same method as described in Preparation example 89 was conducted, except that benzaldehyde was used instead of 3-pentanone, to obtain the title compound (1.7 g, 50~70%).

$^1$H NMR (400 MHz, DMSO) δ 1.61~1.69 (m, 10H), 3.79 (s, 3H), 4.33 (d, J=8.0, 1H), 5.85 (d, J=8.0, 1H), 7.33~7.64 (m, 4H)

Preparation Example 102: ((4S,5S)-5-(2-fluorophenyl)-2-phenyl-1,3-dioxolane-4-yl)methanol

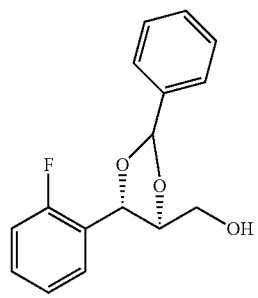

The substantially same method as described in Preparation example 65 was conducted, except that (2R, 3S)-methyl-3-(2-fluorophenyl)-2-phenyl-1,3-dioxolane-4-carboxylate (Preparation example 101) was used instead of (4S,5R)-methyl-5-(2-chlorophenyl)-2,2-diethyl-1.3-dioxolane-4-carboxylate (Preparation example 64), to obtain the title compound (1.1 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.43~7.85 (m, 4H)

Preparation Example 103: (E)-Methyl-3-(2-iodophenyl)acrylate

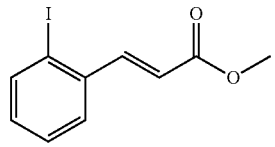

The substantially same method as described in Preparation example 24 was conducted, except that (E)-3(2-iodophenyl)-acrylic acid (Preparation example 17) was used instead of 2-chlorocinnamic acid, to obtain the title compound. (3.2 g, 70~90%)

$^1$H NMR (400 MHz, CDCl$_3$) δ 3.84 (s, 3H), 6.45 (d, J=16.0, 1H), 7.01~7.35 (m, 4H), 8.09 (d, J=16.0, 1H)

Preparation Example 104: (2S,3R)-methyl-3-(2-iodophenyl)-2,3-dihydroxypropanoate

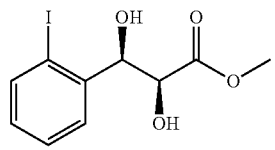

The substantially same method as described in Preparation Example 3 was conducted, except that (E)-Methyl-3-(2-iodophenyl)acrylate (Preparation example 103) was used instead of (E)-1-chloro-2-(3-(methoxymethoxy)prop-1-enyl)benzene (Preparation example 2), to obtain the title compound (3.2 g, 75~90%).

$^1$H NMR (400 MHz, CDCl$_3$): δ=4.31 (s, 3H), 5.44 (m, 4H), 5.89 (s, 1H), 7.30~7.71 (m, 4H).

Preparation Example 105: (2R,3S)-methyl-3-(2-iodophenyl)-2,3-dihydroxypropanoate

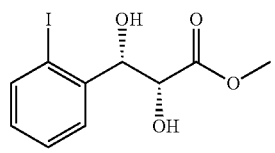

The substantially same method as described in Preparation example 25 was conducted, except that (E)-methyl-3-(2-iodophenyl)acrylate (Preparation example 103) was used instead of (E)-Methyl-3-(2-chlorophenyl)acrylate (Preparation example 24), to obtain the title compound (3.1 g, 60~80%).

$^1$H NMR (400 MHz, CDCl$_3$): δ=4.31 (s, 3H), 5.44 (m, 4H), 5.89 (s, 1H), 7.31~7.72 (m, 4H).

Preparation Example 106: ((4S,5R)-methyl-5-(2-iodophenyl)-2-mehtyl-1.3-dioxolane-4-carboxylate

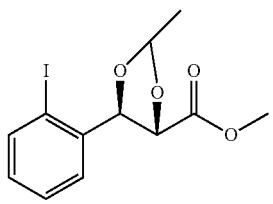

The substantially same method as described in Preparation example 60 was conducted, except that (2S,3R)-methyl-3-(2-iodophenyl)-2,3-dihydroxypropanoate (Preparation example 104) was used instead of (2S,3R)-methyl-3-(2-chlorophenyl)-2,3-dihydroxypropanoate (Preparation example 433), to obtain the title compound (2.7 g, 70~95%).

$^1$H NMR (400 MHz, CDCl$_3$) δ 1.36 (d, J=6.4, 3H), 3.78 (s, 3H), 4.30 (d, J=7.6, 1H), 5.07 (m, 1H), 5.62 (d, J=7.6, 1H), 7.29~7.70 (m, 4H)

Preparation Example 107: ((4R,5R)-5-(2-iodophenyl)-2-mehtyl-1.3-dioxolane-4-yl)methanol

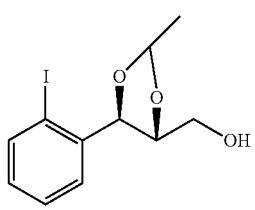

The substantially same method as described in Preparation example 27 was conducted, except that (4S,5R)-methyl-5-(2-iodophenyl)-2-mehtyl-1.3-dioxolane-4-carboxylate (Preparation example 106) was used instead of (4R,5S)-methyl-5-(2-chlorophenyl)-2,2-dimethyl-1.3-dioxolane-4-carboxylate (Preparation example 26), to obtain the title compound (2.3 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.17~7.41 (m, 4H).

Preparation Example 108: ((4R,5S)-methyl-5-(2-iodophenyl)-2-mehtyl-1.3-dioxolane-4-carboxylate

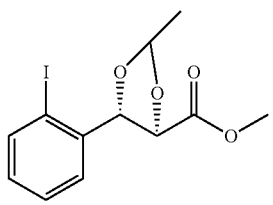

The substantially same method as described in Preparation example 60 was conducted, except that (2R,3S)-methyl-3-(2-iodophenyl)-2.3-dihydroxypropanote (Preparation example 104) was used instead of (2S,3R)-methyl-3-(2-chlorophenyl)-2.3-dihydroxypropanote (Preparation example 433), to obtain the title compound (2.4 g, 70~95%).

$^1$H NMR (400 MHz, CDCl$_3$) δ 1.36 (d, J=6.4, 3H), 3.78 (s, 3H), 4.30 (d, J=7.6, 1H), 5.07 (m, 1H), 5.62 (d, J=7.6, 1H), 7.29~7.70 (m, 4H)

Preparation Example 109: ((4S,5S)-5-(2-iodophenyl)-2-mehtyl-1.3-dioxolane-4-yl)methanol

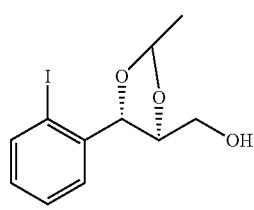

The substantially same method as described in Preparation example 107 was conducted, except that (4R,5S)-methyl-5-(2-iodophenyl)-2-mehtyl-1.3-dioxolane-4-carboxylate (Preparation example 108) was used instead of (4S,5R)-methyl-5-(2-iodophenyl)-2-mehtyl-1.3-dioxolane-4-carboxylate (Preparation example 106), to obtain the title compound (1.9 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.17~7.41 (m, 4H)

Preparation Example 110: (4S, 5R)-methyl-5-(2-iodophenyl)-2,2-diethyl-1.3-dioxolane-4-carboxylate

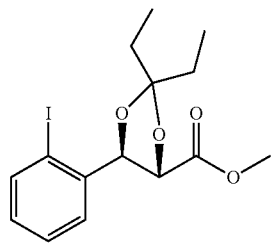 [SMILES: CCC1(CC)O[C@H](C(=O)OC)[C@@H](c2ccccc2I)O1]

The substantially same method as described in Preparation example 64 was conducted, except that (2R,3S)-methyl-3-(2-iodophenyl)-2,3-dihydroxypropanoate (Preparation example 104) was used instead of (2S,3R)-methyl-3-(2-chlorophenyl)-2,3-dihydroxypropanoate (Preparation example 433), to obtain the title compound (2.6 g, 60~85%).

$^1$H NMR (400 MHz, CDCl$_3$) δ 0.96 (m, 6H), 1.59 (m, 4H), 3.67 (s, 3H), 5.11 (d, J=7.6, 1H), 5.81 (d, J=7.6, 1H), 7.23~7.65 (m, 4H)

Preparation Example 111: ((4R,5R)-5-(2-iodophenyl)-2,2-diethyl-1,3-dioxolane-4-yl)methanol

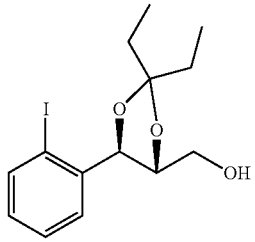 [SMILES: CCC1(CC)O[C@H](c2ccccc2I)[C@@H](CO)O1]

The substantially same method as described in Preparation example 107 was conducted, except that (4S,5R)-methyl-5-(2-iodophenyl)-2,2-diethyl-1,3-dioxolane-4-carboxylate (Preparation example 110) was used instead of (4S,5R)-methyl-5-(2-iodophenyl)-2-mehtyl-1,3-dioxolane-4-carboxylate (Preparation example 106), to obtain the title compound (2.1 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.17~7.41 (m, 4H)

Preparation Example 112: (4R, 5S)-methyl-5-(2-iodophenyl)-2,2-diethyl-1,3-dioxolane-4-carboxylate

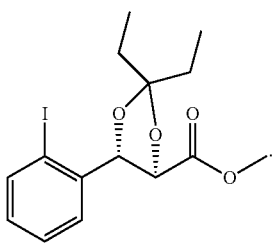 [SMILES: CCC1(CC)O[C@@H](C(=O)OC)[C@H](c2ccccc2I)O1]

The substantially same method as described in Preparation example 110 was conducted, except that (2R,3S)-methyl-3-(2-iodophenyl)-2,3-dihydroxypropanoate (Preparation example 105) was used instead of (2S,3R)-methyl-3-(2-iodophenyl)-2,3-dihydroxypropanoate (Preparation example 104), to obtain the title compound (2.3 g, 60~85%).

$^1$H NMR (400 MHz, CDCl$_3$) δ 0.96 (m, 6H), 1.59 (m, 4H), 3.67 (s, 3H), 5.11 (d, J=7.6, 1H), 5.81 (d, J=7.6, 1H), 7.20~7.61 (m, 4H)

Preparation Example 113: ((4S,5S)-5-(2-iodophenyl)-2,2-diethyl-1,3-dioxolane-4-yl)methanol

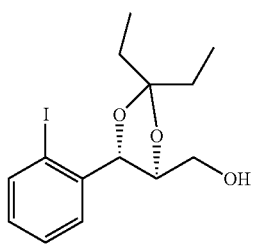 [SMILES: CCC1(CC)O[C@@H](CO)[C@H](c2ccccc2I)O1]

The substantially same method as described in Preparation example 107 was conducted, except that (4R,5S)-methyl-5-(2-iodophenyl)-2,2-diethyl-1,3-dioxolane-4-carboxylate (Preparation example 112) was used instead of (4S,5R)-methyl-5-(2-iodophenyl)-2-mehtyl-1,3-dioxolane-4-carboxylate (Preparation example 106), to obtain the title compound (1.8 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, 17.0, 1H), 7.17~7.41 (m, 4H)

Preparation Example 114: (2S, 3R)-methyl-3-(2-iodophenyl)-1,4-dioxaspiro[4,4]nonane-2-carboxylate

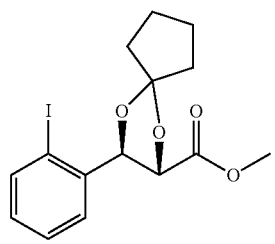 [SMILES: COC(=O)[C@H]1OC2(CCCC2)O[C@@H]1c1ccccc1I]

The substantially same method as described in Preparation example 110 was conducted, except that cyclopentanone was used instead of 3-pentanone, to obtain the title compound (2.7 g, 70~95%).

$^1$H NMR (400 MHz, DMSO) δ 1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.19~7.44 (m, 4H)

Preparation Example 115: ((2R,2R)-3-(2-iodophenyl)-1,4-dioxaspiro[4,4]nonane-2-yl)methanol

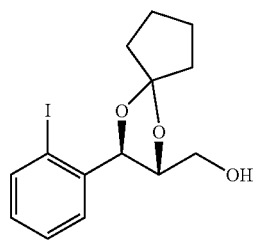 [SMILES: OC[C@H]1OC2(CCCC2)O[C@@H]1c1ccccc1I]

The substantially same method as described in Preparation example 107 was conducted, except that (2S,3R)-methyl-3-(2-iodophenyl)-1,4-dioxaspiro[4,4]nonane-2-carboxylate (Preparation example 114) was used instead of (4S,5R)-methyl-5-(2-iodophenyl)-2-mehtyl-1,3-dioxolane-4-carboxylate (Preparation example 106), to obtain the title compound (2.1 g, 70~95%)

$^1$H NMR (400 MHz, DMSO): δ 1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.20~7.45 (m, 4H)

Preparation Example 116: (2R, 3S)-methyl-3-(2-iodophenyl)-1,4-dioxaspiro[4,4]nonane-2-carboxylate

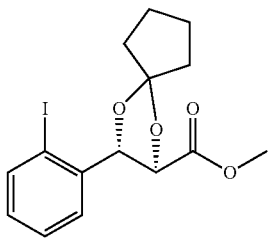 [SMILES: COC(=O)[C@@H]1OC2(CCCC2)O[C@H]1c1ccccc1I]

The substantially same method as described in Preparation example 112 was conducted, except that cyclopentanone was used instead of 3-pentanone, to obtain the title compound (2.9 g, 70~95%).
$^1$H NMR (400 MHz, DMSO) δ 1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.19~7.44 (m, 4H)

Preparation Example 117: ((2S,2S)-3-(2-iodophenyl)-1,4-dioxaspiro[4,4]nonane-2-yl)methanol

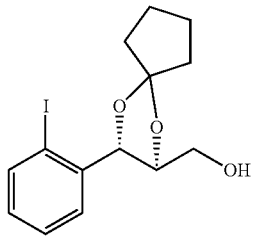 [SMILES: OC[C@@H]1OC2(CCCC2)O[C@H]1c1ccccc1I]

The substantially same method as described in Preparation example 107 was conducted, except that (2R,3S)-methyl-3-(2-iodophenyl)-1,4-dioxaspiro[4,4]nonane-2-carboxylate (Preparation example 116) was used instead of (4S,5R)-methyl-5-(2-iodophenyl)-2-mehtyl-1.3-dioxolane-4-carboxylate (Preparation example 106), to obtain the title compound (1.5 g, 70~95%)
$^1$H NMR (400 MHz, DMSO): δ 1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.20~7.45 (m, 4H)

Preparation Example 118: (2S, 3R)-methyl-3-(2-iodophenyl)-1,4-dioxaspiro[4,5]decane-2-carboxylate

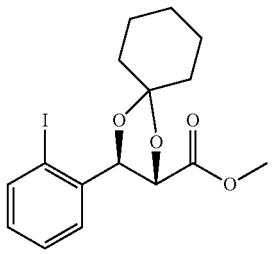

The substantially same method as described in Preparation example 114 was conducted, except that cyclohexanone was used instead of cyclopentanone, to obtain the title compound (1.9 g, 70~95%).
$^1$H NMR (400 MHz, DMSO) δ 1.61~1.69 (m, 10H), 3.79 (s, 3H), 4.33 (d, J=8.0, 1H), 5.85 (d, J=8.0, 1H), 7.17~7.43 (m, 4H)

Preparation Example 119: ((2R,3R)-3-(2-iodophenyl)-1,4-dioxaspiro[4,5]decane-2-yl)methanol

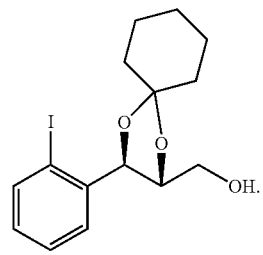 [SMILES: OC[C@H]1OC2(CCCCC2)O[C@@H]1c1ccccc1I]

The substantially same method as described in Preparation example 107 was conducted, except that (2S,3R)-methyl-3-(2-iodophenyl)-1,4-dioxaspiro[4,5]decane-2-carboxylate (Preparation example 118) was used instead of (4S,5R)-methyl-5-(2-iodophenyl)-2-mehtyl-1.3-dioxolane-4-carboxylate (Preparation example 106), to obtain the title compound (1.3 g, 70~95%)
$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.19~7.49 (m, 4H)

Preparation Example 120: (2R, 3S)-methyl-3-(2-iodophenyl)-1,4-dioxaspiro[4,5]decane-2-carboxylate

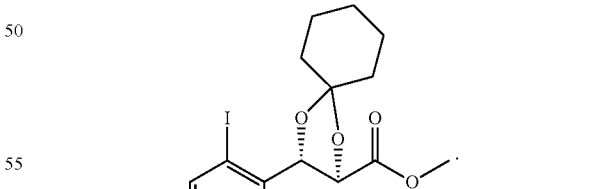

The substantially same method as described in Preparation example 116 was conducted, except that cyclohexanone was used instead of cyclopentanone, to obtain the title compound (2.3 g, 70~95%).
$^1$H NMR (400 MHz, DMSO) δ 1.61~1.69 (m, 10H), 3.79 (s, 3H), 4.33 (d, J=8.0, 1H), 5.85 (d, J=8.0, 1H), 7.17~7.43 (m, 4H)

Preparation Example 121: ((2S,3S)-3-(2-iodophenyl)-1,4-dioxaspiro[4,5]decane-2-yl)methanol

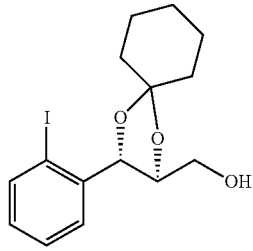 [SMILES: OC[C@@H]1OC2(CCCCC2)O[C@H]1c1ccccc1I]

The substantially same method as described in Preparation example 107 was conducted, except that (2R,3S)-methyl-3-(2-iodophenyl)-1,4-dioxaspiro[4,5]decane-2-carboxylate (Preparation example 120) was used instead of (4S,5R)-methyl-5-(2-iodophenyl)-2-mehtyl-1.3-dioxolane-4-carboxylate (Preparation example 106), to obtain the title compound (1.7 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.19~7.49 (m, 4H)

Preparation Example 122: (4S, 5R)-methyl-5-(2-iodophenyl)-2-phenyl-1,3-dioxolane-4-carboxylate

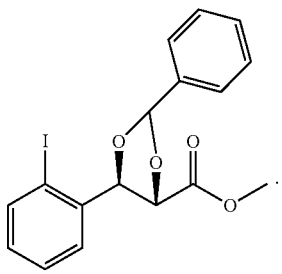

The substantially same method as described in Preparation example 118 was conducted, except that benzaldehyde was used instead of cyclohexanone, to obtain the title compound (1.9 g, 50~70%).

$^1$H NMR (400 MHz, DMSO) δ 3.67 (s, 3H), 5.11 (d, J=8.0, 1H), 5.81 (d, J=8.0, 1H), 6.18 (s, 1H), 6.96~7.57 (m, 9H)

Preparation Example 123: ((4R,5R)-5-(2-iodophenyl)-2-phenyl-1,3-dioxolane-4-yl)methanol

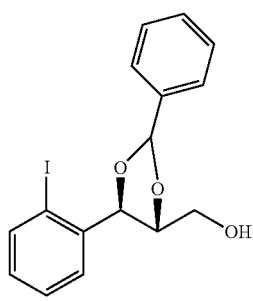

The substantially same method as described in Preparation example 107 was conducted, except that (4S, 5R)-methyl-5-(2-iodophenyl)-2-phenyl-1,3-dioxolane-4-carboxylate (Preparation example 122) was used instead of (4S,5R)-methyl-5-(2-iodophenyl)-2-mehtyl-1.3-dioxolane-4-carboxylate (Preparation example 106), to obtain the title compound (1.4 g, 70~95%)

$^1$H NMR (400 MHz, DMSO): δ 3.66 (d, J=7.6, 2H), 4.36 (m, 1H), 5.17 (d, J=8.0, 1H), 6.18 (s, 1H), 6.94~7.59 (m, 9H)

Preparation Example 124: (4R, 5S)-methyl-5-(2-iodophenyl)-2-phenyl-1,3-dioxolane-4-carboxylate

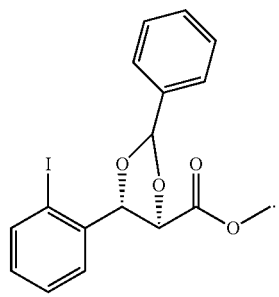

The substantially same method as described in Preparation example 120 was conducted, except benzaldehyde that was used instead of cyclohexanone, to obtain the title compound (2.1 g, 50~70%).

$^1$H NMR (400 MHz, DMSO) δ 3.67 (s, 3H), 5.11 (d, J=8.0, 1H), 5.81 (d, J=8.0, 1H), 6.18 (s, 1H), 6.96~7.57 (m, 9H)

Preparation Example 125: ((4S,5S)-5-(2-iodophenyl)-2-phenyl-1,3-dioxolane-4-yl)methanol

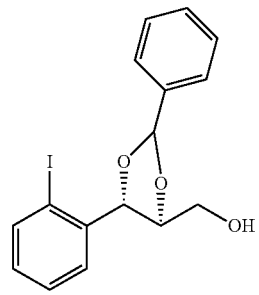

The substantially same method as described in Preparation example 107 was conducted, except that (4R, 5S)-methyl-5-(2-iodophenyl)-2-phenyl-1,3-dioxolane-4-carboxylate (Preparation example 124) was used instead of (4S,5R)-methyl-5-(2-iodophenyl)-2-mehtyl-1.3-dioxolane-4-carboxylate (Preparation example 106), to obtain the title compound (1.3 g, 70~95%)

$^1$H NMR (400 MHz, DMSO): δ 3.66 (d, J=7.6, 2H), 4.36 (m, 1H), 5.17 (d, J=8.0, 1H), 6.18 (s, 1H), 6.94~7.59 (m, 9H)

Preparation Example 126: ((4S,5R)-methyl-5-(2,4-dichlorophenyl)-2-mehtyl-1.3-dioxolane-4-carboxylate

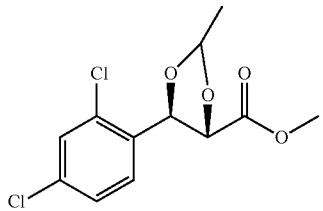

The substantially same method as described in Preparation example 60 was conducted, except that (2S,3R)-methyl-3-(2,4-dichlorophenyl)-2,3-dihydroxypropanoate (Preparation example 36) was used instead of (2S,3R)-methyl-3-(2-chlorophenyl)-2,3-dihydroxypropanoate (Preparation example 433), to obtain the title compound (0.9 g, 70~95%).

$^1$H NMR (400 MHz, CDCl$_3$) δ 1.36 (d, J=6.4, 3H), 3.78 (s, 3H) 4.30 (d, J=7.6, 1H), 5.07 (m, 1H), 5.62 (d, J=7.6, 1H), 7.07~7.21 (m, 3H)

Preparation Example 127: ((4R,5R)-5-(2,4-dichlorophenyl)-2-mehtyl-1.3-dioxolane-4-yl)methanol

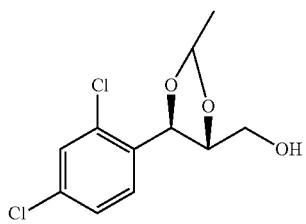

The substantially same method as described in Preparation example 27 was conducted, except that ((4S,5R)-methyl-5-(2,4-dichlorophenyl)-2-mehtyl-1.3-dioxolane-4-carboxylate (Preparation example 126) was used instead of (4R,5S)-methyl-5-(2-chlorophenyl)-2,2-dimethyl-1.3-dioxolane-4-carboxylate (Preparation example 26), to obtain the title compound (0.7 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.08~7.39 (m, 3H).

Preparation Example 128: ((4R,5S)-methyl-5-(2,4-dichlorophenyl)-2-mehtyl-1.3-dioxolane-4-carboxylate

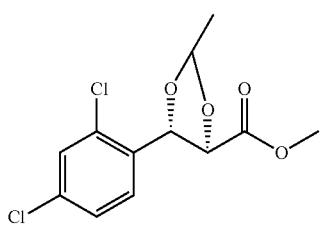

The substantially same method as described in Preparation example 126 was conducted, except that (2R,3S)-methyl-3-(2,4-dichlorophenyl)-2,3-dihydroxypropanoate (Preparation example 29) was used instead of (2S,3R)-methyl-3-(2,4-dichlorophenyl)-2,3-dihydroxypropanoate (Preparation example 36), to obtain the title compound (1.9 g, 70~95%).

$^1$H NMR (400 MHz, CDCl$_3$) δ 1.36 (d, J=6.4, 3H), 3.78 (s, 3H), 4.30 (d, J=7.6, 1H), 5.07 (m, 1H), 5.62 (d, J=7.6, 1H), 7.07~7.21 (m, 3H).

Preparation Example 129: ((4S,5S)-5-(2,4-dichlorophenyl)-2-mehtyl-1.3-dioxolane-4-yl)methanol

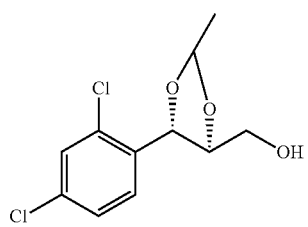

The substantially same method as described in Preparation example 27 was conducted, except that (4R,5S)-methyl-5-(2,4-dichlorophenyl)-2-mehtyl-1.3-dioxolane-4-carboxylate (Preparation example 128) was used instead of (4R,5S)-methyl-5-(2-chlorophenyl)-2,2-dimethyl-1.3-dioxolane-4-carboxylate (Preparation example 26), to obtain the title compound (1.5 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.08~7.39 (m, 3H).

Preparation Example 130: (4S, 5R)-methyl-5-(2,4-dichlorophenyl)-2,2-diethyl-1.3-dioxolane-4-carboxylate

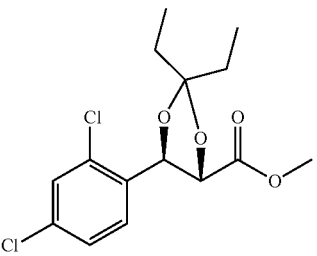 [SMILES: CCC1(CC)O[C@H](C(=O)OC)[C@@H](c2ccc(Cl)cc2Cl)O1]

The substantially same method as described in Preparation example 64 was conducted, except that (2S,3R)-methyl-3-(2,4-dichlorophenyl)-2,3-dihydroxypropanoate (Preparation example 36) was used instead of (2S,3R)-methyl-3-(2-chlorophenyl)-2,3-dihydroxypropanoate (Preparation example 433), to obtain the title compound (2.2 g, 60~85%).

$^1$H NMR (400 MHz, CDCl$_3$) δ 0.96 (m, 6H), 1.59 (m, 4H), 3.67 (s, 3H), 5.11 (d, J=7.6, 1H), 5.81 (d, J=7.6, 1H), 7.12~7.37 (m, 3H)

Preparation Example 131: ((4R,5R)-5-(2,4-dichlorophenyl)-2,2-diethyl-1.3-dioxolane-4-yl)methanol

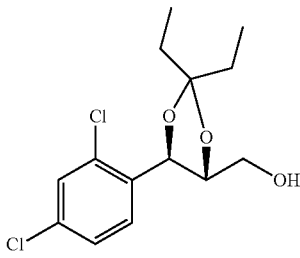 [SMILES: CCC1(CC)O[C@H](c2ccc(Cl)cc2Cl)[C@@H](CO)O1]

The substantially same method as described in Preparation example 27 was conducted, except that (4S,5R)-methyl-5-(2,4-dichlorophenyl)-2,2-diethyl-1.3-dioxolane-4-carboxylate (Preparation example 130) was used instead of (4R,5S)-methyl-5-(2-chlorophenyl)-2,2-dimethyl-1.3-dioxolane-4-carboxylate (Preparation example 26), to obtain the title compound (1.4 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.08~7.39 (m, 3H).

Preparation Example 132: (4R, 5S)-methyl-5-(2,4-chlorophenyl)-2,2-diethyl-1.3-dioxolane-4-carboxylate

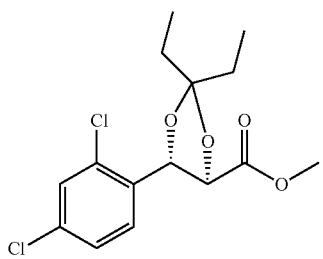 [SMILES: CCC1(CC)O[C@@H](C(=O)OC)[C@H](c2ccc(Cl)cc2Cl)O1]

The substantially same method as described in Preparation example 130 was conducted, except that (2R,3R)-methyl-3-(2,4-dichlorophenyl)-2,3-dihydroxypropanoate (Preparation example 29) was used instead of (2S,3R)-methyl-3-(2,4-dichlorophenyl)-2,3-dihydroxypropanoate (Preparation example 36), to obtain the title compound (2.1 g, 70~95%).

$^1$H NMR (400 MHz, CDCl$_3$) δ 0.96 (m, 6H), 1.59 (m, 4H), 3.67 (s, 3H), 5.11 (d, J=7.6, 1H), 5.81 (d, J=7.6, 1H), 7.12~7.37 (m, 3H)

Preparation Example 133: ((4S, 5S)-5-(2,4-chlorophenyl)-2,2-diethyl-1.3-dioxolane-4-yl)methanol

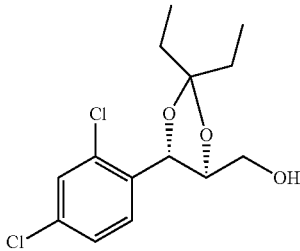 [SMILES: CCC1(CC)O[C@@H](CO)[C@H](c2ccc(Cl)cc2Cl)O1]

The substantially same method as described in Preparation example 131 was conducted, except that (4R,5S)-methyl-5-(2,4-dichlorophenyl)-2,2-diethyl-1.3-dioxolane-4-carboxylate (Preparation example 132) was used instead of ((4S,5R)-methyl-5-(2,4-dichlorophenyl)-2,2-diethyl-1.3-dioxolane-4-carboxylate (Preparation example 130), to obtain the title compound (1.2 g, 70~95%).

$^1$H NMR (400 MHz, CDCl$_3$): δ 1.37 (d, J=6.0, 3H), 3.62~3.70 (m, 2H), 4.36 (dd, J=7.0, J=7.0, 1H); 5.06 (m, 1H), 5.17 (d, J=7.0, 1H), 7.08~7.39 (m, 3H).

Preparation Example 134: (2S, 3R)-methyl-3-(2,4-chlorophenyl)-1,4-dioxaspiro[4,4]nonane-2-carboxylate

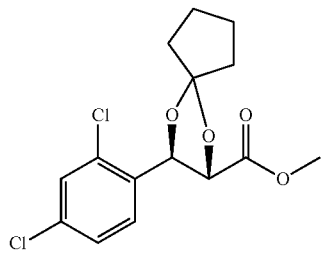 [SMILES: COC(=O)[C@H]1OC2(CCCC2)O[C@@H]1c1ccc(Cl)cc1Cl]

The substantially same method as described in Preparation example 131 was conducted, except that cyclopentanone was used instead of 3-pentanone, to obtain the title compound (2.5 g, 70~95%).

$^1$H NMR (400 MHz, DMSO) δ 1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.03~7.36 (m, 3H)

Preparation Example 135: ((2R,3R)-3-(2,4-chlorophenyl)-1,4-dioxaspiro[4,4]nonane-2-yl)methanol

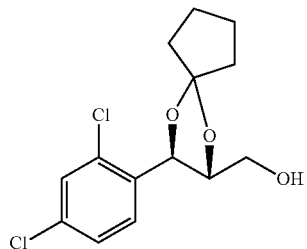 [SMILES: OC[C@H]1OC2(CCCC2)O[C@@H]1c1ccc(Cl)cc1Cl]

The substantially same method as described in Preparation example 65 was conducted, except that (2S,3R)-methyl-3-(2,4-dichlorophenyl)-1,4-dioxaspiro[4,4]nonane-2-carboxylate (Preparation example 134) was used instead of (4S,5R)-methyl-5-(2-chlorophenyl)-2,2-diethyl-1.3-dioxolane-4-carboxylate (Preparation example 64), to obtain the title compound (1.8 g, 70~95%)

$^1$H NMR (400 MHz, DMSO): δ 1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.02~7.37 (m, 3H)

Preparation Example 136: (2R, 3S)-methyl-3-(2,4-chlorophenyl)-1,4-dioxaspiro[4,4]nonane-2-carboxylate

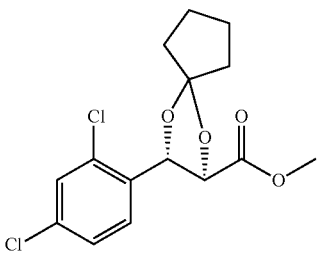 [SMILES: COC(=O)[C@@H]1OC2(CCCC2)O[C@H]1c1ccc(Cl)cc1Cl]

The substantially same method as described in Preparation example 132 was conducted, except that cyclopentanone was used instead of 3-pentanone, to obtain the title compound (2.2 g, 70~95%).

$^1$H NMR (400 MHz, DMSO) δ 1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.03~7.36 (m, 3H)

Preparation Example 137: ((2S,3S)-3-(2,4-chlorophenyl)-1,4-dioxaspiro[4,4]nonane-2-yl)methanol

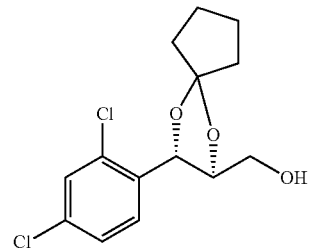 [SMILES: OC[C@@H]1OC2(CCCC2)O[C@H]1c1ccc(Cl)cc1Cl]

The substantially same method as described in Preparation example 135 was conducted, except that (2R,3S)-methyl-3-(2,4-dichlorophenyl)-1,4-dioxaspiro[4,4]nonane-2-carboxylate (Preparation example 136) was used instead of (2S, 3R)-methyl-3-(2,4-dichlorophenyl)-1,4-dioxaspiro[4,4]nonane-2-carboxylate (Preparation example 134), to obtain the title compound (1.2 g, 70~95%)

$^1$H NMR (400 MHz, DMSO): δ 1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.02~7.37 (m, 3H)

Preparation Example 138: (2S, 3R)-methyl-3-(2,4-chlorophenyl)-1,4-dioxaspiro[4,5]decane-2-carboxylate

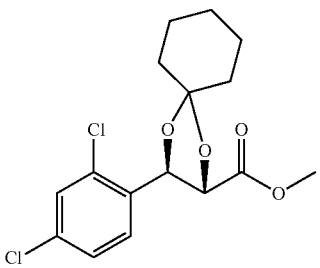 [SMILES: COC(=O)[C@H]1OC2(CCCCC2)O[C@@H]1c1ccc(Cl)cc1Cl]

The substantially same method as described in Preparation example 134 was conducted, except that cyclohexanone was used instead of cyclopentanone, to obtain the title compound (1.8 g, 70~95%).

$^1$H NMR (400 MHz, DMSO) δ 1.61~1.69 (m, 10H), 3.79 (s, 3H), 4.33 (d, J=8.0, 1H), 5.85 (d, J=8.0, 1H), 7.07~7.41 (m, 3H)

Preparation Example 139: ((2R,3R)-3-(2,4-chlorophenyl)-1,4-dioxaspiro[4,5]decane-2-yl)methanol

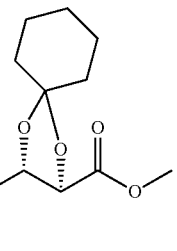

The substantially same method as described in Preparation example 73 was conducted, except that (2S,3R)-methyl-3-(2,4-dichlorophenyl)-1,4-dioxaspiro[4,5]decane-2-carboxylate (Preparation example 138) was used instead of (2S,3R)-methyl-3-(2-chlorophenyl)-1,4-dioxaspiro[4,5]decane-27 carboxylate (Preparation example 72), to obtain the title compound (1.3 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.04~7.40 (m, 3H)

Preparation Example 140: (2R, 3S)-methyl-3-(2,4-chlorophenyl)-1,4-dioxaspiro[4,5]decane-2-carboxylate The substantially same method as described in Preparation example 136 was conducted, except that cyclohexanone was used instead of cyclopentanone, to obtain the title compound (1.6 g, 70~95%).

$^1$H NMR (400 MHz, DMSO) δ 1.61~1.69 (m, 10H), 3.79 (s, 3H), 4.33 (d, J=8.0, 1H), 5.85 (d, J=8.0, 1H), 7.07~7.41 (m, 3H)

Preparation Example 141: ((2S,3S)-3-(2,4-chlorophenyl)-1,4-dioxaspiro[4,5]decane-2-yl)methanol

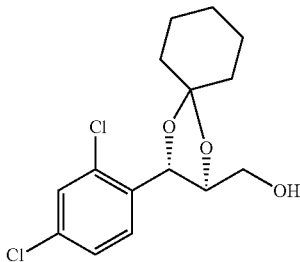 [SMILES: OC[C@@H]1OC2(CCCCC2)O[C@H]1c1ccc(Cl)cc1Cl]

The substantially same method as described in Preparation example 139 was conducted, except that (2R,3S)-methyl-3-(2,4-dichlorophenyl)-1,4-dioxaspiro[4,5]decane-2-carboxylate (Preparation example 140) was used instead of (2S, 3R)-methyl-3-(2,4-dichlorophenyl)-1,4-dioxaspiro[4,5]decane-2-carboxylate (Preparation example 138), to obtain the title compound (1.2 g, 70~95%)

$^1$H NMR (400 MHz, DMSO): δ 1.63~1.75 (m, 10H), 3.52~3 0.81 (m, 2H), 3.95 (t, J=8.0, 1H), 5.43 (d, J=7.6, 1H), 7.04~7.40 (m, 3H)

Preparation Example 142: (4S, 5R)-methyl-5-(2,4-chlorophenyl)-2-phenyl-1,3-dioxolane-4-carboxylate

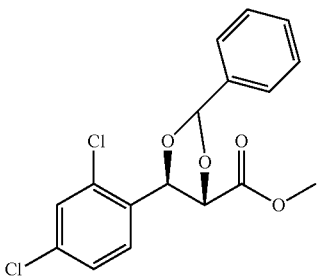

The substantially same method as described in Preparation example 138 was conducted, except that benzaldehyde was used instead of cyclohexanone, to obtain the title compound (1.9 g, 50~70%).

$^1$H NMR (400 MHz, DMSO) δ 1.61~1.69 (m, 10H), 3.79 (s, 3H), 4.33 (d, J=8.0, 1H), 5.85 (d, J=8.0, 1H), 7.03~7.41 (m, 3H)

Preparation Example 143: ((4R,5R)-5-(2,4-chlorophenyl)-2-phenyl-1,3-dioxolane-4-yl)methanol

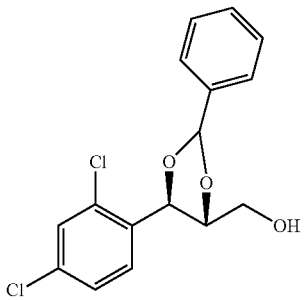

The substantially same method as described in Preparation example 65 was conducted, except that (4S,5R)-methyl-5-(2,4-chlorophenyl)-2-phenyl-1,3-dioxolane-4-carboxylate (Preparation example 142) was used instead of (4S,5R)-methyl-5-(2-chlorophenyl)-2,2-diethyl-1.3-dioxolane-4-carboxylate (Preparation example 64), to obtain the title compound (1.5 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.04~7.42 (m, 3H)

Preparation Example 144: (4R, 5S)-methyl-5-(2,4-chlorophenyl)-2-phenyl-1,3-dioxolane-4-carboxylate

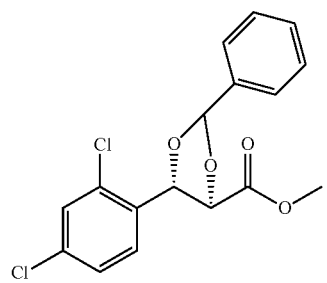

The substantially same method as described in Preparation example 140 was conducted, except that benzaldehyde was used instead of cyclohexanone, to obtain the title compound (1.6 g, 50~70%).

$^1$H NMR (400 MHz, DMSO) δ 1.61~1.69 (m, 10H), 3.79 (s, 3H), 4.33 (d, J=8.0, 1H), 5.85 (d, J=8.0, 1H), 7.03~7.41 (m, 3H)

Preparation Example 145: ((4S,5S)-5-(2,4-chlorophenyl)-2-phenyl-1,3-dioxolane-4-yl)methanol

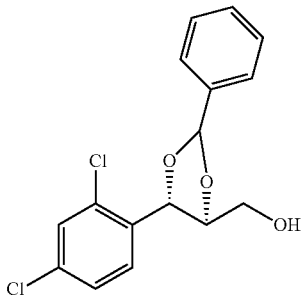

The substantially same method as described in Preparation example 143 was conducted, except that (4R, 5S)-methyl-5-(2,4-chlorophenyl)-2-phenyl-1,3-dioxolane-4-carboxylate (Preparation example 144) was used instead of (2S, 3R)-methyl-3-(2,4-chlorophenyl)-2-phenyl-1,3-dioxolane-4-carboxylate (Preparation example 142), to obtain the title compound (1.2 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.04~7.42 (m, 3H)

Preparation Example 146: ((4S,5R)-ethyl-5-(2,6-dichlorophenyl)-2-methyl-1.3-dioxolane-4-carboxylate

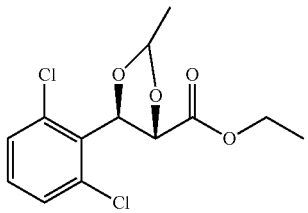

The substantially same method as described in Preparation example 60 was conducted, except that (2S,3R)-ethyl-3-(2,6-dichlorophenyl)-2,3-dihydroxypropanoate (Preparation example 39) was used instead of (2S,3R)-methyl-3-(2-chlorophenyl)-2,3-dihydroxypropanoate (Preparation example 433), to obtain the title compound (1.7 g, 70~95%).

$^1$H NMR (400 MHz, CDCl$_3$) δ 1.36 (d, J=6.4, 3H), 3.78 (s, 3H), 4.15 (m, 2H), 4.30 (d, J=7.6, 1H), 5.07 (m, 1H), 5.62 (d, J=7.6, 1H), 7.17~7.36 (m, 3H)

Preparation Example 147: ((4R,5R)-5-(2,6-dichlorophenyl)-2-methyl-1.3-dioxolane-4-yl)methanol

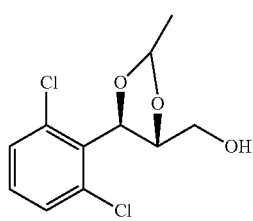

The substantially same method as described in Preparation example 27 was conducted, except that ((4S,5R)-ethyl-5-(2,6-dichlorophenyl)-2-mehtyl-1.3-dioxolane-4-carboxylate (Preparation example 146) was used instead of (4R,5S)-methyl-5-(2-chlorophenyl)-2,2-dimethyl-1.3-dioxolane-4-carboxylate (Preparation example 26), to obtain the title compound (1.2 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.18~7.39 (m, 3H).

Preparation Example 148: ((4R,5S)-ethyl-5-(2,6-dichlorophenyl)-2-methyl-1.3-dioxolane-4-carboxylate

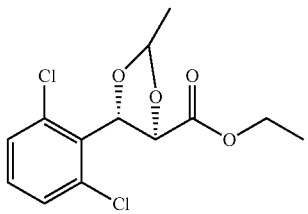

The substantially same method as described in Preparation example 146 was conducted, except that (2R,3S)-ethyl-3-(2,6-dichlorophenyl)-2,3-dihydroxypropanoate (Preparation example 33) was used instead of (2S,3R)-methyl-3-(2,4-dichlorophenyl)-2,3-dihydroxypropanoate (Preparation example 39), to obtain the title compound (1.8 g, 70~95%).

$^1$H NMR (400 MHz, CDCl$_3$) δ 1.36 (d, J=6.4, 3H), 3.78 (s, 3H), 4.15 (m, 2H), 4.30 (d, J=7.6, 1H), 5.07 (m, 1H), 5.62 (d, J=7.6, 1H), 7.17~7.36 (m, 3H).

Preparation Example 149: ((4S,5S)-5-(2,6-dichlorophenyl)-2-methyl-1.3-dioxolane-4-yl)methanol

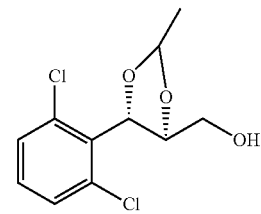

The substantially same method as described in Preparation example 147 was conducted, except that ((4R,5S)-ethyl-5-(2,6-dichlorophenyl)-2-methyl-1.3-dioxolane-4-carboxylate (Preparation example 148) was used instead of ((4S,5R)-ethyl-5-(2,6-dichlorophenyl)-2-mehtyl-1.3-dioxolane-4-carboxylate (Preparation example 146), to obtain the title compound (1.3 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.18~7.39 (m, 3H).

Preparation Example 150: (4S, 5R)-ethyl-5-(2,6-dichlorophenyl)-2,2-diethyl-1.3-dioxolane-4-carboxylate

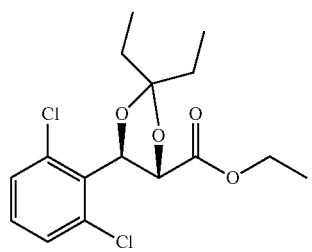 [SMILES: CCOC(=O)[C@H]1OC(CC)(CC)O[C@@H]1c1c(Cl)cccc1Cl]

The substantially same method as described in Preparation example 130 was conducted, except that (2S,3R)-ethyl-3-(2,6-dichlorophenyl)-2,3-dihydroxypropanoate (Preparation example 39) was used instead of (2S,3R)-methyl-3-(2,6-dichlorophenyl)-2,3-dihydroxypropanoate (Preparation example 36), to obtain the title compound (1.8 g, 60~85%).

$^1$H NMR (400 MHz, CDCl$_3$) δ 0.96 (m, 6H), 1.30 (t, J=8.0, 3H), 1.59 (m, 4H), 4.12 (m, 2H), 5.11 (d, J=7.6, 1H), 5.81 (d, J=7.6, 1H), 7.08~7.26 (m, 3H)

Preparation Example 151: ((4R,5R)-5-(2,6-dichlorophenyl)-2,2-diethyl-1,3-dioxolane-4-yl)methanol

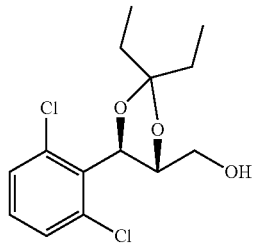 [SMILES: CCC1(CC)O[C@H](c2c(Cl)cccc2Cl)[C@@H](CO)O1]

The substantially same method as described in Preparation example 147 was conducted, except that (4S,5R)-ethyl-5-(2,6-dichlorophenyl)-2,2-diethyl-1,3-dioxolane-4-carboxylate (Preparation example 150) was used instead of ((4S,5R)-ethyl-5-(2,6-dichlorophenyl)-2-mehtyl-1,3-dioxolane-4-carboxylate (Preparation example 146), to obtain the title compound (1.2 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.07~7.29 (m, 3H).

Preparation Example 152: (4R, 5S)-ethyl-5-(2,6-chlorophenyl)-2,2-diethyl-1,3-dioxolane-4-carboxylate

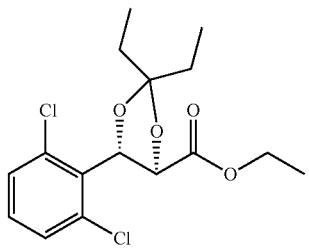 [SMILES: CCOC(=O)[C@@H]1OC(CC)(CC)O[C@H]1c1c(Cl)cccc1Cl]

The substantially same method as described in Preparation example 150 was conducted, except that (2R,3S)-ethyl-3-(2,6-dichlorophenyl)-2,3-dihydroxypropanoate (Preparation example 33) was used instead of (2S,3R)-ethyl-3-(2,6-dichlorophenyl)-2,3-dihydroxypropanoate (Preparation example 39), to obtain the title compound (2.5 g, 70~95%).

$^1$H NMR (400 MHz, CDCl$_3$) δ 0.96 (m, 6H), 1.30 (t, J=8.0, 3H), 1.59 (m, 4H), 4.12 (m, 2H), 5.11 (d, J=7.6, 1H), 5.81 (d, J=7.6, 1H), 7.08~7.26 (m, 3H)

Preparation Example 153: ((4S,5S)-5-(2,6-chlorophenyl)-2,2-diethyl-1,3-dioxolane-4-yl)methanol

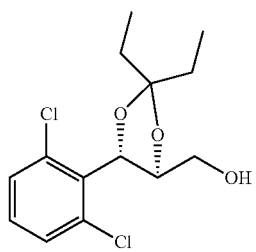 [SMILES: CCC1(CC)O[C@@H](CO)[C@H](c2c(Cl)cccc2Cl)O1]

The substantially same method as described in Preparation example 151 was conducted, except that (4R,5S)-ethyl-5-(2,6-dichlorophenyl)-2,2-diethyl-1,3-dioxolane-4-carboxylate (Preparation example 152) was used instead of (4S,5R)-ethyl-5-(2,6-dichlorophenyl)-2,2-diethyl-1,3-dioxolane-4-carboxylate (Preparation example 150), to obtain the title compound (2.1 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.07~7.29 (m, 3H).

Preparation Example 154: (2S, 3R)-ethyl-3-(2,6-chlorophenyl)-1,4-dioxaspiro[4,4]nonane-2-carboxylate

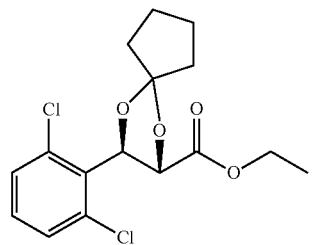 [SMILES: CCOC(=O)[C@H]1OC2(CCCC2)O[C@@H]1c1c(Cl)cccc1Cl]

The substantially same method as described in Preparation example 150 was conducted, except that cyclopentanone was used instead of 3-pentanone, to obtain the title compound (2.1 g, 70~95%).

$^1$H NMR (400 MHz, DMSO) δ 1.30 (t, J=7.8 hz, 3H), 1.69~1.71 (m, 4H), 1.73~1.86 (m, 4H), 4.07~4.14 (m, 2H), 5.11 (d, J=7.2, 1H), 5.81 (d, J=7.2, 1H), 7.07~7.31 (m, 3H)

Preparation Example 155: ((2R,3R)-3-(2,6-chlorophenyl)-1,4-dioxaspiro[4,4]nonane-2-yl)methanol

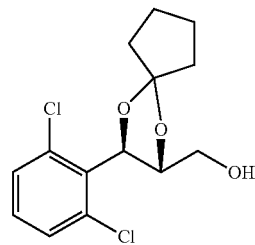 [SMILES: OC[C@H]1OC2(CCCC2)O[C@@H]1c1c(Cl)cccc1Cl]

The substantially same method as described in Preparation example 151 was conducted, except that (2S,3R)-ethyl-3-(2,6-dichlorophenyl)-1,4-dioxaspiro[4,4]nonane-2-carboxylate (Preparation example 154) was used instead of (4S,5R)-ethyl-5-(2,6-dichlorophenyl)-2,2-diethyl-1,3-dioxolane-4-carboxylate (Preparation example 150), to obtain the title compound (1.7 g, 70~95%)

$^1$H NMR (400 MHz, DMSO): δ 1.60~1.72 (m, 4H), 1.83~1.94 (m, 4H), 3.52~3.65 (m, 2H), 4.90 (t, J=5.2, 1H), 5.12 (d, J=7.6, 1H), 7.08~7.32 (m, 3H)

Preparation Example 156: (2R, 3S)-ethyl-3-(2,6-chlorophenyl)-1,4-dioxaspiro[4,4]nonane-2-carboxylate

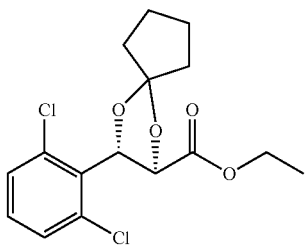 [SMILES: CCOC(=O)[C@@H]1OC2(CCCC2)O[C@H]1c1c(Cl)cccc1Cl]

The substantially same method as described in Preparation example 152 was conducted, except that cyclopentanone was used instead of 3-pentanone, to obtain the title compound (2.5 g, 70~95%).
¹H NMR (400 MHz, DMSO) δ 1.30 (t, J=7.8 hz, 3H), 1.69~1.71 (m, 4H); 1.73~1.86 (m, 4H), 4.07~4.14 (m, 2H), 5.11 (d, J=7.2, 1H), 5.81 (d, J=7.2, 1H), 7.07~7.31 (m, 3H)

Preparation Example 157: ((2S,3S)-3-(2,6-chlorophenyl)-1,4-dioxaspiro[4,4]nonane-2-yl)methanol

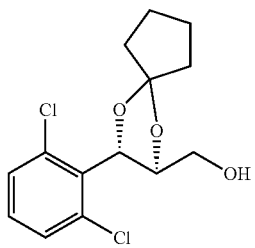 [SMILES: OC[C@@H]1OC2(CCCC2)O[C@H]1c1c(Cl)cccc1Cl]

The substantially same method as described in Preparation example 155 was conducted, except that (2R,3S)-ethyl-3-(2,6-dichlorophenyl)-1,4-dioxaspiro[4,4]nonane-2-carboxylate (Preparation example 156) was used instead of (2S, 3R)-ethyl-3-(2,6-dichlorophenyl)-1,4-dioxaspiro[4,4] nonane-2-carboxylate (Preparation example 154), to obtain the title compound (2.0 g, 70~95%)
¹H NMR (400 MHz, DMSO): δ 1.60~1.72 (m, 4H), 1.83~1.94 (m, 4H), 3.52~3.65 (m, 2H), 4.90 (t, J=5.2, 1H), 5.12 (d, J=7.6, 1H), 7.08~7.32 (m, 3H)

Preparation Example 158: (2S, 3R)-ethyl-3-(2,6-chlorophenyl)-1,4-dioxaspiro[4,5]decane-2-carboxylate

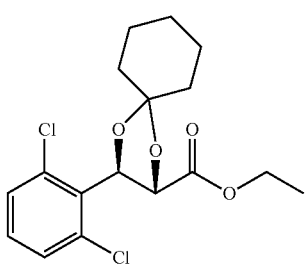 [SMILES: CCOC(=O)[C@H]1OC2(CCCCC2)O[C@@H]1c1c(Cl)cccc1Cl]

The substantially same method as described in Preparation example 154 was conducted, except that cyclohexanone was used instead of cyclopentanone, to obtain the title compound (2.2 g, 70~95%).
¹H NMR (400 MHz, DMSO) δ 1.30 (t, J=7.6, 3H), 1.61~1.69 (m, 10H), 4.08~4.18 (d, 2H), 4.33 (d, J=8.0, 1H), 5.85 (d, J=8.0, 1H), 7.07~7.31 (m, 3H)

Preparation Example 159: ((2R,3R)-3-(2,6-chlorophenyl)-1,4-dioxaspiro[4,5]decane-2-yl)methanol

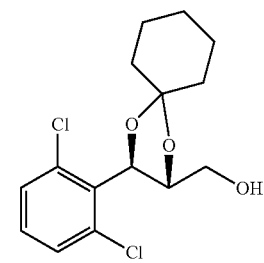 [SMILES: OC[C@H]1OC2(CCCCC2)O[C@@H]1c1c(Cl)cccc1Cl]

The substantially same method as described in Preparation example 155 was conducted, except that (2S,3R)-ethyl-3-(2,6-dichlorophenyl)-1,4-dioxaspiro[4,5]decane-2-carboxylate (Preparation example 158) was used instead of (2S, 3R)-ethyl-3-(2,6-dichlorophenyl)-1,4-dioxaspiro[4,4] nonane-2-carboxylate (Preparation example 154), to obtain the title compound (1.7 g, 70~95%)
¹H NMR (400 MHz, DMSO): δ 1.63~1.75 (m, 10H), 3.52~3.81 (m, 2H), 3.95 (t, J=8.0, 1H), 5.43 (d, J=7.6, 1H), 7.05~7.30 (m, 3H)

Preparation Example 160: (2R, 3S)-ethyl-3-(2,6-chlorophenyl)-1,4-dioxaspiro[4,5]decane-2-carboxylate

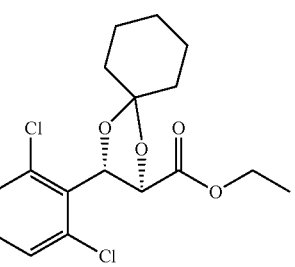

The substantially same method as described in Preparation example 156 was conducted, except that cyclohexanone was used instead of cyclopentanone, to obtain the title compound (1.9 g, 70~95%).
¹H NMR (400 MHz, DMSO) δ 1.30 (t, J=7.6, 3H), 1.61~1.69 (m, 10H), 4.08~4.18 (d, 2H), 4.33 (d, J=8.0, 1H), 5.85 (d, J=8.0, 1H), 7.07~7.31 (m, 3H)

Preparation Example 161: ((2S,3S)-3-(2,6-chlorophenyl)-1,4-dioxaspiro[4,5]decane-2-yl)methanol

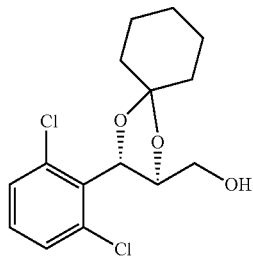 [SMILES: OC[C@@H]1OC2(CCCCC2)O[C@H]1c1c(Cl)cccc1Cl]

The substantially same method as described in Preparation example 159 was conducted, except that (2R,3S)-ethyl-3-(2,6-dichlorophenyl)-1,4-dioxaspiro[4,5]decane-2-carboxylate (Preparation example 160) was used instead of (2S, 3R)-ethyl-3-(2,6-dichlorophenyl)-1,4-dioxaspiro[4,5]decane-2-carboxylate (Preparation example 158), to obtain the title compound (1.5 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.05~7.30 (m, 3H)

Preparation Example 162: (4S, 5R)-ethyl-5-(2,6-chlorophenyl)-2-phenyl-1,3-dioxolane-4-carboxylate

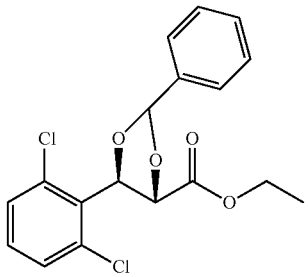

The substantially same method as described in Preparation example 158 was conducted, except that benzaldehyde was used instead of cyclohexanone, to obtain the title compound (2.0 g, 50~70%).

$^1$H NMR (400 MHz, DMSO) δ 1.30 (t, J=7.6, 3H), 4.08~4.18 (d, 2H), 5.13 (d, J=8.0, 1H), 5.85 (d, J=8.0, 1H), 6.18 (s, 1H), 7.03~7.22 (m, 8H)

Preparation Example 163: ((4R,5R)-5-(2,6-chlorophenyl)-2-phenyl-1,3-dioxolane-4-yl)methanol

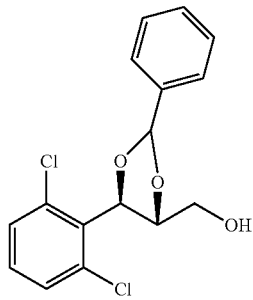

The substantially same method as described in Preparation example 159 was conducted, except that (4S, 5R)-ethyl-5-(2,6-chlorophenyl)-2-phenyl-1,3-dioxolane-4-carboxylate (Preparation example 162) was used instead of (2S, RS)-ethyl-3-(2,6-dichlorophenyl)-1,4-dioxaspiro[4,5]decane-2-carboxylate (Preparation example 158), to obtain the title compound (1.6 g, 70~95%)

$^1$H NMR (400 MHz, DMSO) δ 3.50~3.79 (m, 2H), 5.13 (d, J=8.0, 1H), 5.85 (d, J=8.0, 1H), 6.18 (s, 1H), 7.03~7.22 (m, 8H)

Preparation Example 164: (4R, 5S)-ethyl-5-(2,6-chlorophenyl)-2-phenyl-1,3-dioxolane-4-carboxylate

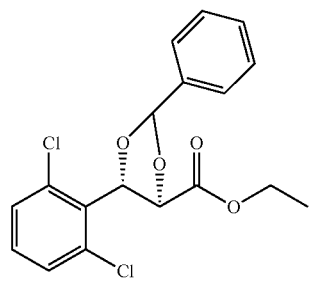

The substantially same method as described in Preparation example 160 was conducted, except that benzaldehyde was used instead of cyclohexanone, to obtain the title compound (1.8 g, 50~70%).

$^1$H NMR (400 MHz, DMSO) δ 1.30 (t, J=7.6, 3H), 4.08~4.18 (d, 2H), 5.13 (d, J=8.0, 1H), 5.85 (d, J=8.0, 1H), 6.18 (s, 1H), 7.03~7.22 (m, 8H)

Preparation Example 165: ((4S,5S)-5-(2,6-chlorophenyl)-2-phenyl-1,3-dioxolane-4-yl)methanol

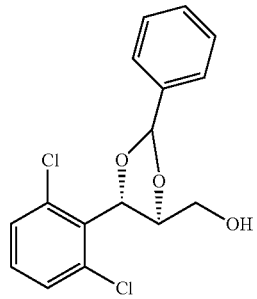

The substantially same method as described in Preparation example 163 was conducted, except that (4R, 5S)-ethyl-5-(2,6-chlorophenyl)-2-phenyl-1,3-dioxolane-4-carboxylate (Preparation example 164) was used instead of (2S, 3R)-ethyl-3-(2,6-chlorophenyl)-2-phenyl-1,3-dioxolane-4-carboxylate (Preparation example 162), to obtain the title compound (1.4 g, 70~95%)

$^1$H NMR (400 MHz, DMSO): δ 3.50~3.79 (m, 2H), 5.13 (d, J=8.0, 1H), 5.85 (d, J=8.0, 1H), 6.18 (s, 1H), 7.03~7.22 (m, 8H)

Preparation Example 166: ((4S,5R)-methyl-5-(2-nitrophenyl)-2-mehtyl-1.3-dioxolane-4-carboxylate

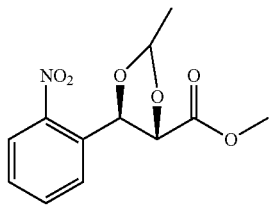

The substantially same method as described in Preparation example 60 was conducted, except that (2S,3R)-methyl-3-(2-nitrophenyl)-2,3-dihydroxypropanoate (Preparation example 44) was used instead of (2S,3R)-methyl-3-(2-chlorophenyl)-2,3-dihydroxypropanoate (Preparation example 433), to obtain the title compound (2.3 g, 70~95%).

$^1$H NMR (400 MHz, CDCl$_3$) δ 1.36 (d, J=6.4, 3H), 3.78 (s, 3H), 4.30 (d, J=7.6, 1H), 5.07 (m, 1H), 5.62 (d, J=7.6, 1H), 7.45~8.12 (m, 4H)

Preparation Example 167: ((4R,5R)-5-(2-nitrophenyl)-2-mehtyl-1.3-dioxolane-4-yl)methanol

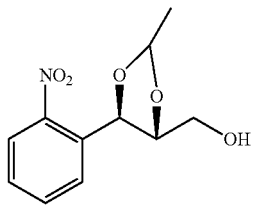

The substantially same method as described in Preparation example 27 was conducted, except that (4S,5R)-methyl-5-(2-nitrophenyl)-2-mehtyl-1.3-dioxolane-4-carboxylate (Preparation example 166) was used instead of (4R,5S)-methyl-5-(2-chlorophenyl)-2,2-dimethyl-1.3-dioxolane-4-carboxylate (Preparation example 26), to obtain the title compound (1.9 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.47~8.11 (m, 4H).

Preparation Example 168: ((4R,5S)-methyl-5-(2-nitrophenyl)-2-mehtyl-1.3-dioxolane-4-carboxylate

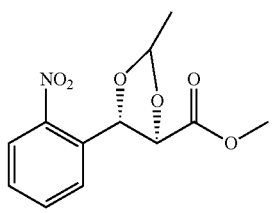

The substantially same method as described in Preparation example 160 was conducted, except that (2R,3S)-methyl-3-(2-nitrophenyl)-2,3-dihydroxypropanoate (Preparation example 48) was used instead of (2S,3R)-methyl-3-(2-nitrophenyl)-2,3-dihydroxypropanoate (Preparation example 44), to obtain the title compound (2.0 g, 70~95%).

$^1$H NMR (400 MHz, CDCl$_3$) δ 1.36 (d, J=6.4, 3H), 3.78 (s, 3H), 4.30 (d, J=7.6, 1H), 5.07 (m, 1H), 5.62 (d, J=7.6, 1H), 7.45~8.12 (m, 4H)

Preparation Example 169: ((4S,5S)-5-(2-nitrophenyl)-2-mehtyl-1.3-dioxolane-4-yl)methanol

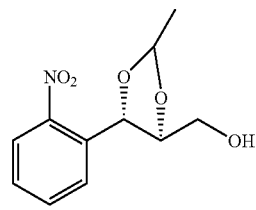

The substantially same method as described in Preparation example 167 was conducted, except that (4R,5S)-methyl-5-(2-nitrophenyl)-2-mehtyl-1.3-dioxolane-4-carboxylate (Preparation example 168) was used instead of (4S,5R)-methyl-5-(2-nitrophenyl)-2-mehtyl-1.3-dioxolane-4-carboxylate (Preparation example 166), to obtain the title compound (1.6 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.47~8.11 (m, 4H).

Preparation Example 170: (4S, 5R)-methyl-5-(2-nitrophenyl)-2,2-diethyl-1.3-dioxolane-4-carboxylate

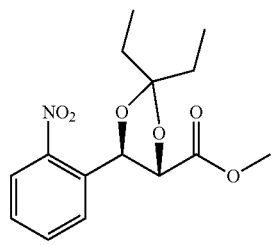 [SMILES: CCC1(CC)O[C@H](C(=O)OC)[C@@H](c2ccccc2[N+](=O)[O-])O1]

The substantially same method as described in Preparation example 150 was conducted, except that (2S,3R)-methyl-3-(2-nitrophenyl)-2,3-dihydroxypropanoate (Preparation example 44) was used instead of (2S,3R)-ethyl-3-(2,6-dichlorophenyl)-2,3-dihydroxypropanoate (Preparation example 39), to obtain the title compound (2.4 g, 60~85%).

$^1$H NMR (400 MHz, CDCl$_3$) δ 0.96 (m, 6H), 1.59 (m, 4H), 3.67 (s, 3H), 5.11 (d, J=7.6, 1H), 5.81 (d, J=7.6, 1H), 7.43~8.10 (m, 4H)

Preparation Example 171: ((4R,5R)-5-(2-nitrophenyl)-2,2-diethyl-1,3-dioxolane-4-yl)methanol

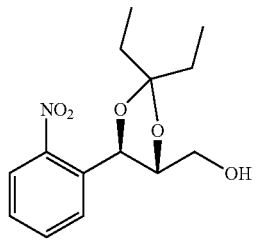 [SMILES: CCC1(CC)O[C@H](c2ccccc2[N+](=O)[O-])[C@@H](CO)O1]

The substantially same method as described in Preparation example 167 was conducted, except that (4S,5R)-methyl-5-(2-nitrophenyl)-2,2-diethyl-1,3-dioxolane-4-carboxylate (Preparation example 170) was used instead of (4S,5R)-methyl-5-(2-nitrophenyl)-2-mehtyl-1,3-dioxolane-4-carboxylate (Preparation example 166), to obtain the title compound (1.9 g, 70~95%)

$^1$H NMR (400 MHz, CDCl$_3$): δ 0.96 (m, 6H), 1.59 (m, 4H), 3.62~3.70 (m, 2H), 4.36 (dd, J=7.0, J=7.0, 1H), 5.17 (d, J=7.0, 1H), 0.7.37~8.09 (m, 4H)

Preparation Example 172: (4R, 5S)-methyl-5-(2-nitrophenyl)-2,2-diethyl-1,3-dioxolane-4-carboxylate

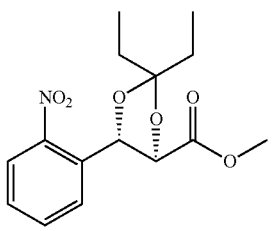 [SMILES: CCC1(CC)O[C@@H](C(=O)OC)[C@H](c2ccccc2[N+](=O)[O-])O1]

The substantially same method as described in Preparation example 170 was conducted, except that (2R,3S)-methyl-3-(2-nitrophenyl)-2,3-dihydroxypropanoate (Preparation example 48) was used instead of (2S,3R)-methyl-3-(2-nitrophenyl)-2,3-dihydroxypropanoate (Preparation example 44), to obtain the title compound (2.5 g, 60~85%).

$^1$H NMR (400 MHz, CDCl$_3$) δ 0.96 (m, 6H), 1.59 (m, 4H), 3.67 (s, 3H), 5.11 (d, J=7.6, 1H), 5.81 (d, J=7.6, 1H), 7.43~8.10 (m, 4H)

Preparation Example 173: ((4S,5S)-5-(2-nitrophenyl)-2,2-diethyl-1,3-dioxolane-4-yl)methanol

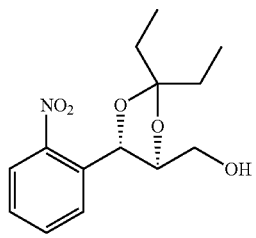 [SMILES: CCC1(CC)O[C@@H](CO)[C@H](c2ccccc2[N+](=O)[O-])O1]

The substantially same method as described in Preparation example 171 was conducted, except that (4R,5S)-methyl-5-(2-nitrophenyl)-2,2-diethyl-1,3-dioxolane-4-carboxylate (Preparation example 172) was used instead of (4S,5R)-methyl-5-(2-nitrophenyl)-2,2-diethyl-1,3-dioxolane-4-carboxylate (Preparation example 170), to obtain the title compound (2.0 g, 70~95%)

$^1$H NMR (400 MHz, CDCl$_3$): δ 0.96 (m, 6H), 1.59 (m, 4H), 3.62~3.70 (m, 2H), 4.36 (dd, J=7.0, J=7.0, 1H), 5.17 (d, J=7.0, 1H), 7.37~8.09 (m, 4H)

Preparation Example 174: (2S, 3R)-methyl-3-(2-nitrophenyl)-1,4-dioxaspiro[4,4]nonane-2-carboxylate

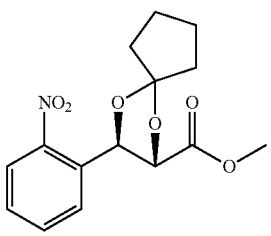 [SMILES: COC(=O)[C@H]1OC2(CCCC2)O[C@@H]1c1ccccc1[N+](=O)[O-]]

The substantially same method as described in Preparation example 170 was conducted, except that cyclopentanone was used instead of 3-pentanone, to obtain the title compound (2.5 g, 70~95%).

$^1$H NMR (400 MHz, DMSO) δ 1.69~1.71 (m, 4H), 1.82~1.86 (m, 4H), 3.68 (s, 3H), 4.40 (d, J=7.2, 1H), 5.39 (d, J=7.2, 1H), 7.44~8.06 (m, 4H)

Preparation Example 175: ((2R,3R)-3-(2-nitrophenyl)-1,4-dioxaspiro[4,4]nonane-2-yl)methanol

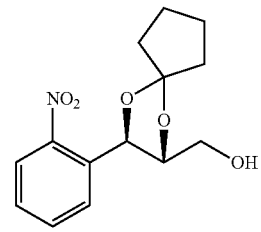 [SMILES: O=[N+]([O-])c1ccccc1[C@H]1OC2(CCCC2)O[C@@H]1CO]

The substantially same method as described in Preparation example 171 was conducted, except that (2S, 3R)-methyl-3-(2-nitrophenyl)-1,4-dioxaspiro[4,4]nonane-2-carboxylate (Preparation example 174) was used instead of (4S,5R)-methyl-5-(2-nitrophenyl)-2,2-diethyl-1,3-dioxolane-4-carboxylate (Preparation example 170), to obtain the title compound (2.1 g, 70~95%)

$^1$H NMR (400 MHz, DMSO): δ 1.60~1.72 (m, 4H), 1.83~1.94 (m, 4H), 3.52~3.65 (m, 2H), 4.90 (t, J=5.2, 1H), 5.12 (d, J=7.6, 1H), 7.46~8.09 (m, 4H)

Preparation Example 176: (2R, 3S)-methyl-3-(2-nitrophenyl)-1,4-dioxaspiro[4,4]nonane-2-carboxylate

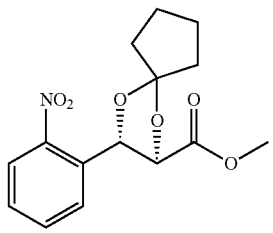 [SMILES: COC(=O)[C@@H]1OC2(CCCC2)O[C@H]1c1ccccc1[N+](=O)[O-]]

The substantially same method as described in Preparation example 172 was conducted, except that cyclopentanone was used instead of 3-pentanone, to obtain the title compound (2.9 g, 70~95%).

$^1$H NMR (400 MHz, DMSO) δ 1.69~1.71 (m, 4H), 1.82~1.86 (m, 4H), 3.68 (s, 3H), 4.40 (d, J=7.2, 1H), 5.39 (d, J=7.2, 1H), 7.44~8.06 (m, 4H)

Preparation Example 177: ((2S,3S)-3-(2-nitrophenyl)-1,4-dioxaspiro[4,4]nonane-2-yl)methanol

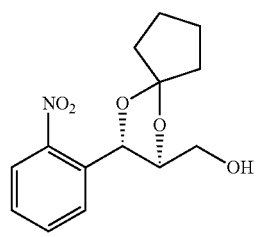 [SMILES: O=[N+]([O-])c1ccccc1[C@@H]1OC2(CCCC2)O[C@H]1CO]

The substantially same method as described in Preparation example 175 was conducted, except that (2R, 3S)-methyl-3-(2-nitrophenyl)-1,4-dioxaspiro[4,4]nonane-2-carboxylate (Preparation example 176) was used instead of (2S, 3R)-methyl-3-(2-nitrophenyl)-1,4-dioxaspiro[4,4]nonane-2-carboxylate (Preparation example 174), to obtain the title compound (2.0 g, 70~95%)

$^1$H NMR (400 MHz, DMSO): δ 1.60~1.72 (m, 4H), 1.83~1.94 (m, 4H), 3.52~3.65 (m, 2H), 4.90 (t, J=5.2, 1H), 5.12 (d, J=7.6, 1H), 7.46~8.09 (m, 4H)

Preparation Example 178: (2S, 3R)-methyl-3-(2-nitrophenyl)-1,4-dioxaspiro[4,5]decane-2-carboxylate

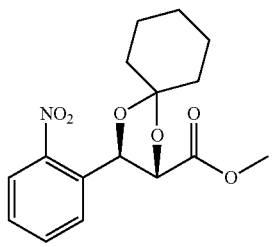 [SMILES: COC(=O)[C@H]1OC2(CCCCC2)O[C@@H]1c1ccccc1[N+](=O)[O-]]

The substantially same method as described in Preparation example 174 was conducted, except that cyclohexanone was used instead of cyclopentanone, to obtain the title compound (1.7 g, 70~95%).

$^1$H NMR (400 MHz, DMSO) δ 1.61~1.69 (m, 10H), 3.79 (s, 3H), 4.33 (d, J=8.0, 1H), 5.85 (d, J=8.0, 1H), 7.45~8.12 (m, 4H)

Preparation Example 179: ((2R,3R)-3-(2-nitrophenyl)-1,4-dioxaspiro[4,5]decane-2-yl)methanol

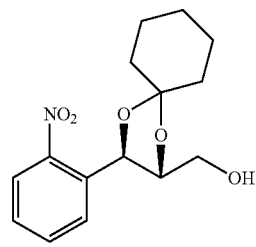 [SMILES: O=[N+]([O-])c1ccccc1[C@H]1OC2(CCCCC2)O[C@@H]1CO]

The substantially same method as described in Preparation example 175 was conducted, except that (2S, 3R)-methyl-3-(2-nitrophenyl)-1,4-dioxaspiro[4,5]decane-2-carboxylate (Preparation example 178) was used instead of (2S, 3R)-methyl-3-(2-nitrophenyl)-1,4-dioxaspiro[4,4]nonane-2-carboxylate (Preparation example 174), to obtain the title compound (1.4 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.46~8.09 (m, 4H)

Preparation Example 180: (2R, 3S)-methyl-3-(2-nitrophenyl)-1,4-dioxaspiro[4,5]decane-2-carboxylate

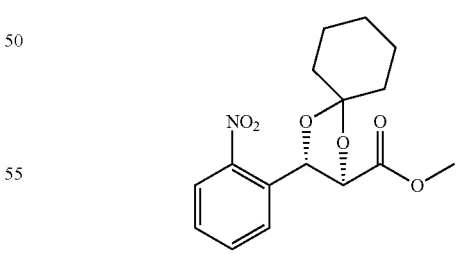

The substantially same method as described in Preparation example 176 was conducted, except that cyclohexanone was used instead of cyclopentanone, to obtain the title compound (2.2 g, 70~95%).

$^1$H NMR (400 MHz, DMSO) δ 1.61~1.69 (m, 10H), 3.79 (s, 3H), 4.33 (d, J=8.0, 1H), 5.85 (d, J=8.0, 1H), 7.45~8.12 (m, 4H)

Preparation Example 181: ((2S,3S)-3-(2-nitrophenyl)-1,4-dioxaspiro[4,5]decane-2-yl)methanol

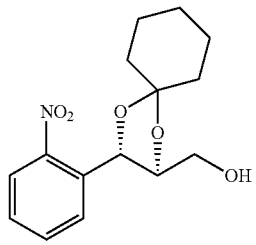 [SMILES: O=[N+]([O-])c1ccccc1[C@@H]1OC2(CCCCC2)O[C@H]1CO]

The substantially same method as described in Preparation example 179 was conducted, except that (2R, 3S)-methyl-3-(2-nitrophenyl)-1,4-dioxaspiro[4,5]decane-2-carboxylate (Preparation example 180) was used instead of (2S, 3R)-methyl-3-(2-nitrophenyl)-1,4-dioxaspiro[4,5]decane-2-carboxylate (Preparation example 178), to obtain the title compound (1.5 g, 70~95%)

$^1$H NMR (400 MHz, DMSO): δ 1.63~1.75 (m, 10H), 3.52~3.81 (m, 2H), 3.95 (t, J=8.0, 1H), 5.43 (d, J=7.6, 1H), 7.19~7.49 (m, 4H)

Preparation Example 182: (4S, 5R)-methyl-5-(2-nitrophenyl)-2-phenyl-1,3-dioxolane-4-carboxylate

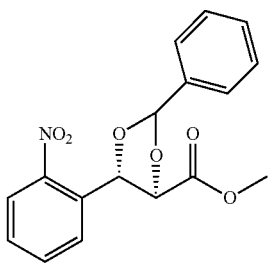

The substantially same method as described in Preparation example 178 was conducted, except that benzaldehyde was used instead of cyclohexanone, to obtain the title compound (1.9 g, 50~70%).

$^1$H NMR (400 MHz, DMSO) δ 3.67 (s, 3H), 5.11 (d, J=8.0, 1H), 5.81 (d, J=8.0, 1H), 6.18 (s, 1H), 6.96~8.12 (m, 9H)

Preparation Example 183: ((4R,5R)-5-(2-nitrophenyl)-2-phenyl-1,3-dioxolane-4-yl)methanol

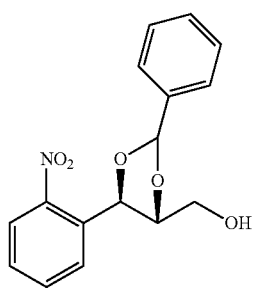

The substantially same method as described in Preparation example 179 was conducted, except that (4S, 5R)-methyl-5-(2-nitrophenyl)-2-phenyl-1,3-dioxolane-4-carboxylate (Preparation example 182) was used instead of (2S, 3R)-methyl-3-(2-nitrophenyl)-1,4-dioxaspiro[4,4]nonane-2-carboxylate (Preparation example 174), to obtain the title compound (1.5 g, 70~95%)

$^1$H NMR (400 MHz, DMSO): δ 3.66 (d, J=7.6, 2H), 4.36 (m, 1H), 5.17 (d, J=8.0, 1H), 6.18 (s, 1H), 7.06~8.14 (m, 9H)

Preparation Example 184: (4R, 5S)-methyl-5-(2-nitrophenyl)-2-phenyl-1,3-dioxolane-4-carboxylate

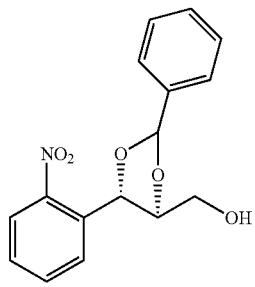

The substantially same method as described in Preparation example 180 was conducted, except benzaldehyde that was used instead of cyclohexanone, to obtain the title compound (1.8 g, 50~70%).

$^1$H NMR (400 MHz, DMSO) δ 3.67 (s, 3H), 5.11 (d, J=8.0, 1H), 5.81 (d, J=8.0, 1H), 6.18 (s, 1H), 6.96~8.12 (m, 9H)

Preparation Example 185: ((4R,5S)-5-(2-nitrophenyl)-2-phenyl-1,3-dioxolane-4-yl)methanol The substantially same method as described in Preparation example 183 was conducted, except that (4R, 5S)-methyl-5-(2-nitrophenyl)-2-phenyl-1,3-dioxolane-4-carboxylate (Preparation example 184) was used instead of (2S, 3R)-methyl-3 (2-nitrophenyl)-2-phenyl-1,3-dioxolane-4-carboxylate (Preparation example 182), to obtain the title compound (1.3 g, 70~95%)

$^1$H NMR (400 MHz, DMSO): δ 3.66 (d, J=7.6, 2H), 4.36 (m, 1H), 5.17 (d, J=8.0, 1H), 6.18 (s, 1H), 7.06~8.14 (m, 9H)

Preparation Example 186: (4S,5R)-methyl-5-(2-methylphenyl)-2-methyl-1,3-dioxolane-4-carboxylate

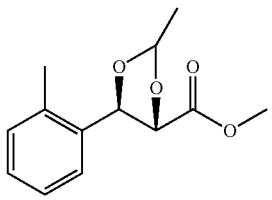

The substantially same method as described in Preparation example 60 was conducted, except that (2S,3R)-methyl-3-(2-methylphenyl)-2,3-dihydroxypropanoate (Preparation example 54) was used instead of (2S,3R)-methyl-3-(2-chlorophenyl)-2,3-dihydroxypropanoate (Preparation example 433), to obtain the title compound (2.1 g, 70~95%).

$^1$H NMR (400 MHz, CDCl$_3$) δ 1.36 (d, J=6.4, 3H), 2.35 (s, 3H), 3.68 (s, 3H), 5.07 (m, 1H), 5.11 (d, J=7.6, 1H), 5.82 (d, J=7.6, 1H), 7.19~7.39 (m, 4H)

Preparation Example 187: ((4R,5R)-5-(2-methylphenyl)-2-methyl-1,3dioxolane-4-yl)methanol

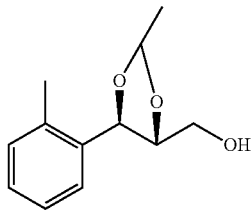

The substantially same method as described in Preparation example 185 was conducted, except that (4S,5R)-methyl-5-(2-methylphenyl)-2-mehtyl-1.3-dioxolane-4-carboxylate (Preparation example 186) was used instead of (2R, 3S)-methyl-37 (2-nitrophenyl)-2-phenyl-1,3-dioxolane-4-carboxylate (Preparation example 184), to obtain the title compound (1.7 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.17~7.41 (m, 4H).

Preparation Example 188: (4R,5S)-methyl-5-(2-methylphenyl)-2-methyl-1,3-dioxolane-4-carboxylate

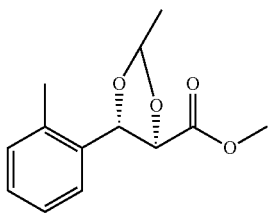

The substantially same method as described in Preparation example 186 was conducted, except that (2R,3S)-methyl-3-(2-methylphenyl)-2,3-dihydroxypropanoate (Preparation example 57) was used instead of (2S,3R)-methyl-3-(2-methylphenyl)-2,3-dihydroxypropanoate (Preparation example 54), to obtain the title compound (1.8 g, 70~95%).

$^1$H NMR (400 MHz, CDCl$_3$) δ 1.36 (d, J=6.4, 3H), 2.35 (s, 3H), 3.68 (s, 3H), 5.07 (m, 1H), 5.11 (d, J=7.6, 1H), 5.82 (d, J=7.6, 1H), 7.19~7.39 (n, 4H)

Preparation Example 189: ((4S,5S)-5-(2-methylphenyl)-2-methyl-1.3-dioxolane-4-yl)methanol

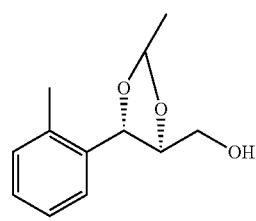

The substantially same method as described in Preparation example 187 was conducted, except that (4R,5S)-methyl-5-(2-methylphenyl)-2-mehtyl-1.3-dioxolane-4-carboxylate (Preparation example 188) was used instead of (4S,5R)-methyl-5-(2-methylphenyl)-2-mehtyl-1.3-dioxolane-4-carboxylate (Preparation example 186), to obtain the title compound (1.6 g, 70~95%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.17~7.41 (m, 4H).

Preparation Example 190: (4S, 5R)-methyl-5-(2-methylphenyl)-2,2-diethyl-1.3-dioxolane-4-carboxylate

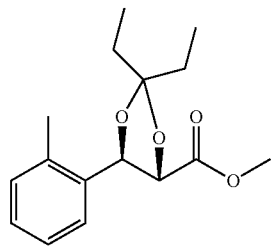 [SMILES: CCC1(CC)O[C@H](C(=O)OC)[C@@H](c2ccccc2C)O1]

The substantially same method as described in Preparation example 170 was conducted, except that (2S,3R)-methyl-3-(2-methylphenyl)-2,3-dihydroxypropanoate (Preparation example 54) was used instead of (2S,3R)-methyl-3-(2-nitrophenyl)-2,3-dihydroxypropanoate (Preparation example 44), to obtain the title compound (2.1 g, 60~85%).

$^1$H NMR (400 MHz, CDCl$_3$) δ 0.96 (m, 6H), 1.59 (m, 4H), 2.33 (s, 1H), 3.67 (s, 3H), 5.11 (d, J=7.6, 1H), 5.81 (d, J=7.6, 1H), 7.00~7.17 (m, 4H)

Preparation Example 191: ((4R,5R)-5-(2-methyl-phenyl)-2,2-diethyl-1.3-dioxolane-4-yl)methanol

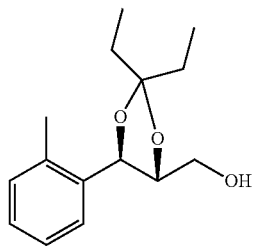 [SMILES: CCC1(CC)O[C@H](c2ccccc2C)[C@@H](CO)O1]

The substantially same method as described in Preparation example 187 was conducted, except that (4S,5R)-methyl-5-(2-methylphenyl)-2,2-diethyl-1,3-dioxolane-4-carboxylate (Preparation example 190) was used instead of (4S,5R)-methyl-5-(2-methylphenyl)-2-mehtyl-1.3-dioxolane-4-carboxylate (Preparation example 186), to obtain the title compound (1.7 g, 70~95%)

$^1$H NMR (400 MHz, CDCl$_3$): δ 0.96 (m, 6H), 1.59 (m, 4H), 2.37 (s, 3H), 3.62~3.70 (m, 2H), 4.36 (dd, J=7.0, J=7.0, 1H), 5.17 (d, J=7.0, 1H), 7.15~7.39 (m, 4H)

Preparation Example 192: (4R, 5S)-methyl-5-(2-methylphenyl)-2,2-diethyl-1.3-dioxolane-4-carboxylate

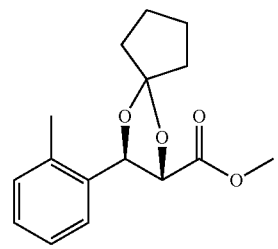

The substantially same method as described in Preparation example 190 was conducted, except that (2R,3S)-methyl-3-(2-methylphenyl)-2,3-dihydroxypropanoate (Preparation example 57) was used instead of (2S,3R)-methyl-3-(2-methylphenyl)-2,3-dihydroxypropanoate (Preparation example 54), to obtain the title compound (2.2 g, 60~85%).

$^1$H NMR (400 MHz, CDCl$_3$) δ 0.96 (m, 6H), 1.59 (m, 4H), 2.33 (s, 1H), 3.67 (s, 3H), 5.11 (d, J=7.6, 1H), 5.81 (d, J=7.6, 1H), 7.00~7.17 (m, 4H)

Preparation Example 193: ((4S,5S)-5-(2-methylphenyl)-2,2-diethyl-1.3-dioxolane-4-yl)methanol

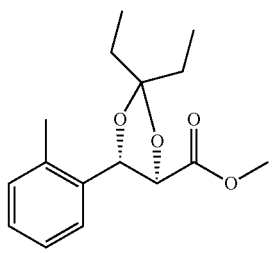 [SMILES: CCC1(CC)O[C@@H](C(=O)OC)[C@H](c2ccccc2C)O1]

The substantially same method as described in Preparation example 191 was conducted, except that (4R,5S)-methyl-5-(2-methylphenyl)-2,2-diethyl-1.3-dioxolane-4-carboxylate (Preparation example 192) was used instead of (4S, 5R)-methyl-5-(2-methylphenyl)-2,2-diethyl-1.3-dioxolane-4-carboxylate (Preparation example 190), to obtain the title compound (1.8 g, 70~95%)

$^1$H NMR (400 MHz, CDCl$_3$): δ 0.96 (m, 6H), 1.59 (m, 4H), 2.37 (s, 3H), 3.62~3.70 (m, 2H), 4.36 (dd, J=7.0, J=7.0, 1H), 5.17 (d, J=7.0, 1H), 7.15~7.39 (m, 4H)

Preparation Example 194: (2S, 3R)-methyl-3-(2-methylphenyl)-1,4-dioxaspiro[4,4]nonane-2-carboxylate

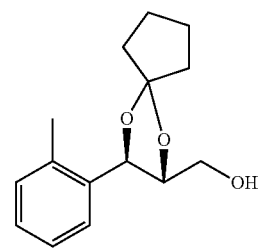

The substantially same method as described in Preparation example 190 was conducted, except that cyclopentanone was used instead of 3-pentanone, to obtain the title compound (2.1 g, 70~95%).

$^1$H NMR (400 MHz, DMSO) δ 1.49~1.57 (m, 4H), 1.72~1.81 (m, 4H), 2.35 (s, 3H), 3.68 (s, 3H), 5.14 (d, J=7.2, 1H), 5.89 (d, J=7.2, 1H), 7.02~7.25 (m, 4H)

Preparation Example 195: ((2R,3R)-3-(2-methylphenyl)-1,4-dioxaspiro[4,4]nonane-2-yl)methanol

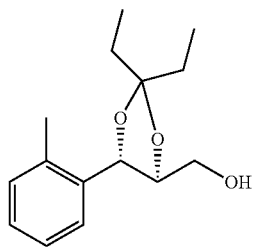 [SMILES: CCC1(CC)O[C@@H](CO)[C@H](c2ccccc2C)O1]

The substantially same method as described in Preparation example 191 was conducted, except that (2S, 3R)-methyl-3-(2-methylphenyl)-1,4-dioxaspiro[4,4]nonane-2-carboxylate (Preparation example 194) was used instead of (4S, 5R)-methyl-5-(2-methylphenyl)-2,2-diethyl-1.3-dioxolane-4-carboxylate (Preparation example 190), to obtain the title compound (1.6 g, 70~95%)

$^1$H NMR (400 MHz, DMSO): δ 1.49~1.57 (m, 4H), 1.72~1.81 (m, 4H), 2.35 (s, 3H), 3.52~3.65 (m, 2H), 4.90 (t, J=5.2, 1H), 5.12 (d, J=7.6, 1H), 7.02~7.25 (m, 4H)

Preparation Example 196: (2R, 3S)-methyl-3-(2-methylphenyl)-1,4-dioxaspiro[4,4]nonane-2-carboxylate

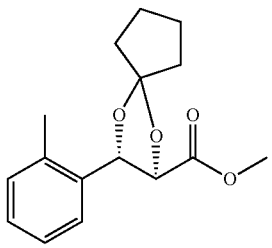 [SMILES: COC(=O)[C@@H]1OC2(CCCC2)O[C@H]1c1ccccc1C]

The substantially same method as described in Preparation example 192 was conducted, except that cyclopentanone was used instead of 3-pentanone, to obtain the title compound (2.5 g, 70~95%).
$^1$H NMR (400 MHz, DMSO) δ 1.49~1.57 (m, 4H), 1.72~1.81 (m, 4H), 2.35 (s, 3H), 3.68 (s, 3H), 5.14 (d, J=7.2, 1H), 5.89 (d, J=7.2, 1H), 7.02~7.25 (m, 4H)

Preparation example 197: ((2S,3S)-3-(2-methylphenyl)-1,4-dioxaspiro[4,4]nonane-2-yl)methanol

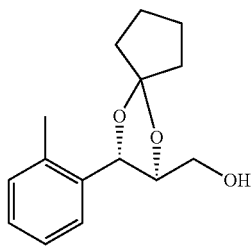 [SMILES: Cc1ccccc1[C@@H]1OC2(CCCC2)O[C@H]1CO]

The substantially same method as described in Preparation example 195 was conducted, except that (2R, 3S)-methyl-3-(2-methylphenyl)-1,4-dioxaspiro[4,4]nonane-2-carboxylate (Preparation example 196) was used instead of (2S, 3R)-methyl-3-(2-methylphenyl)-1,4-dioxaspiro[4,4]nonane-2-carboxylate (Preparation example 194), to obtain the title compound (2.0 g, 70~95%)
$^1$H NMR (400 MHz, DMSO): δ 1.49~1.57 (m, 4H), 1.72~1.81 (m, 4H), 2.35 (s, 3H), 3.52~3.65 (m, 2H), 4.90 (t, J=5.2, 1H), 5.12 (d, J=7.6, 1H), 7.02~7.25 (m, 4H)

Preparation Example 198: (2S, 3R)-methyl-3-(2-methylphenyl)-1,4-dioxaspiro[4,5]decane-2-carboxylate

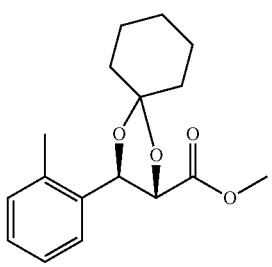 [SMILES: COC(=O)[C@H]1OC2(CCCCC2)O[C@@H]1c1ccccc1C]

The substantially same method as described in Preparation example 194 was conducted, except that cyclohexanone was used instead of cyclopentanone, to obtain the title compound (1.8 g, 70~95%).
$^1$H NMR (400 MHz, DMSO) δ 1.61~1.69 (m, 10H), 2.34 (s, 3H), 3.79 (s, 3H), 4.33 (d, J=8.0, 1H), 5.85 (d, J=8.0, 1H), 7.01~7.30 (m, 4H)

Preparation Example 199: ((2R,3R)-3-(2-methylphenyl)-1,4-dioxaspiro[4,5]decane-2-yl)methanol

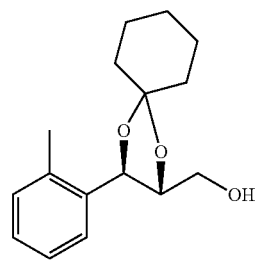 [SMILES: Cc1ccccc1[C@H]1OC2(CCCCC2)O[C@@H]1CO]

The substantially same method as described in Preparation example 195 was conducted, except that (2S, 3R)-methyl-3-(2-methylphenyl)-1,4-dioxaspiro[4,5]decane-2-carboxylate (Preparation example 198) was used instead of (2S, 3R)-methyl-3-(2-methylphenyl)-1,4-dioxaspiro[4,4]nonane-2-carboxylate (Preparation example 194), to obtain the title compound (1.5 g, 70~95%)
$^1$H NMR (400 MHz, DMSO): δ 1.63~1.75 (m, 10H), 2.33 (s, 3H), 3.52~3.81 (m, 2H), 3.95 (t, J=8.0, 1H), 5.43 (d, J=7.6, 1H), 7.02~7.28 (m, 4H)

Preparation Example 200: (2R, 3S)-methyl-3-(2-methylphenyl)-1,4-dioxaspiro[4,5]decane-2-carboxylate

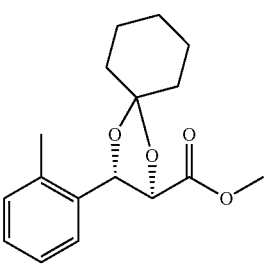 [SMILES: COC(=O)[C@@H]1OC2(CCCCC2)O[C@H]1c1ccccc1C]

The substantially same method as described in Preparation example 196 was conducted, except that cyclohexanone was used instead of cyclopentanone, to obtain the title compound (2.2 g, 70~95%).
$^1$H NMR (400 MHz, DMSO) δ 1.61~1.69 (m, 10H), 2.34 (s, 3H), 3.79 (s, 3H), 4.33 (d, J=8.0, 1H), 5.85 (d, J=8.0, 1H), 7.01~7.30 (m, 4H)

Preparation Example 201: ((2S,3S)-3-(2-methylphenyl)-1,4-dioxaspiro[4,5]decane-2-yl)methanol

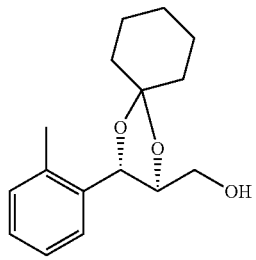 [SMILES: Cc1ccccc1[C@@H]1OC2(CCCCC2)O[C@H]1CO]

The substantially same method as described in Preparation example 199 was conducted, except that (2R, 3S)-methyl-3-(2-methylphenyl)-1,4-dioxaspiro[4,5]decane-2-carboxylate (Preparation example 200) was used instead of (2S, 3R)-methyl-3-(2-methylphenyl)-1,4-dioxaspiro[4,5]decane-2-carboxylate (Preparation example 198), to obtain the title compound (1.5 g, 70~95%)

¹H NMR (400 MHz, DMSO): δ 1.63~1.75 (m, 10H), 2.33 (s, 3H), 3.52~3.81 (m, 2H), 3.95 (t, J=8.0, 1H), 5.43 (d, J=7.6, 1H), 7.02~7.28 (m, 4H)

Preparation Example 202: (4S, 5R)-methyl-5-(2-methylphenyl)-2-phenyl-1,3-dioxolane-4-carboxylate

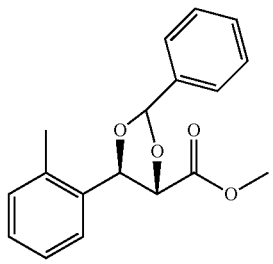

The substantially same method as described in Preparation example 198 was conducted, except that benzaldehyde was used instead of cyclohexanone, to obtain the title compound (2.2 g, 50~70%).

¹H NMR (400 MHz, DMSO) δ 2.33 (s, 3H), 3.67 (s, 3H), 5.11 (d, J=8.0, 1H), 5.81 (d, J=8.0, 1H), 6.18 (s, 1H), 6.96~7.32 (m, 9H)

Preparation Example 203: ((4R,5R)-5-(2-methylphenyl)-2-phenyl-1,3-dioxolane-4-yl)methanol

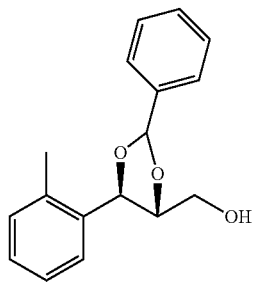

The substantially same method as described in Preparation example 199 was conducted, except that (4S, 5R)-methyl-5-(2-methylphenyl)-2-phenyl-1,3-dioxolane-4-carboxylate (Preparation example 202) was used instead of (2S, 3R)-methyl-3-(2-methylphenyl)-1,4-dioxaspiro[4,5]decane-2-carboxylate (Preparation example 198), to obtain the title compound (1.6 g, 70~95%)

¹H NMR (400 MHz, DMSO): δ 2.32 (s, 3H), 3.66 (d, J=7.6, 2H), 4.36 (m, 1H), 5.17 (d, J=8.0, 1H), 6.18 (s, 1H), 6.99~7.33 (m, 9H)

Preparation Example 204: (4R, 5S)-methyl-5-(2-methylphenyl)-2-phenyl-1,3-dioxolane-4-carboxylate

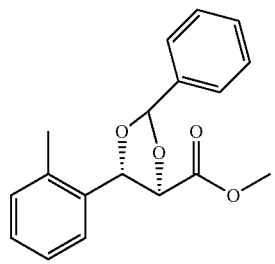

The substantially same method as described in Preparation example 200 was conducted, except benzaldehyde that was used instead of cyclohexanone, to obtain the title compound (1.9 g, 50~70%).

¹H NMR (400 MHz, DMSO) δ 2.33 (s, 3H), 3.67 (s, 3H), 5.11 (d, J=8.0, 1H), 5.81 (d, J=8.0, 1H), 6.18 (s, 1H), 6.96~7.32 (m, 9H)

Preparation Example 205: ((4S,5S)-5-(2-methylphenyl)-2-phenyl-1,3-dioxolane-4-yl)methanol

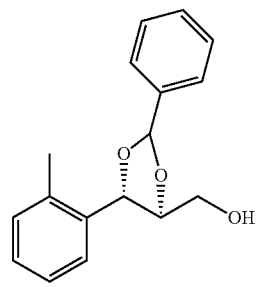

The substantially same method as described in Preparation example 203 was conducted, except that (4R, 5S)-methyl-5-(2-methylphenyl)-2-phenyl-1,3-dioxolane-4-carboxylate (Preparation example 204) was used instead of (4S, 5R)-methyl-5-(2-methylphenyl)-2-phenyl-1,3-dioxolane-4-carboxylate (Preparation example 202), to obtain the title compound (1.3 g, 70~95%)

¹H NMR (400 MHz, DMSO): δ 2.32 (s, 3H), 3.66 (d, J=7.6, 2H), 4.36 (m, 1H), 5.17 (d, J=8.0, 1H), 6.18 (s, 1H), 6.99~7.33 (m, 9H)

Preparation Example 206: ((4R,5R)-5-(2-aminophenyl)-2-mehtyl-1.3-dioxolane-4-yl)methanol

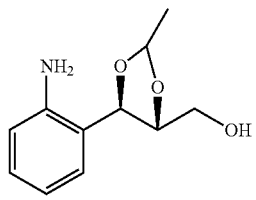

The substantially same method as described in Preparation example 47 was conducted, except that ((4R,5R)-5-(2-nitrophenyl)-2-mehtyl-1.3-dioxolane-4-yl)methanol (Preparation example 167) was used instead of ((4R,5R)-5-(2-nitrophenyl)-2,2-dimethyl-1.3-dioxolane-4-yl)methanol (Preparation example 46), to obtain the title compound (1.5 g, 65~85%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.57~8.08 (m, 4H).

Preparation Example 207: ((4S,5S)-5-(2-aminophenyl)-2-mehtyl-1.3-dioxolane-4-yl)methanol

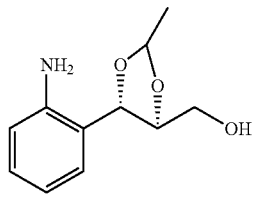

The substantially same method as described in Preparation example 47 was conducted, except that ((4S,5S)-5-(2-nitrophenyl)-2-mehtyl-1.3-dioxolane-4-yl)methanol (Preparation example 169) was used instead of ((4R,5R)-5-(2-nitrophenyl)₇2,2-dimethyl-1.3-dioxolane-4-yl)methanol (Preparation example 46), to obtain the title compound (1.1 g, 65~85%)

$^1$H NMR (400 MHz, CDCl$_3$): δ 1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.57~8.08 (m, 4H).

Preparation Example 208: ((4R,5R)-5-(2-aminohenyl)-2,2-diethyl-1.3-dioxolane-4-yl)methanol

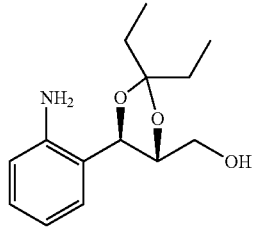 [SMILES: CCC1(CC)O[C@H](c2ccccc2N)[C@@H](CO)O1]

The substantially same method as described in Preparation example 47 was conducted, except that ((4R,5R)-5-(2-nitrophenyl)-2,2-diethyl-1.3-dioxolane-4-yl)methanol (Preparation example 171) was used instead of ((4R,5R)-5-(2-nitrophenyl)-2,2-dimethyl-1.3-dioxolane-4-yl)methanol (Preparation example 46), to obtain the title compound (1.5 g, 65~85%)

$^1$H NMR (400 MHz, CDCl$_3$): δ 0.96 (m, 6H), 1.59 (m, 4H), 3.62~3.70 (m, 2H), 4.36 (dd, J=7.0, J=7.0, 1H), 5.17 (d, J=7.0, 1H), 7.55~8.09 (m, 4H)

Preparation Example 209: ((4S,5S)-5-(2-aminophenyl)-2,2-diethyl-1.3-dioxolane-4-yl)methanol

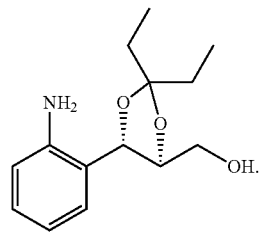 [SMILES: CCC1(CC)O[C@@H](CO)[C@H](c2ccccc2N)O1]

The substantially same method as described in Preparation example 47 was conducted, except that ((4S,5S)-5-(2-nitrophenyl)-2,2-diethyl-1.3-dioxolane-4-yl)methanol (Preparation example 173) was used instead of ((4R,5R)-5-(2-nitrophenyl)-2,2-dimethyl-1.3-dioxolane-4-yl)methanol (Preparation example 46), to obtain the title compound (1.4 g, 65~85%)

$^1$H NMR (400 MHz, CDCl$_3$): δ 0.96 (m, 6H), 1.59 (m, 4H), 3.62~3.70 (m, 2H), 4.36 (dd, J=7.0, J=7.0, 1H), 5.17 (d, J=7.0, 1H), 7.55~8.09 (m, 4H)

Preparation Example 210: ((2R,3R)-3-(2-aminophenyl)-1,4-dioxaspiro[4,4]nonane-2-yl)methanol

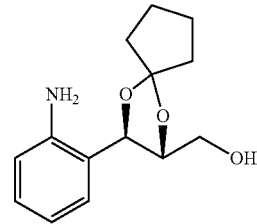 [SMILES: Nc1ccccc1[C@H]1OC2(CCCC2)O[C@@H]1CO]

The substantially same method as described in Preparation example 47 was conducted, except that ((4R,5R)-5-(2-nitrophenyl)-1,4-dioxaspiro[4,4]nonane-2-yl)methanol (Preparation example 175) was used instead of ((4R,5R)-5-(2-nitrophenyl)-2,2-dimethyl-1.3-dioxolane-4-yl)methanol (Preparation example 46), to obtain the title compound (1.7 g, 65~85%)

$^1$H NMR (400 MHz; DMSO): δ 1.62~1.73 (m, 4H), 1.82~1.95 (m, 4H), 3.52~3.65 (m, 2H), 4.90 (t, J=5.2, 1H), 5.12 (d, J=7.6, 1H), 7.56~8.11 (m, 4H)

Preparation Example 211: ((2S,3S)-3-(2-aminophenyl)-1,4-dioxaspiro[4,4]nonane-2-yl)methanol

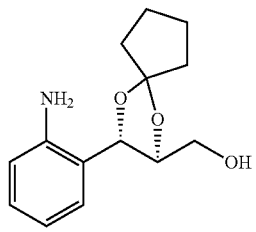 [SMILES: Nc1ccccc1[C@@H]1OC2(CCCC2)O[C@H]1CO]

The substantially same method as described in Preparation example 47 was conducted, except that ((4S,5S)-5-(2-nitrophenyl)-1,4-dioxaspiro[4,4]nonane-2-yl)methanol (Preparation example 177) was used instead of ((4R,5R)-5-(2-nitrophenyl)-2,2-dimethyl-1.3-dioxolane-4-yl)methanol (Preparation example 46), to obtain the title compound (1.6 g, 65~85%)

$^1$H NMR (400 MHz, DMSO): δ 1.62~1.73 (m, 4H), 1.82~1.95 (m, 4H), 3.52~3.65 (m, 2H) 4.90 (t, J=5.2, 1H), 5.12 (d, J=7.6, 1H), 7.56~8.11 (m, 4H)

Preparation Example 212: ((2R,3R)-3-(2-aminophenyl)-1,4-dioxaspiro[4,5]decane-2-yl)methanol

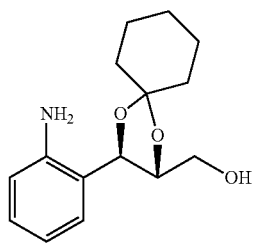 [SMILES: Nc1ccccc1[C@H]1OC2(CCCCC2)O[C@@H]1CO]

The substantially same method as described in Preparation example 47 was conducted, except that ((4R,5R)-5-(2-nitrophenyl)-1,4-dioxaspiro[4,5]decane-2-yl)methanol (Preparation example 179) was used instead of ((4R,5R)-5-(2-nitrophenyl)-2,2-dimethyl-1.3-dioxolane-4-yl)methanol (Preparation example 46), to obtain the title compound (1.1 g, 65~85%)

$^1$H NMR (400 MHz, DMSO): δ 1.61~1.75 (m, 10H), 3.52~3.81 (m, 2H), 3.95 (t, J=8.0, 1H), 5.43 (d, J=7.6, 1H), 7.49~8.12 (m, 4H)

Preparation Example 213: ((2S,3S)-3-(2-aminophenyl)-1,4-dioxaspiro[4,5]decane-2-yl)methanol

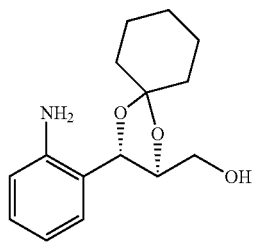 [SMILES: Nc1ccccc1[C@@H]1OC2(CCCCC2)O[C@H]1CO]

The substantially same method as described in Preparation example 47 was conducted, except that ((4S,5S)-5-(2-nitrophenyl)-1,4-dioxaspiro[4,5]decane-2-yl)methanol (Preparation example 181) was used instead of ((4R,5R)-5-(2-nitrophenyl)-2,2-dimethyl-1.3-dioxolane-4-yl)methanol (Preparation example 46), to obtain the title compound (1.0 g, 65~85%)

$^1$H NMR (400 MHz, DMSO): δ 1.61~1.75 (m, 10H), 3.52~3.81 (m, 2H), 3.95 (t, J=8.0, 1H), 5.43 (d, J=7.6, 1H), 7.49~8.12 (m, 4H)

Preparation Example 214: ((4R,5R)-5-(2-aminophenyl)-2-phenyl-1,3-dioxolane-4-yl)methanol

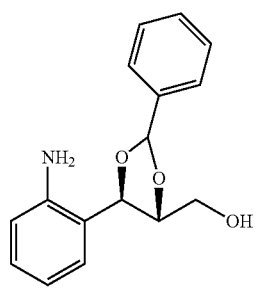

The substantially same method as described in Preparation example 47 was conducted, except that ((4R,5R)-5-(2-nitrophenyl)-2-phenyl-1,3-dioxolane-4-yl)methanol (Preparation example 183) was used instead of ((4R,5R)-5-(2-nitrophenyl)-2,2-dimethyl-1.3-dioxolane-4-yl)methanol (Preparation example 46), to obtain the title compound (1.2 g, 65~85%)

$^1$H NMR (400 MHz, DMSO): δ 3.66 (d, J=7.6, 2H), 4.36 (m, 1H), 5.17 (d, J=8.0, 1H), 6.18 (s, 1H), 7.06~8.14 (m, 9H)

Preparation Example 215: ((4S,5S)-5-(2-aminophenyl)-2-phenyl-1,3-dioxolane-4-yl)methanol

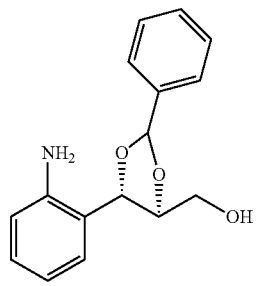

The substantially same method as described in Preparation example 47 was conducted, except that (4S,5S)-5-(2-nitrophenyl)-2-phenyl-1,3-dioxolane-4-yl)methanol (Preparation example 185) was used instead of ((4R,5R)-5-(2-nitrophenyl)-2,2-dimethyl-1.3-dioxolane-4-yl)methanol (Preparation example 46), to obtain the title compound (0.9 g, 65~85%)

$^1$H NMR (400 MHz, DMSO): δ 3.66 (d, J=7.6, 2H), 4.36 (m, 1H), 5.17 (d, J=8.0, 1H), 6.18 (s, 1H), 7.06~8.14 (m, 9H)

Preparation Example 216: (E)-Methyl cinnamate

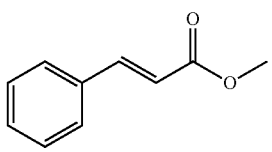

To a round-bottomed flask, trans-cinnamic acid (7 g, 47.25 mmol) and MeOH (70 mL) were added. POCl$_3$ (0.43 mL, 4.73 mmol) was added dropwise. The reaction mixture was stirred under reflux for 3 h. The reaction mixture was cooled to room temperature, quenched with 1N NaOH solution. The mixture was extracted by EtOAc and washed with H$_2$O. The aqueous layer was further extracted with EtOAc. The combined organic layer was dried over anhydrous magnesium sulfate (MgSO$_4$), filtered and concentrated under vacuum (7.1 g, 80~95%)

$^1$H NMR (400 MHz, CDCl$_3$): δ 3.81 (s, 3H), 6.42 (d, J=15.9, 1H), 7.37~7.39 (m, 3H), 7.50~7.53 (m, 2H), 7.67 (d, J=15.9, 1H)

Preparation Example 217: (2S, 3R)-methyl-3-phenyl-2,3-dihydroxypropanoate

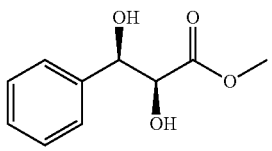

The substantially same method as described in Preparation example 36 was conducted, except that (E)-Methyl cinnamate (Preparation example 216) was used instead of (E)-methyl-3-(2,4-dichlorophenyl)acrylate (Preparation example 28), to obtain the title compound (6.2 g, 70~95%)

$^1$H NMR (400 MHz, CDCl$_3$): δ 2.70 (bs, 1H), 3.08 (bs, 1H), 3.82 (s, 3H), 4.38 (d, J=2.9, 1H), 5.03 (d, J=2.9, 1H), 7.30-7.42 (m, 5H)

Preparation Example 218: (4S, 5R)-methyl-2,2-dimethyl-5-phenyl-1,3-dioxolane-4-carboxylate

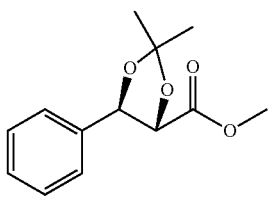 [SMILES: COC(=O)[C@H]1OC(C)(C)O[C@@H]1c1ccccc1]

The substantially same method as described in Preparation example 45 was conducted, except that (2S, 3R)-methyl-3-phenyl-2,3-dihydroxypropanoate (Preparation example 217) was used instead of (2S, 3R)-methyl-3-(2-nitrophenyl)-2,3-dihydroxypropanoate (Preparation example 44), to obtain the title compound (5.6 g, 70~95%)

$^1$H NMR (400 MHz, CDCl$_3$): δ 1.56 (s, 3H), 1.61 (s, 3H), 3.79 (s, 3H), 4.36 (d, J=7.8, 1H), 5.17 (d, J=7.8, 1H), 7.31~7.40 (m, 5H)

Preparation Example 219: ((4R, 5R)-5-phenyl-2,2-dimethyl-1,3-dioxolane-4-yl)methanol

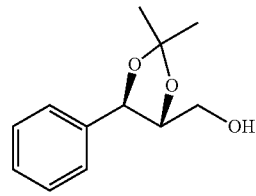

The substantially same method as described in Preparation example 46 was conducted, except that (4S, 5R)-methyl-2,2-dimethyl-5-phenyl-1,3-dioxolane-4-carboxylate (Preparation example 218) was used instead of (4S, 5R)-methyl-5-(2-nitrophenyl)-1,3-dioxolane-4-carboxylate (Preparation example 45), to obtain the title compound (4.4 g, 70~95%)

$^1$H NMR (400 MHz, CDCl$_3$): δ 1.41 (s, 3H), 1.46 (s, 3H), 2.79 (bs, 1H), 3.48~3.52 (m, 1H), 3.68~3.76 (m, 2H), 4.76 (d, J=8.8, 1H), 7.18~7.28 (m, 5H)

Preparation Example 220: (2R, 3S)-methyl-3-phenyl-2,3-dihydroxypropanoate

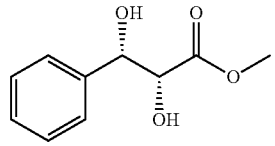

The substantially same method as described in Preparation example 30 was conducted, except that (E)-Methyl cinnamate (Preparation example 216) was used instead of (E)-methyl-3-(2,4-dichlorophenyl)acrylate (Preparation example 28), to obtain the title compound (8.6 g, 70~95%)

$^1$H NMR (400 MHz, CDCl$_3$): δ 2.70 (bs, 1H), 3.08 (bs, 1H), 3.82 (s, 3H), 4.38 (d, J=2.9, 1H), 5.03 (d, J=2.9, 1H), 7.30~7.42 (m, 5H)

Preparation Example 221: (4R, 5S)-methyl-2,2-dimethyl-5-phenyl-1,3-dioxolane-4-carboxylate

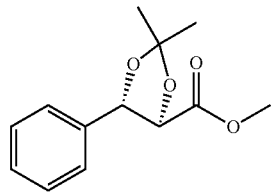 [SMILES: COC(=O)[C@@H]1OC(C)(C)O[C@H]1c1ccccc1]

The substantially same method as described in Preparation example 45 was conducted, except that (2S, 3R)-methyl-3-phenyl-2,3-dihydroxypropanoate (Preparation example 217) was used instead of (2S, 3R)-methyl-3-(2- nitrophenyl)-2,3-dihydroxypropanoate (Preparation example 44), to obtain the title compound (5.6 g, 70~95%)

$^1$H NMR (400 MHz, CDCl$_3$): δ 1.56 (s, 3H), 1.61 (s, 3H), 3.79 (s, 3H), 4.36 (d, J=7.8, 1H), 5.17 (d, J=7.8, 1H), 7.31~7.40 (m, 5H)

Preparation Example 222: ((4S, 5S)-5-phenyl-2,2-dimethyl-1,3-dioxolane-4-yl)methanol

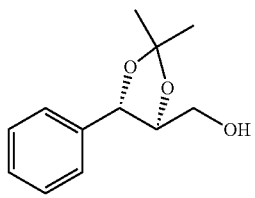

The substantially same method as described in Preparation example 46 was conducted, except that (4R, 5S)-methyl-2,2-dimethyl-5-phenyl-1,3-dioxolane-4-carboxylate (Preparation example 221) was used instead of (4S, 5R)-methyl-5-(2-nitrophenyl)-1,3-dioxolane-4-carboxylate (Preparation example 45), to obtain the title compound (6.5 g, 70~95%)

$^1$H NMR (400 MHz, CDCl$_3$): δ 1.41 (s, 3H), 1.46 (s, 3H), 2.79 (bs, 1H), 3.48~3.52 (m, 1H), 3.68~3.76 (m, 2H), 4.76 (d, J=8.8, 1H), 7.18~7.28 (m, 5H)

Preparation Example 223: (4S, 5R)-methyl-2,2-diethyl-5-phenyl-1,3-dioxolane-4-carboxylate

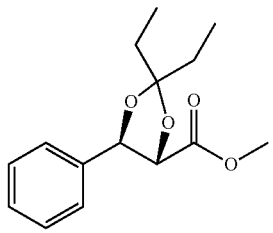 [SMILES: CCC1(CC)O[C@H](C(=O)OC)[C@@H](c2ccccc2)O1]

The substantially same method as described in Preparation example 190 was conducted, except that (2S, 3R)-methyl-3-phenyl-2,3-dihydroxypropanoate (Preparation example 217) was used instead of (2S, 3R)-methyl-3-(2-Methylphenyl)-2,3-dihydroxypropanoate (Preparation example 54), to obtain the title compound (1.9 g, 70~95%)

$^1$H NMR (400 MHz, CDCl$_3$): δ=1.01 (t, J=7.4, 1H), 1.06 (t, J=7.6, 3H), 1.78~1.90 (m, 4H), 3.78 (s, 3H), 5.12 (d, J=8.4, 1H), 7.32~7.45 (m, 5H)

Preparation Example 224: ((4R, 5R)-5-phenyl-2,2-diethyl-1,3-dioxolane-4-yl)methanol

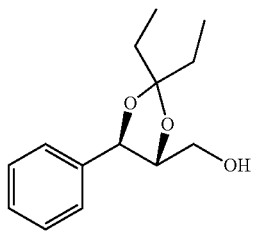 [SMILES: CCC1(CC)O[C@H](c2ccccc2)[C@@H](CO)O1]

The substantially same method as described in Preparation example 219 was conducted, except that (4S, 5R)-methyl-2,2-diethyl-5-phenyl-1,3-dioxolane-4-carboxylate (Preparation example 223) was used instead of (4S, 5R)-methyl-2,2-dimethyl-5-phenyl-1,3-dioxolane-4-carboxylate (Preparation example 218), to obtain the title compound (1.3 g, 70~95%)

$^1$H NMR (400 MHz, CDCl$_3$): δ=1.00 (t, J=7.6, 1H), 1.06 (t, J=7.4, 1H), 1.74~1.90 (m, 4H), 3.64 (ddd, J=3.4, 8.4, 12.1, 1H), 3.84~3.91 (m, 2H), 4.89 (d, J=8.8, 1H), 7.30~7.43 (m, 5H)

Preparation Example 225: (4R, 5S)-methyl-2,2-diethyl-5-phenyl-1,3-dioxolane-4-carboxylate

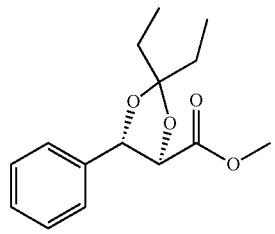 [SMILES: CCC1(CC)O[C@@H](C(=O)OC)[C@H](c2ccccc2)O1]

The substantially same method as described in Preparation example 223 was conducted, except that (2R, 3S)-methyl-3-phenyl-2,3-dihydroxypropanoate (Preparation example 220) was used instead of (2S, 3R)-methyl-3-phenyl-2,3-dihydroxypropanoate (Preparation example 217), to obtain the title compound (5.6 g, 70~95%)

$^1$H NMR (400 MHz, CDCl$_3$): δ=1.01 (t, J=7.4, 1H), 1.06 (t, J=7.6, 3H), 1.78~1.90 (m, 4H), 3.78 (s, 3H), 5.12 (d, J=8.4, 1H), 7.32~7.45 (m, 5H)

Preparation Example 226: ((4S, 5S)-5-phenyl-2,2-dimethyl-1,3-dioxolane-4-yl)methanol

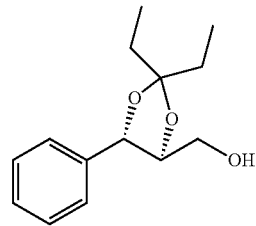 [SMILES: CCC1(CC)O[C@@H](CO)[C@H](c2ccccc2)O1]

The substantially same method as described in Preparation example 224 was conducted, except that (4R, 5S)-methyl-2,2-dimethyl-5-phenyl-1,3-dioxolane-4-carboxylate (Preparation example 225) was used instead of (4S, 5R)-methyl-2,2-dimethyl-5-phenyl-1,3-dioxolane-4-carboxylate (Preparation example 218), to obtain the title compound (6.5 g, 70~95%)

$^1$H NMR (400 MHz, CDCl$_3$): δ=1.00 (t, J=7.6, 1H), 1.06 (t, J=7.4, 1H), 1.74~1.90 (m, 4H), 3.64 (ddd, J=3.4, 8.4, 12.1, 1H), 3.84~3.91 (m, 2H), 4.89 (d, J=8.8, 1H), 7.30~7.43 (m, 5H)

Preparation Example 227: (2S, 3R)-methyl-3-phenyl-1,4-dioxapiro[4,4]nonane-2-carboxylate

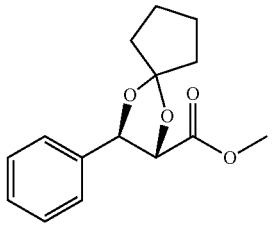 [SMILES: COC(=O)[C@H]1OC2(CCCC2)O[C@@H]1c1ccccc1]

The substantially same method as described in Preparation example 223 was conducted, except that cyclopetanone was used instead of 3-pentanone, to obtain the title compound (0.9 g, 50~75%)
$^1$H NMR (400 MHz, CDCl$_3$): δ=1.71~1.80 (m, 4H), 1.87~1.94 (m, 1H), 2.00~2.08 (m, 3H), 3.79 (s, 3H), 4.35 (d, J=7.2, 1H), 5.08 (d, J=7.2, 1H), 7.32~7.45 (m, 5H)

Preparation Example 228: ((2R, 3R)-3-phenyl-1,4-dioxapiro[4,4]nonan-2-yl)methanol

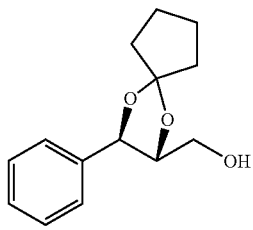 [SMILES: OC[C@H]1OC2(CCCC2)O[C@@H]1c1ccccc1]

The substantially same method as described in Preparation example 224 was conducted, except that (2S, 3R)-methyl-3-phenyl-1,4-dioxapiro[4,4]nonane-2-carboxylate (Preparation example 227) was used instead of (4S, 5R)-methyl-2,2-diethyl-5-phenyl-1,3-dioxolane-4-carboxylate (Preparation example 223), to obtain the title compound (0.7 g, 70~95%)
$^1$H NMR (400 MHz, CDCl$_3$): δ=1.69~1.82 (m, 4H), 1.85~2.03 (m, 4H), 3.66 (ddd, J=3.7, 8.1, 12.1, 1H), 3.83~3.90 (m, 2H), 4.84 (d, J=8.4, 1H), 7.26~7.41 (m, 5H)

Preparation Example 229: (2R, 3S)-methyl-3-phenyl-1,4-dioxapiro[4,4]nonane-2-carboxylate

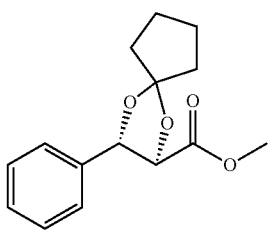 [SMILES: COC(=O)[C@@H]1OC2(CCCC2)O[C@H]1c1ccccc1]

The substantially same method as described in Preparation example 225 was conducted, except that cyclopetanone was used instead of 3-pentanone, to obtain the title compound (0.8 g, 50~75%)
$^1$H NMR (400 MHz, CDCl$_3$): δ=1.71~1.80 (m, 4H), 1.87~1.94 (m, 1H), 2.00~2.08 (m, 3H), 3.79 (s, 3H), 4.35 (d, J=7.2, 1H), 5.08 (d, J=7.2, 1H), 7.32~7.45 (m, 5H)

Preparation Example 230: ((2S, 3S)-3-phenyl-1,4-dioxapiro[4,4]nonan-2-yl)methanol

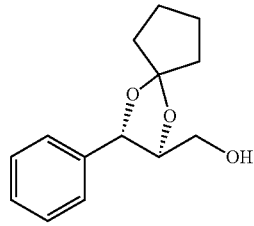 [SMILES: OC[C@@H]1OC2(CCCC2)O[C@H]1c1ccccc1]

The substantially same method as described in Preparation example 228 was conducted, except that (2R, 3S)-methyl-3-phenyl-1,4-dioxapiro[4,4]nonane-2-carboxylate (Preparation example 229) was used instead (2S, 3Rmethyl-3-phenyl-1,4-dioxapiro[4,4]nonane-2-carboxylate (Preparation example 227), to obtain the title compound (0.5 g, 70~95%)
$^1$H NMR (400 MHz, CDCl$_3$): δ=1.69~1.82 (m, 4H), 1.85~2.03 (m, 4H), 3.66 (ddd, J=3.7, 8.1, 12.1, 1H), 3.83~3.90 (m, 2H), 4.84 (d, J=8.4, 1H), 7.26~7.41 (m, 5H)

Preparation Example 231: (2S,3R)-methyl 3-phenyl-1,4-dioxapiro[4,5]decane-2-carboxylate

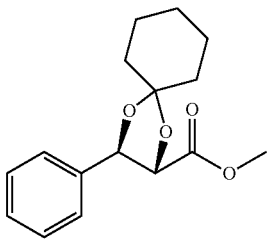 [SMILES: COC(=O)[C@H]1OC2(CCCCC2)O[C@@H]1c1ccccc1]

The substantially same method as described in Preparation example 227 was conducted, except that cyclohexanone was used instead of cyclopetanone, to obtain the title compound (1.4 g, 50~75%)
$^1$H NMR (400 MHz, CDCl$_3$): δ=1.41~1.49 (m, 2H), 1.58~1.76 (m, 4H), 1.79~1.90 (m, 4H), 3.78 (s, 3H), 4.36 (d, J=7.6, 1H), 5.16 (d, J=7.2, 1H), 7.31~7.44 (m, 5H)

Preparation Example 232: ((2R, 3R)-3-phenyl-1,4-dioxapiro[4,5]decan-2-yl)methanol

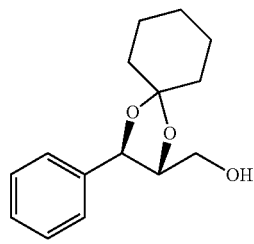 [SMILES: OC[C@H]1OC2(CCCCC2)O[C@@H]1c1ccccc1]

The substantially same method as described in Preparation example 224 was conducted, except that (2S, 3R)-methyl 3-phenyl-1,4-dioxapiro[4,5]decane-2-carboxylate (Preparation example 231) was used instead of (4S, 5R)-methyl-2,2-diethyl-5-phenyl-1,3-dioxolane-4-carboxylate (Preparation example 223), to obtain the title compound (1.0 g, 70~95%)

$^1$H NMR (400 MHz, CDCl$_3$): δ=1.41~1.50 (m, 2H), 1.61~1.89 (m, 8H), 3.60~3.66 (m, 1H), 3.85~3.90 (m, 2H), 4.91 (d, J=8.4, 1H), 7.30~7.42 (m, 5H)

Preparation Example 233: (2R, 3S)-methyl-3-phenyl-1,4-dioxapiro[4,5]decane-2-carboxylate

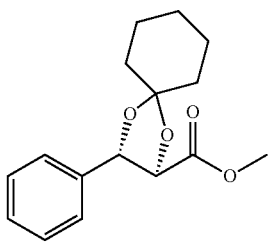 [SMILES: COC(=O)[C@@H]1OC2(CCCCC2)O[C@H]1c1ccccc1]

The substantially same method as described in Preparation example 229 was conducted, except that cyclohexanone was used instead of cyclopetanone, to obtain the title compound (1.2 g, 50~75%)

$^1$H NMR (400 MHz, CDCl$_3$): δ=1.41~1.49 (m, 2H), 1.58~1.76 (m, 4H), 1.79~1.90 (m, 4H), 3.78 (s, 3H), 4.36 (d, J=7.6, 1H), 5.16 (d, J=7.2, 1H), 7.31~7.44 (m, 5H)

Preparation Example 234: ((2S, 3S)-3-phenyl-1,4-dioxapiro[4,5]decane-2-yl)methanol

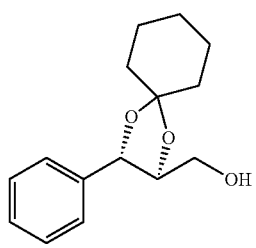 [SMILES: OC[C@@H]1OC2(CCCCC2)O[C@H]1c1ccccc1]

The substantially same method as described in Preparation example 232 was conducted, except that (2R, 3S)-methyl-3-phenyl-1,4-dioxapiro[4,5]decane-2-carboxylate (Preparation example 233) was used instead of (2S, 3R)-methyl-3-phenyl-1,4-dioxapiro[4,5]decane-2-carboxylate (Preparation example 231), to obtain the title compound (0.8 g, 70~95%)

$^1$H NMR (400 MHz, CDCl$_3$): δ=1.41~1.50 (m, 2H), 1.61~1.89 (m, 8H), 3.60~3.66 (m, 1H), 3.85~3.90 (m, 2H), 4.91 (d, J=8.4, 1H), 7.30~7.42 (m, 5H)

Preparation Example 235: (E)-5-phenylpent-3-enoic acid

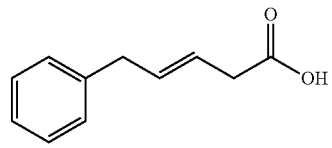 [SMILES: O=C(O)C/C=C/Cc1ccccc1]

A solution of malonic acid (17.06 g, 163.96 mmol) in DMSO (65 mL) was treated with a solution of AcOH (0.1 mL, 1.49 mmol) and piperidine (0.15 mL, 1.49 mmol) in DMSO (4 mL). The reaction solution was warmed to 65° C. and hydrocinnamaldehyde (10 g, 74.53 mmol) was added dropwise within 1.5 hr. After the addition ended, the reaction mixture was stirred for further 2 h at 65° C. The solution was cooled to room temperature, taken up in H$_2$O and extracted with Et$_2$O. The combined organic extracts were washed with 5% aqueous KHSO$_4$ and brine, dried over MgSO$_4$, and evaporated to dryness. The crude compound was purified by a silica gel column to produce the title compound (10.4 g, 75~90%)

$^1$H NMR (400 MHz, CDCl$_3$): δ=3.19 (d, J=6.9, 2H), 3.46 (d, J=6.9, 2H), 5.69~5.78 (m, 1H), 5.83~5.91 (m, 1H), 7.01~7.56 (m, 5H), 11.79 (s, 1H)

Preparation Example 236: (E)-5-phenylpent-3-en-1-ol

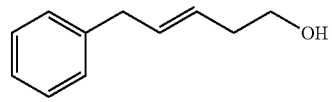 [SMILES: OCC/C=C/Cc1ccccc1]

To stirred solution of LAH (LiAlH$_4$, 3.3 g, 86.73 mmol) in THF (66 mL) was added dropwise a solution (E)-5-phenylpent-3-enoic acid (Preparation example 235, 11.0 g, 57.82 mmol) in THF (44 mL) at 0° C. then stirred at room temperature for 1 h. The reaction mixture was quenched with H$_2$O at 0° C. filtered through celite, washed with EtOAc, dried over anhydrous magnesium sulfate (MgSO$_4$), filtered and concentrated. The crude compound was purified by a silica gel column to produce the title compound (7.2 g, 70~90%)

$^1$H NMR (400 MHz, CDCl$_3$): δ=1.40 (bs, 1H), 2.31 (q, J=6.3, 2H), 3.37 (d, J=6.8, 2H), 3.66 (t, J=6.4, 2H), 5.49 (dt, J=4.9, 11.0, 1H), 5.73 (dt, J=4.8, 10.9, 1H), 7.17~7.31 (m, 5H)

Preparation Example 237: (E)-tert-butyldimethyl(5-phenylpent-3-enyloxy)silane

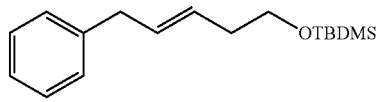 [SMILES: CC(C)(C)[Si](C)(C)OCC/C=C/Cc1ccccc1]

To a stirred solution of (E)-5-phenylpent-3-en-1-ol (Preparation example 236, 6.3 g, 38.83 mmol) in CH$_2$Cl$_2$ was added imidazole (3.4 g, 50.48 mmol) and TBDMS-Cl (7.6 g, 50.48 mmol) at 0° C. then stirred for 1 h at room temperature. The resulting mixture was diluted with EtOAc, washed with water, dried over MgSO₄, filtered, and concentrated under reduced pressure. The crude compound was purified by a silica gel column to produce the title compound (10.6 g, 80~98%)

¹H NMR (400 MHz, CDCl₃): δ=0.00 (s, 6H), 0.84 (s, 9H), 2.21 (ddd, J=6.8, 13.6, 0.8, 2H), 3.29 (d, J=6.8, 2H), 3.59 (t, J=6.8, 2H), 5.41~5.49 (m, 1H), 5.56~5.63 (m, 1H), 7.13~7.26 (m, 5H)

Preparation Example 238: (E)-5-phenylpent-3-enyl pivalate

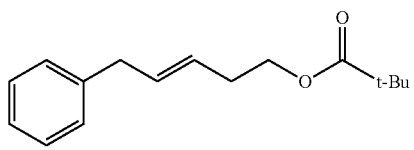 [SMILES: CC(C)(C)C(=O)OCC/C=C/Cc1ccccc1]

To a stirred solution of (E)-5-phenylpent-3-en-1-ol (Preparation example 236, 3.8 g; 23.42 mmol) in CH₂Cl₂ (40 mL) was added pyridine (2.3 mL, 28.1 mmol) and pivaloyl chloride (3.5 mL, 28.1 mmol) at 0° C. under N₂. The mixture was stirred for 14 h. The resulting mixture was diluted with CH₂Cl₂, washed with water, dried over MgSO₄, filtered, and concentrated under reduced pressure. The crude compound was purified by a silica gel column to produce the title compound (5.5 g, 80~95%)

¹H NMR (400 MHz, CDCl₃): δ=1.17 (s, 9H), 2.36 (q, J=6.7, 2H), 3.34 (d, J=6.8, 4.09 (t, J=6.8, 2H), 5.45~5.51 (m, 1H), 5.64~5.69 (m, 1H), 7.16~7.21 (m, 3H), 7.26~7.30 (m, 2H)

Preparation Example 239: (2S,3S)-5-(tert-butyldimethylsilyloxy)-1-phenylpentane-2,3-diol

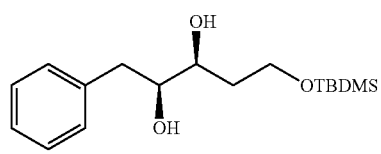 [SMILES: CC(C)(C)[Si](C)(C)OCC[C@H](O)[C@@H](O)Cc1ccccc1]

The substantially same method as described in Preparation example 217 was conducted, except that (E)-tert-butyldimethyl(5-phenylpent-3-enyloxy)silane (Preparation example 237) was used instead of (E)-Methyl cinnamate (Preparation example 216), to obtain the title compound (8.7 g, 70~95%)

¹H NMR (400 MHz, CDCl₃): δ=0.00 (s, 6H), 0.82 (s, 9H), 1.57~1.62 (m, 1H), 1.73~1.80 (m, 1H), 2.51 (d, J=6.0, 1H), 2.77 (dq, J=6.9, 14.9, 2H), 3.50 (d, J=3.6, 1H), 3.59~3.62 (m, 1H), 3.66 (dq, J=3.1, 5.4, 1H), 3.72~3.82 (m, 2H), 7.12~7.25 (m, 5H)

Preparation Example 240: (2-((4S,5S)-5-benzyl-2,2-dimethyl-1,3-dioxolane-4-yl)ethoxy)(tert-butyl)dimethylsilane

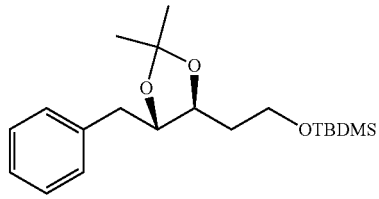 [SMILES: CC1(C)O[C@@H](CCO[Si](C)(C)C(C)(C)C)[C@H](Cc2ccccc2)O1]

The substantially same method as described in Preparation example 218 was conducted, except that (2S,3S)-5-(tert-butyldimethylsilyloxy)-1-phenylpentane-2,3-diol (Preparation example 239) was used instead of (2R, 3S)-methyl-3-phenyl-2,3-dihydroxypropanoate (Preparation example 217), to obtain the title compound (9.5 g, 70~95%)

¹H NMR (400 MHz, CDCl₃): δ=0.00 (s, 6H), 0.85 (s, 9H), 1.29 (s, 3H), 1.34 (s, 3H), 1.52~1.58 (m, 2H), 2.87 (dq, J=5.5, 14.2, 2H), 3.64~3.69 (m, 2H), 3.80~3.88 (m, 2H), 7.18~7.27 (m, 5H)

Preparation Example 241: 2-((4S,5S)-5-benzyl-2,2-dimethyl-1,3-dioxolane-4-yl)ethanol

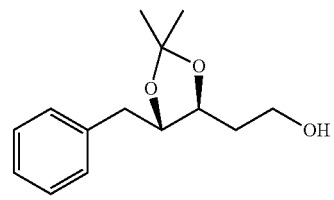 [SMILES: CC1(C)O[C@@H](CCO)[C@H](Cc2ccccc2)O1]

To a stirred solution of (2-((4S,5S)-5-benzyl-2,2-dimethyl-1,3-dioxolan-4-yl)ethoxy)(tert-butyl)dimethylsilane (Preparation example 240, 11.5 g, 32.80 mmol) in THF (115 mL) was slowly added tetrabutylammonium fluoride (TBAF, 1.0M in THF, 48.8 mL, 48.8 mmol) at room temperature. The mixture was stirred for 5 h. The resulting mixture was diluted with EtOAc, washed with water, dried over anhydrous magnesium sulfate, filtered and concentrated. The crude compound was purified by a silica gel column to produce the title compound (7.3 g, 80~95%)

¹H NMR (400 MHz, CDCl₃): δ=1.38 (s, 3H), 1.40 (s, 3H), 1.50~1.63 (m, 2H), 2.29 (t, J=5.4, 1H), 2.82 (dd, J=5.8, 13.8, 1H), 3.01 (dd, J=6.4, 14.0, 1H), 3.72 (q, J=5.5, 2H), 3.86 (dt, J=3.2, 8.4, 1H), 3.92~3.97 (m, 1H), 7.22~7.32 (m, 5H)

Preparation Example 242: (2R,3R)-5-(tert-butyldimethylsilyloxy)-1-phenylpentane-2,3-diol

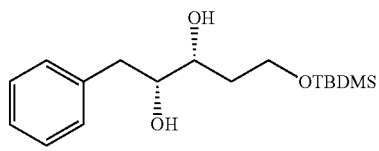 [SMILES: CC(C)(C)[Si](C)(C)OCC[C@@H](O)[C@H](O)Cc1ccccc1]

The substantially same method as described in Preparation example 220 was conducted, except that (E)-tert-butyldimethyl(5-phenylpent-3-enyloxy)silane (Preparation example 237) was used instead of (E)-Methyl cinnamate (Preparation example 216), to obtain the title compound (10.6 g, 70~95%)

¹H NMR (400 MHz, CDCl₃): δ=0.00 (s, 6H), 0.82 (s, 9H), 1.57~1.62 (m, 1H), 1.73~1.80 (m, 1H), 2.51 (d, J=6.0, 1H), 2.77 (dq, J=6.9, 14.9, 2H), 3.50 (d, J=3.6, 1H), 3.59~3.62 (m, 1H), 3.66 (dq, J=3.1, 5.4, 1H), 3.72~3.82 (m, 2H), 7.12~7.25 (m, 5H)

Preparation Example 243: (2-((4R,5R)-5-benzyl-2,2-dimethyl-1,3-dioxolane-4-yl)ethoxy)(tert-butyl)dimethylsilane

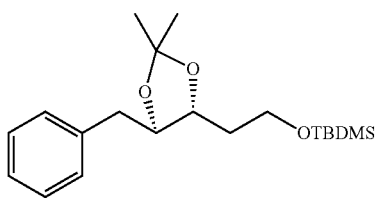 [SMILES: CC1(C)O[C@H](CCO[Si](C)(C)C(C)(C)C)[C@@H](Cc2ccccc2)O1]

The substantially same method as described in Preparation example 221 was conducted, except that (2R,3R)-5-(tert-butyldimethylsilyloxy)-1-phenylpentane-2,3-diol (Preparation example 242) was used instead of (2R, 3S)-methyl-3-phenyl-2,3-dihydroxypropanoate (Preparation example 217), to obtain the title compound (11.5 g, 70~95%)

¹H NMR (400 MHz, CDCl₃): δ=0.00 (s, 6H), 0.85 (s, 9H), 1.29 (s, 3H), 1.34 (s, 3H), 1.52~1.58 (m, 2H), 2.87 (dq, J=5.5, 14.2, 2H), 3.64~3.69 (m, 2H), 3.80~3.88 (m, 2H), 7.18~7.27 (m, 5H)

Preparation Example 244: 2-((4R,5R)-5-benzyl-2,2-dimethyl-1,3-dioxolane-4-yl)ethanol

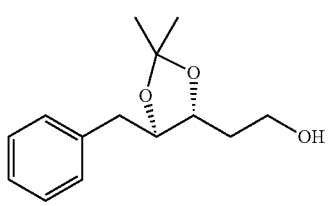 [SMILES: CC1(C)O[C@H](CCO)[C@@H](Cc2ccccc2)O1]

The substantially same method as described in Preparation example 241 was conducted, except that (2-((4R,5R)-5-benzyl-2,2-dimethyl-1,3-dioxolan-4-yl)ethoxy)(tert-butyl)dimethylsilane (Preparation example 243) was used instead of (2-((4S,5S)-5-benzyl-2,2-dimethyl-1,3-dioxolan-4-yl)ethoxy)(tert-butyl)dimethylsilane (Preparation example 240), to obtain the title compound (7.4 g, 80~95%)

¹H NMR (400 MHz, CDCl₃): δ=1.38 (s, 3H), 1.40 (s, 3H), 1.50~1.63 (m, 2H), 2.29 (t, J=5.4, 1H), 2.82 (dd, J=5.8, 13.8, 1H), 3.01 (dd, J=6.4, 14.0, 1H), 3.72 (q, J=5.5, 2H), 3.86 (dt, J=3.2, 8.4, 1H), 3.92~3.97 (m, 1H), 7.22~7.32 (m, 5H)

Preparation Example 245: (3S,4S)-3,4-dihydroxy-5-phenylpentyl pivalate

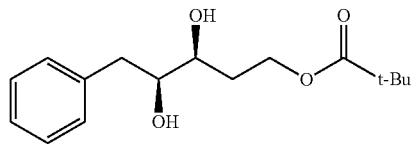 [SMILES: CC(C)(C)C(=O)OCC[C@H](O)[C@@H](O)Cc1ccccc1]

The substantially same method as described in Preparation example 239 was conducted, except that (E)-5-phenylpent-3-enyl pivalate (Preparation example 238) was used instead of (E)-tert-butyldimethyl(5-phenylpent-3-enyloxy)silane (Preparation example 237), to obtain the title compound (5.5 g, 70~95%)

¹H NMR (400 MHz, CDCl₃): δ=1.16 (s, 9H), 1.83~1.88 (m, 2H), 2.08 (d, J=4.8, 1H), 2.67 (d, J=5.2, 1H), 2.80 (dd, J=8.0, 13.6, 1H), 2.92 (dd, J=5.2, 13.6, 1H), 3.50~3.55 (m, 1H), 3.66~3.71 (m, 1H), 4.09~4.19 (m, 1H), 4.35~4.41 (m, 1H), 7.22~7.25 (m, 3H), 7.29~7.33 (m, 2H)

Preparation Example 246: (2-((4S,5S)-5-benzyl-2,2-diethyl-1,3-dioxolane-4-yl)ethyl pivalate

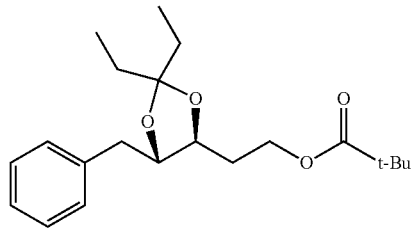 [SMILES: CCC1(CC)O[C@@H](CCOC(=O)C(C)(C)C)[C@H](Cc2ccccc2)O1]

The substantially same method as described in Preparation example 223 was conducted, except that (3S,4S)-3,4-dihydroxy-5-phenylpentyl pivalate (Preparation example 245) was used instead of (2R, 3S)-methyl-3-phenyl-2,3-dihydroxypropanoate (Preparation example 217), to obtain the title compound (0.9 g, 70~95%)

¹H NMR (400 MHz, CDCl₃): δ=1.15 (s, 9H), 1.76 (q, J=7.6, 2H), 1.84~1.90 (m, 2H), 2.00~2.07 (m, 2H), 3.85 (dt, J=3.7, 8.5, 1H), 4.14~4.27 (m, 2H), 5.17 (d, J=8.4, 1H), 7.22~7.28 (m, 1H), 7.32~7.38 (m, 2H), 7.64 (dd, J=1.4, 7.8, 1H)

Preparation Example 247: 2-((4S,5S)-5-benzyl-2,2-diethyl-1,3-dioxolane-4-yl)ethanol

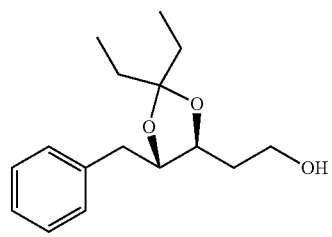 [SMILES: CCC1(CC)O[C@@H](CCO)[C@H](Cc2ccccc2)O1]

To a stirred solution of (2-((4S,5S)-5-benzyl-2,2-diethyl-1,3-dioxolan-4-yl)ethyl pivalate (Preparation example 246, 1.0 g, 2.87 mmol) in MeOH (10 mL) was added NaOMe (0.47 g, 8.61 mmol) and then warm to 45° C. The mixture was stirred for 14 h. The resulting mixture was diluted with EtOAc, washed with water, dried over MgSO4, filtered, and concentrated under reduced pressure. The crude compound was purified by a silica gel column to produce the title compound (0.7 g, 80~95%);

$^1$H NMR (400 MHz, CDCl$_3$): δ=0.89 (t, J=7.4, 6H), 1.44~1.50 (m, 1H), 1.54~1.66 (m, 5H), 2.37 (t, J=5.6, 1H), 2.80 (dd, J=5.6, 14.0, 1H), 3.03 (dd, J=6.4, 14.0, 1H), 3.72 (q, J=5.5, 2H), 3.80~3.85 (m, 1H), 3.89~3.94 (m, 1H), 7.21~7.24 (m, 3H), 7.28~7.31 (m, 2H).

Preparation Example 248: (3R,4R)-3,4-dihydroxy-5-phenylpentyl pivalate

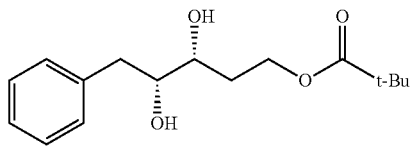 [SMILES: CC(C)(C)C(=O)OCC[C@@H](O)[C@H](O)Cc1ccccc1]

The substantially same method as described in Preparation example 242 was conducted, except that (E)-5-phenyl-pent-3-enyl pivalate (Preparation example 238) was used instead of (E)-tert-butyldimethyl (5-phenylpent-3-enyloxy) silane (Preparation example 237), to obtain the title compound (4.5 g, 70~95%)

$^1$H NMR (400 MHz, CDCl$_3$): δ=1.16 (s, 9H), 1.83~1.88 (m, 2H), 2.08 (d, J=4.8, 1H), 2.67 (d, J=5.2, 1H), 2.80 (dd, J=8.0, 13.6, 1H), 2.92 (dd, J=5.2, 13.6, 1H), 3.50~3.55 (m, 1H), 3.66~3.71 (m, 1H), 4.09~4.19 (m, 1H), 4.35~4.41 (m, 1H), 7.22~7.25 (m, 3H), 7.29~7.33 (m, 2H)

Preparation Example 249: (2-((4R, 5R)-5-benzyl-2,2-diethyl-1,3-dioxolane-4-yl)ethyl pivalate

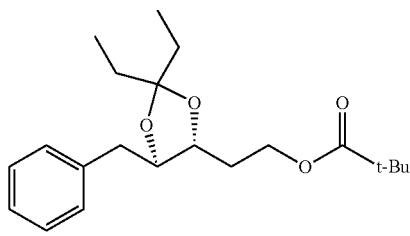 [SMILES: CCC1(CC)O[C@H](CCOC(=O)C(C)(C)C)[C@@H](Cc2ccccc2)O1]

The substantially same method as described in Preparation example 246 was conducted, except that (3R,4R)-3,4-dihydroxy-5-phenylpentyl pivalate (Preparation example 248) was used instead of (3S,4S)-3,4-dihydroxy-5-phenyl-pentyl pivalate (Preparation example 245), to obtain the title compound (1.1 g, 70~95%)

$^1$H NMR (400 MHz, CDCl$_3$): δ=1.15 (s, 9H) 1.76 (q, J=7.6, 2H), 1.84~1.90 (m, 2H), 2.00~2.07 (m, 2H), 3.85 (dt, J=3.7, 8.5, 1H), 4.14~4.27 (m, 2H), 5.17 (d, J=8.4, 1H), 7.22~7.28 (m, 1H), 7.32~7.38 (m, 2H), 7.64 (dd, J=1.4, 7.8, 1H)

Preparation Example 250: 2-((4R, 5R)-5-benzyl-2,2-diethyl-1,3-dioxolane-4-yl)ethanol

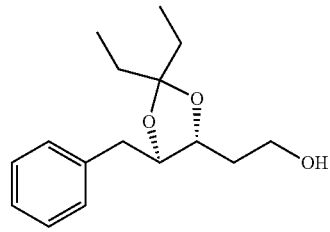 [SMILES: CCC1(CC)O[C@H](CCO)[C@@H](Cc2ccccc2)O1]

The substantially same method as described in Preparation example 247 was conducted, except that (2-((4R,5R)-5-benzyl-2,2-diethyl-1,3-dioxolan-4-yl)ethyl pivalate (Preparation example 249) was used instead of (2-((4S,5S)-5-benzyl-2,2-diethyl-1,3-dioxolan-4-yl)ethyl pivalate (Preparation example 246), to obtain the title compound (0.9 g, 80~95%)

$^1$H NMR (400 MHz, CDCl$_3$): δ=0.89 (t, J=7.4, 6H), 1.44~1.50 (m, 1H), 1.54~1.66 (m, 5H), 2.37 (t, J=5.6, 1H), 2.80 (dd, J=5.6, 14.0, 1H), 3.03 (dd, J=6.4, 14.0, 1H), 3.72 (q, J=5.5, 2H), 3.80~3.85 (m, 1H), 3.89~3.94 (m, 1H), 7.21~7.24 (m, 3H), 7.28~7.31 (m, 2H)

Preparation Example 251: 2-((2S, 3S)-3-benzyl-1,4-dioxaspiro[4.4]nonane-2-yl)ethyl pivalate

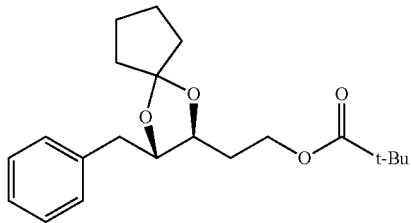 [SMILES: CC(C)(C)C(=O)OCC[C@@H]1OC2(CCCC2)O[C@H]1Cc1ccccc1]

The substantially same method as described in Preparation example 246 was conducted, except that cyclopetanone was used instead of 3-pentanone, to obtain the title compound (1.2 g, 60~85%)

$^1$H NMR (400 MHz, CDCl$_3$): δ=1.18 (s, 9H), 1.53~1.80 (m, 10H), 2.81 (dd, J=6.0, 13.6, 1H), 3.00 (dd, J=6.4, 14.0, 1H), 3.75~3.80 (m, 1H), 3.84~3.89 (m, 1H), 4.05~4.16 (m, 2H), 7.20~7.24 (m, 3H), 7.27~7.31 (m, 2H)

Preparation Example 252: 2-((2S, 3S)-3-benzyl-1,4-dioxaspiro[4.4]nonane-2-yl)ethanol

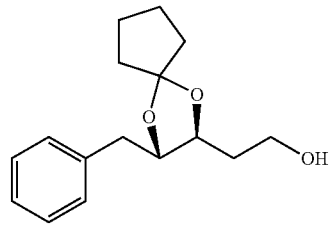 [SMILES: OCC[C@@H]1OC2(CCCC2)O[C@H]1Cc1ccccc1]

The substantially same method as described in Preparation example 247 was conducted, except that 2-((2S,3S)-3-benzyl-1,4-dioxaspiro[4.4]nonan-2-yl)ethyl pivalate (Preparation example 251) was used instead of (2-((4S,5S)-5-benzyl-2,2-diethyl-1,3-dioxolan-4-yl)ethyl pivalate (Preparation example 246), to obtain the title compound (0.7 g, 80~95%)

$^1$H NMR (400 MHz, CDCl$_3$): δ=1.44~1.51 (m, 1H), 1.56~1.60 (m, 1H), 1.63~1.70 (m, 4H), 1.72~1.81 (m, 4H), 2.26 (t, J=5.4, 1H), 2.80 (dd, J=6.0, 14.0, 1H), 3.03 (dd, J=6.4, 14.0, 1H), 3.71 (q, J=5.5, 2H), 3.81~3.92 (m, 2H), 7.22~7.24 (m, 3H), 7.28~7.32 (m, 2H)

Preparation Example 253: 2-((2R, 3R)-3-benzyl-1,4-dioxaspiro[4.4]nonane-2-yl)ethyl pivalate

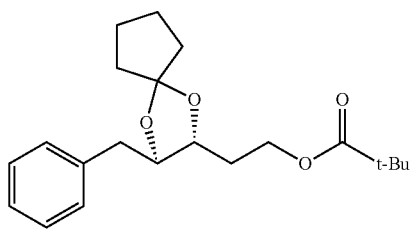 [SMILES: CC(C)(C)C(=O)OCC[C@H]1OC2(CCCC2)O[C@@H]1Cc1ccccc1]

The substantially same method as described in Preparation example 249 was conducted, except that cyclopetanone was used instead of 3-pentanone, to obtain the title compound (1.7 g, 60~85%)

$^1$H NMR (400 MHz, CDCl$_3$): δ=1.18 (s, 9H), 1.53~1.80 (m, 10H), 2.81 (dd, J=6.0, 13.6, 1H), 3.00 (dd, J=6.4, 14.0, 1H), 3.75~3.80 (m, 1H), 3.84~3.89 (m, 1H), 4.05~4.16 (m, 2H), 7.20~7.24 (m, 3H), 7.27~7.31 (m, 2H)

Preparation Example 254: 2-((2R, 3R)-3-benzyl-1,4-dioxaspiro[4,4]nonane-2-yl)ethanol

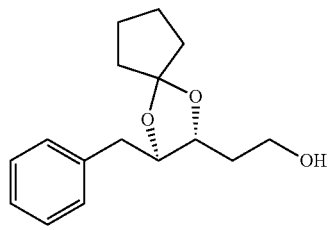 [SMILES: OCC[C@H]1OC2(CCCC2)O[C@@H]1Cc1ccccc1]

The substantially same method as described in Preparation example 252 was conducted, except that 2-((2R,3R)-3-benzyl-1,4-dioxaspiro[4.4]nonan-2-yl)ethyl pivalate (Preparation example 253) was used instead of 2-((2S,3S)-3-benzyl-1,4-dioxaspiro[4.4]nonan-2-yl)ethyl pivalate (Preparation example 251), to obtain the title compound (0.8 g, 80~95%)

$^1$H NMR (400 MHz, CDCl$_3$): δ=1.44~1.51 (m, 1H), 1.56~1.60 (m, 1H), 1.63~1.70 (m, 4H), 1.72~1.81 (m, 4H), 2.26 (t, J=5.4, 1H), 2.80 (dd, J=6.0, 14.0, 1H), 3.03 (dd, J=6.4, 14.0, 1H), 3.71 (q, J=5.5, 2H), 3.81~3.92 (m, 2H), 7.22~7.24 (m, 3H), 7.28~7.32 (m, 2H)

Preparation Example 255: 2-((2S, 3S)-3-benzyl-1,4-dioxaspiro[4.5]decane-2-yl)ethyl pivalate

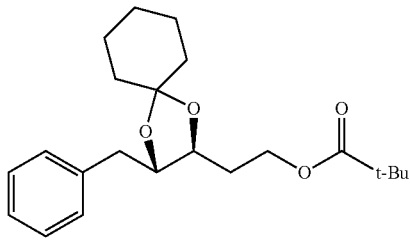 [SMILES: CC(C)(C)C(=O)OCC[C@@H]1OC2(CCCCC2)O[C@H]1Cc1ccccc1]

The substantially same method as described in Preparation example 251 was conducted, except that cyclohexanone was used instead of cyclopetanone, to obtain the title compound (1.4 g, 60~85%)

$^1$H NMR (400 MHz, CDCl$_3$): δ=1.18 (s, 9H), 1.53~1.60 (m, 10H), 1.61~1.66 (m, 2H), 2.83 (dd, J=5.6, 14.0, 1H), 2.98 (dd, J=6.0, 14.0, 1H), 3.78 (dt, J=3.5, 8.2, 1H), 3.86~3.91 (m, 1H), 4.11~4.15 (m, 2H), 7.20~7.31 (m, 5H)

Preparation Example 256: 2-((2S, 3S)-3-benzyl-1,4-dioxaspiro[4.5]decane-2-yl)ethanol

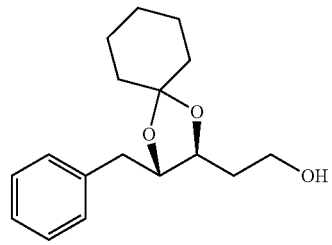 [SMILES: OCC[C@@H]1OC2(CCCCC2)O[C@H]1Cc1ccccc1]

The substantially same method as described in Preparation example 254 was conducted, except that 2-((2S, 3S)-3-benzyl-1,4-dioxaspiro[4.5]decan-2-yl)ethyl pivalate (Preparation example 255) was used instead of 2-((2R,3R)-3-benzyl-1,4-dioxaspiro[4.4]nonan-2-yl)ethyl pivalate (Preparation example 253), to obtain the title compound (1.0 g, 80~95%)

$^1$H NMR (400 MHz, CDCl$_3$): δ=1.34~1.43 (m, 2H), 1.48~1.61 (m, 10H), 2.42 (t, J=5.6, 1H), 2.81 (dd, J=5.6, 14.0, 1H), 3.02 (dd, J=6.2, 13.8, 1H), 3.72 (q, J=5.5, 2H), 3.82~3.87 (m, 1H), 3.91~3.96 (m, 1H), 7.21~7.31 (m, 5H)

Preparation Example 257: 2-((2R, 3R)-3-benzyl-1,4-dioxaspiro[4.5]decane-2-yl)ethyl pivalate

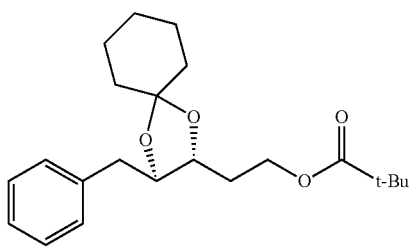 [SMILES: CC(C)(C)C(=O)OCC[C@H]1OC2(CCCCC2)O[C@@H]1Cc1ccccc1]

The substantially same method as described in Preparation example 253 was conducted, except that cyclohexanone was used instead of cyclopetanone, to obtain the title compound (1.6 g, 60~85%)

¹H NMR (400 MHz, CDCl₃): δ=1.18 (s, 9H), 1.53~1.60 (m, 10H), 1.61~1.66 (m, 2H), 2.83 (dd, J=5.6, 14.0, 1H), 2.98 (dd, J=6.0, 14.0, 1H), 3.78 (dt, J=3.5, 8.2, 1H), 3.86~3.91 (m, 1H), 4.11~4.15 (m, 2H), 7.20~7.31 (m, 5H)

Preparation Example 258: 2-((2R, 3R)-3-benzyl-1,4-dioxaspiro[4.5]decane-2-yl)ethanol

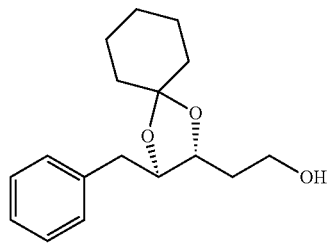 [SMILES: OCC[C@H]1OC2(CCCCC2)O[C@@H]1Cc1ccccc1]

The substantially same method as described in Preparation example 256 was conducted, except that 2-((2R, 3R)-3-benzyl-1,4-dioxaspiro[4.5]decan-2-yl)ethyl pivalate (Preparation example 257) was used instead of 2-((2S, 3S)-3-benzyl-1,4-dioxaspiro[4.5]decan-2-yl)ethyl pivalate (Preparation example 255), to obtain the title compound (1.1 g, 80~95%)

¹H NMR (400 MHz, CDCl₃): δ=1.34~1.43 (m, 2H), 1.48~1.61 (m, 10H), 2.42 (t, J=5.6, 1H), 2.81 (dd, J=5.6, 14.0, 1H), 3.02 (dd, J=6.2, 13.8, 1H), 3.72 (q, J=5.5, 2H), 3.82~3.87 (m, 1H), 3.91~3.96 (m, 1H), 7.21~7.31 (m, 5H)

Preparation Example 259: (E)-methyl-4-phenylbut-2-enoate

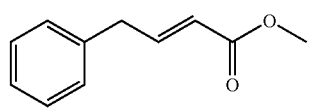

To a solution of phenyl acetaldehyde (5.0 g, 41.61 mmol) in toluene (500 mL) was added methyl (triphenylphosphoranylidene) acetate (13.9 g, 41.61 mmol). The reaction mixture was stirred at reflux for 3 h. The resulting mixture was diluted with EtOAc, washed with water, dried over MgSO₄, filtered, and concentrated under reduced pressure. The crude product was added ether/hexane(=1:1, v/v) at 0° C. then stirred for 30 min. The filtrate was concentrated then purified by a silica gel column to produce the title compound (5.9 g, 70~90%)

¹H NMR (400 MHz, CDCl₃): δ=3.47 (d, J=6.8, 2H), 3.67 (s, 3H), 5.79 (d, J=15.4, 1H), 7.06 (dt, J=15.4, 6.8, 1H), 7.28~7.12 (m, 5H)

Preparation Example 260: (2R, 3S)-methyl 2,3-dihydroxy-4-phenylbutanoate

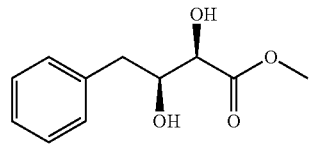

The substantially same method as described in Preparation example 245 was conducted, except that (E)-methyl-4-phenylbut-2-enoate (Preparation example 259) was used instead of (E)-5-phenylpent-3-enyl pivalate (Preparation example 238), to obtain the title compound (3.5 g, 70~95%)

¹H NMR (400 MHz, CDCl₃): δ=2.96 (ddd, J=7.3, 13.5, 17.1, 2H), 3.10 (d, J=5.2, 1H), 3.80 (s, 3H), 4.08 (dd, J=1.4, 5.4, 1H), 7.23~7.34 (m, 5H)

Preparation Example 261: (4R,5S)-methyl-5-benzyl-2,2-dimethyl-1,3-dioxolane-4-carboxylate

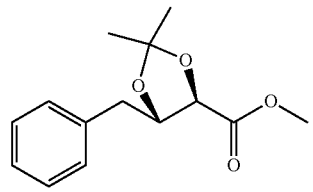 [SMILES: COC(=O)[C@@H]1OC(C)(C)O[C@H]1Cc1ccccc1]

The substantially same method as described in Preparation example 240 was conducted, except that (2R, 3S)-methyl 2,3-dihydroxy-4-phenylbutanoate (Preparation example 260) was used instead of (2S,3S)-5-(tert-butyldimethylsilyloxy)-1-phenylpentane-2,3-diol (Preparation example 239), to obtain the title compound (3.1 g, 70~95%)

¹H NMR (400 MHz, CDCl₃): δ=1.42 (s, 3H), 1.43 (s, 3H), 3.01 (dd, J=6.8, 14.4, 1H), 3.12 (dd, J=4.4, 14.4, 1H), 3.72 (s, 3H), 4.19 (d, J=7.6, 1H), 4.40 (ddd, J=4.4, 7.0, 7.8, 1H), 7.22~7.33 (m, 5H)

Preparation Example 262: ((4S, 5S)-5-benzyl-2,2-dimethyl-1,3-dioxolan-4-yl)methanol

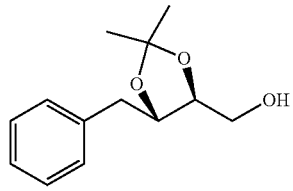 [SMILES: CC1(C)O[C@@H](CO)[C@H](Cc2ccccc2)O1]

The substantially same method as described in Preparation example 234 was conducted, except that (4R,5S)-methyl 5-benzyl-2,2-dimethyl-1,3-dioxolane-4-carboxylate (Preparation example 261) was used instead of (4S, 5R)-methyl-3-phenyl-1,4-dioxapiro[4,5]decane-2-carboxylate (Preparation example 233), to obtain the title compound (2.3 g, 70~95%)

$^1$H NMR (400 MHz, CDCl$_3$): δ=1.41 (s, 6H), 1.79 (q, J=4.3, 1H), 2.83 (dd, J=6.2, 13.8, 1H), 3.07 (dd, J=6.4, 14.0, 1H), 3.29 (ddd, J=4.7, 7.5, 12.1, 1H), 3.54 (ddd, J=2.8, 5.2, 12.0, 1H), 3.83 (ddd, J=3.9, 3.9, 7.1, 1H), 4.15 (q, J=7.1, 1H), 7.22~7.32 (m, 5H)

Preparation Example 263: (4R,5S)-methyl-5-benzyl-2,2-diethyl-1,3-dioxolane-4-carboxylate

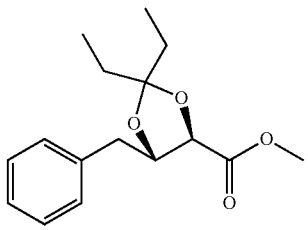 [SMILES: CCC1(CC)O[C@@H](Cc2ccccc2)[C@H](C(=O)OC)O1]

To a stirred solution of (2R, 3S)-methyl 2,3-dihydroxy-4-phenylbutanoate (Preparation example 260, 2.0 g, 9.51 mmol) in 3-pentanone (5 mL, 47.55 mmol) was added a catalytic amount of H$_2$SO$_4$ (0.051 mL, 0.951 mmol) at room temperature. The mixture was stirred for 20 h. The resulting mixture was diluted with EtOAc, washed with water, dried over MgSO$_4$, filtered, and concentrated under reduced pressure. The crude compound was purified by a silica gel column to produce the title compound (1.2 g, 50~75%)

$^1$H NMR (400 MHz, CDCl$_3$): δ=0.85 (t, J=6.0, 3H), 0.92 (t, J=7.6, 3H), 1.66 (dq, J=7.6, 14.7, 4H), 3.01 (dd, J=6.6, 14.2, 1H), 3.10 (dd, J=4.4, 14.4, 1H), 3.71 (s, 3H), 4.17 (d, J=8.4, 1H), 4.32~4.37 (m, 1H), 7.23~7.32 (m, 5H)

Preparation Example 264: ((4S, 5S)-5-benzyl-2,2-diethyl-1,3-dioxolan-4-yl)methanol

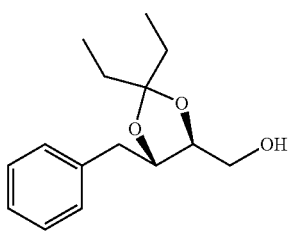 [SMILES: CCC1(CC)O[C@@H](CO)[C@H](Cc2ccccc2)O1]

The substantially same method as described in Preparation example 262 was conducted, except that (4R,5S)-methyl-5-benzyl-2,2-dimethyl-1,3-dioxolane-4-carboxylate (Preparation example 263) was used instead of (4R,5S)-methyl 5-benzyl-2,2-dimethyl-1,3-dioxolane-4-carboxylate (Preparation example 261), to obtain the title compound (0.8 g, 70~95%)

$^1$H NMR (400 MHz, CDCl$_3$): δ=0.91 (dt, J=1.9, 7.5, 6H), 1.61~1.68 (m, 4H), 1.77 (t, J=6.2, 1H), 2.81 (dd, J=6.4, 14.0, 1H), 3.09 (dd, J=6.2, 13.8, 1H), 3.24~3.30 (m, 1H), 3.49~3.54 (m, 1H), 3.78~3.82 (m, 1H), 4.08~4.13 (m, 1H), 7.21~7.32 (m, 5H)

Preparation Example 265: (2R, 3S)-methyl 3-benzyl-1,4-dioxaspiro[4.4]nonane-2-carboxylate

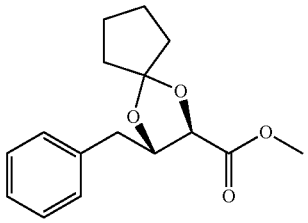 [SMILES: COC(=O)[C@@H]1OC2(CCCC2)O[C@H]1Cc1ccccc1]

The substantially same method as described in Preparation example 263 was conducted, except that cyclopetanone was used instead of 3-pentanone, to obtain the title compound (1.3 g, 60~85%)

$^1$H NMR (400 MHz, CDCl$_3$): δ=1.61~1.79 (m, 5H), 1.85~1.92 (m, 3H), 3.00~3.11 (m, 2H), 3.70 (s, 3H), 4.17 (d, J=7.2, 1H), 4.32 (dt, J=4.9, 7.0, 1H), 7.21~7.33 (m, 5H)

Preparation Example 266: ((2S, 3S)-3-benzyl-1,4-dioxaspiro[4.4]nonane-2-yl)methanol

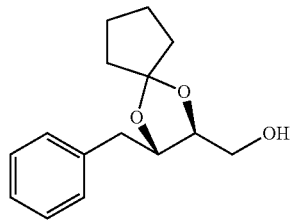 [SMILES: OC[C@@H]1OC2(CCCC2)O[C@H]1Cc1ccccc1]

The substantially same method as described in Preparation example 264 was conducted, except that (2R, 3S)-methyl 3-benzyl-1,4-dioxaspiro[4.4]nonane-2-carboxylate (Preparation example 265) was used instead of (4R,5S)-methyl-5-benzyl-2,2-dimethyl-1,3-dioxolane-4-carboxylate (Preparation example 263), to obtain the title compound (0.8 g, 70~95%)

$^1$H NMR (400 MHz, CDCl$_3$): δ=1.57~1.88 (m, 8H), 2.82 (dd, J=6.6, 13.8, 1H), 3.08 (dd, J=6.4, 14.0, 1H), 3.27~3.33 (m, 1H), 3.47~3.52 (m, 1H), 3.79~3.83 (m, 1H), 4.07 (q, J=6.8, 1H), 7.21~7.32 (m, 5H)

Preparation Example 267: (2R,3S)-methyl-3-benzyl-1,4-dioxaspiro[4.5]decane-2-carboxylate

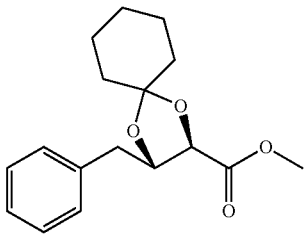 [SMILES: COC(=O)[C@@H]1OC2(CCCCC2)O[C@H]1Cc1ccccc1]

The substantially same method as described in Preparation example 265 was conducted, except that cyclohexanone was used instead of cyclopetanone, to obtain the title compound (1.5 g, 60~85%)

¹H NMR (400 MHz, CDCl₃): δ=1.54~1.74 (m, 10H), 2.99~3.12 (m, 2H), 3.70 (s, 3H), 4.18 (d, J=7.6, 1H), 4.36~4.41 (m, 1H), 7.21~7.32 (m, 5H)

Preparation Example 268: ((2S, 3S)-3-benzyl-1,4-dioxaspiro[4.4]decan-2-yl)methanol

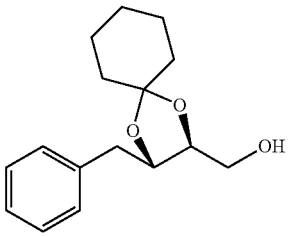 [SMILES: OC[C@@H]1OC2(CCCCC2)O[C@H]1Cc1ccccc1]

The substantially same method as described in Preparation example 266 was conducted, except that (2R, 3S)-methyl-3-benzyl-1,4-dioxaspiro[4.5]decane-2-carboxylate (Preparation example 267) was used instead of (2R, 3S)-methyl 3-benzyl-1,4-dioxaspiro[4.4]nonane-2-carboxylate (Preparation example 265), to obtain the title compound (0.8 g, 70~95%)

¹H NMR (400 MHz, CDCl₃): δ=1.53~1.65 (m, 10H), 2.82 (dd, J=6.2, 13.8, 1H), 3.07 (dd, J=6.4, 13.6, 1H), 3.24~3.30 (m, 1H), 3.52~3.56 (m, 1H), 3.80~3.84 (m, 114), 4.10~4.15 (m, 1H), 7.21~7.31 (m, 5H)

Preparation Example 269: (2S, 3R)-methyl-2,3-dihydroxy-4-phenylbutanoate

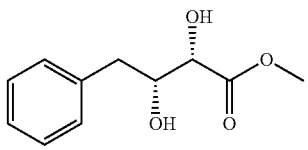

The substantially same method as described in Preparation example 242 was conducted, except that (E)-methyl-4-phenylbut-2-enoate (Preparation example 259) was used instead of (E)-tert-butyldimethyl(5-phenylpent-3-enyloxy)silane (Preparation example 237), to obtain the title compound (3.5 g, 70~95%)

¹H NMR (400 MHz, CDCl₃): δ=2.96 (ddd, J=7.3, 13.5, 17.1, 2H), 3.10 (d, J=5.2, 1H), 3.80 (s, 3H), 4.08 (dd, J=1.4, 5.4, 1H), 7.23~7.34 (m, 5H)

Preparation Example 270: (4S, 5R)-methyl-5-benzyl-2,2-dimethyl-1,3-dioxolane-4-carboxylate

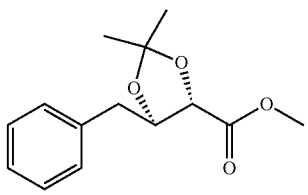 [SMILES: COC(=O)[C@H]1OC(C)(C)O[C@@H]1Cc1ccccc1]

The substantially same method as described in Preparation example 261 was conducted, except that (2S, 3R)-methyl-2,3-dihydroxy-4-phenylbutanoate (Preparation example 269) was used instead of (2R, 3S)-methyl 2,3-dihydroxy-4-phenylbutanoate (Preparation example 260), to obtain the title compound (3.4 g, 70~95%)

¹H NMR (400 MHz, CDCl₃): δ=1.41 (s, 6H), 1.79 (q, J=4.3, 1H), 2.83 (dd, J=6.2, 13.8, 1H), 3.07 (dd, J=6.4, 14.0, 1H), 3.29 (ddd, J=4.7, 7.5, 12.1, 1H), 3.54 (ddd, J=2.8, 5.2, 12.0, 1H), 3.83 (ddd, J=3.9, 3.9, 7.1, 1H), 4.15 (q, J=7.1, 1H), 7.22~7.32 (m, 5H)

Preparation Example 271: ((4R, 5R)-5-benzyl-2,2-dimethyl-1,3-dioxolan-4-yl)methanol

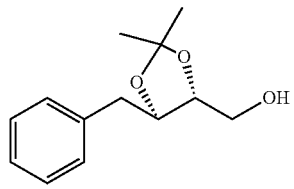 [SMILES: CC1(C)O[C@H](CO)[C@@H](Cc2ccccc2)O1]

The substantially same method as described in Preparation example 262 was conducted, except that (4S,5R)-methyl-5-benzyl-2,2-dimethyl-1,3-dioxolane-4-carboxylate (Preparation example 270) was used instead of (4R,5S)-methyl 5-benzyl-2,2-dimethyl-1,3-dioxolane-4-carboxylate (Preparation example 261), to obtain the title compound (2.7 g, 70~95%)

¹H NMR (400 MHz, CDCl₃): δ=1.41 (s, 6H), 1.79 (q, J=4.3, 1H), 2.83 (dd, J=6.2, 13.8, 1H), 3.07 (dd, J=6.4, 14.0, 1H), 3.29 (ddd, J=4.7, 7.5, 12.1, 1H), 3.54 (ddd, J=2.8, 5.2, 12.0, 1H), 3.83 (ddd, J=3.9, 3.9, 7.1, 1H), 4.15 (q, J=7.1, 1H), 7.22~7.32 (m, 5H)

Preparation Example 272: (4S, 5R)-methyl-5-benzyl-2,2-diethyl-1,3-dioxolane-4-carboxylate

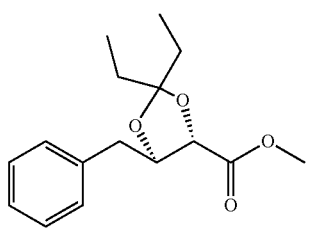 [SMILES: CCC1(CC)O[C@H](C(=O)OC)[C@@H](Cc2ccccc2)O1]

The substantially same method as described in Preparation example 263 was conducted, except that (2S, 3R)-methyl-2,3-dihydroxy-4-phenylbutanoate (Preparation example 269) was used instead of (2,3-dihydroxy-4-phenylbutanoate (Preparation example 260), to obtain the title compound (1.5 g, 50~75%)

¹H NMR (400 MHz, CDCl₃): δ=0.85 (t, J=6.0, 3H), 0.92 (t, J=7.6, 3H), 1.66 (dq, J=7.6, 14.7, 4H), 3.01 (dd, J=6.6, 14.2, 1H), 3.10 (dd, J=4.4, 14.4, 1H), 3.71 (s, 3H), 4.17 (d, J=8.4, 1H), 4.32~4.37 (m, 1H), 7.23~7.32 (m, 5H)

Preparation Example 273: ((4R, 5R)-5-benzyl-2,2-diethyl-1,3-dioxolan-4-yl)methanol

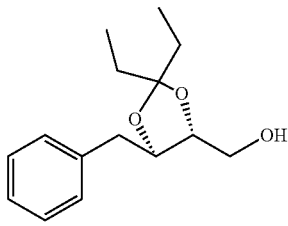 [SMILES: CCC1(CC)O[C@H](CO)[C@@H](Cc2ccccc2)O1]

The substantially same method as described in Preparation example 264 was conducted, except that (4S,5R)-methyl-5-benzyl-2,2-dimethyl-1,3-dioxolane-4-carboxylate (Preparation example 272) was used instead of (4R,5S)-methyl-5-benzyl-2,2-dimethyl-1,3-dioxolane-4-carboxylate (Preparation example 263), to obtain the title compound (1.2 g, 70~95%)

$^1$H NMR (400 MHz, CDCl$_3$): δ=0.91 (dt, J=1.9, 7.5, 6H), 1.61~1.68 (m, 4H), 1.77 (t, J=6.2, 1H), 2.81 (dd, J=6.4, 14.0, 1H), 3.09 (dd, J=6.2, 13.8, 1H), 3.24~3.30 (m, 1H), 3.49~3.54 (m, 1H), 3.78~3.82 (m, 1H), 4.08~4.13 (m, 1H), 7.21~7.32 (m, 5H)

Preparation Example 274: (2S, 3R)-methyl-3-benzyl-1,4-dioxaspiro[4.4]nonane-2-carboxylate

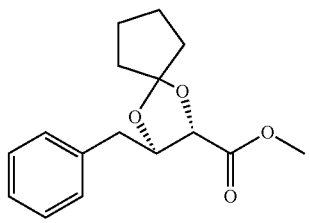 [SMILES: COC(=O)[C@H]1OC2(CCCC2)O[C@@H]1Cc1ccccc1]

The substantially same method as described in Preparation example 272 was conducted, except that cyclopetanone was used instead of 3-pentanone, to obtain the title compound (1.2 g, 60~85%)

$^1$H NMR (400 MHz, CDCl$_3$): δ=1.61~1.79 (m, 5H), 1.85~1.92 (m, 3H), 3.00~3.11 (m, 2H), 3.70 (s, 3H), 4.17 (d, J=7.2, 1H), 4.32 (dt, J=4.9, 7.0, 1H), 7.21~7.33 (m, 5H)

Preparation Example 275: ((2R, 3R)-3-benzyl-1,4-dioxaspiro[4.4]nonane-2-yl)methanol

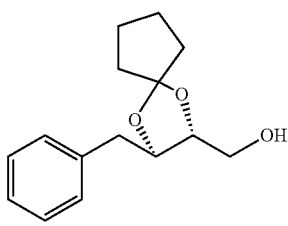 [SMILES: OC[C@H]1OC2(CCCC2)O[C@@H]1Cc1ccccc1]

The substantially same method as described in Preparation example 266 was conducted, except that (2S, 3R)-methyl-3-benzyl-1,4-dioxaspiro[4.4]nonane-2-carboxylate (Preparation example 274) was used instead of (2R, 3S)-methyl-3-benzyl-1,4-dioxaspiro[4.4]nonane-2-carboxylate (Preparation example 265), to obtain the title compound (1.1 g, 70~95%)

$^1$H NMR (400 MHz, CDCl$_3$): δ=1.57~1.88 (m, 8H), 2.82 (dd, J=6.6, 13.8, 1H), 3.08 (dd, J=6.4, 14.0, 1H), 3.27~3.33 (m, 1H), 3.47~3.52 (m, 1H), 3.79~3.83 (m, 1H), 4.07 (q, J=6.8, 1H), 7.21~7.32 (m, 5H)

Preparation Example 276: (2S, 3R)-methyl-3-benzyl-1,4-dioxaspiro[4.5]decane-2-carboxylate

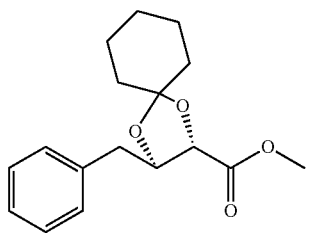 [SMILES: COC(=O)[C@H]1OC2(CCCCC2)O[C@@H]1Cc1ccccc1]

The substantially same method as described in Preparation example 274 was conducted, except that cyclohexanone was used instead of cyclopetanone, to obtain the title compound (1.4 g, 60~85%)

$^1$H NMR (400 MHz, CDCl$_3$): δ=1.54~1.74 (m, 10H), 2.99~3.12 (m, 2H), 3.70 (s, 3H), 4.18 (d, J=7.6, 1H), 4.36~4.41 (m, 1H), 7.21~7.32 (m, 5H)

Preparation Example 277: ((2R, 3R)-3-benzyl-1,4-dioxaspiro[4.4]nonane-2-yl)methanol

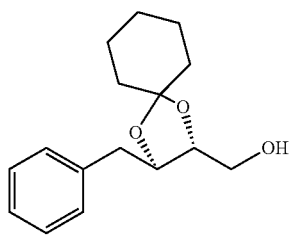 [SMILES: OC[C@H]1OC2(CCCCC2)O[C@@H]1Cc1ccccc1]

The substantially same method as described in Preparation example 268 was conducted, except that (2S, 3R)-methyl-3-benzyl-1,4-dioxaspiro[4.5]decane-2-carboxylate (Preparation example 276) was used instead of (2R, 3S)-methyl-3-benzyl-1,4-dioxaspiro[4.5]decane-2-carboxylate (Preparation example 267), to obtain the title compound (1.4 g, 70~95%)

$^1$H NMR (400 MHz, CDCl$_3$): δ=1.53~1.65 (m, 10H), 2.82 (dd, J=6.2, 13.8, 1H), 3.07 (dd, J=6.4, 13.6, 1H), 3.24~3.30 (m, 1H), 3.52~3.56 (m, 1H), 3.80~3.84 (m, 1H), 4.10~4.15 (m, 1H), 7.21~7.31 (m, 5H)

Preparation Example 278: (E)-4-phenylbut-3-enoic acid

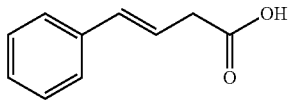 [SMILES: O=C(O)C/C=C/c1ccccc1]

To a stirred solution of 2-phenylacetaldehyde (5.0 g, 32.3 mmol) and malonic acid (4.0 g, 38.8 mmol) in pyridine (25.0 mL) was added a catalytic amount of piperidine (0.64 mL, 6.46 mmol) then heated to reflux. After 3 h, the resulting mixture was cooled to room temperature and concentrated under reduced pressure. The crude product was slowly added 2N HCl. The white precipitate was filtered off and dried under vacuum to produce the title compound (3.5 g, 55~80%)

$^1$H NMR (400 MHz, CDCl$_3$): δ=3.39 (d, J=8.8, 2H), 6.31 (td, J=7.9, 14.8, 1H), 6.94 (d, J=16, 1H), 7.17~7.45 (m, 3H), 7.56~7.59 (m, 1H)

Preparation Example 279: (E)-4-phenylbut-3-en-1-ol

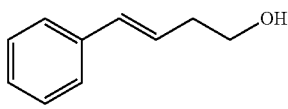 [SMILES: OCC/C=C/c1ccccc1]

To stirred solution of Zn(BH$_4$)$_2$ (40.0 mL, 20.0 mmol) in THF (40 mL) was added dropwise a solution (E)-4-phenyl-but-3-enoic acid (Preparation example 278, 2.0 g, 10.0 mmol) in THF (5 mL) at 0° C. then heated to reflux for 0.5 h. The reaction mixture was quenched with H$_2$O at 0° C., filtered through celite, washed with EtOAc, dried over anhydrous magnesium sulfate (MgSO$_4$), filtered and concentrated. The crude compound was purified by a silica gel column to produce the title compound (1.0 g, 50~75%)

$^1$H NMR (400 MHz, CDCl$_3$): δ=2.55 (ddd, J=4.1, 11.9, 21.5, 2H), 3.82 (t, J=5.8, 2H), 6.24 (td, J=7.2, 15.7, 1H), 6.87 (d, J=14.8, 1H), 7.12~7.25 (m, 3H), 7.36 (dd, J=1.2, 8.0, 1H), 7.52 (dd, J=1.6, 9.2, 1H)

Preparation Example 280: (E)-tert-butyldimethyl(4-phenylbut-3-enyloxy)silane

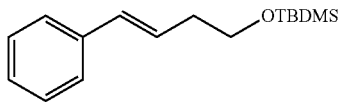 [SMILES: CC(C)(C)[Si](C)(C)OCC/C=C/c1ccccc1]

The substantially same method as described in Preparation example 237 was conducted, except that (E)-4-phenyl-but-3-en-1-ol (Preparation example 279) was used instead of (E)-5-phenylpent-3-en-1-ol (Preparation example 236), to obtain the title compound (1.7 g, 80~98%)

$^1$H NMR (400 MHz, CDCl$_3$): δ=0.07 (s, 3H), 0.10 (s, 3H), 0.92 (d, J=6.4, 9H), 2.51 (q, J=4.5, 2H), 3.78 (t, J=6.6, 2H), 6.26 (td, J=7.2, 15.7, 1H), 6.84 (d, J=15.6, 1H), 7.13~7.24 (m, 3H), 7.36 (dd, J=5.6, 12.4, 1H), 7.53 (dd, J=1.4, 7.8, 1H)

Preparation Example 281: (E)-4-phenylbut-3-enyl pivalate

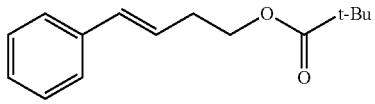 [SMILES: CC(C)(C)C(=O)OCC/C=C/c1ccccc1]

The substantially same method as described in Preparation example 238 was conducted, except that (E)-4-phenyl-but-3-en-1-ol (Preparation example 279) was used instead of (E)-5-phenylpent-3-en-1-ol (Preparation example 236), to obtain the title compound (10.8 g, 75~95%)

$^1$H NMR (400 MHz, CDCl$_3$): δ=1.22 (s, 9H), 2.57 (ddd, J=1.3, 6.7, 13.5, 2H), 4.22 (t, J=6.6, 2H), 6.19 (td, J=7.0, 16.0, 1H), 6.49 (d, J=16.0, 1H), 7.23~7.26 (m, 1H), 7.31~7.41 (m, 4H)

Preparation Example 282: (1R, 2R)-4-(tert-butyldimethylsilyloxy)-1-phenylbutane-1,2-diol

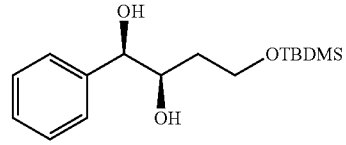 [SMILES: CC(C)(C)[Si](C)(C)OCC[C@@H](O)[C@H](O)c1ccccc1]

The substantially same method as described in Preparation example 239 was conducted, except that (E)-tert-butyldimethyl(4-phenylbut-3-enyloxy)silane (Preparation example 280) was used instead of (E)-tert-butyldimethyl(5-phenylpent-3-enyloxy)silane (Preparation example 237), to obtain the title compound (0.8 g, 70~95%)

$^1$H NMR (400 MHz, CDCl$_3$): δ=0.10 (s, 3H), 0.11 (s, 3H), 0.92 (s, 9H), 1.69~1.70 (m, 1H), 1.93~2.07 (m, 1H), 3.51 (d, J=4.8, 1H), 3.86 (d, J=3.2, 1H), 3.87 (dd, J=3.2, 9.2, 1H), 3.91~3.96 (m, 1H), 4.01~4.06 (m, 1H), 5.05 (t, J=4.6, 1H), 7.22~7.26 (m, 1H), 7.31~7.37 (m, 2H), 7.59 (dd, J=1.2, 7.6, 1H)

Preparation Example 283: (3R, 4R)-3,4-dihydroxy-4-phenylbutyl pivalate

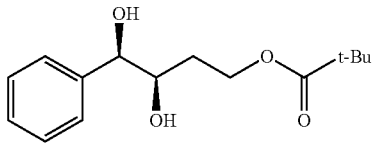 [SMILES: CC(C)(C)C(=O)OCC[C@@H](O)[C@H](O)c1ccccc1]

The substantially same method as described in Preparation example 282 was conducted, except that (E)-4-phenyl-but-3-enyl pivalate (Preparation example 281) was used instead of (E)-tert-butyldimethyl(4-phenylbut-3-enyloxy)silane (Preparation example 280), to obtain the title compound (8.7 g, 70~95%)

$^1$H NMR (400 MHz, CDCl$_3$): δ=1.18 (s, 9H), 1.65~1.74 (m, 2H), 2.83 (d, J=2.4, 1H), 2.96 (d, J=3.2, 1H), 3.74~3.79 (m, 1H), 4.10~4.17 (m, 1H), 4.33 (ddd, J=4.0, 7.2, 12.6, 1H), 4.49 (d, J=5.6, 1H), 7.31~7.41 (m, 5H)

Preparation Example 284: tert-butyl(2-((4R, 5R)-5-phenyl-2,2-dimethyl-1,3-dioxolan-4-yl)ethoxy)dimethylsilane

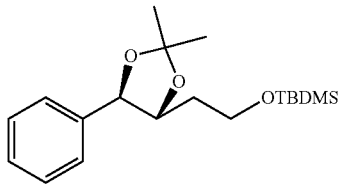 [SMILES: CC1(C)O[C@H](c2ccccc2)[C@@H](CCO[Si](C)(C)C(C)(C)C)O1]

The substantially same method as described in Preparation example 218 was conducted, except that (1R, 2R)-4-(tert-butyldimethylsilyloxy)-1-phenylbutane-1,2-diol (Preparation example 282) was used instead of (2R, 3S)-methyl-3-phenyl-2,3-dihydroxypropanoate (Preparation example 217), to obtain the title compound (1.6 g, 70~95%)

$^1$H NMR (400 MHz, CDCl$_3$): δ=0.02 (s, 3H), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7, 1H), 5.16 (d, J=8.4, 1H), 7.21~7.27 (m, 1H), 7.31~7.38 (m, 2H), 7.60 (dd, J=1.6, 7.6, 1H)

Preparation Example 285: 2-((4R, 5R)-5-phenyl-2,2-dimethyl-1,3-dioxolan-4-yl)ethanol

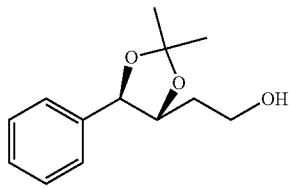 [SMILES: CC1(C)O[C@H](c2ccccc2)[C@@H](CCO)O1]

The substantially same method as described in Preparation example 244 was conducted, except that tert-butyl(2-((4R,5R)-5-phenyl-2,2-dimethyl-1,3-dioxolan-4-yl)ethoxy)dimethylsilane (Preparation example 284) was used instead of (2-((4R,5R)-5-benzyl-2,2-dimethyl-1,3-dioxolan-4-yl)ethoxy)(tert-butyl)dimethylsilane (Preparation example 243), to obtain the title compound (1.4 g, 80~95%).

$^1$H NMR (400 MHz, CDCl$_3$): δ=1.56 (s, 3H), 1.62 (s, 3H), 1.92~2.04 (m, 2H), 2.26 (q, J=3.7, 1H), 3.75~3.90 (m, 2H), 3.94 (td, J=3.9, 8.5, 1H), 5.23 (d, J=15.6, 1H), 7.22~7.27 (m, 1H), 7.33~7.39 (m, 2H), 7.62 (dd, J=1.6, 7.6, 1H)

Preparation Example 286: (1S, 2S)-4-(tert-butyldimethylsilyloxy)-1-phenylbutane-1,2-diol

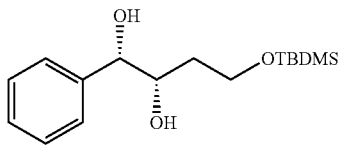 [SMILES: CC(C)(C)[Si](C)(C)OCC[C@H](O)[C@@H](O)c1ccccc1]

The substantially same method as described in Preparation example 242 was conducted, except that (E)-tert-butyldimethyl(4-phenylbut-3-enyloxy)silane (Preparation example 280) was used instead of (E)-tert-butyldimethyl(5-phenylpent-3-enyloxy)silane (Preparation example 237), to obtain the title compound (0.7 g, 70~95%)

$^1$H NMR (400 MHz, CDCl$_3$): δ=0.10 (s, 3H), 0.11 (s, 3H), 0.92 (s, 9H), 1.69~1.70 (m, 1H), 1.93~2.07 (m, 1H), 3.51 (d, J=4.8, 1H), 3.86 (d, J=3.2, 1H), 3.87 (dd, J=3.2, 9.2, 1H), 3.91~3.96 (m, 1H), 4.01~4.06 (m, 1H), 5.05 (t, J=4.6, 1H), 7.22~7.26 (m, 1H), 7.31~7.37 (m, 2H), 7.59 (dd, J=1.2, 7.6, 1H)

Preparation Example 287: (3S, 4S)-3,4-dihydroxy-4-phenylbutyl pivalate

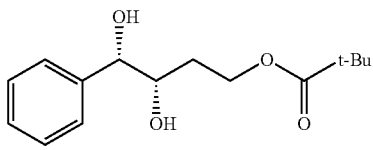 [SMILES: CC(C)(C)C(=O)OCC[C@H](O)[C@@H](O)c1ccccc1]

The substantially same method as described in Preparation example 286 was conducted, except that (E)-4-phenyl-but-3-enyl pivalate (Preparation example 281) was used instead of (E)-tert-butyldimethyl(4-phenylbut-3-enyloxy)silane (Preparation example 280), to obtain the title compound (10.4 g, 70~95%)

$^1$H NMR (400 MHz, CDCl$_3$): δ=1.18 (s, 9H), 1.65~1.74 (m, 2H), 2.83 (d, J=2.4, 1H), 2.96 (d, J=3.2, 1H), 3.74~3.79 (m, 1H), 4.10~4.17 (m, 1H), 4.33 (ddd, J=4.0, 7.2, 12.6, 1H), 4.49 (d, J=5.6, 1H), 7.31~7.41 (m, 5H)

Preparation Example 288: tert-butyl(2-((4S, 5S)-5-phenyl-2,2-dimethyl-1,3-dioxolan-4-yl)ethoxy)dimethylsilane

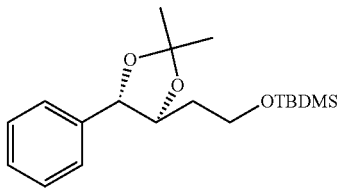 [SMILES: CC1(C)O[C@@H](CCO[Si](C)(C)C(C)(C)C)[C@H](c2ccccc2)O1]

The substantially same method as described in Preparation example 284 was conducted, except that (1S, 2S)-4-(tert-butyldimethylsilyloxy)-1-phenylbutane-1,2-diol (Preparation example 286) was used instead of (1R, 2R)-4-(tert-butyldimethylsilyloxy)-1-phenylbutane-1,2-diol (Preparation example 282), to obtain the title compound (0.7 g, 70~95%)

$^1$H NMR (400 MHz, CDCl$_3$): δ=0.02 (s, 36), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7, 1H), 5.16 (d, J=8.4, 1H), 7.21~7.27 (m, 1H), 7.31~7.38 (m, 2H), 7.60 (dd, J=1.6, 7.6, 1H)

Preparation Example 289: 2-((4S, 5S)-5-phenyl-2,2-dimethyl-1,3-dioxolan-4-yl)ethanol

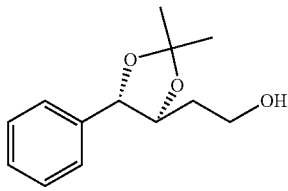 [SMILES: CC1(C)O[C@@H](CCO)[C@H](c2ccccc2)O1]

The substantially same method as described in Preparation example 285 was conducted, except that tert-butyl(2-((4S,5S)-5-phenyl-2,2-dimethyl-1,3-dioxolan-4-yl)ethoxy)dimethylsilane (Preparation example 288) was used instead of that tert-butyl(2-((4R,5R)-5-phenyl-2,2-dimethyl-1,3-dioxolan-4-yl)ethoxy)dimethylsilane (Preparation example 284), to obtain the title compound (0.4 g, 80~95%)

$^1$H NMR (400 MHz, CDCl$_3$): δ=1.56 (s, 3H), 1.62 (s, 3H), 1.92~2.04 (m, 2H), 2.26 (q, J=3.7, 1H), 3.75~3.90 (m, 2H), 3.94 (td, J=3.9, 8.5, 1H), 5.23 (d, J=15.6, 1H), 7.22~7.27 (m, 1H), 7.33~7.39 (m, 2H), 7.62 (dd, J=1.6, 7.6, 1H)

Preparation Example 290: 2-((4R, 5R)-2,2-diethyl-5-phenyl-1,3-dioxolan-4-yl)ethyl pivalate

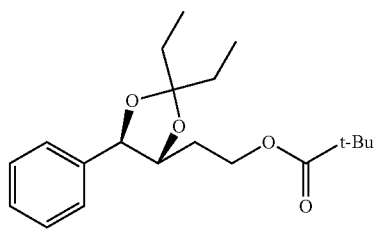 [SMILES: CCC1(CC)O[C@H](c2ccccc2)[C@@H](CCOC(=O)C(C)(C)C)O1]

The substantially same method as described in Preparation example 264 was conducted, except that (3R, 4R)-3,4-dihydroxy-4-phenylbutyl pivalate (Preparation example 283) was used instead of (4R,5S)-methyl-5-benzyl-2,2-dimethyl-1,3-dioxolane-4-carboxylate (Preparation example 263), to obtain the title compound (1.8 g, 70~95%)

$^1$H NMR (400 MHz, CDCl$_3$): δ=1.00 (t, J=7.4, 3H), 1.08 (t, J=7.6, 3H), 1.14 (s, 9H), 1.76 (q, J=7.5, 2H), 1.81~1.89 (m, 2H), 1.91~1.98 (m, 2H), 3.87 (td, J=5.8, 8.8, 1H), 4.13~4.18 (m, 1H), 4.22~4.28 (m, 1H), 4.58 (d, J=8.8, 1H), 7.31~7.43 (m, 5H)

Preparation Example 291: 2-((4R, 5R)-2,2-diethyl-5-phenyl-1,3-dioxolan-4-yl)ethyl pivalate

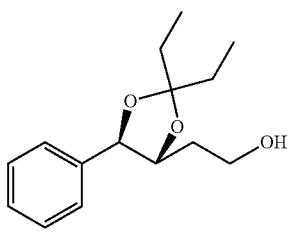 [SMILES: CCC1(CC)O[C@H](c2ccccc2)[C@@H](CCO)O1]

The substantially same method as described in Preparation example 258 was conducted, except that 2-((4R, 5R)-2,2-diethyl-5-phenyl-1,3-dioxolan-4-yl)ethyl pivalate (Preparation example 290) was used instead of 2-((2R, 3R)-3-benzyl-1,4-dioxaspiro[4.5]decan-2-yl)ethyl pivalate (Preparation example 257), to obtain the title compound (0.9 g, 80~95%)

$^1$H NMR (400 MHz, CDCl$_3$): δ=1.01 (t, J=7.4, 3H), 1.07 (t, J=7.6, 3H), 1.79 (q, J=7.5, 2H), 1.83~1.90 (m, 4H), 2.38 (q, J=3.7, 1H), 3.75~3.87 (m, 2H), 3.90~3.95 (m, 1H), 4.63 (d, J=8.8, 1H), 7.32~7.43 (m, 5H)

Preparation Example 292: 2-((2R, 3R)-3-phenyl-1,4-dioxaspiro[4.4]nonan-2-yl)ethyl pivalate

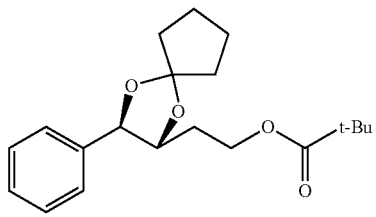 [SMILES: CC(C)(C)C(=O)OCC[C@H]1OC2(CCCC2)O[C@@H]1c1ccccc1]

The substantially same method as described in Preparation example 290 was conducted, except that cyclopetanone was used instead of 3-pentanone, to obtain the title compound (1.8 g, 60~85%)

$^1$H NMR (400 MHz, CDCl$_3$): δ=1.14 (s, 9H), 1.67~1.83 (m, 4H), 1.88~2.07 (m, 6H), 3.84 (td, J=6.0, 8.4, 1H), 4.13 (td, J=7.0, 11.1, 1H), 4.24 (td, J=6.4, 11.2, 11~0, 4.55 (d, J=8.4, 1H), 7.31~7.39 (m, 5H)

Preparation Example 293: 2-((2R, 3R)-3-phenyl-1,4-dioxaspiro[4.4]nonan-2-yl)ethanol

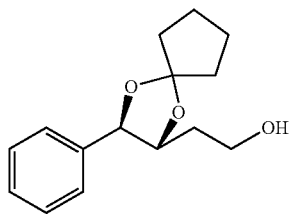 [SMILES: OCC[C@H]1OC2(CCCC2)O[C@@H]1c1ccccc1]

The substantially same method as described in Preparation example 291 was conducted, except that 2-((2R, 3R)-3-phenyl-1,4-dioxaspiro[4.4]nonan-2-yl)ethyl pivalate (Preparation example 292) was used instead of that 2-((4S, 5S)-2,2-diethyl-5-phenyl-1,3-dioxolan-4-yl)ethyl pivalate (Preparation example 290), to obtain the title compound (0.9 g, 80~95%)

$^1$H NMR (400 MHz, CDCl$_3$): δ=1.71~1.81 (m, 4H), 1.87~2.07 (m, 6H), 2.27 (q, J=3.7, 1H), 3.79~3.85 (m, 2H), 3.89~3.92 (m, 1H), 4.59 (d, J=8.4, 1H), 7.32~7.41 (m, 5H)

Preparation Example 294: 2-((2R, 3R)-3-phenyl-1,4-dioxaspiro[4.5]decan-2-yl)ethyl pivalate

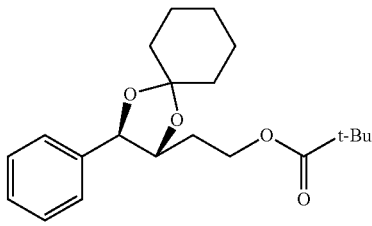 [SMILES: CC(C)(C)C(=O)OCC[C@H]1OC2(CCCCC2)O[C@@H]1c1ccccc1]

The substantially same method as described in Preparation example 292 was conducted, except that cyclohexanone was used instead of cyclopetanone, to obtain the title compound (2.0 g, 60~85%)

$^1$H NMR (400 MHz, CDCl$_3$): δ=1.14 (s, 9H), 1.67~1.83 (m, 4H), 1.88~2.07 (m, 6H), 3.84 (td, J=6.0, 8.4, 1H), 4.10~4.17 (m, 1H), 4.21~4.27 (m, 1H), 4.55 (d, J=8.4, 1H), 7.31~7.39 (m, 5H)

Preparation Example 295: 2-((2R, 3R)-3-phenyl-1,4-dioxaspiro[4.5]decan-2-yl)ethanol

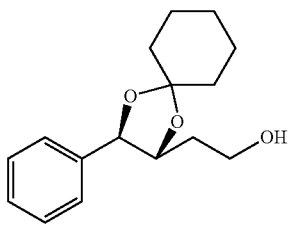 [SMILES: OCC[C@H]1OC2(CCCCC2)O[C@@H]1c1ccccc1]

The substantially same method as described in Preparation example 293 was conducted, except that 2-((2R, 3R)-3-phenyl-1,4-dioxaspiro[4.5]decan-2-yl)ethyl pivalate (Preparation example 294) was used instead of that 2-((2R, 3R)-3-phenyl-1,4-dioxaspiro[4.4]nonan-2-yl)ethyl pivalate (Preparation example 292), to obtain the title compound (1.2 g, 80~95%)

$^1$H NMR (400 MHz, CDCl$_3$): δ=1.71~1.83 (m, 4H), 1.87~2.05 (m, 6H), 2.27 (q, J=3.7, 1H), 3.79~3.85 (m, 2H), 3.86~3.91 (m, 1H), 4.59 (d, J=8.4, 1H), 7.32~7.41 (m, 5H)

Preparation Example 296: 2-((4S, 5S)-2,2-diethyl-5-phenyl-1,3-dioxolan-4-yl)ethyl pivalate

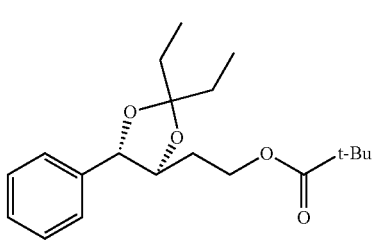 [SMILES: CCC1(CC)O[C@@H](CCOC(=O)C(C)(C)C)[C@H](c2ccccc2)O1]

The substantially same method as described in Preparation example 290 was conducted, except that (3S, 4S)-3,4-dihydroxy-4-phenylbutyl pivalate (Preparation example 287) was used instead of (3R, 4R)-3,4-dihydroxy-4-phenylbutyl pivalate (Preparation example 283), to obtain the title compound (2.2 g, 70~95%)

$^1$H NMR (400 MHz, CDCl$_3$): δ=1.00 (t, J=7.4, 3H), 1.08 (t, J=7.6, 3H), 1.14 (s, 9H), 1.76 (q, J=7.5, 2H), 1.81~1.89 (m, 2H), 1.91~1.98 (m, 2H), 3.87 (td, J=5.8, 8.8, 1H), 4.13~4.18 (m, 1H), 4.22~4.28 (m, 1H), 4.58 (d, J=8.8, 1H), 7.31~7.43 (m, 5H)

Preparation Example 297: 2-((4S, 5S)-2,2-diethyl-5-phenyl-1,3-dioxolan-4-yl)ethyl pivalate

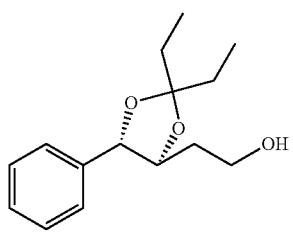 [SMILES: CCC1(CC)O[C@@H](CCO)[C@H](c2ccccc2)O1]

The substantially same method as described in Preparation example 295 was conducted, except 2-((4S, 5S)-2,2-diethyl-5-phenyl-1,3-dioxolan-4-yl)ethyl pivalate (Preparation example 296) was used instead of 2-((2R, 3R)-3-phenyl-1,4-dioxaspiro[4.5]decan-2-yl)ethyl pivalate (Preparation example 294), to obtain the title compound (0.7 g, 80~95%)

$^1$H NMR (400 MHz, CDCl$_3$): δ=1.01 (t, J=7.4, 3H), 1.07 (t, J=7.6, 3H), 1.79 (q, J=7.5, 2H), 1.83~1.90 (m, 4H), 2.38 (q, J=3.7, 1H), 3.75~3.87 (m, 2H), 3.90~3.95 (m, 1H), 4.63 (d, J=8.8, 1H), 7.32~7.43 (m, 5H)

Preparation Example 298: 2-((2S, 3S)-3-phenyl-1,4-dioxaspiro[4.4]nonan-2-yl)ethyl pivalate

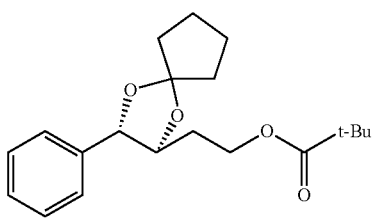 [SMILES: CC(C)(C)C(=O)OCC[C@@H]1OC2(CCCC2)O[C@H]1c1ccccc1]

The substantially same method as described in Preparation example 296 was conducted, except that cyclopetanone was used instead of 3-pentanone, to obtain the title compound (2.4 g, 60~85%)

$^1$H NMR (400 MHz, CDCl$_3$): δ=1.14 (s, 9H), 1.67~1.83 (m, 4H), 1.88~2.07 (m, 6H), 3.84 (td, J=6.0, 8.4, 1H), 4.13 (td, J=7.0, 11.1, 1H), 4.24 (td, J=6.4, 11.2, 1H), 4.55 (d, J=8.4, 1H), 7.31~7.39 (m, 5H)

Preparation Example 299: 2-((2S, 3S)-3-phenyl-1,4-dioxaspiro[4.4]nonan-2-yl)ethanol

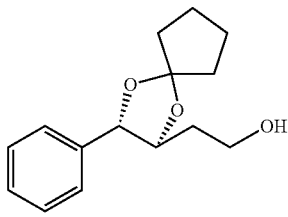 [SMILES: OCC[C@@H]1OC2(CCCC2)O[C@H]1c1ccccc1]

The substantially same method as described in Preparation example 297 was conducted, except that 2-((2S, 3S)-3-phenyl-1,4-dioxaspiro[4.4]nonan-2-yl)ethyl pivalate (Preparation example 298) was used instead of that 2-((4S, 5S)-2,2-diethyl-5-phenyl-1,3-dioxolan-4-yl)ethyl pivalate (Preparation example 296), to obtain the title compound (07 g, 80~95%)
$^1$H NMR (400 MHz, CDCl$_3$): δ=1.71~1.81 (m, 4H), 1.87~2.07 (m, 6H), 2.27 (q, J=3.7, 1H), 3.79~3.85 (m, 2H), 3.89~3.92 (m, 1H), 4.59 (d, J=8.4, 1H), 7.32~7.41 (m, 5H)

Preparation Example 300: 2-((2S, 3S)-3-phenyl-1,4-dioxaspiro[4.5]decan-2-yl)ethyl pivalate

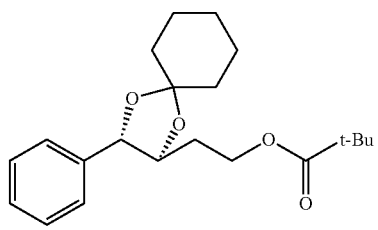 [SMILES: CC(C)(C)C(=O)OCC[C@@H]1OC2(CCCCC2)O[C@H]1c1ccccc1]

The substantially same method as described in Preparation example 298 was conducted, except that cyclohexanone was used instead of cyclopetanone, to obtain the title compound (2.4 g, 60~85%)
$^1$H NMR (400 MHz, CDCl$_3$): δ=1.14 (s, 9H), 1.67~1.83 (m, 4H), 1.88~2.07 (m, 6H), 3.84 (td, J=6.0, 8.4, 1H), 4.10~4.17 (m, 1H), 4.21~4.27 (m, 1H), 4.55 (d, J=8.4, 1H), 7.31~7.39 (m, 5H)

Preparation Example 301: 2-((2S, 3S)-3-phenyl-1,4-dioxaspiro[4.5]decan-2-yl)ethanol

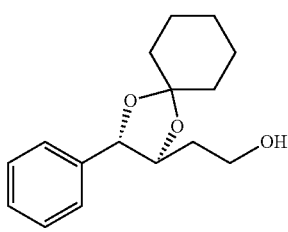 [SMILES: OCC[C@@H]1OC2(CCCCC2)O[C@H]1c1ccccc1]

The substantially same method as described in Preparation example 299 was conducted, except that 2-((2S, 3S)-3-phenyl-1,4-dioxaspiro[4.5]decan-2-yl)ethyl pivalate (Preparation example 300) was used instead of that 2-((2S, 3S)-3-phenyl-1,4-dioxaspiro[4.4]nonan-2-yl)ethyl pivalate (Preparation example 298), to obtain the title compound (1.2 g, 80~95%)
$^1$H NMR (400 MHz, CDCl$_3$): δ=1.71~1.83 (m, 4H), 1.87~2.05 (m, 6H), 2.27 (q, J=3.7, 1H), 3.79~3.85 (m, 2H), 3.86~3.91 (m, 1H), 4.59 (d, J=8.4, 1H), 7.32~7.41 (m, 5H)

Preparation Example 302: (E)-5-(2-chlorophenyl)pent-3-enoic acid

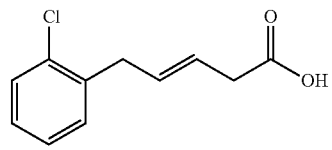 [SMILES: O=C(O)C/C=C/Cc1ccccc1Cl]

The substantially same method as described in Preparation example 235 was conducted, except that 3-(2-chlorophenyl)propanal was used instead of that hydrocinnamaldehyde (6.1 g, 70~90%)
$^1$H NMR (400 MHz, CDCl$_3$): δ=3.15 (dd, J=0.8, 6.8, 2H), 3.53 (d, J=6.4, 2H), 5.61~5.69 (m, 1H), 5.75~5.82 (m, 1H), 7.16~7.28 (m, 3H), 7.36~7.38 (m, 1H)

Preparation Example 303: (E)-5-(2-chlorophenyl)pent-3-en-1-ol

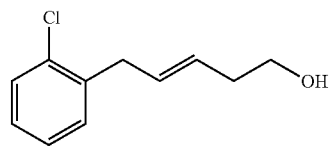 [SMILES: OCC/C=C/Cc1ccccc1Cl]

The substantially same method as described in Preparation example 236 was conducted, except that (E)-5-(2-chlorophenyl)pent-3-enoic acid (Preparation example 302) was used instead of that (E)-5-phenylpent-3-enoic acid (Preparation example 235), to obtain the title compound (4.6 g, 70~90%)
$^1$H NMR (400 MHz, CDCl$_3$): δ=2.33 (dq, J=1.0, 6.5, 2H), 3.50 (dd, J=1.8, 5.0, 2H), 3.67 (q, J=6.0, 2H), 5.45~5.53 (m, 1H), 5.70~5.77 (m, 1H), 7.15~7.37 (m, 4H)

Preparation Example 304: (E)-tert-butyl(5-(2-chlorophenyl)pent-3-enyloxy)dimethylsilane

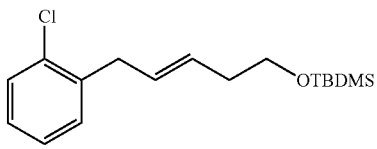 [SMILES: CC(C)(C)[Si](C)(C)OCC/C=C/Cc1ccccc1Cl]

The substantially same method as described in Preparation example 237 was conducted, except that (E)-5-(2-chlorophenyl)pent-3-en-1-ol (Preparation example 303) was used instead of that (E)-5-phenylpent-3-en-1-ol (Preparation example 236), to obtain the title compound (4.9 g, 75~95%)

¹H NMR (400 MHz, CDCl₃): δ=0.60 (s, 6H), 0.90 (s, 9H), 2.28 (dq, J=1.0, 6.7, 2H), 3.47 (d, J=6.4, 2H), 3.65 (t, J=6.8, 2H), 5.49~5.56 (m, 1H), 5.62~5.70 (m, 1H), 7.14~7.36 (m, 4H)

Preparation Example 305:
(E)-5-(2-chlorophenyl)pent-3-enyl pivalate

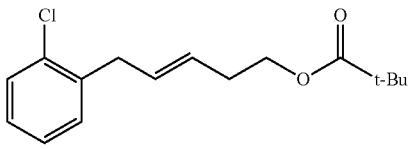

The substantially same method as described in Preparation example 238 was conducted, except that (E)-5-(2-chlorophenyl)pent-3-en-1-ol (Preparation example 303) was used instead of that (E)-5-phenylpent-3-en-1-ol (Preparation example 236), to obtain the title compound (7.2 g, 75~95%)

¹H NMR (400 MHz, CDCl₃): δ=1.18 (s, 9H), 2.36 (q, J=6.7, 2H), 3.45 (d, J=6.4, 2H), 4.08 (t, J=6.6, 2H), 5.43~5.50 (m, 1H), 5.63~5.70 (m, 1H), 7.12~7.35 (m, 4H)

Preparation Example 306: (2S, 3S)-5-(tert-butyldimethylsilyloxy)-1-(2-chlorophenyl)pentane-2,3-diol

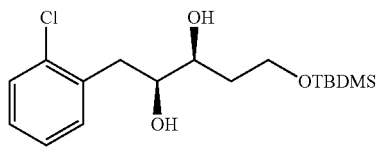 [SMILES: CC(C)(C)[Si](C)(C)OCC[C@H](O)[C@@H](O)Cc1ccccc1Cl]

The substantially same method as described in Preparation example 239 was conducted, except that (E)-tert-butyl (5-(2-chlorophenyl)pent-3-enyloxy)dimethylsilane (Preparation example 304) was used instead of that (E)-tert-butyldimethyl(5-phenylpent-3-enyloxy)silane (Preparation example 237), to obtain the title compound (2.8 g, 90%)

¹H NMR (400 MHz, CDCl₃): δ=0.11 (s, 6H), 0.92 (s, 9H), 1.68~1.77 (m, 1H), 1.87~1.96 (m, 1H), 2.64 (d, J=6.0, 1H), 2.93 (dd, J=8.2, 13.4, 1H), 3.07 (dd, J=4.8, 13.6, 1H), 3.68 (d, J=3.2, 1H), 3.76~3.96 (m, 4H), 7.17~7.25 (m, 2H), 7.35~7.39 (m, 2H)

Preparation Example 307: (2-(4S, 5S)-5-(2-chlorobenzyl)-2,2-dimethyl-1,3-dioxolan-4-yl)ethoxy)(tert-butyl)dimethylsilane

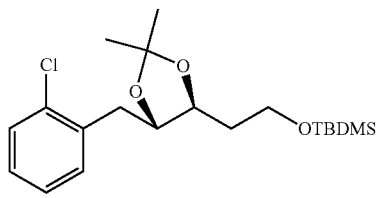 [SMILES: CC1(C)O[C@@H](CCO[Si](C)(C)C(C)(C)C)[C@H](Cc2ccccc2Cl)O1]

The substantially same method as described in Preparation example 240 was conducted, except that (2S, 3S)-5-(tert-butyldimethylsilyloxy)-1-(2-chlorophenyl)pentane-2,3-diol (Preparation example 306) was used instead of that (2S,3S)-5-(tert-butyldimethylsilyloxy)-1-phenylpentane-2,3-diol (Preparation example 239), to obtain the title compound (3.6 g, 75~90%)

¹H NMR (400 MHz, CDCl₃): δ=0.06 (s, 6H), 0.91 (s, 9H), 1.39 (s, 3H), 1.40 (s, 3H), 1.69 (q, J=6.5, 2H), 3.05 (dq, J=5.8, 15.1, 2H), 3.70~3.80 (m, 2H), 3.86~3.93 (m, 1H), 3.97~4.02 (m, 1H), 7.17~7.25 (m, 2H), 7.36~7.38 (m, 2H)

Preparation Example 308: 2-((4S,5S)-5-(2-chlorobenzyl)-2,2-dimethyl-1,3-dioxolan-4-yl)ethanol

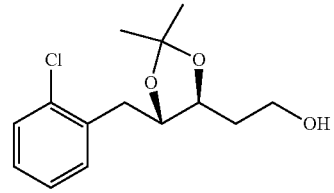 [SMILES: CC1(C)O[C@@H](CCO)[C@H](Cc2ccccc2Cl)O1]

The substantially same method as described in Preparation example 241 was conducted, except that (2-(4S, 5S)-5-(2chlorobenzyl)-2,2-dimethyl-1,3-dioxolan-4-yl)ethoxy)(tert-butyl)dimethylsilane (Preparation example 307) was used instead of that (2-(4S,5S)-5-benzyl-2,2-dimethyl-1,3-dioxolan-4-yl)ethoxy)(tert-butyl) dimethylsilane (Preparation example 240), to obtain the title compound (3.2 g, 80~95%)

¹H NMR (400 MHz, CDCl₃): δ=1.38 (s, 3H), 1.40 (s, 3H), 1.50~1.63 (m, 2H), 2.29 (t, J=5.4, 1H), 2.82 (dd, J=5.8, 13.8, 1H), 3.01 (dd, J=6.4, 14.0, 1H), 3.72 (q, J=5.5, 2H), 3.86 (dt, J=3.2, 8.4, 1H), 3.92~3.97 (m, 1H), 7.17~7.25 (m, 2H), 7.36~7.38 (m, 2H)

Preparation Example 309: (2R, 3R)-5-(tert-butyldimethylsilyloxy)-1-(2-chlorophenyl)pentane-2,3-diol

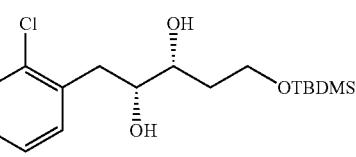

The substantially same method as described in Preparation example 242 was conducted, except that (E)-tert-butyl (5-(2-chlorophenyl)pent-3-enyloxy)dimethylsilane (Preparation example 304) was used instead of that (E)-tert-butyldimethyl(5-phenylpent-3-enyloxy)silane (Preparation example 237), to obtain the title compound (4.4 g, 90%)

¹H NMR (400 MHz, CDCl₃): δ=0.11 (s, 6H), 0.92 (s, 9H), 1.68~1.77 (m, 1H), 1.87~1.96 (m, 1H), 2.64 (d, J=6.0, 1H), 2.93 (dd, J=8.2, 13.4, 1H), 3.07 (dd, J=4.8, 13.6, 1H), 3.68 (d, J=3.2, 1H), 3.76~3.96 (m, 4H), 7.17~7.25 (m, 2H), 7.35~7.39 (m, 2H)

Preparation Example 310: (2-(4R, 5R)-5-(2chlorobenzyl)-2,2-dimethyl-1,3-dioxolan-4-yl)ethoxy)(tert-butyl)dimethylsilane

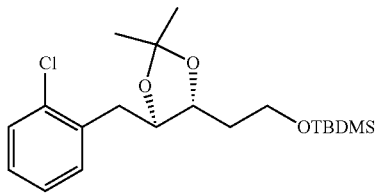 [SMILES: CC1(C)O[C@H](CCO[Si](C)(C)C(C)(C)C)[C@@H](Cc2ccccc2Cl)O1]

The substantially same method as described in Preparation example 307 was conducted, except that (2R, 3R)-5-(tert-butyldimethylsilyloxy)-1-(2-chlorophenyl)pentane-2,3-diol (Preparation example 309) was used instead of (2S, 3S)-5-(tert-butyldimethylsilyloxy)-1-(2-chlorophenyl)pentane-2,3-diol (Preparation example 306), to obtain the title compound (4.6 g, 70~95%)

$^1$H NMR (400 MHz, CDCl$_3$): δ=0.06 (s, 6H), 0.91 (s, 9H), 1.39 (s, 3H), 1.40 (s, 3H), 1.69 (q, J=6.5, 2H), 3.05 (dq, J=5.8, 15.1, 2H), 3.70~3.80 (m, 2H), 3.86~3.93 (m, 1H), 3.97~4.02 (m, 1H), 7.17~7.25 (m, 2H), 7.36~7.38 (m, 2H)

Preparation Example 311: 2-((4R,5R)-5-(2-chlorobenzyl)-2,2-dimethyl-1,3-dioxolan-4-yl)ethanol

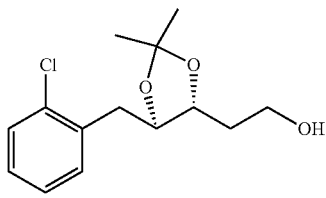 [SMILES: CC1(C)O[C@H](CCO)[C@@H](Cc2ccccc2Cl)O1]

The substantially same method as described in Preparation example 241 was conducted, except that (2-(4S, 5S)-5-(2chlorobenzyl)-2,2-dimethyl-1,3-dioxolan-4-yl)ethoxy)(tert-butyl)dimethylsilane (Preparation example 307) was used instead of that (2-(4S, 5S)-5-benzyl-2,2-dimethyl-1,3-dioxolan-4-yl)ethoxy)(tert-butyl)dimethylsilane (Preparation example 240), to obtain the title compound (3.0 g, 80~95%)

$^1$H NMR (400 MHz, CDCl$_3$): δ=1.38 (s, 3H), 1.40 (s, 3H), 1.50~1.63 (m, 2H), 2.29 (t, J=5.4, 1H), 2.82 (dd, J=5.8, 13.8, 1H), 3.01 (dd, J=6.4, 14.0, 1H), 3.72 (q, J=5.5, 2H), 3.86 (dt, J=3.2, 8.4, 1H), 3.92~3.97 (m, 1H), 7.17~7.25 (m, 2H), 7.36~7.38 (m, 2H)

Preparation Example 312: (3S,4S)-3,4-dihydroxy-5-(2chlorophenyl)pentyl pivalate

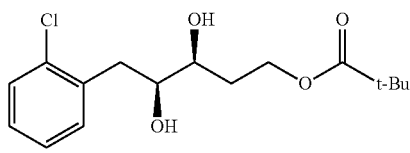 [SMILES: CC(C)(C)C(=O)OCC[C@H](O)[C@@H](O)Cc1ccccc1Cl]

The substantially same method as described in Preparation example 306 was conducted, except that (E)-5-(2-chlorophenyl)pent-3-enyl pivalate (Preparation example 305) was used instead of (E)-tert-butyl(5-(2-chlorophenyl)pent-3-enyloxy)dimethylsilane (Preparation example 304), to obtain the title compound (6.0 g, 70~95%)

$^1$H NMR (400 MHz, CDCl$_3$): δ=1.16 (s, 9H), 1.85~1.91 (m, 2H), 2.17 (d, J=6.0, 1H), 2.73 (d, J=5.2, 1H), 2.91 (dd, J=8.4, 13.6, 1H), 3.08 (dd, J=5.6, 13.6, 1H), 3.52~3.55 (m, 1H), 3.77~3.80 (m, 1H), 4.11~4.19 (m, 1H), 4.37~4.41 (m, 1H), 7.18~7.23 (m, 2H), 7.31 (dd, J=2.2, 7.0, 1H), 7.36 (dd, J=1.8, 7.4, 1H)

Preparation Example 313: 2-((4S,5S)-5-(2-chlorobenzyl)-2,2-diethyl-1,3-dioxolan-4-yl)ethyl pivalate

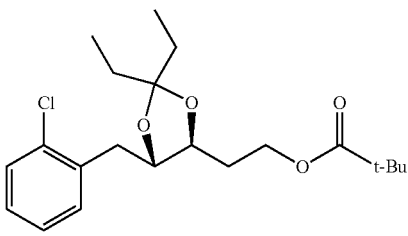 [SMILES: CCC1(CC)O[C@@H](CCOC(=O)C(C)(C)C)[C@H](Cc2ccccc2Cl)O1]

The substantially same method as described in Preparation example 246 was conducted, except that (3S,4S)-3,4-dihydroxy-5-(2chlorophenyl)pentyl pivalate (Preparation example 312) was used instead of (3S,4S)-3,4-dihydroxy-5-phenylpentyl pivalate (Preparation example 245), to obtain the title compound (1.7 g, 70~95%)

$^1$H NMR (400 MHz, CDCl$_3$): δ=0.90 (t, J=7.4, 6H), 1.21 (s, 9H), 1.58~1.66 (m, 4H), 1.70~1.77 (m, 2H), 3.06 (d, J=5.6, 2H), 3.81~3.86 (m, 1H), 3.94~3.99 (m, 1H), 4.15~4.25 (m, 2H), 7.18~7.24 (m, 2H), 7.36~7.38 (m, 2H)

Preparation Example 314: 2-((4S,5S)-5-(2-chlorobenzyl)-2,2-dimethyl-1,3-dioxolan-4-yl)ethanol

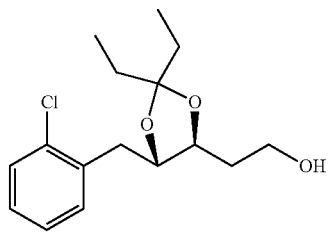 [SMILES: CCC1(CC)O[C@@H](CCO)[C@H](Cc2ccccc2Cl)O1]

The substantially same method as described in Preparation example 247 was conducted, except that 2-((4S,5S)-5-(2-chlorobenzyl)-2,2-diethyl-1,3-dioxolan-4-yl)ethyl pivalate (Preparation example 313) was used instead of 2-((4S, 5S)-5-benzyl-2,2-diethyl-1,3-dioxolan-4-yl)ethyl pivalate (Preparation example 246), to obtain the title compound (0.9 g, 80~95%);

$^1$H NMR (400 MHz, CDCl$_3$): δ=0.91 (dt, J=2.5, 7.5, 6H), 1.46~1.79 (m, 6H), 2.42 (t, J=5.6, 1H), 3.01~3.12 (m, 2H), 3.79 (q, J=5.6, 2H), 3.88~3.93 (m, 1H), 3.98~4.06 (m, 1H), 7.18~7.25 (m, 2H), 7.35~7.39 (m, 2H)

Preparation Example 315: (3R,4R)-3,4-dihydroxy-5-(2-chlorophenyl)pentyl pivalate

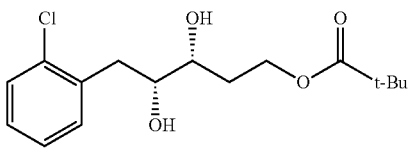 [SMILES: CC(C)(C)C(=O)OCC[C@@H](O)[C@H](O)Cc1ccccc1Cl]

The substantially same method as described in Preparation example 309 was conducted, except that (E)-5-(2-chlorophenyl)pent-3-enyl pivalate (Preparation example 305) was used instead of (E)-tert-butyl(5-(2-chlorophenyl)pent-3-enyloxy)dimethylsilane (Preparation example 304), to obtain the title compound (4.4 g, 70~95%)

$^1$H NMR (400 MHz, CDCl$_3$): δ=0.11 (s, 6H), 0.92 (s, 9H), 1.68~1.77 (m, 1H), 1.87~1.96 (m, 1H), 2.64 (d, J=6.0, 1H), 2.93 (dd, J=8.2, 13.4, 1H), 3.07 (dd, J=4.8, 13.6, 1H), 3.68 (d, J=3.2, 1H), 3.76~3.96 (m, 4H), 7.17~7.25 (m, 2H), 7.35~7.39 (m, 2H)

Preparation Example 316: 2-((4R, 5R)-5-(2-chlorobenzyl)-2-diethyl-1,3-dioxolan-4-yl)ethyl pivalate

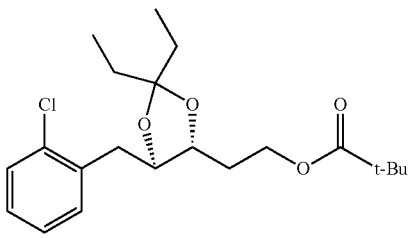 [SMILES: CCC1(CC)O[C@H](CCOC(=O)C(C)(C)C)[C@@H](Cc2ccccc2Cl)O1]

The substantially same method as described in Preparation example 313 was conducted, except that (3R, 4R)-3,4-dihydroxy-5-(2chlorophenyl)pentyl pivalate (Preparation example 315) was used instead of (3S, 4S)-3,4-dihydroxy-5-(2chlorophenyl)pentyl pivalate (Preparation example 312), to obtain the title compound (1.7 g, 70~95%)

$^1$H NMR (400 MHz, CDCl$_3$): δ=0.90 (t, J=7.4, 6H), 1.21 (s, 9H), 1.58~1.66 (m, 4H), 1.70~1.77 (m, 2H), 3.06 (d, J=5.6, 2H), 3.81~3.86 (m, 1H), 3.94~3.99 (m, 1H), 4.15~4.25 (m, 2H), 7.18~7.24 (m, 2H), 7.36~7.38 (m, 2H)

Preparation Example 317: 2-((4R, 5R)-5-(2-chlorobenzyl)-2,2-dimethyl-1,3-dioxolan-4-yl)ethanol

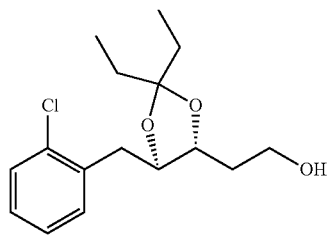 [SMILES: CCC1(CC)O[C@H](CCO)[C@@H](Cc2ccccc2Cl)O1]

The substantially same method as described in Preparation example 314 was conducted, except that 2-((4R, 5R)-5-(2-chlorobenzyl)-2,2-diethyl-1,3-dioxolan-4-yl)ethyl pivalate (Preparation example 316) was used instead of 2-((4S, 5S)-5-(2-chlorobenzyl)-2,2-diethyl-1,3-dioxolan-4-yl)ethyl pivalate (Preparation example 313), to obtain the title compound (0.9 g, 80~95%)

$^1$H NMR (400 MHz, CDCl$_3$): δ=0.91 (dt, J=2.5, 7.5, 6H), 1.46~1.79 (m, 6H), 2.42 (t, J=5.6, 1H), 3.01~3.12 (m, 2H), 3.79 (q, J=5.6, 2H), 3.88~3.93 (m, 1H), 3.98~4.06 (m, 1H), 7.18~7.25 (m, 2H), 7.35~7.39 (m, 2H)

Preparation Example 318: 2-((2S, 3S)-3-(2-chlorobenzyl)-1,4-dioxaspiro[4.4]nonan-2-yl)ethyl pivalate

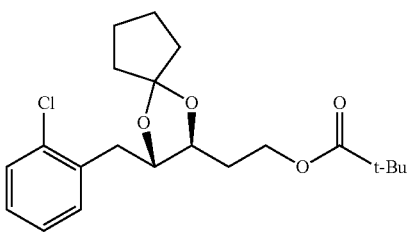 [SMILES: CC(C)(C)C(=O)OCC[C@@H]1OC2(CCCC2)O[C@H]1Cc1ccccc1Cl]

The substantially same method as described in Preparation example 313 was conducted, except that cyclopetanone was used instead of 3-pentanone, to obtain the title compound (1.2 g, 60~85%)

$^1$H NMR (400 MHz, CDCl$_3$): δ=1.21 (s, 9H), 1.64~1.74 (m, 5H), 1.75~1.88 (m, 5H), 3.03~3.11 (m, 2H), 3.81~3.86 (m, 1H), 3.97 (q, J=6.5, 1H), 4.12~4.22 (m, 2H), 7.18~7.25 (m, 2H), 7.34~7.39 (m, 2H)

Preparation Example 319: 2-((2S, 3S)-3-(2-chlorobenzyl)-1,4-dioxaspiro[4.4]nonan-2-yl)ethanol

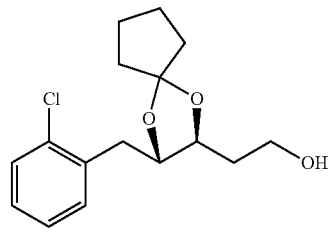 [SMILES: OCC[C@@H]1OC2(CCCC2)O[C@H]1Cc1ccccc1Cl]

The substantially same method as described in Preparation example 317 was conducted, except that 2-((2S,3S)-3-(2-chlorobenzyl)-1,4-dioxaspiro[4.4]nonan-2-yl)ethyl pivalate (Preparation example 318) was used instead of 2-((4R, 5R)-5-(2-chlorobenzyl)-2,2-diethyl-1,3-dioxolan-4-yl)ethyl pivalate (Preparation example 316), to obtain the title compound (0.7 g, 80~95%)

$^1$H NMR (400 MHz, CDCl$_3$): δ=1.62~1.74 (m, 6H), 1.75~1.88 (m, 4H), 2.28 (t, J=5.6, 1 H), 3.03~3.12 (m, 2H), 3.78 (q, J=5.6, 1H), 3.88~3.95 (m, 1H), 3.97~4.06 (m, 1H), 7.18~7.26 (m, 2H), 7.34~7.39 (m, 2H)

Preparation Example 320: 2-((2R, 3R)-3-(2-chlorobenzyl)-1,4-dioxaspiro[4.4]nonan-2-yl)ethyl pivalate

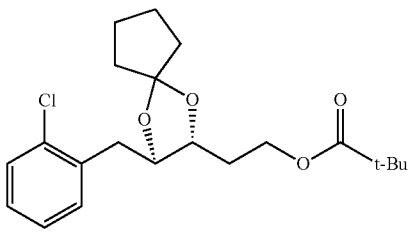 [SMILES: CC(C)(C)C(=O)OCC[C@H]1OC2(CCCC2)O[C@@H]1Cc1ccccc1Cl]

The substantially same method as described in Preparation example 316 was conducted, except that cyclopetanone was used instead of 3-pentanone, to obtain the title compound (1.4 g, 60~85%)

$^1$H NMR (400 MHz, CDCl$_3$): δ=1.21 (s, 9H), 1.64~1.74 (m, 5H), 1.75~1.88 (m, 5H), 3.03~3.11 (m, 2H), 3.81~3.86 (m, 1H), 3.97 (q, J=6.5, 1H), 4.12~4.22 (m, 2H), 7.18~7.25 (m, 2H), 7.34~7.39 (m, 2H)

Preparation Example 321: 2-((2R, 3R)-3-(2-chlorobenzyl)-1,4-dioxaspiro[4.4]nonan-2-yl)ethanol

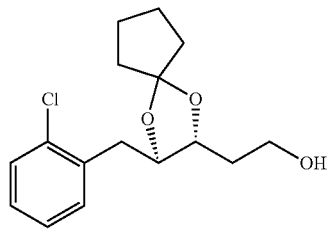 [SMILES: OCC[C@H]1OC2(CCCC2)O[C@@H]1Cc1ccccc1Cl]

The substantially same method as described in Preparation example 319 was conducted, except that 2-((2R, 3R)-3-(2-chlorobenzyl)-1,4-dioxaspiro[4.4]nonan-2-yl)ethyl pivalate (Preparation example 320) was used instead of 2-((2S,3S)-3-(2-chlorobenzyl)-1,4-dioxaspiro[4.4]nonan-2-yl)ethyl pivalate (Preparation example 318), to obtain the title compound (0.8 g, 80~95%)

$^1$H NMR (400 MHz, CDCl$_3$): δ=1.62~1.74 (m, 6H), 1.75~1.88 (m, 4H), 2.28 (t, J=5.6, 1H), 3.03~3.12 (m, 2H), 3.78 (q, J=5.6, 1H), 3.88~3.95 (m, 16), 3.97~4.06 (m, 1H), 7.18~7.26 (m, 2H), 7.34~7.39 (m, 2H)

Preparation Example 322: 2-((2S, 3S)-3-(2-chlorobenzyl)-1,4-dioxaspiro[4.5]decan-2-yl)ethyl pivalate

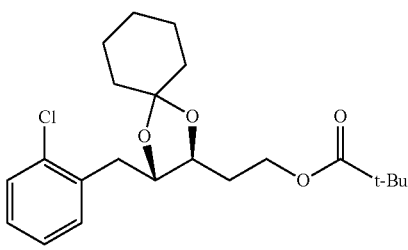 [SMILES: CC(C)(C)C(=O)OCC[C@@H]1OC2(CCCCC2)O[C@H]1Cc1ccccc1Cl]

The substantially same method as described in Preparation example 318 was conducted, except that cyclohexanone was used instead of cyclopetanone, to obtain the title compound (1.1 g, 60~85%)

$^1$H NMR (400 MHz, CDCl$_3$): δ=1.21 (s, 9H), 1.58~1.61 (m, 8H), 1.77 (q, J=6.8, 2H), 3.07 (d, J=6.0, 2H), 3.81~3.88 (m, 1H), 3.96~4.01 (m, 1H), 4.16~4.22 (m, 2H), 7.17~7.25 (m, 2H), 7.36~7.39 (m, 2H)

Preparation Example 323: 2-((2S, 3S)-3-(2-chlorobenzyl)-1,4-dioxaspiro[4.5]decan-2-yl)ethanol

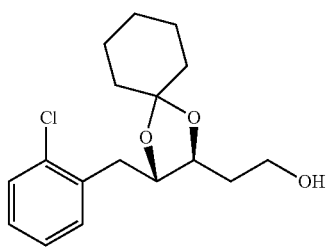 [SMILES: OCC[C@@H]1OC2(CCCCC2)O[C@H]1Cc1ccccc1Cl]

The substantially same method as described in Preparation example 321 was conducted, except that 2-((2S, 3S)-3-(2-chlorobenzyl)-1,4-dioxaspiro[4.5]decan-2-yl)ethyl pivalate (Preparation example 322) was used instead of 2-((2R, 3R)-3-(2-chlorobenzyl)-1,4-dioxaspiro[4.4]nonan-2-yl)ethyl pivalate (Preparation example 320), to obtain the title compound (0.7 g, 80~95%)

$^1$H NMR (400 MHz, CDCl$_3$): δ=1.51~1.64 (m, 8H), 1.65~1.74 (m, 2H), 2.59~2.63 (m, 1H), 3.06 (d, J=6.0, 2H), 3.76~3.78 (m, 2H), 3.89~3.94 (m, 1H), 3.99~4.04 (m, 1H), 7.16~7.24 (m, 2H), 7.35~7.38 (m, 2H)

Preparation Example 324: 2-((2R, 3R)-3-(2-chlorobenzyl)-1,4-dioxaspiro[4.5]decan-2-yl)ethyl pivalate

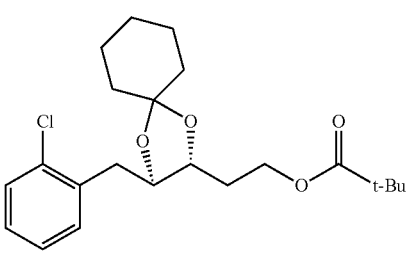 [SMILES: CC(C)(C)C(=O)OCC[C@H]1OC2(CCCCC2)O[C@@H]1Cc1ccccc1Cl]

The substantially same method as described in Preparation example 320 was conducted, except that cyclohexanone was used instead of cyclopetanone, to obtain the title compound (1.5 g, 60~85%)

$^1$H NMR (400 MHz, CDCl$_3$): δ=1.21 (s, 9H), 1.58~1.61 (m, 8H), 1.77 (q, J=6.8, 2H), 3.07 (d, J=6.0, 21~1), 3.81~3.88 (m, 1H), 3.96~4.01 (m, 1H), 4.16~4.22 (m, 2H), 7.17~7.25 (m, 2H), 7.36~7.39 (m, 2H)

Preparation Example 325: 2-((2R, 3R)-3-(2-chlorobenzyl)-1,4-dioxaspiro[4.5]decan-2-yl)ethanol

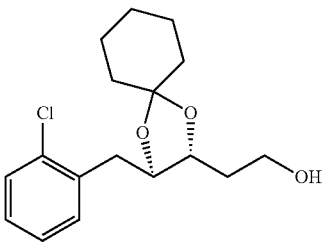 [SMILES: OCC[C@H]1OC2(CCCCC2)O[C@@H]1Cc1ccccc1Cl]

The substantially same method as described in Preparation example 323 was conducted, except that 2-((2R, 3R)-3-(2-chlorobenzyl)-1,4-dioxaspiro[4.5]decan-2-yl)ethyl pivalate (Preparation example 324) was used instead of 2-((2S, 3S)-3-(2-chlorobenzyl)-1,4-dioxaspiro[4.5]decan-2-yl)ethyl pivalate (Preparation example 322), to obtain the title compound (0.9 g, 80~95%)

$^1$H NMR (400 MHz, CDCl$_3$): δ=1.51~1.64 (m, 8H), 1.65~1.74 (m, 2H), 2.59~2.63 (m, 1H), 3.06 (d, J=6.0, 2H), 3.76~3.78 (m, 2H), 3.89~3.94 (m, 1H), 3.99~4.04 (m, 1H), 7.16~7.24 (m, 2H), 7.35~7.38 (m, 2H)

Preparation Example 326: (E)-methyl-4-(2-chlorophenyl)but-2-enoate

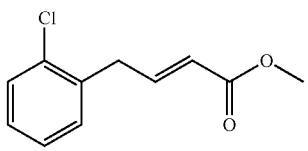

The substantially same method as described in Preparation example 259 was conducted, except that 2-chlorophenyl acetaldehyde was used instead of phenyl acetaldehyde, to obtain the title compound (5.0 g, 65~85%)

$^1$H NMR (400 MHz, CDCl$_3$): δ=3.47 (d, J=6.8, 2H), 3.67 (s, 3H), 5.79 (d, J=15.4, 1H), 7.06 (dt, J=15.4, 6.8, 1H), 7.12~7.28 (m, 4H)

Preparation Example 327: (2R, 3S)-methyl-4-(2chlorophenyl)-2,3-dihydroxybutanoate

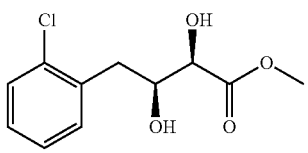 [SMILES: COC(=O)[C@H](O)[C@@H](O)Cc1ccccc1Cl]

The substantially same method as described in Preparation example 260 was conducted, except that (E)-methyl-4-(2-chlorophenyl)but-2-enoate (Preparation example 326) was used instead of (E)-methyl-4-phenylbut-2-enoate (Preparation example 259), to obtain the title compound (3.0 g, 70~95%)

$^1$H NMR (400 MHz, CDCl$_3$): δ=3.08~3.17 (m, 2H), 3.84 (s, 3H), 4.12 (dd, J=1.6, 5.2, 1H), 4.28~4.34 (m, 1H), 7.20~7.27 (m, 2H), 7.33~7.36 (m, 1H), 7.39~7.41 (m, 1H)

Preparation Example 328: (4R, 5S)-methyl-5-(2-chlorobenzyl)-2,2-dimethyl-1,3-dioxolane-4-carboxylate

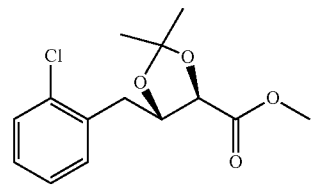 [SMILES: COC(=O)[C@@H]1OC(C)(C)O[C@H]1Cc1ccccc1Cl]

The substantially same method as described in Preparation example 261 was conducted, except that (2R, 3S)-methyl-4-(2chlorophenyl)-2,3-dihydroxybutanoate (Preparation example 327) was used instead of (2R, 3S)-methyl 2,3-dihydroxy-4-phenylbutanoate (Preparation example 260), to obtain the title compound (0.6 g, 70~95%)

$^1$H NMR (400 MHz, CDCl$_3$): δ=1.45 (s, 3H), 1.49 (s, 3H), 3.11 (dd, J=7.6, 14.4, 1H), 3.35 (dd, J=4.4, 14.4, 1H), 3.74 (s, 3H), 4.30 (d, J=7.6, 1H), 4.50 (dt, J=4.0, 7.6, 1H), 7.19~7.26 (m, 2H), 7.36~7.40 (m, 2H)

Preparation Example 329: ((4S, 5S)-5-(2-chlorobenzyl)-2,2-dimethyl-1,3-dioxolan-4-yl)methanol

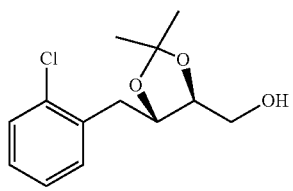 [SMILES: CC1(C)O[C@@H](CO)[C@H](Cc2ccccc2Cl)O1]

The substantially same method as described in Preparation example 262 was conducted, except that (4R,5S)-methyl-5-(2-chlorobenzyl)-2,2-dimethyl-1,3-dioxolane-4-carboxylate (Preparation example 328) was used instead of (4R,5S)-methyl 5-benzyl-2,2-dimethyl-1,3-dioxolane-4-carboxylate (Preparation example 261), to obtain the title compound (0.5 g, 70~95%)

$^1$H NMR (400 MHz, CDCl$_3$): δ=1.43 (s, 6H), 1.83 (q, J=4.3, 1H), 3.06~3.17 (m, 2H), 3.45 (ddd, J=4.6, 7.4, 12.0, 1H), 3.68 (ddd, J=3.2, 5.2, 12.0, 1H), 3.91 (ddd, J=3.3, 4.7, 8.0, 1H), 4.22~4.27 (m, 1H), 7.20~7.26 (m, 2H), 7.35~7.40 (m, 2H)

Preparation Example 330: (4R,5S)-methyl-5-(2-chlorobenzyl)-2,2-diethyl-1,3-dioxolane-4-carboxylate

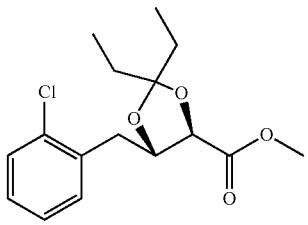 [SMILES: CCC1(CC)O[C@@H](Cc2ccccc2Cl)[C@H](C(=O)OC)O1]

The substantially same method as described in Preparation example 263 was conducted, except that (2R, 3S)-methyl-4-(2chlorophenyl)-2,3-dihydroxybutanoate (Preparation example 327) was used instead of (2R, 3S)-methyl 2,3-dihydroxy-4-phenylbutanoate (Preparation example 260), to obtain the title compound (0.8 g, 50~75%)

$^1$H NMR (400 MHz, CDCl$_3$): δ=0.93 (t, J=7.4, 6H), 1.67~1.74 (m, 4H), 3.10 (dd, J=8.0, 14.4, 1H), 3.35 (dd, J=4.0, 14.4, 1H), 3.73 (s, 3H), 4.27 (d, J=8.4, 1H), 4.42~4.47 (m, 1H), 7.18~7.26 (m, 2H), 7.37~7.40 (m, 2H)

Preparation Example 331: ((4S, 5S)-5-(2-chlorobenzyl)-2,2-diethyl-1,3-dioxolan-4-yl)methanol

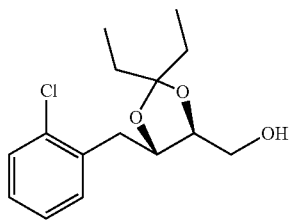 [SMILES: CCC1(CC)O[C@@H](CO)[C@H](Cc2ccccc2Cl)O1]

The substantially same method as described in Preparation example 329 was conducted, except that (4R,5S)-methyl-5-(2-chlorobenzyl)-2,2-dimethyl-1,3-dioxolane-4-carboxylate (Preparation example 330) was used instead of (4R,5S)-methyl-5-(2-chlorobenzyl)-2,2-dimethyl-1,3-dioxolane-4-carboxylate (Preparation example 328), to obtain the title compound (0.6 g, 70~95%)

$^1$H NMR (400 MHz, CDCl$_3$): δ=0.93 (dt, J=2.1, 7.5, 6H), 1.62~1.70 (m, 414), 1.83 (q, J=4.3, 1H), 3.11 (ddd, J=6.0, 14.2, 28.0, 2H), 3.44 (ddd, J=4.8, 7.2, 12.0, 1H), 3.64~3.69 (m, 1H), 3.88 (ddd, J=3.3, 4.9, 8.3, 1H), 4.18~4.24 (m, 1H), 7.19~7.26 (m, 2H), 7.36~7.39 (m, 2H)

Preparation Example 332: (2R, 3S)-methyl-3-(2-chlorobenzyl)-1,4-dioxaspiro[4.4]nonane-2-carboxylate

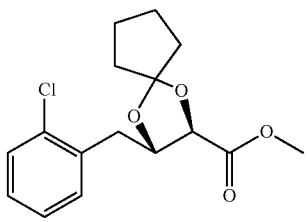 [SMILES: COC(=O)[C@@H]1OC2(CCCC2)O[C@H]1Cc1ccccc1Cl]

The substantially same method as described in Preparation example 330 was conducted, except that cyclopetanone was used instead of 3-pentanone, to obtain the title compound (0.8 g, 60~85%)

$^1$H NMR (400 MHz, CDCl$_3$): δ=1.65~1.80 (m, 5H), 1.89~2.00 (m, 3H), 3.13 (dd, J=7.8, 14.2, 1H), 3.32 (dd, J=4.6, 14.2, 1H), 3.72 (s, 3H), 4.28 (d, J=7.2, 1H), 4.41~4.46 (m, 1H), 7.19~7.26 (m, 2H), 7.35~7.40 (m, 2H)

Preparation Example 333: ((2S, 3S)-3-(-2chlorobenzyl)-1,4-dioxaspiro[4.4]nonan-2-yl)methanol

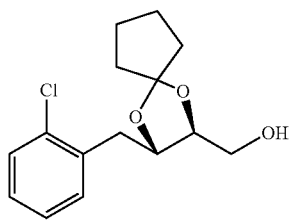 [SMILES: OC[C@@H]1OC2(CCCC2)O[C@H]1Cc1ccccc1Cl]

The substantially same method as described in Preparation example 331 was conducted, except that (2R, 3S)-methyl-3-(2-chlorobenzyl)-1,4-dioxaspiro[4.4]nonane-2-carboxylate (Preparation example 332) was used instead of (4R,5S)-methyl-5-(2-chlorobenzyl)-2,2-dimethyl-1,3-dioxolane-4-carboxylate (Preparation example 330), to obtain the title compound (0.6 g, 70~95%)

$^1$H NMR (400 MHz, CDCl$_3$): δ=1.69~1.74 (m, 3H), 1.77~1.85 (m, 5H), 3.11 (ddd, J=6.3, 14.1, 31.3, 2H), 3.42~3.48 (m, 1H), 3.61~3.66 (m, 1H), 3.87~3.91 (m, 1H), 4.19 (q, J=6.8, 1H), 7.19~7.26 (m, 2H), 7.34~7.40 (m, 2H)

Preparation Example 334: (2R,3S)-methyl-3-(2-chlorobenzyl)-1,4-dioxaspiro[4.5]decane-2-carboxylate

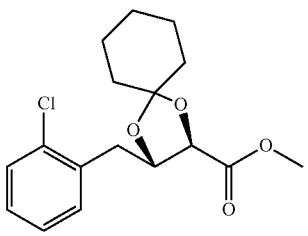 [SMILES: COC(=O)[C@@H]1OC2(CCCCC2)O[C@H]1Cc1ccccc1Cl]

The substantially same method as described in Preparation example 332 was conducted, except that cyclohexanone was used instead of cyclopetanone, to obtain the title compound (0.5 g, 60~85%)

$^1$H NMR (400 MHz, CDCl$_3$): δ=1.54~1.77 (m, 10H), 3.12 (dd, J=7.6, 14.4, 1H), 3.32 (dd, J=4.4, 14.4, 1H), 3.72 (s, 3H), 4.30 (d, J=7.6, 1H), 4.46~4.51 (m, 1H), 7.18~7.26 (m, 2H), 7.37~7.39 (m, 2H)

Preparation Example 335: ((2S, 3S)-3-(-2chlorobenzyl)-1,4-dioxaspiro[4.5]decan-2-yl)methanol

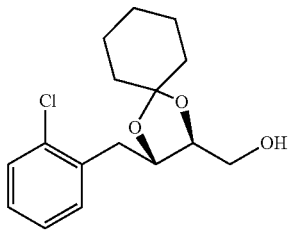 [SMILES: OC[C@@H]1OC2(CCCCC2)O[C@H]1Cc1ccccc1Cl]

The substantially same method as described in Preparation example 333 was conducted, except that (2R, 3S)-methyl-3-(2-chlorobenzyl)-1,4-dioxaspiro[4.5]decane-2-carboxylate (Preparation example 334) was used instead of (2R, 33)-methyl-3-(2-chlorobenzyl)-1,4-dioxaspiro[4.4]nonane-2-carboxylate (Preparation example 332), to obtain the title compound (0.5 g, 70~95%)

$^1$H NMR (400 MHz, CDCl$_3$): δ=1.38~1.45 (m, 2H), 1.58~1.63 (m, 8H), 1.84 (q, J=4.3, 1H), 3.11 (ddd, J=7.9, 15.9, 22.1, 2H), 3.43 (ddd, J=4.6, 7.6, 12.1, 1H), 3.66~3.71 (m, 1H), 3.88~3.92 (m, 1H), 4.21~4.26 (m, 1H), 7.18~7.26 (m, 2H), 7.37~7.39 (m, 2H)

Preparation Example 336: (2S, 3R)-methyl-4-(2chlorophenyl)-2,3-dihydroxybutanoate

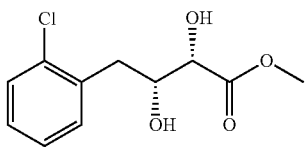 [SMILES: COC(=O)[C@@H](O)[C@H](O)Cc1ccccc1Cl]

The substantially same method as described in Preparation example 269 was conducted, except that (E)-methyl-4-(2-chlorophenyl)but-2-enoate (Preparation example 326) was used instead of (E)-methyl-4-phenylbut-2-enoate (Preparation example 259), to obtain the title compound (3.5 g, 70~95%)

$^1$H NMR (400 MHz, CDCl$_3$): δ=3.08~3.17 (m, 2H), 3.84 (s, 3H), 4.12 (dd, J=1.6, 5.2, 1H), 4.28~4.34 (m, 1H), 7.20~7.27 (m, 2H), 7.33~7.36 (m, 1H), 7.39~7.41 (m, 1H)

Preparation Example 337: (4S, 5R)-methyl-5-(2-chlorobenzyl)-2,2-dimethyl-1,3-dioxolane-4-carboxylate

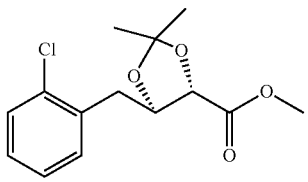 [SMILES: COC(=O)[C@H]1OC(C)(C)O[C@@H]1Cc1ccccc1Cl]

The substantially same method as described in Preparation example 328 was conducted, except that (2S, 3R)-methyl-4-(2chlorophenyl)-2,3-dihydroxybutanoate (Preparation example 336) was used instead of (2R, 3S)-methyl-4-(2chlorophenyl)-2,3-dihydroxybutanoate (Preparation example 327), to obtain the title compound (3.4 g, 70~95%)

$^1$H NMR (400 MHz, CDCl$_3$): δ=1.41 (s, 6H), 1.79 (q, J=4.3, 1H), 2.83 (dd, J=6.2, 13.8, 1H), 3.07 (dd, J=6.4, 14.0, 1H), 3.29 (ddd, J=4.7, 7.5, 12.1, 1H), 3.54 (ddd, J=2.8, 5.2, 12.0, 1H), 3.83 (ddd, J=3.9, 3.9, 7.1, 1H), 4.15 (q, J=7.1, 1H), 7.22~7.32 (m, 5H)

Preparation Example 338: ((4R, 5R)-5-(-2chlorobenzyl)-2,2-dimethyl-1,3-dioxolan-4-yl)methanol

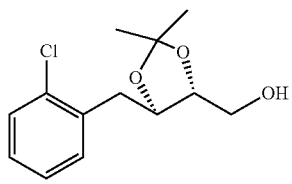 [SMILES: CC1(C)O[C@H](CO)[C@@H](Cc2ccccc2Cl)O1]

The substantially same method as described in Preparation example 335 was conducted, except that (4S,5R)-methyl-5-(2-chlrobenzyl)-2,2-dimethyl-1,3-dioxolane-4-carboxylate (Preparation example 337) was used instead of (2R, 3S)-methyl-3-(2-chlorobenzyl)-1,4-dioxaspiro[4.5]decane-2-carboxylate (Preparation example 334), to obtain the title compound (2.7 g, 70~95%).

$^1$H NMR (400 MHz, CDCl$_3$): δ=1.41 (s, 6H), 1.79 (q, J=4.3, 1H), 2.83 (dd, J=6.2, 13.8, 1H), 3.07 (dd, J=6.4, 14.0, 1H), 3.29 (ddd, J=4.7, 7.5, 12.1, 1H), 3.54 (ddd, J=2.8, 5.2, 12.0, 1H), 3.83 (ddd, J=3.9, 3.9, 7.1, 1H), 4.15 (q, J=7.1, 1H), 7.22~7.32 (m, 5H)

Preparation Example 339: (4S, 5R)-methyl-(5-2-chloro)benzyl-2,2-diethyl-1,3-dioxolane-4-carboxylate

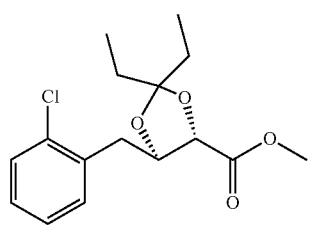 [SMILES: CCC1(CC)O[C@H](C(=O)OC)[C@@H](Cc2ccccc2Cl)O1]

The substantially same method as described in Preparation example 330 was conducted, except that (2S, 3R)-methyl-2,3-dihydroxy-4-phenylbutanoate (Preparation example 336) was used instead of that (2R, 3S)-methyl-4-(2chlorophenyl)-2,3-dihydroxybutanoate (Preparation example 327), to obtain the title compound (0.6 g, 50~75%)

$^1$H NMR (400 MHz, CDCl$_3$): δ=0.93 (t, J=7.4, 6H), 1.67~1.74 (m, 4H), 3.10 (dd, J=8.0, 14.4, 1H), 3.35 (dd, J=4.0, 14.4, 1H), 3.73 (s, 3H), 4.27 (d, J=8.4, 1H), 4.42~4.47 (m, 1H), 7.18~7.26 (m, 2H), 7.37~7.40 (m, 2H)

Preparation Example 340: ((4R, 5R)-5-(2-chlorobenzyl)-2,2-diethyl-1,3-dioxolan-4-yl)methanol

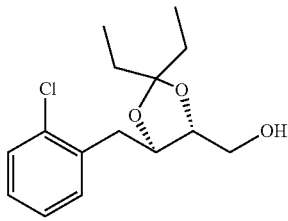 [SMILES: CCC1(CC)O[C@H](CO)[C@@H](Cc2ccccc2Cl)O1]

The substantially same method as described in Preparation example 338 was conducted, except that (4S, 5R)-methyl-(5-2-chloro)benzyl-2,2-diethyl-1,3-dioxolane-4-carboxylate (Preparation example 339) was used instead of (4S,5R)-methyl-5-(2-chlorbenzyl)-2,2-dimethyl-1,3-dioxolane-4-carboxylate (Preparation example 337), to obtain the title compound (0.5 g, 70~95%)

$^1$H NMR (400 MHz, CDCl$_3$): δ=0.93 (dt, J=2.1, 7.5, 6H), 1.62~1.70 (m, 4H), 1.83 (q, J=4.3, 1H), 3.11 (ddd, J=6.0, 14.2, 28.0, 2H), 3.44 (ddd, J=4.8, 7.2, 12.0, 1H), 3.64~3.69 (m, 1H), 3.88 (ddd, J=3.3, 4.9, 8.3, 1H), 4.18~4.24 (m, 1H), 7.19~7.26 (m, 2H), 7.36~7.39 (m, 2H)

Preparation Example 341: (2S, 3R)-methyl-3-(2-chlorobenzyl)-1,4-dioxaspiro[4.4]nonane-2-carboxylate

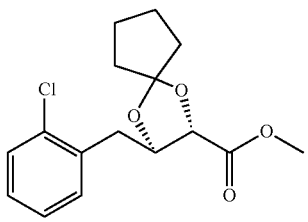 [SMILES: COC(=O)[C@H]1OC2(CCCC2)O[C@@H]1Cc1ccccc1Cl]

The substantially same method as described in Preparation example 339 was conducted, except that cyclopetanone was used instead of 3-pentanone, to obtain the title compound (0.5 g, 60~85%)

$^1$H NMR (400 MHz, CDCl$_3$): δ=1.65~1.80 (m, 5H), 1.89~2.00 (m, 3H), 3.13 (dd, J=7.8, 14.2, 1H), 3.32 (dd, J=4.6, 14.2, 1H), 3.72 (s, 3H), 4.28 (d, J=7.2, 1H), 4.41~4.46 (m, 1H), 7.19~7.26 (m, 2H), 7.35~7.40 (m, 2H)

Preparation Example 342: ((2R, 3R)-3-(2-chlorobenzyl)-1,4-dioxaspiro[4.4]nonan-2-yl)methanol

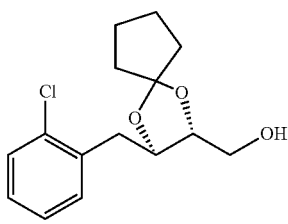 [SMILES: OC[C@H]1OC2(CCCC2)O[C@@H]1Cc1ccccc1Cl]

The substantially same method as described in Preparation example 340 was conducted, except that (2S, 3R)-methyl-3-(2-chlorobenzyl)-1,4-dioxaspiro[4.4]nonane-2-carboxylate (Preparation example 341) was used instead of that (4S, 5R)-methyl-(5-2-chloro)benzyl-2,2-diethyl-1,3-dioxolane-4-carboxylate (Preparation example 339), to obtain the title compound (0.4 g, 70~95%)

$^1$H NMR (400 MHz, CDCl$_3$): δ=1.69~1.74 (m, 3H), 1.77~1.85 (m, 5H), 3.11 (ddd, J=6.3, 14.1, 31.3, 2H), 3.42~3.48 (m, 1H), 3.61~3.66 (m, 1H), 3.87~3.91 (m, 1H), 4.19 (q, J=6.8, 1H), 7.19~7.26 (m, 2H), 7.34~7.40 (m, 2H)

Preparation Example 343: (2S, 3R)-methyl-3-(2-chlorobenzyl)-1,4-dioxaspiro[4.5]decane-2-carboxylate

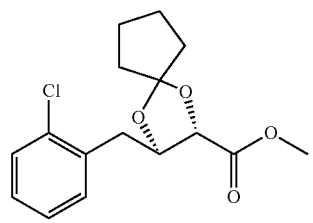 [SMILES: COC(=O)[C@H]1OC2(CCCC2)O[C@@H]1Cc1ccccc1Cl]

The substantially same method as described in Preparation example 341 was conducted, except that cyclohexanone was used instead of cyclopetanone, to obtain the title compound (0.9 g, 60~85%)

$^1$H NMR (400 MHz, CDCl$_3$): δ=1.54~1.77 (m, 10H), 3.12 (dd, J=7.6, 14.4, 1H), 3.32 (dd, J=4.4, 14.4, 1H), 3.72 (s, 3H), 4.30 (d, J=7.6, 1H), 4.46~4.51 (m, 1H), 7.18~7.26 (m, 2H), 7.37~7.39 (m, 2H)

Preparation Example 344: ((2R, 3R)-3-(2-chlorobenzyl)-1,4-dioxaspiro[4.5]decan-2-yl)methanol

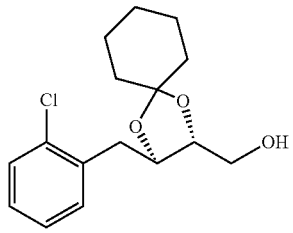 [SMILES: OC[C@H]1OC2(CCCCC2)O[C@@H]1Cc1ccccc1Cl]

The substantially same method as described in Preparation example 342 was conducted, except that (2S, 3R)-methyl-3-(2-chlorobenzyl)-1,4-dioxaspiro[4.5]decane-2-carboxylate (Preparation example 343) was used instead of (2S, 3R)-methyl-3-(2-chlorobenzyl)-1,4-dioxaspiro[4.4]nonane-2-carboxylate (Preparation example 341), to obtain the title compound (0.7 g, 70~95%)

$^1$H NMR (400 MHz, CDCl$_3$): δ=1.38~1.45 (m, 2H), 1.58~1.63 (m, 8H), 1.84 (q, J=4.3, 1H), 3.11 (ddd, J=7.9, 15.9, 22.1, 2H), 3.43 (ddd, J=4.6, 7.6, 12.1; 1H), 3.66~3.71 (m, 1H), 3.88~3.92 (m, 1H), 4.21~4.26 (m, 1H), 7.18~7.26 (m, 2H), 7.37~7.39 (m, 2H)

Preparation Example 345: (E)-4-(2chlorophenyl)but-3-enoic acid

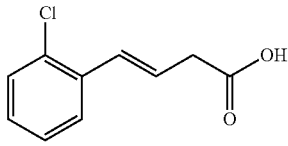 [SMILES: O=C(O)C/C=C/c1ccccc1Cl]

The substantially same method as described in Preparation example 278 was conducted, except that 2-(2-chlorophenyl)acetaldehyde was used instead of phenylacetaldehyde, to obtain the title compound (4.0 g, 55~80%)

$^1$H NMR (400 MHz, CDCl$_3$): δ=3.39 (d, J=8.8, 2H), 6.31 (td, J=7.9, 14.8, 1H), 6.94 (d, J=16, 1H), 7.17~7.45 (m, 3H), 7.56~7.59 (m, 1H)

Preparation Example 346: (E)-4-(2-chlorophenyl)but-3-en-1-ol

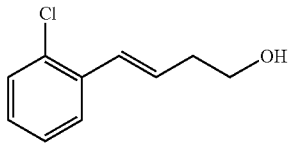 [SMILES: OCC/C=C/c1ccccc1Cl]

The substantially same method as described in Preparation example 279 was conducted, except that (E)-4-(2chlorophenyl)but-3-enoic acid (Preparation example 345) was used instead of (E)-4-phenylbut-3-enoic acid (Preparation example 278), to obtain the title compound (1.2 g, 55~80%)

$^1$H NMR (400 MHz, CDCl$_3$): δ=2.55 (ddd, J=4.1, 11.9, 21.5, 2H), 3.82 (t, J=5.8, 2H), 6.24 (td, J=7.2, 15.7, 1H), 6.87 (d, J=14.8, 1H), 7.12~7.25 (m, 3H), 7.36 (dd, J=1.2, 8.0, 1H), 7.52 (dd, J=1.6, 9.2, 1H)

Preparation Example 347: (E)-tert-butyldimethyl(4-(2-chlorophenyl)but-3-enyloxy)silane

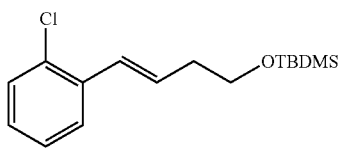 [SMILES: CC(C)(C)[Si](C)(C)OCC/C=C/c1ccccc1Cl]

The substantially same method as described in Preparation example 280 was conducted, except that (E)-4-(2-chlorophenyl)but-3-en-1-ol (Preparation example 346) was used instead of (E)-4-phenylbut-3-en-1-ol (Preparation example 279), to obtain the title compound (1.1 g, 80~98%)

$^1$H NMR (400 MHz, CDCl$_3$): δ=0.07 (s, 3H), 0.10 (s, 3H), 0.92 (d, J=6.4, 9H), 2.51 (q, J=4.5, 2H), 3.78 (t, J=6.6, 2H), 6.26 (td, J=7.2, 15.7, 1H), 6.84 (d, J=15.6, 1H), 7.13~7.24 (m, 3H), 7.36 (dd, J=5.6, 12.4, 1H), 7.53 (dd, J=1.4, 7.8, 1H)

Preparation Example 348: (E)-4-(2-chlorophenyl)but-3-enyl pivalate

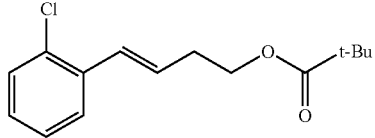 [SMILES: CC(C)(C)C(=O)OCC/C=C/c1ccccc1Cl]

The substantially same method as described in Preparation example 281 was conducted, except that (E)-4-(2-chlorophenyl)but-3-en-1-ol (Preparation example 346) was used instead of (E)-4-phenylbut-3-en-1-ol (Preparation example 279), to obtain the title compound (3.5 g, 75~95%)

$^1$H NMR (400 MHz, CDCl$_3$): δ=1.21 (s, 9H), 2.55~2.64 (m, 2H), 4.24 (t, J=6.4, 2H), 6.18 (td, J=7.9, 14.8, 1H), 6.86 (d, J=16.0, 1H), 7.22~7.26 (m, 2H), 7.38 (dd, J=3.6, 10.8, 1H), 7.51 (dd, J=1.6, 7.6, 1H)

Preparation Example 349: (1R, 2R)-4-(tert-butyldimethylsilyloxy)-1-(2-chlorophenyl)butane-1,2-diol

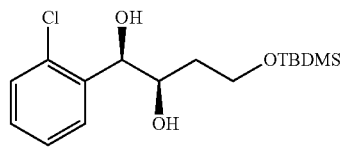 [SMILES: CC(C)(C)[Si](C)(C)OCC[C@@H](O)[C@H](O)c1ccccc1Cl]

The substantially same method as described in Preparation example 282 was conducted, except that (E)-tert-butyldimethyl(4~2-chlorophenyl)but-3-enyloxy)silane (Preparation example 347) was used instead of (E)-tert-butyldimethyl (5-phenylpent-3-enyloxy)silane (Preparation example 237), to obtain the title compound (0.7 g, 70~95%)

$^1$H NMR (400 MHz, CDCl$_3$): δ=0.10 (s, 3H), 0.11 (s, 3H), 0.92 (s, 9H), 1.69~1.70 (m, 1H), 1.93~2.07 (m, 1H), 3.51 (d, J=4.8, 1H), 3.86 (d, J=3.2, 1H), 3.87 (dd, J=3.2, 9.2, 1H), 3.91~3.96 (m, 1H), 4.01~4.06 (m, 1H), 5.05 (t, J=4.6, 1H), 7.22~7.26 (m, 1H), 7.31~7.37 (m, 2H), 7.59 (dd, J=1.2, 7.6, 1H)

Preparation Example 350: (3R, 4R)-3,4-dihydroxy-4-(2-chlorophenyl)butyl pivalate

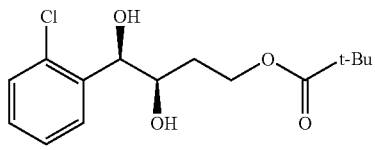 [SMILES: CC(C)(C)C(=O)OCC[C@@H](O)[C@H](O)c1ccccc1Cl]

The substantially same method as described in Preparation example 349 was conducted, except that (E)-4-(2-chlorophenyl)but-3-enyl pivalate (Preparation example 348) was used instead of (E)-tert-butyldimethyl(4-2-chlorophenyl)but-3-enyloxy)silane (Preparation example 347), to obtain the title compound (3.2 g, 70~95%)

¹H NMR (400 MHz, CDCl₃): δ=1.19 (s, 9H), 1.76~1.84 (m, 1H), 1.90~1.98 (m, 1H), 2.70 (d, J=4.4, 1H), 2.86 (d, J=5.2, 1H), 3.84~3.90 (m, 1H), 4.14~4.21 (m, 1H), 4.35~4.41 (m, 1H), 5.05 (t, J=5.0, 1H), 7.23~7.39 (m, 3H), 7.54 (dd, J=1.6, 7.6, 1H)

Preparation Example 351: tert-butyl(2-((4R, 5R)-5-(2-chlorophenyl)-2,2-dimethyl-1,3-dioxolan-4-yl)ethoxy)dimethylsilane

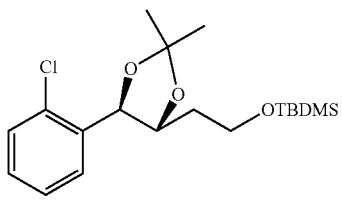 [SMILES: CC1(C)O[C@H](c2ccccc2Cl)[C@@H](CCO[Si](C)(C)C(C)(C)C)O1]

The substantially same method as described in Preparation example 284 was conducted, except that (1R, 2R)-4-(tert-butyldimethylsilyloxy)-1-(2-chlorophenyl)butane-1,2-diol (Preparation example 349) was used instead of (1R, 2R)-4-(tert-butyldimethylsilyloxy)-1-phenylbutane-1,2-diol (Preparation example 282), to obtain the title compound (0.8 g, 70~95%)

¹H NMR (400 MHz, CDCl₃): δ=0.02 (s, 3H), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7, 1H), 5.16 (d, J=8.4, 1H), 7.21~7.27 (m, 1H), 7.31~7.38 (m, 2H), 7.60 (dd, J=1.6, 7.6, 1H)

Preparation Example 352: 2-((4R, 5R)-5-(2-chlorophenyl)-2,2-dimethyl-1,3-dioxolan-4-yl)ethanol

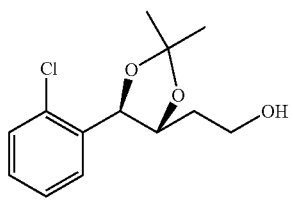 [SMILES: CC1(C)O[C@H](c2ccccc2Cl)[C@@H](CCO)O1]

The substantially same method as described in Preparation example 285 was conducted, except tert-butyl(2-((4R, 5R)-5-(2-chlorophenyl)-2,2-dimethyl-1,3-dioxolan-4-yl)ethoxy)dimethylsilane (Preparation example 351) was used instead of tert-butyl(2-((4R,5R)-5-phenyl-2,2-dimethyl-1,3-dioxolan-4-yl)ethoxy)dimethylsilane (Preparation example 284), to obtain the title compound (0.7 g, 80~95%)

¹H NMR (400 MHz, CDCl₃): δ=1.56 (s, 3H), 1.62 (s, 3H), 1.92~2.04 (m, 2H), 2.26 (q, J=3.7, 1H), 3.75~3.90 (m, 2H), 3.94 (td, J=3.9, 8.5, 1H), 5.23 (d, J=15.6, 1H), 7.22~7.27 (m, 1H), 7.33~7.39 (m, 2H), 7.62 (dd, J=1.6, 7.6, 1H)

Preparation Example 353: (1S, 2S)-4-(tert-butyldimethylsilyloxy)-1-(2-chlorophenyl)butane-1,2-diol

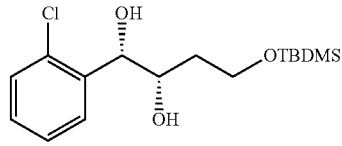 [SMILES: CC(C)(C)[Si](C)(C)OCC[C@H](O)[C@@H](O)c1ccccc1Cl]

The substantially same method as described in Preparation example 286 was conducted, except that (E)-tert-butyldimethyl(4-(2-chlorophenyl)but-3-enyloxy)silane (Preparation example 347) was used instead of (E)-tert-butyldimethyl(4-phenylbut-3-enyloxy)silane (Preparation example 280), to obtain the title compound (0.7 g, 70~95%)

¹H NMR (400 MHz, CDCl₃): δ=1.19 (s, 9H), 1.76~1.84 (m, 1H), 1.90~1.98 (m, 1H), 2.70 (d, J=4.4, 1H), 2.86 (d, J=5.2, 1H), 3.84~3.90 (m, 1H), 4.14~4.21 (m, 1H), 4.35~4.41 (m, 1H), 5.05 (t, J=5.0, 1H), 7.23~7.39 (m, 3H), 7.54 (dd, J=1.6, 7.6, 1H)

Preparation Example 354: (3S, 4S)-3,4-dihydroxy-4-(2-chlorophenyl)butyl pivalate

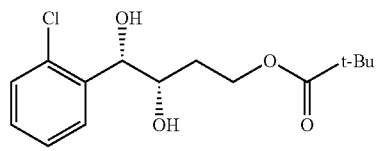 [SMILES: CC(C)(C)C(=O)OCC[C@H](O)[C@@H](O)c1ccccc1Cl]

The substantially same method as described in Preparation example 353 was conducted, except that (E)-4-(2-chlorophenyl)but-3-enyl pivalate (Preparation example 348) was used instead of ((E)-tert-butyldimethyl(4-(2-chlorophenyl)but-3-enyloxy)silane (Preparation example 347), to obtain the title compound (3.0 g, 70~95%)

¹H NMR (400 MHz, CDCl₃): δ=1.19 (s, 9H), 1.76~1.84 (m, 1H), 1.90~1.98 (m, 1H), 2.70 (d, J=4.4, 1H), 2.86 (d, J=5.2, 1H), 3.84~3.90 (m, 1H), 4.14~4.21 (m, 1H), 4.35~4.41 (m, 1H), 5.05 (t, J=5.0, 1H), 7.23~7.39 (m, 3H), 7.54 (dd, J=1.6, 7.6, 1H)

Preparation Example 355: tert-butyl(2-((4S, 5S)-5-(2-chlorophenyl)-2,2-dimethyl-1,3-dioxolan-4-yl)ethoxy)dimethylsilane

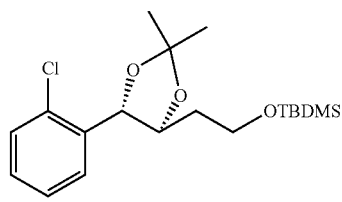 [SMILES: CC1(C)O[C@@H](CCO[Si](C)(C)C(C)(C)C)[C@H](c2ccccc2Cl)O1]

The substantially same method as described in Preparation example 351 was conducted, except that (1S, 2S)-4-(tert-butyldimethylsilyloxy)-1-(2-chlorophenyl)butane-1,2- diol (Preparation example 353) was used instead of 1R, 2R)-4-(tert-butyldimethylsilyloxy)-1-(2-chlorophenyl)butane-1,2-diol (Preparation example 349), to obtain the title compound (0.7 g, 70~95%)

$^1$H NMR (400 MHz, CDCl$_3$): δ=0.02 (s, 3H), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7, 1H), 5.16 (d, J=8.4, 1H); 7.21~7.27 (m, 1H), 7.31~7.38 (m, 2H), 7.60 (dd, J=1.6, 7.6, 1H)

Preparation Example 356: 2-((4S, 5S)-5-(2-chlorophenyl)-2,2-dimethyl-1,3-dioxolan-4-yl)ethanol

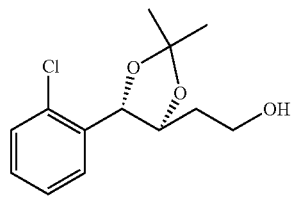 [SMILES: CC1(C)O[C@@H](CCO)[C@H](c2ccccc2Cl)O1]

The substantially same method as described in Preparation example 352 was conducted, except that tert-butyl(2-((4S, 5S)-5-(2-chlorophenyl)-2,2-dimethyl-1,3-dioxolan-4-yl)ethoxy)dimethylsilane (Preparation example 355) was used instead of that tert-butyl(2-((4R,5R)-5-(2-chlorophenyl)-2,2-dimethyl-1,3-dioxolan-4-yl)ethoxy)dimethyl silane (Preparation example 351), to obtain the title compound (0.3 g, 80~95%).

$^1$H NMR (400 MHz, CDCl$_3$): δ=1.56 (s, 3H), 1.62 (s, 3H), 1.92~2.04 (m, 2H), 2.26 (q, J=3.7, 1H), 3.75~3.90 (m, 2H), 3.94 (td, J=3.9, 8.5, 1H), 5.23 (d, J=15.6, 1H), 7.22~7.27 (m, 1H), 7.33~7.39 (m, 2H), 7.62 (dd, J=1.6, 7.6, 1H)

Preparation Example 357: 2-((4R, 5R)-2,2-diethyl-5-(2-chlorophenyl)-1,3-dioxolan-4-yl)ethyl pivalate

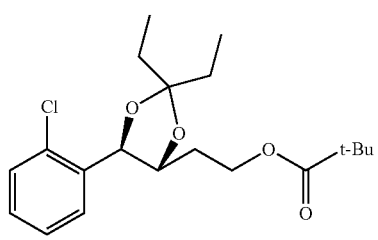 [SMILES: CCC1(CC)O[C@H](c2ccccc2Cl)[C@@H](CCOC(=O)C(C)(C)C)O1]

The substantially same method as described in Preparation example 290 was conducted, except that (3R, 4R)-3,4-dihydroxy-4-(2-chlorophenyl)butyl pivalate (Preparation example 350) was used instead of (3R, 4R)-3,4-dihydroxy-4-phenylbutyl pivalate (Preparation example 233), to obtain the title compound (0.8 g, 70~95%)

$^1$H NMR (400 MHz, CDCl$_3$): δ=1.15 (s, 9H), 1.76 (q, J=7.6, 2H), 1.84~1.90 (m, 2H), 2.00~2.07 (m, 2H), 3.85 (dt, J=3.7, 8.5, 1H), 4.14~4.27 (m, 2H), 5.17 (d, J=8.4, 1H), 7.22~7.28 (m, 1H), 7.32~7.38 (m, 2H), 7.64 (dd, J=1.4, 7.8, 1H)

Preparation Example 358: 2-((4R, 5R)-2,2-diethyl-5-(2-chlorophenyl)-1,3-dioxolan-4-yl)ethyl pivalate

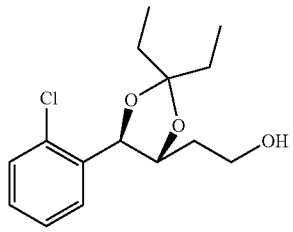 [SMILES: CCC1(CC)O[C@H](c2ccccc2Cl)[C@@H](CCO)O1]

The substantially same method as described in Preparation example 291 was conducted, except that 2-((4R, 5R)-2,2-diethyl-5-(2-chlorophenyl)-1,3-dioxolan-4-yl)ethyl pivalate (Preparation example 357) was used instead of 2-((4R, 5R)-2,2-diethyl-5-phenyl-1,3-dioxolan-4-yl)ethyl pivalate (Preparation example 290), to obtain the title compound (0.6 g, 80~95%)

$^1$H NMR (400 MHz, CDCl$_3$): δ=1.02 (t, J=7.4, 3H), 1.08 (t, J=7.4, 3H), 1.80 (q, J=7.5, 2H), 1.86~1.91 (m, 2H), 1.96~2.00 (m, 2H), 2.37 (q, J=3.7, 1H), 3.76~3.95 (m, 3H), 5.23 (d, J=8.4, 1H), 7.25~7.27 (m, 1H), 7.32~7.39 (m, 2H), 7.65 (dd, J=1.8, 7.8, 1H)

Preparation Example 359: 2-((2R, 3R)-3-(2-chlorophenyl)-1,4-dioxaspiro[4.4]nonan-2-yl)ethyl pivalate

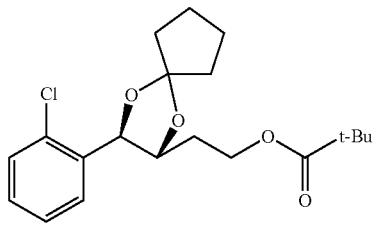 [SMILES: CC(C)(C)C(=O)OCC[C@H]1OC2(CCCC2)O[C@@H]1c1ccccc1Cl]

The substantially same method as described in Preparation example 357 was conducted, except that cyclopetanone was used instead of 3-pentanone, to obtain the title compound (0.8 g, 60~85%)

$^1$H NMR (400 MHz, CDCl$_3$): δ=1.17 (s, 9H), 1.58~2.02 (m, 10H), 3.86 (ddd, J=3.8, 8.2, 8.2, 1H), 4.11~4.28 (m, 2H), 5.13 (d, J=8.0, 1H), 7.20~7.39 (m, 3H), 7.58 (dd, J=1.6, 8.0, 1H)

Preparation Example 360: 2-((2R, 3R)-3-(2-chlorophenyl)-1,4-dioxaspiro[4.4]nonan-2-yl)ethanol

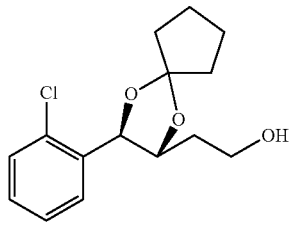 [SMILES: OCC[C@H]1OC2(CCCC2)O[C@@H]1c1ccccc1Cl]

The substantially same method as described in Preparation example 358 was conducted, except that 2-((2R, 3R)-3-(2-chlorophenyl)-1,4-dioxaspiro[4.4]nonan-2-yl)ethyl pivalate (Preparation example 359) was used instead of that 2-((4R, 5R)-2,2-diethyl-5-(2-chlorophenyl)-1,3-dioxolan-4-yl)ethyl pivalate (Preparation example 357), to obtain the title compound (0.5 g, 80~95%)

¹H NMR (400 MHz, CDCl₃): δ=1.72~1.90 (m, 4H), 1.93~1.98 (m, 6H), 2.28 (q, J=3.7, 1H), 3.76~3.93 (m, 3H), 5.18 (d, J=8.0, 1H), 7.24~7.29 (m, 1H), 7.32~7.38 (m, 2H), 7.60 (dd, J=1.8, 7.8, 1H)

Preparation Example 361: 2-((2R, 3R)-3-(2-chlorophenyl)-1,4-dioxaspiro[4.5]decan-2-yl)ethyl pivalate

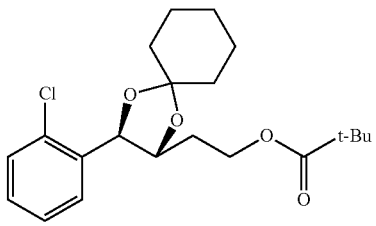 [SMILES: CC(C)(C)C(=O)OCC[C@H]1OC2(CCCCC2)O[C@@H]1c1ccccc1Cl]

The substantially same method as described in Preparation example 359 was conducted, except that cyclohexanone was used instead of cyclopetanone, to obtain the title compound (1.0 g, 60~85%)

¹H NMR (400 MHz, CDCl₃): δ=1.15 (s, 9H), 1.70~1.94 (m, 10H), 2.06~2.09 (m, 2H), 3.86 (dt, J=3.5, 8.5, 1H), 4.16~4.26 (m, 2H), 5.18 (d, J=8.4, 1H), 7.22~7.28 (m, 1H), 7.32~7.38 (m, 2H), 7.61 (dd, J=1.4, 7.8, 1H)

Preparation Example 362: 2-((2R, 3R)-3-(2-chlorophenyl)-1,4-dioxaspiro[4.5]decan-2-yl)ethanol

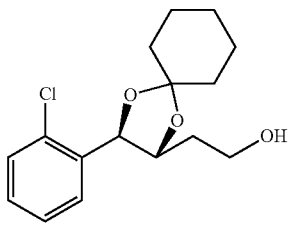 [SMILES: OCC[C@H]1OC2(CCCCC2)O[C@@H]1c1ccccc1Cl]

The substantially same method as described in Preparation example 360 was conducted, except that 2-((2R, 3R)-3-(2-chlorophenyl)-1,4-dioxaspiro[4:5]decan-2-yl)ethyl pivalate (Preparation example 361) was used instead of that 2-((2R, 3R)-3-(2-chlorophenyl)-1,4-dioxaspiro[4.4]nonan-2-yl)ethyl pivalate (Preparation example 359), to obtain the title compound (0.6 g, 80~95%)

¹H NMR (400 MHz, CDCl₃): δ=1.42~1.50 (m, 2H), 1.63~1.77 (m, 5H), 1.82~1.89 (m, 5H), 2.41 (q, J=3.9, 1H), 3.78~3.96 (m, 3H), 5.25 (d, J=8.4, 1H), 7.21~7.28 (m, 1H), 7.32~7.38 (m, 2H), 7.63 (dd, J=1.4, 7.8, 1H)

Preparation Example 363: 2-((4S, 5S)-2,2-diethyl-5-(2-chlorophenyl)-1,3-dioxolan-4-yl)ethyl pivalate

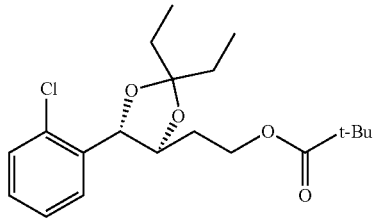 [SMILES: CCC1(CC)O[C@@H](CCOC(=O)C(C)(C)C)[C@H](c2ccccc2Cl)O1]

The substantially same method as described in Preparation example 357 was conducted, except that (3S, 4S)-3,4-dihydroxy-4-(2-chlorophenyl)butyl pivalate (Preparation example 354) was used instead of (3R, 4R)-3,4-dihydroxy-4-(2-chlorophenyl)butyl pivalate (Preparation example 350), to obtain the title compound (0.7 g, 70~95%).

¹H NMR (400 MHz, CDCl₃): δ=1.15 (s, 9H), 1.76 (q, J=7.6, 2H), 1.84~1.90 (m, 2H), 2.00~2.07 (m, 2H), 3.85 (dt, J=3.7, 8.5, 1H), 4.14~4.27 (m, 2H), 5.17 (d, J=8.4, 1H), 7.22~7.28 (m, 1H), 7.32~7.38 (m, 2H), 7.64 (dd, J=1.4, 7.8, 1H)

Preparation Example 364: 2-((4S, 5S)-2,2-diethyl-5-(2-chlorophenyl)-1,3-dioxolan-4-yl)ethanol

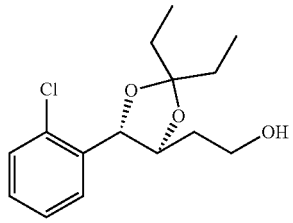 [SMILES: CCC1(CC)O[C@@H](CCO)[C@H](c2ccccc2Cl)O1]

The substantially same method as described in Preparation example 358 was conducted, except that 2-((4S, 5S)-2,2-diethyl-5-(2-chlorophenyl)-1,3-dioxolan-4-yl)ethyl pivalate (Preparation example 363) was used instead of 2-((4R, 5R)-2,2-diethyl-5-(2-chlorophenyl)-1,3-dioxolan-4-yl)ethyl pivalate (Preparation example 357), to obtain the title compound (0.5 g, 80~95%)

¹H NMR (400 MHz, CDCl₃): δ=1.02 (t, J=7.4, 3H), 1.08 (t, J=7.4, 3H), 1.80 (q, J=7.5, 2H), 1.86~1.91 (m, 2H), 1.96~2.00 (m, 2H), 2.37 (q, J=3.7, 1H), 3.76~3.95 (m, 3H), 5.23 (d, J=8.4, 1H), 7.25~7.27 (m, 1H), 7.32~7.39 (m, 2H), 7.65 (dd, J=1:8, 7.8, 1H)

Preparation Example 365: 2-((2S, 3S)-3-(2-chlorophenyl)-1,4-dioxaspiro[4.4]nonan-2-yl)ethyl pivalate

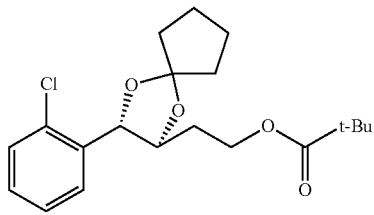 [SMILES: CC(C)(C)C(=O)OCC[C@@H]1OC2(CCCC2)O[C@H]1c1ccccc1Cl]

The substantially same method as described in Preparation example 363 was conducted, except that cyclopetanone was used instead of 3-pentanone, to obtain the title compound (0.6 g, 60~85%)

¹H NMR (400 MHz, CDCl₃): δ=1.17 (s, 9H), 1.58~2.02 (m, 108), 3.86 (ddd, J=3.8, 8.2, 8.2, 1H), 4.11~4.28 (m, 2H), 5.13 (d, J=8.0, 1H), 7.20~7.39 (m, 3H), 7.58 (dd, J=1.6, 8.0, 1H)

Preparation Example 366: 2-((2S, 3S)-3-(2-chlorophenyl)-1,4-dioxaspiro[4.4]nonan-2-yl)ethanol

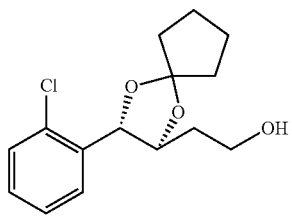 [SMILES: OCC[C@@H]1OC2(CCCC2)O[C@H]1c1ccccc1Cl]

The substantially same method as described in Preparation example 364 was conducted, except that 2-((2S, 3S)-3-(2-chlorophenyl)-1,4-dioxaspiro[4.4]nonan-2-yl)ethyl pivalate (Preparation example 365) was used instead of that 2-((4S, 5S)-2,2-diethyl-5-(2-chlorophenyl)-1,3-dioxolan-4-yl)ethyl pivalate (Preparation example 363), to obtain the title compound (0.4 g, 80~95%)

¹H NMR (400 MHz, CDCl₃): δ=1.72~1.90 (m, 4H), 1.93~1.98 (m, 6H), 2.28 (q, J=3.7, 1H), 3.76~3.93 (m, 3H), 5.18 (d, J=8.0, 1H), 7.24~7.29 (m, 1H), 7.32~7.38 (m, 2H), 7.60 (dd, J=1.8, 7.8, 1H)

Preparation Example 367: 2-((2S, 3S)-3-(2-chlorophenyl)-1,4-dioxaspiro[4.5]decan-2-yl)ethyl pivalate

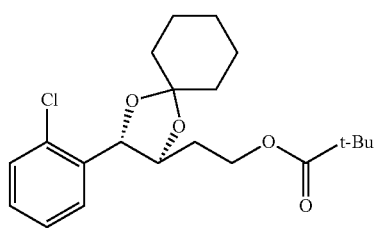 [SMILES: CC(C)(C)C(=O)OCC[C@@H]1OC2(CCCCC2)O[C@H]1c1ccccc1Cl]

The substantially same method as described in Preparation example 366 was conducted, except that cyclohexanone was used instead of cyclopetanone, to obtain the title compound (0.7 g, 60~85%)

¹H NMR (400 MHz, CDCl₃): δ=1.15 (s, 9H), 1.70~1.94 (m, 10H), 2.06~2.09 (m, 2H), 3.86 (dt, J=3.5, 8.5, 1H), 4.16~4.26 (m, 2H), 5.18 (d, J=8.4, 1H), 7.22~7.28 (m, 1H), 7.32~7.38 (m, 2H), 7.61 (dd, J=1.4, 7.8, 1H)

Preparation Example 368: 2-((2R, 3R)-3-(2-chlorophenyl)-1,4-dioxaspiro[4.5]decan-2-yl)ethanol

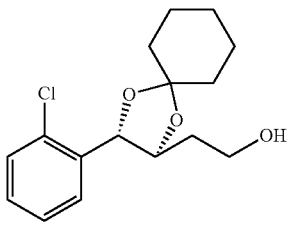 [SMILES: OCC[C@@H]1OC2(CCCCC2)O[C@H]1c1ccccc1Cl]

The substantially same method as described in Preparation example 366 was conducted, except that 2-((2S,3S)-3-(2-chlorophenyl)-1,4-dioxaspiro[4.5]decan-2-yl)ethyl pivalate (Preparation example 367) was used instead of that 2-((2S, 3S)-3-(2-chlorophenyl)-1,4-dioxaspiro[4.4]nonan-2-yl)ethyl pivalate (Preparation example 365), to obtain the title compound (0.4 g, 80~95%).

¹H NMR (400 MHz, CDCl₃): δ=1.42~1.50 (m, 2H), 1.63~1.77 (m, 5H), 1.82~1.89 (m, 5H), 2.41 (q, J=3.9, 1H), 3.78~3.96 (m, 3H), 5.25 (d, J=8.4, 1H), 7.21~7.28 (m, 1H), 7.32~7.38 (m, 2H), 7.63 (dd, J=1.4, 7.8, 1H)

Preparation Example 369: (E)-1-(3(benzyloxy)prop-1enyl)2-chlorobenzene

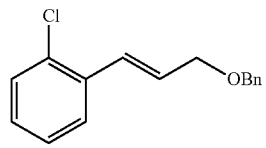 [SMILES: Clc1ccccc1/C=C/COCc1ccccc1]

To a solution of (E)-3-(2-chlorophenyl) prop-2-en-1-ol (Preparation example 1, 5.3 g, 31.6 mmole) in THF was added NaH (60% in mineral oil, 0.91 g, 37.7 mmole) and Benzyl bromide (4.12 mL, 34.8 mmole), sequentially at 0° C. The reaction mixture was stirred at room temperature for 18 hr. The TLC showed complete consumption of SM. The reaction mixture was quenched with H₂O at 0° C. then extracted with EtOAc. The aqueous layer was extracted with EtOAc and separated. The combined organic layer was washed with H₂O, then dried over MgSO₄ and evaporated under reduced pressure. The crude compound was purified by silica gel column to produce the title compound (4.94 g, 70~90%).

¹H NMR (400 MHz, CDCl₃) δ 7.57 (dd, J=7.76, 2, 1H), 7.42-7.13 (m, 3H), 7.05 (d, J=16 Hz, 1H), 6.37-6.30 (m, 1H), 4.62 (s, 2H), 4.26 (dd, J=6, 1.6, 2H).

Preparation Example 370: (±)-2-(benzyloxymethyl)-3-(2-chlorophenyl)oxirane

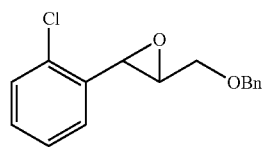 [SMILES: Clc1ccccc1C1OC1COCc1ccccc1]

To a solution of (E)-1-(3-(benzyloxy)prop-1-enyl)-2-chlorobenzene (Preparation example 369, 4.94 g, 22 mmole) in CH$_2$Cl$_2$ (110 mL) was added 3-chloroperoxybenzoic acid (70~75%, 8 g, 33 mmole) portionwise at 0° C. The mixture was stirred for 18 hr at room temperature. The TLC showed complete consumption of SM. The reaction mixture was quenched with H$_2$O at 0° C. then extracted with EtOAc. The aqueous layer was extracted with EtOAc and separated. The combined organic layer was washed with sat' NaHCO$_3$, H$_2$O, then dried over MgSO$_4$ and evaporated under reduced pressure. The crude compound was purified by silica gel column to produce the title compound (4.3 g, 60~80%).

$^1$H NMR (400 MHz, CDCl$_3$) δ 7.42-7.24 (n, 9H), 4.68 (d, J=14.8, 2H), 4.18 (d, J=2 Hz, 1H), 3.96 (dd, J=11.6, 2.8 Hz, 1H), 3.69-3.64 (m, 1H), 3.14 (qt, J=2.4 Hz, 1H)

Preparation Example 371: (±)-3-(benzyloxy)-1-(2-chlorophenyl)-2-hydroxypropyl & (±)-3-(benzyloxy)-1-(2-chlorophenyl)-1-hydroxypropan-2-yl acetate

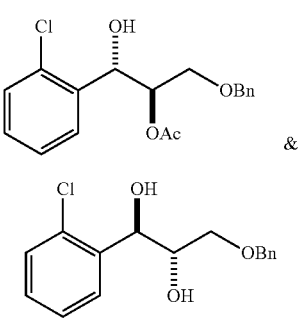

To a solution of (±)-2-(benzyloxymethyl)-3-(2-chlorophenyl)oxirane (Preparation example 370, 4.3 g, 15.6 mmole) in Acetic acid (78 mL) was added Cerium Ammonium Nitrate (1.71 g, 3.1 mmole) at room temperature. The mixture was stirred for 18 hr at room temperature. The TLC showed complete consumption of SM. The reaction mixture was quenched with sat' NaHCO$_3$ to pH7 at 0° C. then extracted with EtOAc. The aqueous layer was extracted with EtOAc and separated. The combined organic layer was washed with H$_2$O, then dried over MgSO$_4$ and evaporated under reduced pressure. The crude compound was purified by silica gel column to produce the title compound (1) (1.2 g, 23%). (2)(1.8 g, 34%).

(1) $^1$H NMR (400 MHz, CDCl$_3$) δ 7.55-7.22 (m, 9H), 5.41 (t, J=5 Hz, 1H), 5.33-5.29 (m, 1H), 4.61-4.47 (m, 2H), 3.70-3.63 (m, 2H, —OH), 2.09 (s, 3H).

(2) $^1$H NMR (400 MHz, CDCl$_3$) δ 7.46-7.24 (m, 9H), 6.31 (d. J=5.6 Hz, 1H), 4.55 (d, J=9.6 Hz, 2H), 4.24-4.22 (m, 1H), 3.67-3.55 (m, 2H), 2.52 (d, J=5.2 Hz, —OH), 2.10 (s, 3H).

Preparation Example 372: (±)-3-(benzyloxy)-1-(2-chlorophenyl)propane-1,2-diol(Anti mixture)

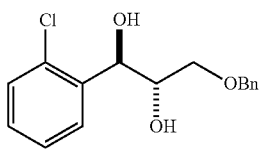 [SMILES: O[C@H](c1ccccc1Cl)[C@@H](O)COCc1ccccc1]

To a solution of (±)-3-(benzyloxy)-1-(2-chlorophenyl)-2-hydroxypropyl and (±)-3-(benzyloxy)-1-(2-chlorophenyl)-1-hydroxypropan-2-yl acetate (Preparation example 371, 3 g, 8.9 mmole) in MeOH (36 mL) and H$_2$O (4 mL) was added K$_2$CO$_3$ (3.69 g, 26.7 mmole) at 0° C. The mixture was stirred for 1.5 hr at 0° C. The TLC showed complete consumption of SM. The reaction mixture was quenched with H$_2$O at 0° C. then extracted with EtOAc. The aqueous layer was extracted with EtOAc and separated. The combined organic layer was washed with H$_2$O, then dried over MgSO$_4$ and evaporated under reduced pressure. The crude compound was purified by silica gel column to produce the title compound (2.4 g, 80~95%).

$^1$H NMR (400 MHz, CDCl$_3$) δ 7.50 (dd, J=7.6, 1.2 Hz, 1H), 7.35-7.19 (m, 8H), 5.28 (t, J=4.8 Hz, 1H), 4.46 (d, J=6 Hz, 2H), 4.18-4.13 (m, 1H), 3.55-3.42 (m, 3H, —OH), 3.02 (d, J=5.2 Hz, —OH).

Preparation Example 373: (±)-4-(benzyloxymethyl)-5-(2-chlorophenyl)-2,2-dimethyl-1,3-dioxolane

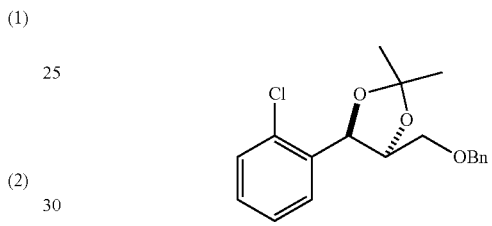

To a solution of (±)-3-(benzyloxy)-1-(2-chlorophenyl)propane-1,2-diol (Preparation example 372, 2.4 g, 8.2 mmole) in CH$_2$Cl$_2$ (40 mL) was added p-toluenesulfonyl chloride (15.2 g, 0.08 mole), and 2,2-dimethoxypropan (8.4 mL, 9.84 mmole) at 0° C. sequentially. The mixture was stirred for 1.5 hr at room temperature. The TLC showed complete consumption of SM. The reaction mixture was quenched with H$_2$O then extracted with EtOAc. The aqueous layer was extracted with EtOAc and separated. The combined organic layer was washed with H$_2$O, then dried over MgSO$_4$ and evaporated under reduced pressure. The crude compound was purified by silica gel column to produce the title compound (2.2 g, 75~90%).

$^1$H NMR (400 MHz, CDCl$_3$) δ 7.61 (dd, J=7.4, 1.6 Hz, 1H), 7.35-7.16 (m, 8H), 5.63 (d, J=6.8, 1H), 4.83-4.78 (m, 1H), 4.26 (d, J=12 Hz, 2H), 3.14-3.06 (m, 2H), 1.66 (s, 3H), 1.53 (s, 3H).

Preparation Example 374: 5-(2-chlorophenyl)-2,2-dimethyl-1,3-dioxolan-4-yl)methanol (SR & RS mixture)

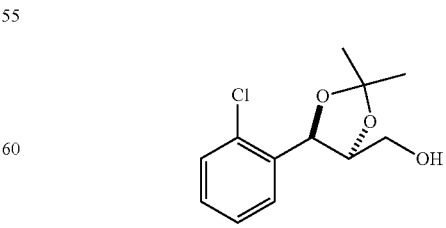

To a solution of (±)-4-(benzyloxymethyl)-5-(2-chlorophenyl)-2,2-dimethyl-1,3-dioxolane (Preparation example 375, 2.2 g, 6.6 mmole) in EtOAc (33 mL) was added 10% Pd/C on carbon (0.11 g) at room temperature. The mixture was stirred for 1 hr at room temperature under H₂ (g). The TLC showed complete consumption of SM. The reaction mixture was filtered through celite pad then evaporated under reduced pressure. The crude compound was purified by silica gel column to produce the title compound (1.5 g, 80~95%).

¹H NMR (400 MHz, CDCl₃) δ 7.61 (dd, J=7.4, 1.6, 1H), 7.35-7.16 (m, 8H), 5.63 (d, J=6.8 Hz, 1H), 4.83-4.78 (m, 1H), 4.26 (d, J=12, 2H), 3.14-3.06 (m, 2H), 1.66 (s, 3H), 1.53 (s, 3H).

Preparation Example 375: (2R,3R)-2-(benzyloxymethyl)-3-(2-chlorophenyl)oxirane

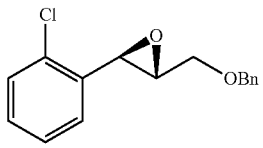 [SMILES: Clc1ccccc1[C@H]1O[C@@H]1COCc1ccccc1]

To a solution of (E)-1-(3-(benzyloxy)prop-1-enyl)-2-chlorobenzene (Preparation example 369, 4.16 g, 18.58 mmole) and 1,2:4,5-di-O-isopropylidene-β-D-erythro-2,3-hexodiulo-2,6-pyranose (5.76 g, 22.30 mmole) in ACN-DMM (3:1, v/v) (185 mL) was added buffer (0.2M K₂CO₃—AcOH in 4×10⁻⁴ M aq. EDTA, buffer pH=8.0) (185 mL) and Bu₄NHSO₄, (0.26 g, 0.75 mmole). After the mixture was cooled to 0° C., a solution of Oxone (15.76 g, 25.64 mmole) in 4×10⁻⁴M aq. EDTA (100 mL) and a solution of K₂CO₃ (13.6 g, 98.47 mmole) H₂O (100 mL) were added dropwise separately over a period of 3.5 hr via a syringe pump at 0° C. The reaction mixture was stirred for 14 hr at 0° C. The reaction mixture was quenched with H₂O then extracted with EtOAc. The aqueous layer was extracted with EtOAc and separated. The combined organic layer was washed with H₂O then dried over MgSO₄ and evaporated under reduced pressure The crude compound was purified by silica gel column to produce the title compound (2.9 g, 50~65%).

¹H NMR (400 MHz, CDCl₃) δ 3.14 (qt, J=2.4 Hz, 1H), 3.69-3.64 (m, 1H), 3.96 (dd, J=11.6, 2.8 Hz, 1H), 4.18 (d, J=2 Hz, 1H), 4.68 (d, J=14.8, 2H), 7.42-7.24 (m, 9H),

Preparation Example 376: (1S, 2R)-3-(benzyloxy)-1-(2-chlorophenyl)-2-hydroxypropyl acetate

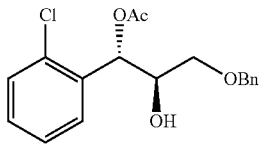 [SMILES: CC(=O)O[C@@H](c1ccccc1Cl)[C@H](O)COCc1ccccc1]

To a solution of (2R,3R)-2-(benzyloxymethyl)-3-(2-chlorophenyl)oxirane (Preparation example 375, 2.9 g, 10.55 mmole) in Acetic acid (55 mL) was added Cerium Ammonium Nitrate (1.15 g, 2.11 mmole) at room temperature. The mixture was stirred for 18 hr at room temperature. The TLC showed complete consumption of SM. The reaction mixture was quenched with sat' NaHCO₃ to pH7 at 0° C. then extracted with EtOAc. The aqueous layer was extracted with EtOAc and separated. The combined organic layer was washed with H₂O, then dried over MgSO₄ and evaporated under reduced pressure. The crude compound was purified by silica gel column to produce the title compound (1.2 g, 30~50%).

¹H NMR (400 MHz, CDCl₃) δ 2.10 (s, 3H), 2.52 (d, J=5.2 Hz, —OH), 3.67-3.55 (m, 2H), 4.24-4.22 (m, 1H), 4.55 (d, J=9.6 Hz, 2H), 6.31 (d, J=5.6 Hz, 1H), 7.46-7.24 (m, 9H).

Preparation Example 377: (1S, 2R)-3-(benzyloxy)-1-(2-chlorophenyl)propane-1.2-diol

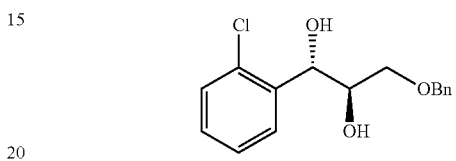

To a solution of (1S, 2R)-3-(benzyloxy)-1-(2-chlorophenyl)-2-hydroxypropyl acetate (Preparation example 376, 1.2 g, 3.58 mmole) in MeOH (16.2 mL) and H₂O (1.8 mL) was added K₂CO₃ (1.48 g, 10.74 mmole) at 0° C. The mixture was stirred for 1.5 hr at 0° C. The TLC showed complete consumption of SM. The reaction mixture was quenched with H₂O at 0° C. then extracted with EtOAc. The aqueous layer was extracted with EtOAc and separated. The combined organic layer was washed with H₂O, then dried over MgSO₄ and evaporated under reduced pressure. The crude compound was purified by silica gel column to produce the title compound (1.0 g, 80~100%).

¹H NMR (400 MHz, CDCl₃) δ 3.02 (d, J=5.2 Hz, 1H), 3.55-3.42 (m, 3H, —OH), 4.18-4.13 (m, 1H), 4.46 (d, J=6 Hz, 2H), 5.28 (t, J=4.8 Hz, 1H), 7.35-7.19 (m, 8H), 7.50 (dd, J=7.6, 1.2 Hz, 1H).

Preparation Example 378: (4R, 5S)-4-(benzyloxymethyl)-5-(2-chlorophenyl)-2.2-dimethyl-1,3-dioxolane

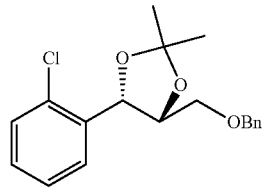 [SMILES: CC1(C)O[C@H](COCc2ccccc2)[C@H](c2ccccc2Cl)O1]

The substantially same method as described in Preparation example 373 was conducted, except that (1S, 2R)-3-(benzyloxy)-1-(2-chlorophenyl)propane-1,2-diol (Preparation example 377) was used instead of that (±)-3-(benzyloxy)-1-(2-chlorophenyl)propane-1,2-diol (Preparation example 372), to obtain the title compound (0.77 g, 80~100%).

¹H NMR (400 MHz, CDCl₃) δ 1.53 (s, 3H), 1.66 (s, 3H), 3.14-3.06 (m, 2H), 4.26 (d, J=12 Hz, 2H), 4.83-4.78 (m, 1H), 5.63 (d, J=6.8, 1H) 7.35-7.16 (m, 8H), 7.61 (dd, J=7.4, 1.6 Hz, 1H).

Preparation Example 379: ((4R, 5S)-5-(2-chlorophenyl)-2,2-dimethyl-1,3-dioxolan-4-yl)methanol

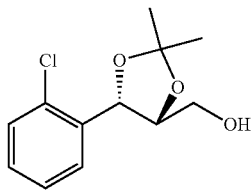 [SMILES: CC1(C)O[C@H](CO)[C@H](c2ccccc2Cl)O1]

The substantially same method as described in Preparation example 374 was conducted, except that ((4R, 5S)-4-(benzyloxymethyl)-5-(2-chlorophenyl)-2,2-dimethyl-1,3-dioxolane (Preparation example 378) was used instead of that (±)-4-(benzyloxymethyl)-5-(2-chlorophenyl)-2,2-dimethyl-1,3-dioxolane (Preparation example 373), to obtain the title compound (0.58 g, 80~100%).

$^1$H NMR (400 MHz, CDCl$_3$) δ 1.66 (s, 3H), 1.53 (s, 3H), 3.14-3.06 (m, 2H), 4.26 (d, J=12, 2H), 4.83-4.78 (m, 1H), 5.63 (d, J=6.8 Hz, 1H), 7.35-7.16 (m, 8H), 7.61 (dd, J=7.4, 1.6, 1H).

Preparation Example 380: (E)-ethyl 3-(2,4-dichlorothiazol-5-yl)acrylate

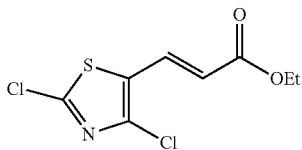 [SMILES: CCOC(=O)/C=C/c1sc(Cl)nc1Cl]

To a stirred solution of 2,4-dichlorothiazole-5-carbaldehyde (5.0 g, 27.5 mmol) in THF (200 mL) was added triethylphosphonoacetate (6.6 mL, 32.9 mmol) and Lithiumhydroxide (0.79 mL, 32.9 mmol), 4A molecular sieve 5 g at room temperature under N$_2$. The mixture was stirred for 3 h. The resulting mixture was diluted with EtOAc, washed with water, dried over anhydrous magnesium sulfate (MgSO$_4$), filtered, and concentrated under reduced pressure. The crude compound was purified by a silica gel column to produce the title compound (6.1 g, 80~95%)

$^1$H NMR (400 MHz, DMSO): δ=1.22 (q, J=12.5, 3H), 4.23 (q, J=7.0, 2H), 6.54 (d, J=16, 1H), 7.54 (d, J=16, 1H).

Preparation Example 381: (2S,3S)-ethyl 3-(2,4-dichlorothiazol-5-yl)-2,3-dihydroxypropanoate

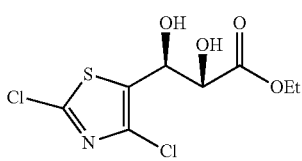 [SMILES: CCOC(=O)[C@@H](O)[C@H](O)c1sc(Cl)nc1Cl]

The substantially same method as described in Preparation Example 3 was conducted, except that (E)-ethyl 3-(2,4-dichlorothiazol-5-yl)acrylate (Preparation example 380) was used instead of (E)-1-chloro-2-(3-(methoxymethoxy)prop-1-enyl)benzene (Preparation example 2), to obtain the title compound (3.94 g, 50~70%); $^1$H NMR (400 MHz, DMSO): δ=1.22 (q, J=12.5, 3H), 4.18 (q, J=7.0, 2H), 4.20 (dd, J=2.4, J=7.6, 1H), 5.19 (dd, J=2.6, J=5.8, 1H), 6.03 (d, J=7.6, 1H), 6.37 (d, J=5.6, 1H).

Preparation Example 382: (4S,5S)-ethyl 5-(2,4-dichlorothiazol-5-yl)-2,2-dimethyl-1,3-dioxolane-4-carboxylate

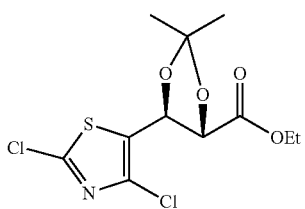 [SMILES: CCOC(=O)[C@H]1OC(C)(C)O[C@@H]1c1sc(Cl)nc1Cl]

The substantially same method as described in Preparation example 26 was conducted, except that (2S,3S)-ethyl 3-(2,4-dichlorothiazol-5-yl)-2,3-dihydroxypropanoate (Preparation example 381) was used instead of (2S,3R)-methyl-3-(2-chlorophenyl)-2,3-dihydroxypropanoate (Preparation example 25), to obtain the title compound (0.13 g, 65~80%)

$^1$H NMR (400 MHz, DMSO): δ=1.20 (t, J=7.2, 3H), 1.42 (s, 3H), 1.49 (s, 3H), 4.18 (m, 2H), 4.66 (d, J=6.8, 1H), 5.44 (d, J=6.8, 1H).

Preparation Example 383: ((4R,5S)-5-(2,4-dichlorothiazol-5-yl)-2,2-dimethyl-1,3-dioxolan-4-yl)methanol

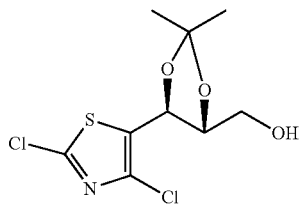 [SMILES: CC1(C)O[C@H](c2sc(Cl)nc2Cl)[C@@H](CO)O1]

The substantially same method as described in Preparation example 27 was conducted, except that (4R,5S)-ethyl 5-(2,4-dichlorothiazol-5-yl)-2,2-dimethyl-1,3-dioxolane-4-carboxylate (Preparation example 382) was used instead of (4S,5R)-methyl-5-(2-chlorophenyl)-2,2-dimethyl-1.3-dioxolane-4-carboxylate (Preparation example 26), to obtain the title compound (0.05 g, 50~70%)

$^1$H NMR (400 MHz, DMSO): δ=1.42 (d, J=6.0, 6H), 3.59 (m, 1H), 3.67 (m, 1H), 3.97 (m, 1H), 5.04 (t, J=5.4, 1H), 5.10 (d, J=8.4, 1H).

Preparation Example 384: (2R, 3R)-ethyl 3-(2,4-dichlorothiazol-5-yl)-2,3-dihydroxypropanoate

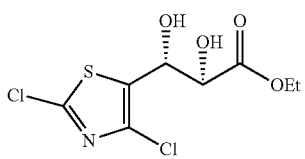 [SMILES: CCOC(=O)[C@H](O)[C@@H](O)c1sc(Cl)nc1Cl]

The substantially same method as described in Preparation Example 381 was conducted, except that (DHQ)₂-PHAL was used instead of (DHQD)₂-PHAL, to obtain the title compound (3.9 g, 50~70%).

¹H NMR (400 MHz, DMSO): δ=1.22 (q, J=12.5, 3H), 4.18 (q, J=7.0, 2H), 4.20 (dd, J=2.4, J=7.6, 1H), 5.19 (dd, J=2.6, J=5.8, 1H), 6.03 (d, J=7.6, 1H), 6.37 (d, J=5.6, 1H).

Preparation Example 385: (4R, 5R)-ethyl 5-(2,4-dichlorothiazol-5-yl)-2,2-dimethyl-1,3-dioxolane-4-carboxylate

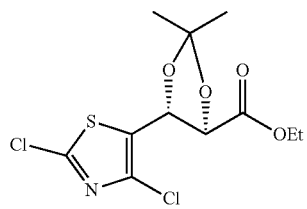 [SMILES: CCOC(=O)[C@@H]1OC(C)(C)O[C@H]1c1sc(Cl)nc1Cl]

The substantially same method as described in Preparation Example 382 was conducted, except that (2R, 3R)-ethyl 3-(2,4-dichlorothiazol-5-yl)-2,3-dihydroxypropanoate (Preparation example 384) was used instead of (2S, 3S)-ethyl 3-(2,4-dichlorothiazol-5-yl)-2,3-dihydroxypropanoate (Preparation example 381), to obtain the title compound (0.13 g, 65~80%).

¹H NMR (400 MHz, DMSO): δ=1.20 (t, J=7.2, 3H), 1.42 (s, 3H), 1.49 (s, 3H), 4.18 (m, 2H), 4.66 (d, J=6.8, 1H), 5.44 (d, J=6.8, 1H).

Preparation Example 386: ((4S, 5R)-5-(2,4-dichlorothiazol-5-yl)-2,2-dimethyl-1,3-dioxolan-4-yl)methanol

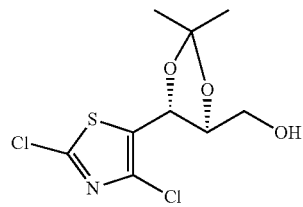 [SMILES: CC1(C)O[C@@H](CO)[C@H](c2sc(Cl)nc2Cl)O1]

The substantially same method as described in Preparation Example 383 was conducted, except that (4R, 5R)-ethyl 5-(2,4-dichlorothiazol-5-yl)-2,2-dimethyl-1,3-dioxolane-4-carboxylate (Preparation example 385) was used instead of (4S, 5S)-ethyl 5-(2,4-dichlorothiazol-5-yl)-2,2-dimethyl-1,3-dioxolane-4-carboxylate (Preparation example 382), to obtain the title compound (0.05 g, 50~70%).

¹H NMR (400 MHz, DMSO): δ=1.42 (d, J=6.0, 6H), 3.59 (m, 1H), 3.67 (m, 1H), 3.97 (m, 1H), 0.5.04 (t, J=5.4, 1H), 5.10 (d, J=8.4, 1H).

Preparation Example 387: (E)-ethyl 3-(2-chlorothiazol-5-yl)acrylate

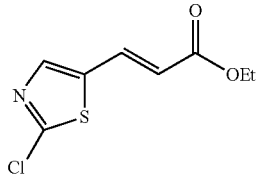 [SMILES: CCOC(=O)/C=C/c1cnc(Cl)s1]

The substantially same method as described in Preparation Example 380 was conducted, except that 2-chlorothiazole-5-carbaldehyde was used instead of 2,4-dichlorothiazole-5-carbaldehyde, to obtain the title compound (4.7 g, 80~95%)

¹H NMR (400 MHz, DMSO): δ=1.25 (t, J=7.0, 3H), 4.19 (q, J=7.2, 2H), 6.40 (d, J=16, 1H), 7.81 (d, J=16, 1H), 8.11 (s, 1H)

Preparation Example 388: (2S,3S)-ethyl-3-(2-chlorothiazol-5-yl)-2,3-dihydroxypropanoate

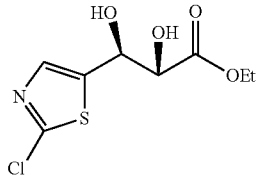 [SMILES: CCOC(=O)[C@@H](O)[C@H](O)c1cnc(Cl)s1]

The substantially same method as described in Preparation Example 381 was conducted, except that (E)-ethyl 3-(2-chlorothiazol-5-yl)acrylate (Preparation example 387) was used instead of (E)-ethyl 3-(2,4-dichlorothiazol-5-yl) acrylate (Preparation example 380), to obtain the title compound (4.1 g, 50~70%).

¹H NMR (400 MHz, DMSO): δ=1.20 (t, J=7.0, 3H), 4.12 (q, J=7.2, 2H), 5.18 (d, J=1.6, 1H), 5.87 (s, 1H), 6.12 (s, 1H), 7.63 (s, 1H).

Preparation Example 389: (4S,5S)-ethyl-5-(2-chlorothiazol-5-yl)-2,2-dimethyl-1,3-dioxolane-4-carboxylate

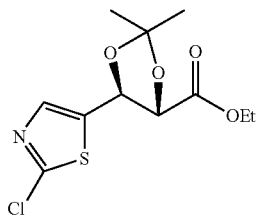 [SMILES: CCOC(=O)[C@H]1OC(C)(C)O[C@@H]1c1cnc(Cl)s1]

The substantially same method as described in Preparation Example 382 was conducted, except that (2S, 3S)-ethyl 3-(2-chlorothiazol-5-yl)-2,3-dihydroxypropanoate (Preparation example 388) was used instead of (2S, 3S)-ethyl 3-(2,4-dichlorothiazol-5-yl)-2,3-dihydroxypropanoate (Preparation example 381), to obtain the title compound (1.0 g, 65~80%).

¹H NMR (400 MHz, DMSO): δ=1.44 (d, J=16.8, 3H), 4.18 (m, 2H), 4.62 (d, J=7.6, 1H), 5.50 (d, J=7.2, 1H), 7.74 (s, 1H).

Preparation Example 390: (4R, 5S)-5-(2-chlorothiazol-5-yl)2,2-dimethyl-1,3-dioxolan-4-yl)methanol

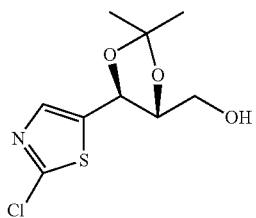

The substantially same method as described in Preparation Example 386 was conducted, except that (4S, 5S)-ethyl 5-(2-chlorothiazol-5-yl)-2,2-dimethyl-1,3-dioxolane-4-carboxylate (Preparation example 389) was used instead of (4R, 5R)-ethyl 5-(2,4-dichlorothiazol-5-yl)-2,2-dimethyl-1,3-dioxolane-4-carboxylate (Preparation example 385), to obtain the title compound (0.84 g, 70~90%).

¹H NMR (400 MHz, DMSO): δ=1.40 (d, J=2.0, 6H), 3.59 (q, J=4.7, 2H), 3.94 (m, 1H), 5.06 (t, J=6.6, 1H), 5.09 (d, J=0.8, 1H), 7.69 (s, 1H).

Preparation Example 391: (2S, 3R)-ethyl 3-(2-chlorothiazol-5-yl)-2,3-dihydroxypropanoate

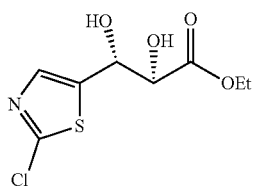

The substantially same method as described in Preparation Example 384 was conducted, except that (E)-ethyl-3-(2-chlorothiazol-5-yl)acrylate (Preparation example 387) was used instead of (E)-ethyl 3-(2,4-dichlorothiazol-5-yl)acrylate (Preparation example 380), to obtain the title compound (3.9 g, 50~70%).

¹H NMR (400 MHz, DMSO): δ=1.20 (t, J=7.0, 3H), 4.12 (q, J=7.2, 2H), 5.18 (d, J=1.6, 1H), 5.87 (s, 1H), 6.12 (s, 1H), 7.63 (s, 1H).

Preparation Example 392: (4R, 5R)-ethyl-5-(2-chlorothiazol-5-yl)-2,2-dimethyl-1,3-dioxolane-4-carboxylate

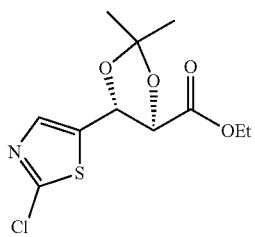 [SMILES: CCOC(=O)[C@@H]1OC(C)(C)O[C@H]1c1cnc(Cl)s1]

The substantially same method as described in Preparation Example 382 was conducted, except that (2R, 3R)-ethyl-3-(2-chlorothiazol-5-yl)-2,3-dihydroxypropanoate (Preparation example 391) was used instead of (2S, 3S)-ethyl 3-(2,4-dichlorothiazol-5-yl)-2,3-dihydroxypropanoate (Preparation example 381), to obtain the title compound (0.73 g, 65~80%).

¹H NMR (400 MHz, DMSO): δ=1.44 (d, J=16.8, 3H), 4.18 (m, 2H), 4.62 (d, J=7.6, 1H), 5.50 (d, J=7.2, 1H), 7.74 (s, 1H).

Preparation Example 393: (43, 5R)-5-(2-chlorothiazol-5-yl)2,2-dimethyl-1,3-dioxolan-4-yl)methanol

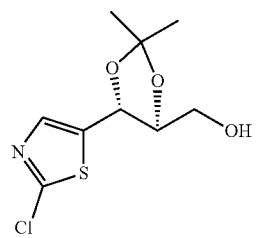

The substantially same method as described in Preparation Example 386 was conducted, except that (4R, 5R)-ethyl-5-(2-chlorothiazol-5-yl)-2,2-dimethyl-1,3-dioxolane-4-carboxylate (Preparation example 392) was used instead of (4R, 5R)-ethyl 5-(2,4-dichlorothiazol-5-yl)-2,2-dimethyl-1,3-dioxolane-4-carboxylate (Preparation example 385), to obtain the title compound (0.60 g, 70~90%).

¹H NMR (400 MHz, DMSO): δ=1.40 (d, J=2.0, 6H), 3.59 (q, J=4.7, 2H), 3.94 (m, 1H), 5.06 (t, J=6.6, 1H), 5.09 (d, J=0.8, 1H), 7.69 (s, 1H).

Preparation Example 394: (E)-ethyl-3-(4-methylthiazol-5-yl)acrylate

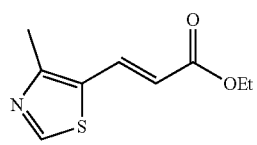

The substantially same method as described in Preparation Example 380 was conducted, except that 4-methylthiazole-5-carbaldehyde was used instead of 2,4-dichlorothiazole-5-carbaldehyde, to obtain the title compound (15 g, 80~95%)

¹H NMR (400 MHz, DMSO): δ=1.25 (t, J=7.0, 3H), 1.45 (s 3H), 4.19 (q, J=7.0, 2H), 6.12 (d, J=16, 1H), 7.77 (d, J=16, 1H), 9.09 (s, 1H).

Preparation Example 395: (2S,3S)-ethyl-3-(4-methylthiazol-5-yl)-2,3-dihydroxypropanoate

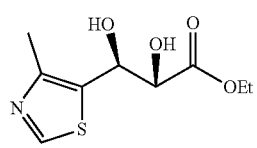

The substantially same method as described in Preparation Example 2 was conducted, except that (E)-ethyl-3-(4-methylthiazol-5-yl)acrylate (Preparation example 394) was used instead of (E)-ethyl-3-(2,4-dichlorothiazol-5-yl)acrylate (Preparation example 381), to obtain the title compound (4.0 g, 50~70%).

$^1$H NMR (400 MHz, DMSO): δ=1.11 (t, J=7.0, 3H), 1.43 (s, 3H), 4.04 (m, 2H), 5.11 (t, J=3.8, 1H), 5.70 (d, J=20.7, 1H), 5.92 (d, J=4.0, 1H), 6.81 (s, 1H), 8.86 (s, 1H).

Preparation Example 396: (4S,5S)-ethyl-5-(4-methylthiazol-5-yl)-2,2-dimethyl-1,3-dioxolane-4-carboxylate

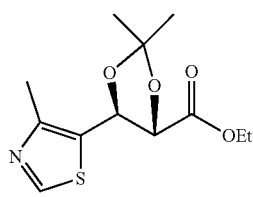 [SMILES: CCOC(=O)[C@H]1OC(C)(C)O[C@@H]1c1scnc1C]

The substantially same method as described in Preparation Example 382 was conducted, except that (2S, 3S)-ethyl-3-(4-methylthiazol-5-yl)-2,3-dihydroxypropanoate (Preparation example 395) was used instead of (2S, 3S)-ethyl 3-(2,4-dichlorothiazol-5-yl)-2,3-dihydroxypropanoate (Preparation example 381), to obtain the title compound (2.6 g, 55~70%).

$^1$H NMR (400 MHz, DMSO): δ=1.17 (t, J=3.6, 3H), 1.43 (S, 3H), 1.49 (s, 3H), 2.34 (s, 3H), 4.17 (q, J=7.0 2H), 4.40 (d, J=14.0, 1H), 5.53 (d, J=7.2, 1H), 9.01 (s, 1H).

Preparation Example 397: (4R, 5S)-5-(4-methylthiazol-5-yl)2,2-dimethyl-1,3-dioxolan-4-yl)methanol

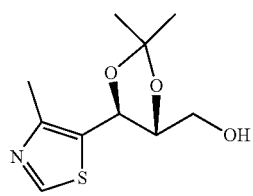

The substantially same method as described in Preparation Example 386 was conducted, except that (4S, 5S)-ethyl-5-(4-methylthiazol-5-yl)-2,2-dimethyl-1,3-dioxolane-4-carboxylate (Preparation example 396) was used instead of (4R, 5R)-ethyl 5-(2,4-dichlorothiazol-5-yl)-2,2-dimethyl-1,3-dioxolane-4-carboxylate (Preparation example 385), to obtain the title compound (1.7 g, 70~90%).

$^1$H NMR (400 MHz, DMSO): δ=1.42 (d, J=7.6, 6H), 2.36 (s, 3H), 3.58 (m, 2H), 3.80 (d, J=3.2, 1H), 5.02 (t, J=5.4, 1H), 5.17 (d, J=8.4, 1H), 8.98 (s, 1H).

Preparation Example 398: (2R, 3R)-ethyl-3-(4-methylthiazol-5-yl)-2,3-dihydroxypropanoate

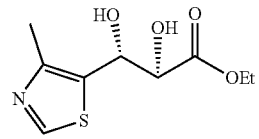

The substantially same method as described in Preparation Example 384 was conducted, except that (E)-ethyl-3-(4-methylthiazol-5-yl)acrylate (Preparation example 394) was used instead of (E)-ethyl13-(2,4-dichlorothiazol-5-yl)acrylate (Preparation example 380), to obtain the title compound (6.0 g, 50~70%).

$^1$H NMR (400 MHz, DMSO): δ=1.11 (t, J=7.0, 3H), 1.43 (s, 3H), 4.04 (m, 2H), 5.11 (t, J=3.8, 1H), 5.70 (d, J=20.7, 1H), 5.92 (d, J=4.0, 1H), 6.81 (s, 1H), 8.86 (s, 1H).

Preparation Example 399: (4R, 5R)-ethyl-5-(4-methylthiazol-5-yl)-2,2-dimethyl-1,3-dioxolane-4-carboxylate

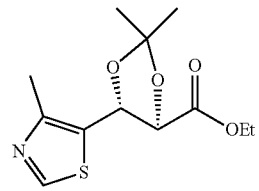 [SMILES: CCOC(=O)[C@@H]1OC(C)(C)O[C@H]1c1scnc1C]

The substantially same method as described in Preparation Example 382 was conducted, except that (2R, 3R)-ethyl-3-(4-methylthiazol-5-yl)-2,3-dihydroxypropanoate (Preparation example 398) was used instead of (2S, 3S)-ethyl 3-(2,4-dichlorothiazol-5-yl)-2,3-dihydroxypropanoate (Preparation example 381), to obtain the title compound (5.0 g, 65~80%).

$^1$H NMR (400 MHz, DMSO): δ=1.17 (t, J=3.6, 3H), 1.43 (S, 3H), 1.49 (s, 3H), 2.34 (s, 3H), 4.17 (q, J=7.0 2H), 4.40 (d, J=14.0, 1H), 5.53 (d, J=7.2, 1H), 9.01 (s, 1H).

Preparation Example 400: (4S, 5R)-5-(4-methylthiazol-5-yl)2,2-dimethyl-1,3-dioxolan-4-yl)methanol

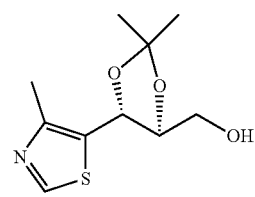

The substantially same method as described in Preparation Example 386 was conducted, except that (4R, 5R)-ethyl-5-(4-methylthiazol-5-yl)-2,2-dimethyl-1,3-dioxolane-4-carboxylate (Preparation example 399) was used instead of (4R, 5R)-ethyl-5-(2,4-dichlorothiazol-5-yl)-2,2-dimethyl-1,3-dioxolane-4-carboxylate (Preparation example 385), to obtain the title compound (4.1 g, 70~90%).

¹H NMR (400 MHz, DMSO): δ=1.42 (d, J=7.6, 6H), 2.36 (s, 3H), 3.58 (m, 2H), 3.80 (d, J=3.2, 1H), 5.02 (t, J=5.4, 1H), 5.17 (d, J=8.4, 1H), 8.98 (s, 1H).

Preparation Example 401: (4R, 5S)-ethyl-5-(2-chloro-4-methylthiazol-5-yl)-2,2-dimethyl-1,3-dioxolane-4-carboxylate

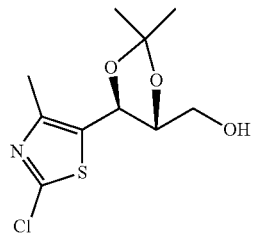 [SMILES: Cc1nc(Cl)sc1[C@H]1OC(C)(C)O[C@@H]1CO]

To a stirred solution of (4R, 5S)-5-(4-methylthiazol-5-yl) 2,2-dimethyl-1,3-dioxolan-4-yl)methanol (Preparation example 397, 3.1 g, 14.3 mmol) in THF (20 mL) was added n-Butyllithium (14.3 mL, 35.7 mmol) and CCl₄ (4.1 mL, 42.8 mmol) at −78° C. The mixture was stirred for 0.5 h. The resulting mixture was diluted with EtOAc, washed with water, dried over MgSO₄, filtered, and concentrated-under reduced pressure. The crude compound was purified by a silica gel column to produce the title compound (2.8 g, 70~90%)

¹H NMR (400 MHz, DMSO): δ=1.40 (d, J=5.6, 6H), 2.28 (s, 3H), 3.58 (m, 2H), 3.80 (m, 1H), 5.06 (m, 1H), 5.13 (d, J=8.4, 1H).

Preparation Example 402: (4S, 5R)-ethyl-5-(2-chloro-4-methylthiazol-5-yl)-2,2-dimethyl-1,3-dioxolane-4-carboxylate

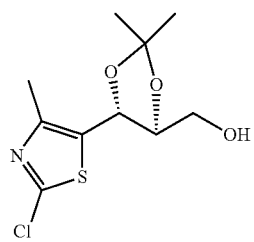 [SMILES: Cc1nc(Cl)sc1[C@@H]1OC(C)(C)O[C@H]1CO]

The substantially same method as described in Preparation. Example 401 was conducted, except that (4S, 5R)-5-(4-methylthiazol-5-yl)2,2-dimethyl-1,3-dioxolan-4-yl)methanol (Preparation example 400) was used instead of (4R, 5S)-5-(4-methylthiazol-5-yl)2,2-dimethyl-1,3-dioxolan-4-yl)methanol (Preparation example 397), to obtain the title compound (1.5 g, 70~90%).

¹H NMR (400 MHz, DMSO): δ=1.40 (d, J=5.6, 6H), 2.28 (s, 3H), 3.58 (m, 2H), 3.80 (m, 1H), 5.06 (m, 1H), 5.13 (d, J=8.4, 1H).

Preparation Example 403: (E)-ethyl 3-(thiophen-3-yl)acrylate

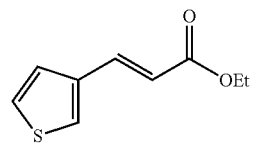 [SMILES: CCOC(=O)/C=C/c1ccsc1]

To a stirred solution of triethylphosphonoacetate (5.36 ml, 26.7 mmol) in THF (40 ml) was added to t-BuOK (3 g, 26.7 mmol) dropwise at rt and stirred at this temperature for 30 min. Then thiophene-3-carbaldehyde (3 g, 26.7 mmol) was added and stirred at 90° C. and stirred at this temperature for 30 min. The product was quenched with 1M HCl solution. The resulting mixture was extracted with ethyl acetate form water. The combined organic layer was dried (Na₂SO₄), filtered and concentrated. The residue was purified by silica gel column to produce the title compound (3.9 g, 70~90%).

¹H NMR (400 MHz, CDCl₃): δ=1.34 (t, J=7.2, 3H), 4.26 (q, J=7.2, 2H), 6.31 (d, J=15.6, 1H), 6.89 (d, J=4, 1H), 7.69 (s, 1H), 7.73 (d, J=4, 1H), 7.80 (d, J=15.6, 1H)

Preparation Example 404: (2R,3S)-ethyl 2,3-dihydroxy-3-(thiophen-3-yl)propanoate

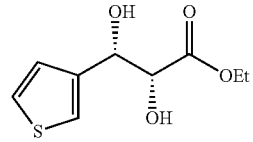 [SMILES: CCOC(=O)[C@H](O)[C@@H](O)c1ccsc1]

The substantially same method as described in Preparation Example 384 was conducted, except that (E)-ethyl 3-(thiophen-3-yl)acrylate (Preparation example 403) was used instead of (E)-ethyl3-(2,4-dichlorothiazol-5-yl)acrylate (Preparation example 380), to obtain the title compound (6.0 g, 60~80%).

¹H NMR (400 MHz, CDCl₃): δ=1.34 (t, J=7.2, 3H), 4.26 (q, J=7.2, 2H), 4.65 (d, J=5.5, 1H), 5.13 (d, J=5.5, 1H), 6.93 (dd, J=6.09, J=1.32, 1H), 7.47 (dd, J=6.09, J=1.73, 1H), 7.88 (dd, J=1.73, J=1.32, 1H)

Preparation Example 405: (4R,5S)-ethyl 2,2-dimethyl-5-(thiophen-3-yl)-1,3-dioxolane-4-carboxylate

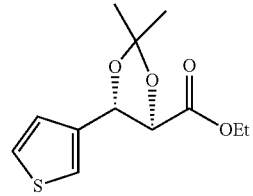 [SMILES: CCOC(=O)[C@@H]1OC(C)(C)O[C@H]1c1ccsc1]

The substantially same method as described in Preparation Example 382 was conducted, except that (2R,3S)-ethyl 2,3-dihydroxy-3-(thiophen-3-yl)propanoate (Preparation example 404) was used instead of (2S, 3S)-ethyl 3-(2,4- dichlorothiazol-5-yl)-2,3-dihydroxypropanoate (Preparation example 381), to obtain the title compound (3.0 g, 65~80%).

¹H NMR (400 MHz, CDCl₃): δ=1.18 (t, J=7.1, 3H), 1.41 (S, 3H), 1.43 (S, 3H), 4.16 (q, J=7.1, 2H), 4.21 (d, J=7.0, 1H), 4.94 (d, J=7.0, 1H) 6.95 (dd, J=6.0, J=1.3, 1H), 7.48 (dd, J=6.0, J=1.7, 1H), 7.90 (dd, J=1.7, J=1.3, 1H)

Preparation Example 406: ((4S,5S)-2,2-dimethyl-5-(thiophen-3-yl)-1,3-dioxolan-4-yl)methanol

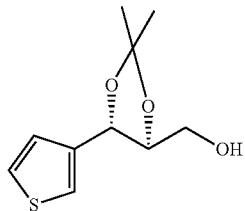

The substantially same method as described in Preparation Example 386 was conducted, except that (4R, 5R)-ethyl 2,2-dimethyl-5-(thiopheh-3-yl)-1,3-dioxolane-4-carboxylate (Preparation example 405) was used instead of (4R, 5R)-ethyl-5-(2,4-dichlorothiazol-5-yl)-2,2-dimethyl-1,3-dioxolane-4-carboxylate (Preparation example 385), to obtain the title compound (2.2 g, 70~90%).

¹H NMR (400 MHz, CDCl₃): δ=1.39 (S, 3H), 1.42 (S, 3H), 3.47~3.6 (m, 2H,) 3.84~3.88 (m, 1H) 4.82 (d, J=7.0, 1H), 6.93 (dd, J=6.1, J=1.3, 1H), 7.47 (dd, J=6.1, J=1.7, 1H,), 7.89 (dd, J=1.7, J=1.3, 1H)

Preparation Example 407: (E)-ethyl 3-(5-chlorothiophen-2-yl)acrylate

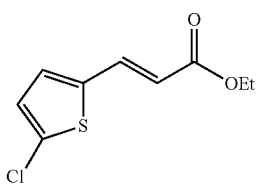 [SMILES: CCOC(=O)/C=C/c1ccc(Cl)s1]

The substantially same method as described in Preparation Example 403 was conducted, except that 5-chlorothiophene-2-carbaldehyde was used instead of thiophene-3-carbaldehyde, to obtain the title compound (4.0 g, 70~90%).

¹H NMR (400 MHz, CDCl₃): δ=1.36 (t, J=7.2, 3H), 4.20 (q, J=7.2, 2H), 6.13 (d, J=15.6, 1H), 6.89 (d, J=4, 1H), 7.65 (d, J=15.6, 1H), 7.83 (d, J=4.2, 1H)

Preparation Example 408: (2R,3S)-ethyl 2,3-dihydroxy-3-(5-chlorothiophen-2-yl)propanoate

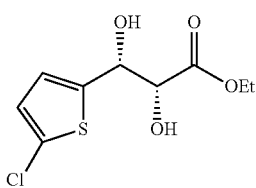 [SMILES: CCOC(=O)[C@H](O)[C@@H](O)c1ccc(Cl)s1]

The substantially same method as described in Preparation Example 404 was conducted, except that (E)-ethyl 3-(5-chlorothiophen-2-yl)acrylate (Preparation example 407) was used instead of (E)-ethyl 3-(thiophen-3-yl)acrylate (Preparation example 403), to obtain the title compound (2.8 g, 60~80%).

¹H NMR (400 MHz, CDCl₃) δ 1.34 (t, J=7.2, 3H), 2.76 (d, J=8.4, 1H), 3.32 (d, J=5.6, 1H), 4.33 (q, J=7.2 2H), 4.4 (dd, J=2.4 J=5.2 1H), 5.16 (dd, J=2 1=8, 1H), 6.82 (d, J=4, 1H), 6.88 (dd, J=0.8 J=3.6, 1H)

Preparation Example 409: (4R,5S)-ethyl 2,2-dimethyl-5-(5-chlorothiophen-2-yl)-1,3-dioxolane-4-carboxylate

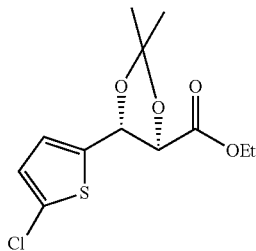 [SMILES: CCOC(=O)[C@@H]1OC(C)(C)O[C@H]1c1ccc(Cl)s1]

The substantially same method as described in Preparation Example 405 was conducted, except that (2R,3S)-ethyl 2,3-dihydroxy-3-(5-chlorothiophen-2-yl)propanoate (Preparation example 408) was used instead of (2R,3S)-ethyl 2,3-dihydroxy-3-(thiophen-3-yl)propanoate (Preparation example 404), to obtain the title compound (0.85 g, 65~80%).

¹H NMR (400 MHz, CDCl₃): δ=1.31 (t, J=7.2 3H), 1.54 (s, 3H), 1.58 (s, 3H), 4.29~4.36 (m, 2H), 4.42 (d, J=7.2 1H), 5.29 (d, J=7.2 1H), 6.81 (q, J=4 1H), 6.88 (d, J=3.2 1H)

Preparation Example 410: ((4S,5S)-2,2-dimethyl-5-(5-chlorothiophen-2-yl)-1,3-dioxolan-4-yl)methanol

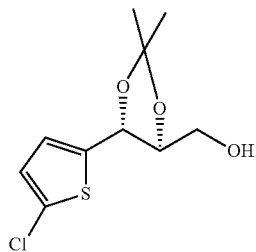

The substantially same method as described in Preparation Example 406 was conducted, except that (4R, 5R)-ethyl 2,2-dimethyl-5-(5-chlorothiophen-2-yl)-1,3-dioxolane-4-carboxylate (Preparation example 409) was used instead of (4R, 5R)-ethyl 2,2-dimethyl-5-(thiophen-3-yl)-1,3-dioxolane-4-carboxylate (Preparation example 405), to obtain the title compound (0.8 g, 70~90%).

¹H NMR (400 MHz, CDCl₃): δ=1.39 (S, 3H), 1.42 (S, 3H), 3.54~3.79 (m, 2H,) 4.28~4.42 (m, 1H), 5.17 (d, J=7.2, 1H), 6.47 (d, J=6.1, 1H,), 6.51 (d, J=6.1, 1H)

Preparation Example 411: 3-chloroisonicotinaldehyde

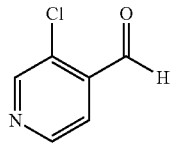

To a 250 ml round-bottomed flask, LDA (11 ml, 22.02 mmol) was added to 3-chloropyridine (1 g, 8.80 mmol) in THF (20 ml) dropwise at −78° C. and stirred at same temperature for 1~2 hr. Then DMF (822 μl, 10.56 mmol) was added and stirred at room temperature for 1 hr. EA (Ethyl acetate) and water were added to the reaction mixture, and after the separation of the layers, the aqueous phase was further extracted with the organic solvent. The combined organic extracts were dried over anhydrous Sodium sulfate (Na$_2$SO$_4$), filtered and concentrated under vacuum. The crude compound was purified by a silica gel column to produce the title compound (0.33 g, 30~65%)

$^1$H NMR (400 MHz, CDCl$_3$) δ 7.73 (d, J=8.0, 1H) 8.71 (d, J=4.0, 1H) 8.81 (s, 1H) 10.52 (s, 1H)

Preparation Example 412: (E)-ethyl 3-(3-chloropyridin-4-yl)acrylate

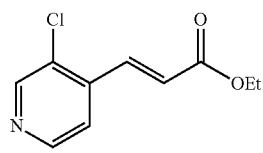

3-chloroisonicotinaldehyde (Preparation example 411, 0.54 g, 3.79 mmol) was dissolved in benzene. At the room temperature, triethyl phosphoacetate (753 μl, 3.79 mmol) and potassium tert-butoxide (468 mg, 4.17 mmol) were added and stirred. When the reaction was completed, the obtained product was washed with water and ethylacetate (EA). Then, the organic layer was dehydrated with anhydrous magnesium sulfate (MgSO$_4$), filtrated, and concentrated under reduced pressure. The crude compound was purified by a silica gel column to produce the title compound (0.57 g, 70~90%).

$^1$H NMR (400 MHz, CDCl$_3$) δ 1.40 (t, J=12, 3H) 4.13 (q, J=6.6, 2H) 6.61 (d, J=16.0, 1H) 7.46 (d, J=16.0, 1H) 7.97 (d J=8.0, 1H) 8.51 (d, J=4.0, 1H) 8.66 (s, 1H).

Preparation Example 413: Ethyl 3-(3-chloropyridin-4-yl)-2,3-dihydroxypropanoate

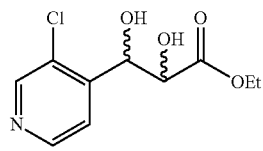 [SMILES: CCOC(=O)C(O)C(O)c1ccncc1Cl]

(E)-ethyl 3-(3-chloropyridin-4-yl)acrylate (Preparation example 412, 0.57 g, 2.69 mmol) was dissolved in the mixture of acetone (11.4 ml)/water (2.3 ml)/t-BuOH (2.3 ml). NMO (0.47 g, 4.03 mmol), Osmium tetroxide (13.6 mg, 0.05 mmol) were added thereto and stirred at 40° C. When the reaction was completed, the obtained product was washed with water and ethylacetate (EA). Then, the organic layer was dehydrated with anhydrous magnesium sulfate (MgSO$_4$), filtrated, and concentrated under reduced pressure. The crude compound was purified by a silica gel column to produce the title compound (0.44 g, 60~80%).

$^1$H NMR (400 MHz, CDCl$_3$) δ 1.28 (t, J=12.0, 3H) 4.15 (q, J=6.6, 2H) 4.26 (d, J=4.0, 1H) 5.24 (d, J=4.0, 1H) 5.44 (br s, 1H) 5.98 (br s, 1H) 7.59 (d, J=8.0, 1H) 8.52 (d, J=4.0, 1H) 8.56 (s, 1H)

Preparation Example 414: Ethyl 5-(3-chloropyridin-4-yl)-2,2-dimethyl-1,3-dioxolane-4-carboxylate

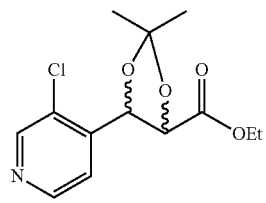 [SMILES: CCOC(=O)C1OC(C)(C)OC1c1ccncc1Cl]

The substantially same method as described in Preparation Example 405 was conducted, except that Ethyl 3-(3-chloropyridin-4-yl)-2,3-dihydroxypropanoate (Preparation example 413) was used instead of (2R,3S)-ethyl 2,3-dihydroxy-3-(thiophen-3-yl)propanoate (Preparation example 404), to obtain the title compound (5.26 g, 70~90%).

$^1$H NMR (400 MHz, CDCl$_3$) δ 1.28 (t, J=12.0, 3H) 1.61 (s, 3H) 1.65 (s, 3H) 4.23 (q, J=6.0 2H) 4.38 (d, J=7.2 1H) 5.67 (d, J=8.0, 1H) 7.55 (d, J=8.0, 1H) 8.56 (d, J=4.0, 1H) 8.57 (s, 1H)

Preparation Example 415: (5-(3-chloropyridin-4-yl)-2,2-dimethyl-1,3-dioxolan-4-yl)methanol

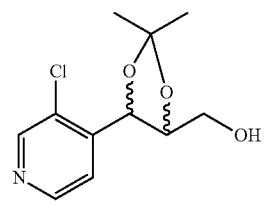 [SMILES: CC1(C)OC(CO)C(c2ccncc2Cl)O1]

The substantially same method as described in Preparation Example 406 was conducted, except that Ethyl 5-(3-chloropyridin-4-yl)-2,2-dimethyl-1,3-dioxolane-4-carboxylate (Preparation example 414) was used instead of (4R, 5R)-ethyl 2,2-dimethyl-5-(thiophen-3-yl)-1,3-dioxolane-4-carboxylate (Preparation example 405), to obtain the title compound (0.18 g, 70~90%).

$^1$H NMR (400 MHz, CDCl$_3$) δ 1.56 (s, 3H) 1.59 (s, 3H) 3.79~3.67 (m, 1H) 3.85 (dd, J=8.0, 6.0, 1 H) 4.06~3.90 (m, 1H) 4.14 (dd, J=8.0, 6.0, 1H) 5.37 (d, J=8.0, 1H) 0.7.57 (d, J=6.0, 1H) 8.57 (d, J=12, 2H)

Preparation Example 416: 4-chloroisonicotinaldehyde

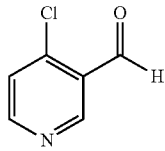

The substantially same method as described in Preparation Example 411 was conducted, except that Ethyl 4-chloropyridine was used instead of 3-chloropyridine, to obtain the title compound (3.0 g, 60~80%).

$^1$H NMR (400 MHz, CDCl$_3$): δ=7.45 (d, J=5.2, 1H), 8.70 (d, J=5.2, 1H), 9.06 (s, 1H), 10.52 (s, 1H)

Preparation Example 417: (E)-ethyl 3-(4-chloropyridin-3-yl)acrylate

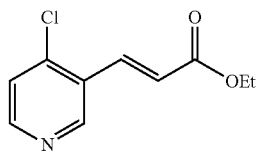 [SMILES: CCOC(=O)/C=C/c1cnccc1Cl]

The substantially same method as described in Preparation Example 412 was conducted, except that Ethyl 4-chloronicotinealdehyde (Preparation example 416) was used instead of 3-chloroisonicotinaldehyde (Preparation example 411), to obtain the title compound (4.0 g, 70~90%).

$^1$H NMR (400 MHz, CDCl$_3$): δ=1.37 (t, J=7.0, 3H), 4.33 (q, J=6.6, 2H), 6.57 (d, J=16.4, 1H), 7.39 (d, J=5.2, 1H), 7.98 (d, J=16.0, 1H), 8.49 (d, J=5.2, 1H), 8.82 (s, 1H)

Preparation Example 418: Ethyl 3-(4-chloropyridin-3-yl)-2,3-dihydroxypropanoate

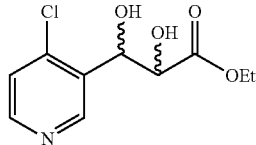 [SMILES: CCOC(=O)C(O)C(O)c1cnccc1Cl]

The substantially same method as described in Preparation Example 413 was conducted, except that (E)-ethyl 3-(4-chloropyridin-3-yl)acrylate (Preparation example 417) was used instead of (E)-ethyl 3-(3-chloropyridin-4-yl)acrylate (Preparation example 412), to obtain the title compound (2.4 g, 60~80%).

$^1$H NMR (400 MHz, CDCl$_3$) δ=1.34 (t, J=7.2, 3H), 4.35 (q, J=7.0, 2H), 4.45 (d, J=2.4, 1H), 5.49 (d, J=2.0, 1H), 7.32 (d, J=5.2, 1H), 8.46 (d, J=4.4, 1H), 8.79 (s, 1H)

Preparation Example 419: Ethyl 5-(4-chloropyridin-3-yl)-2,2-dimethyl-1,3-dioxolane-4-carboxylate

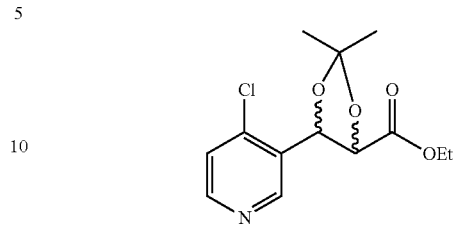

The substantially same method as described in Preparation Example 414 was conducted, except that Ethyl 3-(4-chloropyridin-3-yl)-2,3-dihydroxypropanoate (Preparation example 418) was used instead of Ethyl 3-(3-chloropyridin-4-yl)-2,3-dihydroxypropanoate (Preparation example 413), to obtain the title compound (1.3 g, 70~90%).

$^1$H NMR (400 MHz, CDCl$_3$): δ=1.25 (t, J=7.2 3H), 1.59 (s, 3H), 1.64 (s, 39), 4.22 (q, J=8.27 2H), 4.37 (d, J=7.6, 1H), 5.56 (d, J=7.6, 1H), 7.31 (d, J=5.2, 1H), 8.48 (d, J=5.2, 1H), 8.78 (s, 1H)

Preparation Example 420: (5-(4-chloropyridin-3-yl)-2,2-dimethyl-1,3-dioxolan-4-yl)methanol

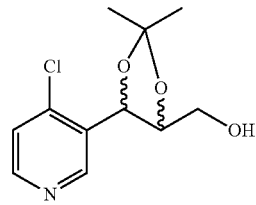 [SMILES: CC1(C)OC(CO)C(c2cnccc2Cl)O1]

The substantially same method as described in Preparation Example 415 was conducted, except that Ethyl 5-(4-chloropyridin-3-yl)-2,2-dimethyl-1,3-dioxolane-4-carboxylate (Preparation example 419) was used instead of Ethyl 5-(3-chloropyridin-4-yl)-2,2-dimethyl-1,3-dioxolane-4-carboxylate (Preparation example 414), to obtain the title compound (0.8 g, 70~90%).

$^1$H NMR (400 MHz, CDCl$_3$): δ=1.56 (s, 3H), 1.63 (s, 3H), 1.64 (s, 3H), 3.73~3.77 (m, 1H), 3.95~3.99 (m, 3H) 5.39 (d, J=8.4, 1H), 7.32 (d, J=5.6, 1H), 8.46 (d, J=5.2, 1H), 8.82 (s, 1H)

Preparation Example 421: (E)-ethyl 3-(pyrimidin-5-yl)acrylate

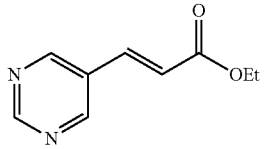 [SMILES: CCOC(=O)/C=C/c1cncnc1]

5-bromopyrimidine (5 g, 31.4 mmol) in DMF (75 ml) was added ethyl acrylate (9.5 ml, 94.4 mmol) at room temperature. Diisopropylamine (7.5 ml, 42.8 mmol), trimethyl phosphate (0.19 ml, 1.6 mmole), Pd(Pac)$_2$ (0.18 g, 0.78 mmol)

were added. The reaction mixture was heated at 110° C. for 2 hr. The reaction mixture was cooled to room temperature and quenched with H₂O then extracted with EA (Ethyl acetate). The aqueous layer was extracted with EA and separated. The combined organic layer was washed with H₂O, then dried over anhydrous magnesium sulfate (MgSO₄) and evaporated under reduced. The crude compound was purified by a silica gel column to produce the title compound (3.9 g, 70~90%).

¹H NMR (400 MHz, CDCl₃) δ 1.38 (t, J=6.8, 3H), 4.29-4.35 (m, 1H), 6.61 (d, J=17.2, 1H), 7.63 (d, J=16.4, 1H), 8.90 (s, 2H), 9.22 (s, 1H).

Preparation Example 422: Ethyl 3-(pyrimidin-5-yl)-2,3-dihydroxypropanoate

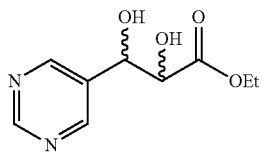 [SMILES: CCOC(=O)C(O)C(O)c1cncnc1]

The substantially same method as described in Preparation Example 418 was conducted, except that (E)-ethyl 3-(pyrimidin-5-yl)acrylate (Preparation example 421) was used instead of (E)-ethyl 3-(4-chloropyridin-3-yl)acrylate (Preparation example 417), to obtain the title compound (1.6 g, 40~60%).

¹H NMR (400 MHz, CDCl₃) δ 1.07-1.39 (m, 3H), 4.16-4.34 (m, 2H), 4.39 (s, 1H), 4.69 (s, 1H), 5.04 (s, 1H), 5.10 (s, 1H), 8.98 (s, 2H), 9.01 (s, 1H).

Preparation Example 423: Ethyl 2,2-dimethyl-5-(pyrimidin-5-yl)-1,3-dioxolane-4-carboxylate

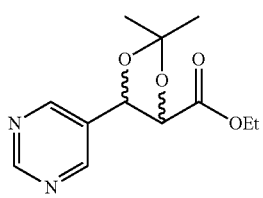 [SMILES: CCOC(=O)C1OC(C)(C)OC1c1cncnc1]

The substantially same method as described in Preparation Example 419 was conducted, except that Ethyl 3-(pyrimidin-5-yl)-2,3-dihydroxypropanoate (Preparation example 422) was used instead of Ethyl 3-(4-chloropyridin-3-yl)-2,3-dihydroxypropanoate (Preparation example 418), to obtain the title compound (0.97 g, 40~60%).

¹H NMR (400 MHz, CDCl₃) δ 1.30 (t, J=7.2, 3H), 1.55 (s, 3H), 1.61 (s, 3H), 4.25-4.32 (m, 1H), 4.35 (d, J=8.0, 1H), 5.18 (d, J=7.6, 1H), 8.82 (s, 2H), 9.20 (s, 1H).

Preparation Example 424: (2,2-dimethyl-5-(pyrimidin-5-yl)-1,3-dioxolan-4-yl)methanol

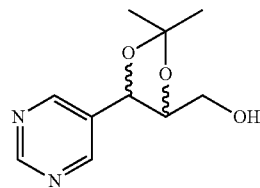

The substantially same method as described in Preparation Example 420 was conducted, except that Ethyl 2,2-dimethyl-5-(pyrimidin-5-yl)-1,3-dioxolane-4-carboxylate (Preparation example 423) was used instead of Ethyl 5-(4-chloropyridin-3-yl)-2,2-dimethyl-1,3-dioxolane-4-carboxylate (Preparation example 419), to obtain the title compound (0.65 g, 70~90%).

¹H NMR (400 MHz, CDCl₃) δ 1.53 (s, 3H), 1.56 (s, 3H), 2.75 (s, —OH), 3.68-3.73 (m, 1H), 3.69-3.64 (m, 1H), 3.89-3.93 (m, 2H), 5.0 (d, J=8.4, 1H), 8.79 (s, 2H), 9.18 (s, 1H).

Preparation Example 425: (E)-ethyl 3-(2-chloropyrimidin-5-yl)acrylate

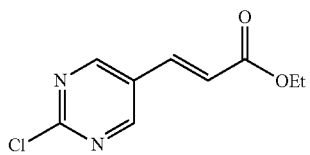 [SMILES: CCOC(=O)/C=C/c1cnc(Cl)nc1]

The substantially same method as described in Preparation Example 421 was conducted, except that 2-chloro-5-bromopyrimidine was used instead of 5-bromopyrimidine, to obtain the title compound (9.7 g, 50~70%).

¹H NMR (400 MHz, CDCl₃) δ 1.37 (t, J=6.8, 3H), 4.32 (qt, J=7.2, 2H), 6.59 (d, J=16.4, 1H), 7.60 (d, J=16.4, 1H), 8.77 (s, 2H).

Preparation Example 426: Ethyl 3-(2-chloropyrimidin-5-yl)-2,3-dihydroxypropanoate

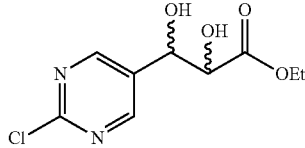 [SMILES: CCOC(=O)C(O)C(O)c1cnc(Cl)nc1]

The substantially same method as described in Preparation Example 422 was conducted, except that (E)-ethyl 3-(2-chloropyrimidin-5-yl)acrylate (Preparation example 425) was used instead of (E)-ethyl 3-(pyrimidin-5-yl)acrylate (Preparation example 421), to obtain the title compound (2.1 g, 40~60%).

¹H NMR (400 MHz, CDCl₃) δ 1.33~1.37 (m, 3H), 2.97 (d, J=7.2, 1H), 3.31 (d, J=18.4, 1H), 4.34~4.55 (m, 3H), 5.10 (d, J=7.2, 1H), 8.72 (s, 2H).

Preparation Example 427: Ethyl 2,2-dimethyl-5-(2-chloropyrimidin-5-yl)-1,3-dioxolane-4-carboxylate

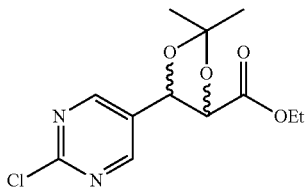 [SMILES: CCOC(=O)C1OC(C)(C)OC1c1cnc(Cl)nc1]

The substantially same method as described in Preparation Example 423 was conducted, except that Ethyl 3-(2-chloropyrimidin-5-yl)-2,3-dihydroxypropanoate (Preparation example 426) was used instead of Ethyl 3-(pyrimidin-5-yl)-2,3-dihydroxypropanoate (Preparation example 422), to obtain the title compound (0.98 g, 40~60%).

$^1$H NMR (400 MHz, CDCl$_3$) δ 1.32 (t, J=7.2 3H), 1.55 (s, 3H), 1.60 (s, 3H), 4.27-4.34 (m, 3H), 5.19 (d, J=7.6, 1H), 8.71 (s, 2H).

Preparation Example 428: (2,2-dimethyl-5-(2-chloropyrimidin-5-yl)-1,3-dioxolan-4-yl)methanol

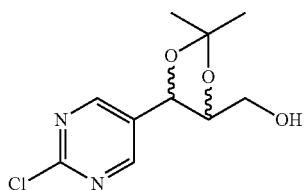 [SMILES: CC1(C)OC(CO)C(c2cnc(Cl)nc2)O1]

The substantially same method as described in Preparation Example 424 was conducted, except that Ethyl 2,2-dimethyl-5-(2-chloropyrimidin-5-yl)-1,3-dioxolane-4-carboxylate (Preparation example 427) was used instead of Ethyl 2,2-dimethyl-5-(pyrimidin-5-yl)-1,3-dioxolane-4-carboxylate (Preparation example 423), to obtain the title compound (0.71 g, 70~90%).

$^1$H NMR (400 MHz, CDCl$_3$) δ 1.54 (s, 3H), 1.56 (s, 3H), 2.21 (s, —OH), 3.71-3.76 (M, 1H), 3.69-3.64 (m, 1H), 3.88-3.96 (m, 2H), 5.02 (d, J=8.0, 1H), 8.68 (s, 2H).

Preparation Example 429: (1R, 2S)-3-(benzyloxy)-1-(2-chlorophenyl)-1-hydroxypropan-2-yl acetate

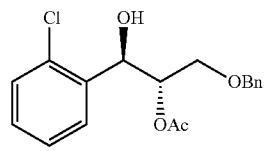 [SMILES: CC(=O)O[C@@H](COCc1ccccc1)[C@H](O)c1ccccc1Cl]

A regioisomer of acetate was separated and purified by conducting the silica gel column chromatography as described in Preparation example 376, to obtain the title compound (0.42 g, yield 10~30%)

$^1$H NMR (400 MHz, CDCl$_3$) δ 2.09 (s, 3H), 3.63-3.70 (m, 2H), 4.47-4.61 (m, 2H), 5.29-5.33 (m, 1H), 5.41 (t, J=5.0 Hz, 1H), 7.22-7.55 (m, 9H).

Preparation Example 430: (1R, 2S)-3-(benzyloxy)-1-(2-chlorophenyl)propane

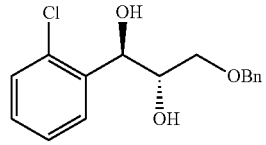 [SMILES: O[C@H](c1ccccc1Cl)[C@@H](O)COCc1ccccc1]

The substantially same method as described in Preparation Example 377 was conducted, except that (1R, 2S)-3-(benzyloxy)-1-(2-chlorophenyl)-1-hydroxypropan-2-yl acetate (Preparation example 429) was used instead of (1S, 2R)-3-(benzyloxy)-1-(2-chlorophenyl)-2-hydroxypropyl acetate (Preparation example 376), to obtain the title compound (0.31 g, 80~95%).

$^1$H NMR (400 MHz, CDCl$_3$) δ 3.02 (d, J=5.2 Hz, 1H), 3.55-3.42 (m, 3H, —OH), 4.18-4.13 (m, 1H), 4.46 (d, J=6 Hz, 2H), 5.28 (t, J=4.8 Hz, 1H), 7.35-7.19 (m, 8H), 7.50 (dd, J=7.6, 1.2 Hz, 1H).

Preparation Example 431: (4S, 5R)-4-(benzyloxymethyl)-5-(2-chlorophenyl)-2,2-dimethyl-1,3-dioxolane

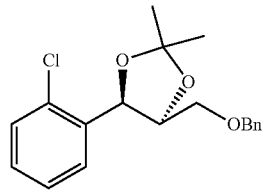 [SMILES: CC1(C)O[C@@H](COCc2ccccc2)[C@@H](c2ccccc2Cl)O1]

The substantially same method as described in Preparation example 373 was conducted, except that (1R, 2S)-3-(benzyloxy)-1-(2-chlorophenyl)propane-1,2-diol (Preparation example 430) was used instead of that (±)-3-(benzyloxy)-1-(2-chlorophenyl)propane-1,2-diol (Preparation example 372), to obtain the title compound (0.84 g, 80~100%).

$^1$H NMR (400 MHz, CDCl$_3$) δ 1.53 (s, 3H), 1.66 (s, 3H), 3.14-3.06 (m, 2H), 4.26 (d, J=12 Hz, 2H), 4.83-4.78 (m, 1H), 5.63 (d, J=6.8, 1H), 7.35-7.16 (m, 8H), 7.61 (dd, J=7.4, 1.6 Hz, 1H).

Preparation Example 432: ((4S, 5R)-5-(2-chlorophenyl)-2,2-dimethyl-1,3-dioxolan-4-yl)methanol

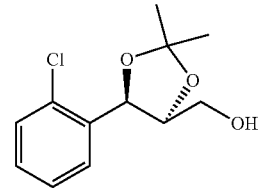 [SMILES: CC1(C)O[C@@H](CO)[C@@H](c2ccccc2Cl)O1]

The substantially same method as described in Preparation example 374 was conducted, except that ((4S, 5R)-4-(benzyloxymethyl)-5-(2-chlorophenyl)-2,2-dimethyl-1,3-dioxolane (Preparation example 431) was used instead of that (±)-4-(benzyloxymethyl)-5-(2-chlorophenyl)-2,2-dimethyl-1,3-dioxolane (Preparation example 373), to obtain the title compound (0.82 g, 80~100%).

$^1$H NMR (400 MHz, CDCl$_3$) δ 1.66 (s, 3H), 1.53 (s, 3H), 3.14-3.06 (m, 2H), 4.26 (d, J=12, 2H), 4.83-4.78 (m, 1H), 5.63 (d, J=6.8 Hz, 1H), 7.35-7.16 (m, 8H), 7.61 (dd, J=7.4, 1.6, 1H).

Preparation Example 433: (2S,3R)-methyl-3-(2-chlorophenyl)-2,3-dihydroxypropanoate

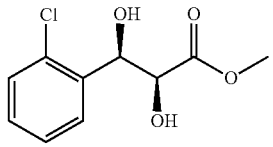

The substantially same method as described in Preparation example 3 was conducted, except that (E)-methyl-3-(2-chlorophenyl)acrylate (Preparation example 24) was used instead of that (E)-1-chloro-2-(3-(methoxymethoxy)prop-1-enyl)benzene (Preparation example 2), to obtain the title compound (14.2 g, 70~90%)

$^1$H NMR (400 MHz, CDCl$_3$) δ 2.79 (d, J=7.2, 1H), 3.13 (d, J=6.0, 1H), 3.86 (s, 3H), 4.50 (dd, J=5.6, 2.4, 1H), 5.51 (dd, J=7.2, 2.4, 1H), 7.62~7.26 (m, 4H)

TABLE 1

| | Example of sulfamate compound (A = Phenyl) | | | | | | | | | |
|---|---|---|---|---|---|---|---|---|---|---|
| No | A = Phenyl | n | l | m | R$^1$ | R$^2$ | R$^3$ | R$^4$ | Chiral-1 | Chiral-2 |
| 1 | 2-Cl | 1 | 0 | 0 | Me | Me | H | H | R | R |
| 2 | 2-Cl | 1 | 0 | 0 | Me | Me | H | H | S | S |
| 3 | 2-Cl | 1 | 0 | 0 | Me | Me | H | H | Rac. (syn) | Rac. (syn) |
| 4 | 2-Cl | 1 | 0 | 0 | Me | Me | H | H | Rac. (anti) | Rac. (anti) |
| 5 | 2-Cl | 1 | 0 | 0 | Me | H | H | H | R | R |
| 6 | 2-Cl | 1 | 0 | 0 | Me | H | H | H | S | S |
| 7 | 2-Cl | 1 | 0 | 0 | Et | Et | H | H | R | R |
| 8 | 2-Cl | 1 | 0 | 0 | Et | Et | H | H | S | S |
| 9 | 2-Cl | 1 | 0 | 0 | Cyclopentyl | H | H | R | R |
| 10 | 2-Cl | 1 | 0 | 0 | Cyclopentyl | H | H | S | S |
| 11 | 2-Cl | 1 | 0 | 0 | Cyclohexyl | H | H | R | R |
| 12 | 2-Cl | 1 | 0 | 0 | Cyclohexyl | H | H | S | S |
| 13 | 2-Cl | 1 | 0 | 0 | Methylbenzene | H | H | R | R |
| 14 | 2-Cl | 1 | 0 | 0 | Methylbenzene | H | H | S | S |
| 15 | 2-F | 1 | 0 | 0 | Me | Me | H | H | R | R |
| 16 | 2-F | 1 | 0 | 0 | Me | Me | H | H | S | S |
| 17 | 2-F | 1 | 0 | 0 | Me | H | H | H | R | R |
| 18 | 2-F | 1 | 0 | 0 | Me | H | H | H | S | S |
| 19 | 2-F | 1 | 0 | 0 | Et | Et | H | H | R | R |
| 20 | 2-F | 1 | 0 | 0 | Et | Et | H | H | S | S |
| 21 | 2-F | 1 | 0 | 0 | Cyclopentyl | H | H | R | R |
| 22 | 2-F | 1 | 0 | 0 | Cyclopentyl | H | H | S | S |
| 23 | 2-F | 1 | 0 | 0 | Cyclohexyl | H | H | R | R |
| 24 | 2-F | 1 | 0 | 0 | Cyclohexyl | H | H | S | S |
| 25 | 2-F | 1 | 0 | 0 | Methylbenzene | H | H | R | R |
| 26 | 2-F | 1 | 0 | 0 | Methylbenzene | H | H | S | S |
| 27 | 2-I | 1 | 0 | 0 | Me | Me | H | H | R | R |
| 28 | 2-I | 1 | 0 | 0 | Me | Me | H | H | S | S |
| 29 | 2-I | 1 | 0 | 0 | Me | H | H | H | R | R |
| 30 | 2-I | 1 | 0 | 0 | Me | H | H | H | S | S |
| 31 | 2-I | 1 | 0 | 0 | Et | Et | H | H | R | R |
| 32 | 2-I | 1 | 0 | 0 | Et | Et | H | H | S | S |
| 33 | 2-I | 1 | 0 | 0 | Cyclopentyl | H | H | R | R |
| 34 | 2-I | 1 | 0 | 0 | Cyclopentyl | H | H | S | S |
| 35 | 2-I | 1 | 0 | 0 | Cyclohexyl | H | H | R | R |
| 36 | 2-I | 1 | 0 | 0 | Cyclohexyl | H | H | S | S |
| 37 | 2-I | 1 | 0 | 0 | Methylbenzene | H | H | R | R |
| 38 | 2-I | 1 | 0 | 0 | Methylbenzene | H | H | S | S |
| 39 | 2,4-Cl | 2 | 0 | 0 | Me | Me | H | H | R | R |
| 40 | 2,4-Cl | 2 | 0 | 0 | Me | Me | H | H | S | S |
| 41 | 2,4-Cl | 2 | 0 | 0 | Me | H | H | H | R | R |
| 42 | 2,4-Cl | 2 | 0 | 0 | Me | H | H | H | S | S |
| 43 | 2,4-Cl | 2 | 0 | 0 | Et | Et | H | H | R | R |
| 44 | 2,4-Cl | 2 | 0 | 0 | Et | Et | H | H | S | S |
| 45 | 2,4-Cl | 2 | 0 | 0 | Cyclopentyl | H | H | R | R |
| 46 | 2,4-Cl | 2 | 0 | 0 | Cyclopentyl | H | H | S | S |
| 47 | 2,4-Cl | 2 | 0 | 0 | Cyclohexyl | H | H | R | R |
| 48 | 2,4-Cl | 2 | 0 | 0 | Cyclohexyl | H | H | S | S |
| 49 | 2,4-Cl | 2 | 0 | 0 | Methylbenzene | H | H | R | R |
| 50 | 2,4-Cl | 2 | 0 | 0 | Methylbenzene | H | H | S | S |
| 51 | 2,6-Cl | 2 | 0 | 0 | Me | Me | H | H | R | R |
| 52 | 2,6-Cl | 2 | 0 | 0 | Me | Me | H | H | S | S |
| 53 | 2,6-Cl | 2 | 0 | 0 | Me | H | H | H | R | R |
| 54 | 2,6-Cl | 2 | 0 | 0 | Me | H | H | H | S | S |
| 55 | 2,6-Cl | 2 | 0 | 0 | Et | Et | H | H | R | R |
| 56 | 2,6-Cl | 2 | 0 | 0 | Et | Et | H | H | S | S |
| 57 | 2,6-Cl | 2 | 0 | 0 | Cyclopentyl | H | H | R | R |
| 58 | 2,6-Cl | 2 | 0 | 0 | Cyclopentyl | H | H | S | S |
| 59 | 2,6-Cl | 2 | 0 | 0 | Cyclohexyl | H | H | R | R |

TABLE 1-continued

Example of sulfamate compound (A = Phenyl)

| No | A = Phenyl | n | l | m | R¹ | R² | R³ | R⁴ | Chiral-1 | Chiral-2 |
|---|---|---|---|---|---|---|---|---|---|---|
| 60 | 2,6-Cl | 2 | 0 | 0 | Cyclohexyl | H | H | | S | S |
| 61 | 2,6-Cl | 2 | 0 | 0 | Methylbenzene | H | H | | R | R |
| 62 | 2,6-Cl | 2 | 0 | 0 | Methylbenzene | H | H | | S | S |
| 63 | 2-NH2 | 1 | 0 | 0 | Me | Me | H | H | R | R |
| 64 | 2-NH2 | 1 | 0 | 0 | Me | Me | H | H | S | S |
| 65* | 2-NH2 | 1 | 0 | 0 | Me | Me | H | H | R | R |
| 66* | 2-NH2 | 1 | 0 | 0 | Me | Me | H | H | S | S |
| 67 | 2-NH2 | 1 | 0 | 0 | Me | H | H | H | R | R |
| 68 | 2-NH2 | 1 | 0 | 0 | Me | H | H | H | S | S |
| 69 | 2-NH2 | 1 | 0 | 0 | Et | Et | H | H | R | R |
| 70 | 2-NH2 | 1 | 0 | 0 | Et | Et | H | H | S | S |
| 71 | 2-NH2 | 1 | 0 | 0 | Cyclopentyl | H | H | | R | R |
| 72 | 2-NH2 | 1 | 0 | 0 | Cyclopentyl | H | H | | S | S |
| 73 | 2-NH2 | 1 | 0 | 0 | Cyclohexyl | H | H | | R | R |
| 74 | 2-NH2 | 1 | 0 | 0 | Cyclohexyl | H | H | | S | S |
| 75 | 2-NH2 | 1 | 0 | 0 | Methylbenzene | H | H | | R | R |
| 76 | 2-NH2 | 1 | 0 | 0 | Methylbenzene | H | H | | S | S |
| 77 | 2-NO2 | 1 | 0 | 0 | Me | Me | H | H | R | R |
| 78 | 2-NO2 | 1 | 0 | 0 | Me | Me | H | H | S | S |
| 79 | 2-NO2 | 1 | 0 | 0 | Me | H | H | H | R | R |
| 80 | 2-NO2 | 1 | 0 | 0 | Me | H | H | H | S | S |
| 81 | 2-NO2 | 1 | 0 | 0 | Et | Et | H | H | R | R |
| 82 | 2-NO2 | 1 | 0 | 0 | Et | Et | H | H | S | S |
| 83 | 2-NO2 | 1 | 0 | 0 | Cyclopentyl | H | H | | R | R |
| 84 | 2-NO2 | 1 | 0 | 0 | Cyclopentyl | H | H | | S | S |
| 85 | 2-NO2 | 1 | 0 | 0 | Cyclohexyl | H | H | | R | R |
| 86 | 2-NO2 | 1 | 0 | 0 | Cyclohexyl | H | H | | S | S |
| 87 | 2-NO2 | 1 | 0 | 0 | Methylbenzene | H | H | | R | R |
| 88 | 2-NO2 | 1 | 0 | 0 | Methylbenzene | H | H | | S | S |
| 89 | 2-NO2 | 1 | 0 | 0 | Cyclocarbonyl | H | H | | R | R |
| 90 | 2-NO2 | 1 | 0 | 0 | Cyclocarbonyl | H | H | | S | S |
| 91 | 2-Me | 1 | 0 | 0 | Me | Me | H | H | R | R |
| 92 | 2-Me | 1 | 0 | 0 | Me | Me | H | H | S | S |
| 93 | 2-Me | 1 | 0 | 0 | Me | H | H | H | R | R |
| 94 | 2-Me | 1 | 0 | 0 | Me | H | H | H | S | S |
| 95 | 2-Me | 1 | 0 | 0 | Et | Et | H | H | R | R |
| 96 | 2-Me | 1 | 0 | 0 | Et | Et | H | H | S | S |
| 97 | 2-Me | 1 | 0 | 0 | Cyclopentyl | H | H | | R | R |
| 98 | 2-Me | 1 | 0 | 0 | Cyclopentyl | H | H | | S | S |
| 99 | 2-Me | 1 | 0 | 0 | Cyclohexyl | H | H | | R | R |
| 100 | 2-Me | 1 | 0 | 0 | Cyclohexyl | H | H | | S | S |
| 101 | 2-Me | 1 | 0 | 0 | Methylbenzene | H | H | | R | R |
| 102 | 2-Me | 1 | 0 | 0 | Methylbenzene | H | H | | S | S |
| 103 | 2-MeNH | 1 | 0 | 0 | Me | Me | Me | H | R | R |
| 104 | 2-MeNH | 1 | 0 | 0 | Me | Me | Me | H | S | S |
| 105 | H | 1 | 0 | 0 | Me | Me | H | H | R | R |
| 106 | H | 1 | 0 | 0 | Me | Me | H | H | S | S |
| 107 | H | 1 | 0 | 0 | Et | Et | H | H | R | R |
| 108 | H | 1 | 0 | 0 | Et | Et | H | H | S | S |
| 109 | H | 1 | 0 | 0 | Cyclopentyl | H | H | | R | R |
| 110 | H | 1 | 0 | 0 | Cyclopentyl | H | H | | S | S |
| 111 | H | 1 | 0 | 0 | Cyclohexyl | H | H | | R | R |
| 112 | H | 1 | 0 | 0 | Cyclohexyl | H | H | | S | S |
| 113 | H | 1 | 1 | 1 | Me | Me | H | H | R | R |
| 114 | H | 1 | 1 | 1 | Me | Me | H | H | S | S |
| 115 | H | 1 | 1 | 1 | Et | Et | H | H | R | R |
| 116 | H | 1 | 1 | 1 | Et | Et | H | H | S | S |
| 117 | H | 1 | 1 | 1 | Cyclopentyl | H | H | | R | R |
| 118 | H | 1 | 1 | 1 | Cyclopentyl | H | H | | S | S |
| 119 | H | 1 | 1 | 1 | Cyclohexyl | H | H | | R | R |
| 120 | H | 1 | 1 | 1 | Cyclohexyl | H | H | | S | S |
| 121 | H | 1 | 1 | 0 | Me | Me | H | H | R | R |
| 122 | H | 1 | 1 | 0 | Me | Me | H | H | S | S |
| 123 | H | 1 | 1 | 0 | Et | Et | H | H | R | R |
| 124 | H | 1 | 1 | 0 | Et | Et | H | H | S | S |
| 125 | H | 1 | 1 | 0 | Cyelopentyl | H | H | | R | R |
| 126 | H | 1 | 1 | 0 | Cyclopentyl | H | H | | S | S |
| 127 | H | 1 | 1 | 0 | Cyclohexyl | H | H | | R | R |
| 128 | H | 1 | 1 | 0 | Cyclohexyl | H | H | | S | S |
| 129 | H | 1 | 0 | 1 | Me | Me | H | H | R | R |
| 130 | H | 1 | 0 | 1 | Me | Me | H | H | S | S |
| 131 | H | 1 | 0 | 1 | Et | Et | H | H | R | R |
| 132 | H | 1 | 0 | 1 | Et | Et | H | H | S | S |
| 133 | H | 1 | 0 | 1 | Cyclopentyl | H | H | | R | R |
| 134 | H | 1 | 0 | 1 | Cyclopentyl | H | H | | R | S |

TABLE 1-continued

Example of sulfamate compound (A = Phenyl)

| No | A = Phenyl | n | l | m | R¹ | R² | R³ | R⁴ | Chiral-1 | Chiral-2 |
|---|---|---|---|---|---|---|---|---|---|---|
| 135 | H | 1 | 0 | 1 | Cyclohexyl | H | H | H | S | R |
| 136 | H | 1 | 0 | 1 | Cyclohexyl | H | H | H | R | S |
| 137 | Cl | 1 | 1 | 1 | Me | Me | H | H | R | R |
| 138 | Cl | 1 | 1 | 1 | Me | Me | H | H | S | S |
| 139 | Cl | 1 | 1 | 1 | Et | Et | H | H | R | R |
| 140 | Cl | 1 | 1 | 1 | Et | Et | H | H | S | S |
| 141 | Cl | 1 | 1 | 1 | Cyclopentyl | | H | H | R | R |
| 142 | Cl | 1 | 1 | 1 | Cyclopentyl | | H | H | S | S |
| 143 | Cl | 1 | 1 | 1 | Cyclohexyl | | H | H | R | R |
| 144 | Cl | 1 | 1 | 1 | Cyclohexyl | | H | H | S | S |
| 145 | Cl | 1 | 1 | 0 | Me | Me | H | H | R | R |
| 146 | Cl | 1 | 1 | 0 | Me | Me | H | H | S | S |
| 147 | Cl | 1 | 1 | 0 | Et | Et | H | H | R | R |
| 148 | Cl | 1 | 1 | 0 | Et | Et | H | H | S | S |
| 149 | Cl | 1 | 1 | 0 | Cyclopentyl | | H | H | R | R |
| 150 | Cl | 1 | 1 | 0 | Cyclopentyl | | H | H | S | S |
| 151 | Cl | 1 | 1 | 0 | Cyclohexyl | | H | H | R | R |
| 152 | Cl | 1 | 1 | 0 | Cyclohexyl | | H | H | S | S |
| 153 | Cl | 1 | 0 | 1 | Me | Me | H | H | R | R |
| 154 | Cl | 1 | 0 | 1 | Me | Me | H | H | S | S |
| 155 | Cl | 1 | 0 | 1 | Et | Et | H | H | R | R |
| 156 | Cl | 1 | 0 | 1 | Et | Et | H | H | S | S |
| 157 | Cl | 1 | 0 | 1 | Cyclopentyl | | H | H | R | R |
| 158 | Cl | 1 | 0 | 1 | Cyclopentyl | | H | H | S | S |
| 159 | Cl | 1 | 0 | 1 | Cyclohexyl | | H | H | R | R |
| 160 | Cl | 1 | 0 | 1 | Cyclohexyl | | H | H | S | S |
| 161 | Cl | 1 | 0 | 0 | Me | Me | H | H | R | S |
| 162 | Cl | 1 | 0 | 0 | Me | Me | H | H | S | R |
| 177* | 2-Cl | 1 | 0 | 0 | Me | Me | H | H | S | S |

*Sodium salt

TABLE 2

Example of sulfamate compound (A = Heterocyclic ring)

| No | A | X | n | l | m | R¹ | R² | R³ | R⁴ | Chiral-1 | Chiral-2 |
|---|---|---|---|---|---|---|---|---|---|---|---|
| 163 | Thiazole | 2,4-Cl | 2 | 0 | 0 | Me | Me | H | H | R | S |
| 164 | Thiazole | 2,4-Cl | 2 | 0 | 0 | Me | Me | H | H | S | R |
| 165 | Thiazole | 2-Cl | 1 | 0 | 0 | Me | Me | H | H | R | S |
| 166 | Thiazole | 2-Cl | 1 | 0 | 0 | Me | Me | H | H | S | R |
| 167 | Thiazole | 4-Me | 1 | 0 | 0 | Me | Me | H | H | R | S |
| 168 | Thiazole | 4-Me | 1 | 0 | 0 | Me | Me | H | H | S | R |
| 169 | Thiazole | 2-Cl, 4-Me | 2 | 0 | 0 | Me | Me | H | H | R | S |
| 170 | Thiazole | 2-Cl, 4-Me | 2 | 0 | 0 | Me | Me | H | H | S | R |
| 171 | Thiophene | H | 1 | 0 | 0 | Me | Me | H | H | S | S |
| 172 | Thiophene | 2-Cl | 1 | 0 | 0 | Me | Me | H | H | S | R |
| 173 | Pyridine | 3-Cl | 1 | 0 | 0 | Me | Me | H | H | Rac. (syn) | Rac. (syn) |
| 174 | Pyridine | 4-Cl | 1 | 0 | 0 | Me | Me | H | H | Rac. (syn) | Rac. (syn) |
| 175 | Pyrimidine | H | 1 | 0 | 0 | Me | Me | H | H | Rac. (syn) | Rac. (syn) |
| 176 | Pyrimidine | 2-Cl | 1 | 0 | 0 | Me | Me | H | H | Rac. (syn) | Rac. (syn) |

Example 1-1: ((4R,5R)-5-(2-chlorophenyl)-2,2-dimethyl-1,3-dioxolan-4-yl)methyl sulfamate

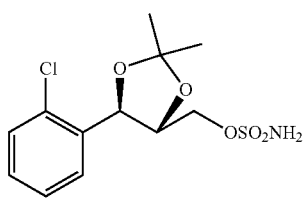

To a 100 ml flask, Acetonitrile (2.26 ml, 43.2 mmol) was added and cooled to 0° C. Chlorosulfonyl isocyanate (1.5 ml, 17.3 mmol), and formic acid (0.65 ml, 17.3 mmol) was added dropwise and stirred at room temperature for 6 hours. ((4R,5R)-5-(2-chlorophenyl)-2,2-dimethyl-1,3-dioxolan-4-yl)methanol (Preparation example 6, 1.05 g, 4.3 mmol) in N,N-dimethyl acetamide (13.2 ml, 142.7 mmol) was slowly added at 0° C. and stirred at room temperature for 1 hours. The reaction mixture was quenched with $H_2O$, extracted with EtOAc, and washed with $H_2O$. The organic layer was dried over anhydrous magnesium sulfate ($MgSO_4$), filtered and concentrated. The crude compound was purified by a silica gel column to produce the title compound (1.00 g, 50~80%).

¹H NMR (400 MHz, CDCl₃) δ 1.57 (s, 3H), 1.63 (s, 3H), 4.11~4.10 (m, 1H), 4.53~4.42 (m, 2H), 4.88 (s, 2H), 5.37 (d, J=8.4, 1H), 7.28~7.56 (m, 4H)

Example 1-2: ((4R,5R)-5-(2-chlorophenyl)-2,2-dimethyl-1,3-dioxolan-4-yl)methyl sulfamate To a 100 mL RB flask, ((4R,5R)-5-(2-chlorophenyl)-2,2-dimethyl-1,3-dioxolan-4-yl)methanol (Preparation example 6, 10.0 g, 41.2 mmol), 50 ml of toluene, 7.92 g (82.4 mmol) of sulfamide and 13.0 g (165 mmol) of pyridine were added at RT. The mixture was refluxed for 1.5 hr (bath temperature 135° C.). The reaction mixture cooled to room temperature then solution was extracted with 27.5 ml (82.4 mmol) of 3N NaOH solution. The aqueous layer was washed with 50 mL of toluene. To the mixture 50 ml of methanol and 35 ml of water was added then acidified to pH 6.0 by slow adding acetic acid to give title compound. (9.9 g 60~80%).

According to the method described in Example 1, the following compounds of Examples 2 to 64, 67 to 88, 91 to 102, 105 to 176 were prepared:

TABLE 3

Characterization of the examples of sulfamate compounds

| Example No. | Structure | Name | Starting material | ¹H NMR (400 MHz) |
|---|---|---|---|---|
| 2 | 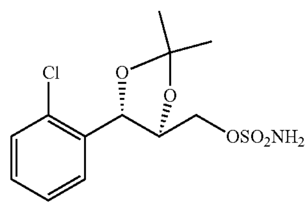 | ((4S,5S)-5-(2-chlorophenyl)-2,2-dimethyl-1,3-dioxolan-4-yl)methyl sulfamate | Preparation example 7, 27 | $^C$δ 1.59 (s, 3H), 1.65 (s, 3H), 4.12~4.07 (m, 1H), 4.54~4.42 (m, 2H), 4.91 (s, 2H), 5.37 (d, J = 8.8, 1H), 7.29~7.65 (m, 4H) |
| 3 | 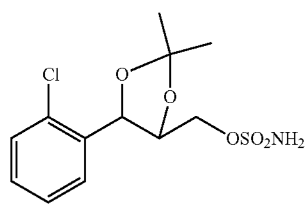 | (5-(2-chlorophenyl)-2,2-dimethyl-1,3-dioxolan-4-yl)methyl sulfamate(SS & RR mixture) | Prepartation example 8 | $^C$δ 1.57 (s, 3H), 1.63 (s, 3H), 4.11~4.10 (m, 1H), 4.53~4.42 (m, 2H), 4.88 (s, 2H), 5.37 (d, J = 8.4, 1H) 7.28~7.65 (m, 4H) |
| 4 | 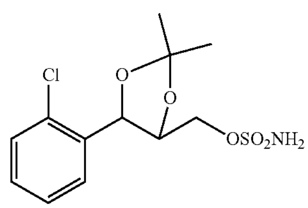 | (5-(2-chlorophenyl)-2,2-dimethyl-1,3-dioxolan-4-yl)methyl sulfamate(SR & RS mixture) | Preparation example 374 | $^C$δ 1.59 (s, 3H), 1.65 (s, 3H), 4.11~4.10 (m, 1H), 4.50~4.42 (m, 2H), 4.85 (s, 2H), 5.35 (d, J = 8.4, 1H) 7.28~7.65 (m, 4H) |
| 5 | 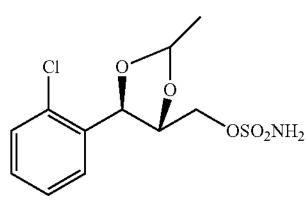 | ((4R,5R)-5-(2-chlorophenyl)-2-methyl-1,3-dioxolan-4-yl)methyl sulfamate | Preparation example 61 | $^D$δ 1.40 (d, J = 6.4, 3H), 4.22 (dt, J = 7.0, J = 3.3, 1H), 4.7 (d, J = 3.2, 2H), 5.08 (d, J = 7.0, 1H), 5.46 (m, J = 6.4, 1H), 7.26-7.40 (m, 3H), 7.49 (s, 2H), 7.61 (dd, J = 1.2, J = 7.6, 1H). |
| 6 | 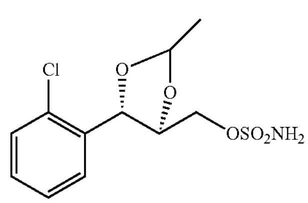 | ((4S,5S)-5-(2-chlorophenyl)-2-methyl-1,3-dioxolan-4-yl)methyl sulfamate | Preparation example 63 | $^D$δ 1.40 (d, J = 6.4, 3H), 4.22 (dt, J = 7.0, J = 3.3, 1H), 4.7 (d, J = 3.2, 2H), 5.08 (d, J = 7.0, 1H), 5.46 (m, J = 6.4, 1H), 7.26-7.40 (m, 3H), 7.49 (s, 2H), 7.61 (dd, J = 1.2, J = 7.6, 1H). |

TABLE 3-continued

Characterization of the examples of sulfamate compounds

| Example No. | Structure | Name | Starting material | $^1$H NMR (400 MHz) |
|---|---|---|---|---|
| 7 | 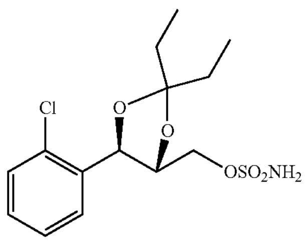 | ((4R,5R)-5-(2-chlorophenyl)-2,2-diethyl-1,3-dioxolan-4-yl)methyl sulfamate | Preparation example 65 | $^C$δ 1.59 (s, 10H), 4.17 (m, 3H), 4.98 (d, J = 8.4, 1H), 5.08 (s, 2H), 6.59 (t, J = 8.4, 1H), 6.68 (d, J = 8.4, 1H), 7.04~7.56 (m, 4H) |
| 8 | 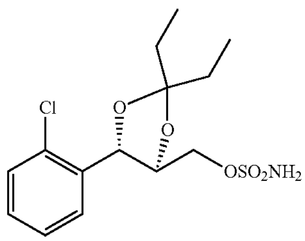 | ((4S,5S)-5-(2-chlorophenyl)-2,2-diethyl-1,3-dioxolan-4-yl)methyl sulfamate | Preparation example 67 | $^C$δ 1.59 (s, 10H), 4.17 (m, 3H), 4.96 (d, J = 3.4, 1H), 5.08 (s, 2H), 6.59 (t, J = 8.4, 1H), 6.68 (d, J = 8.4, 1H), 7.04~7.56 (m, 4H) |
| 9 | 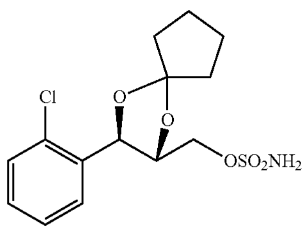 | ((2R,3R)-3-(2-chlorophenyl)-1,4-dioxaspiro[4,4]nonan-2-yl)methyl sulfamate | Preparation example 69 | $^D$δ 1.64~1.72 (m, 4H), 1.85~19.8 (m, 4H), 4.10~4.16 (m, 2H), 4.17~4.25 (m, 1H), 5.20 (d, J = 7.2, 1H), 7.34~7.62 (m, 6H) |
| 10 | 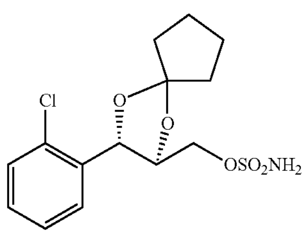 | ((2S,3S)-3-(2-chlorophenyl)-1,4-dioxaspiro[4,4]nonan-2-yl)methyl sulfamate | Preparation example 71 | $^D$δ 1.64~1.75 (m, 4H), 1.85~19.9 (m, 4H), 4.10~4.16 (m, 2H), 4.17~4.25 (m, 1H), 5.20 (d, J = 7.2, 1H), 7.34~7.62 (m, 6H) |
| 11 | 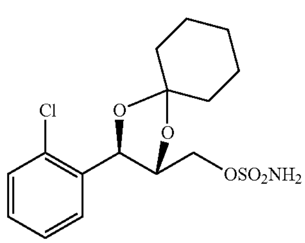 | ((2R,3R)-3-(2-chlorophenyl)-1,4-dioxaspiro[4,5]decan-2-yl)methyl sulfamate | Preparation example 73 | $^D$δ 1.51~1.67 (m, 10H), 4.11~4.23 (m, 3H), 4.98 (d, J = 8.0, 2H), 5.08 (s, 1H), 6.59 (t, J = 8.0, 1H), 6.68 (d, J = 8.0, 1H), 7.04~7.56 (m, 4H) |
| 12 | 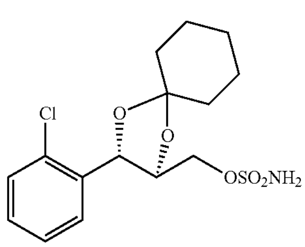 | ((2S,3S)-3-(2-chlorophenyl)-1,4-dioxaspiro[4,5]decan-2-yl)methyl sulfamate | Preparation example 75 | $^D$δ 1.51~1.67 (m, 10H), 4.11~4.23 (m, 3H), 4.98 (d, J = 8.0, 2H), 5.08 (s, 1H), 6.59 (t, J = 8.0, 1H), 6.68 (d, J = 8.0, 1H), 7.04~7.56 (m, 4H) |

TABLE 3-continued

Characterization of the examples of sulfamate compounds

| Example No. | Structure | Name | Starting material | $^1$H NMR (400 MHz) |
|---|---|---|---|---|
| 13 | 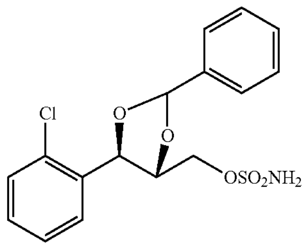 | ((4R,5R)-5-(2-chlorophenyl)-2-phenyl-1,3-dioxolan-4-yl)methyl sulfamate | Preparation example 77 | $^D$δ 4.25 (dt, J = 3.3, J = 5.7, 1H), 4.55 (d, J = 5.7, 1H), 4.75 (d, J = 3.3, 2H), 5.59 (m, 1H), 6.72~7.75 (m, 2H), 6.92~7.33 (m, 5H), 7.29 (m, 1H), 7.76 (m, 1H) |
| 14 | 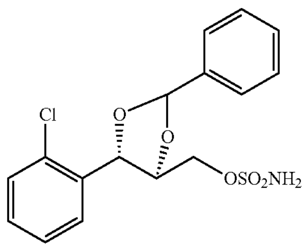 | ((4S,5S)-5-(2-chlorophenyl)-2-phenyl-1,3-dioxolan-4-yl)methyl sulfamate | Preparation example 79 | $^D$δ 4.28 (dt, J = 3.3, J = 5.7, 1H), 4.58 (d, J = 5.7, 1H), 4.75 (d, J = 3.3, 2H), 5.62 (m, 1H), 6.72~7.75 (m, 2H), 6.92~7.33 (m, 5H), 7.29 (m, 1H), 7.76 (m, 1H) |
| 15 | 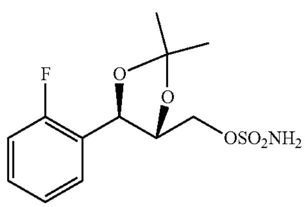 | ((4R,5R)-5-(2-fluorophenyl)-2,2-dimethyl-1,3-dioxolan-4-yl)methyl sulfamate | Preparation example 13 | $^D$δ 1.47 (d, J = 11.6, 6H), 3.35~3.94 (m, 1H), 4.02~4.20 (m, 1H), 4.23 (d, J = 2.0 1H), 5.07 (d, J = 8.4, 1H), 7.21~7.58 (m, 4H) |
| 16 | 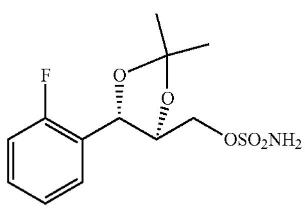 | ((4S,5S)-5-(2-fluorophenyl)-2,2-dimethyl-1,3-dioxolan-4-yl)methyl sulfamate | Preparation example 15 | $^D$δ 1.47 (d, J = 11.6, 6H), 3.35~3.94 (m, 1H), 4.02~4.20 (m, 1H), 4.23 (d, J = 2.0 1H), 5.07 (d, J = 8.4, 1H), 7.21~7.58 (m, 4H) |
| 17 | 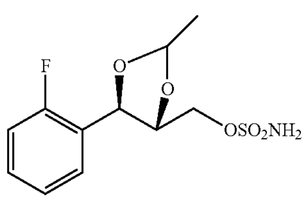 | ((4R,5R)-5-(2-fluorophenyl)-2-methyl-1,3-dioxolan-4-yl)methyl sulfamate | Preparation example 84 | $^D$δ 1.40 (d, J = 6.4, 3H), 4.7 (d, J = 3.2, 2H), 5.46 (m, J = 6.4, 1H), 4.22 (dt, J = 3.3, J = 7.0, 1H), 5.08 (d, J = 7.0, 1H), 7.26~7.40 (m, 3H), 7.49 (s, 2H), 7.61 (dd, J = 1.2, J = 7.6, 1H). |
| 18 | 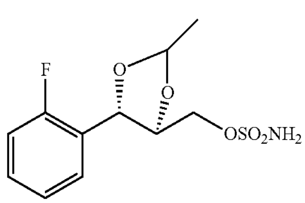 | (4S,5S)-5-(2-fluorophenyl)-2-methyl-1,3-dioxolan-4-yl)methyl sulfamate | Preparation example 86 | $^D$δ 1.40 (d, J = 6.4, 3H), 4.7 (d, J = 3.2, 2H), 5.46 (m, J = 6.4, 1H), 4.22 (dt, J = 3.3, J = 7.0, 1H), 5.18 (d, J = 7.0, 1H), 7.26-7.40 (m, 3H), 7.52 (s, 2H), 7.61 (dd, J = 1.2, J = 7.6, 1H). |

TABLE 3-continued

Characterization of the examples of sulfamate compounds

| Example No. | Structure | Name | Starting material | $^1$H NMR (400 MHz) |
|---|---|---|---|---|
| 19 | 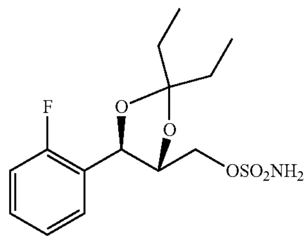 | ((4R,5R)-5-(2-fluorophenyl)-2,2-diethyl-1,3-dioxolan-4-yl)methyl sulfamate | Preparation example 88 | $^C$δ 1.59 (s, 10H), 4.17 (m, 3H), 4.98 (d, J = 8.4, 1H), 5.08 (s, 2H), 6.59 (t, J = 8.4, 1H), 6.68 (d, J = 8.4, 1H), 7.04-7.56 (m, 4H) |
| 20 | 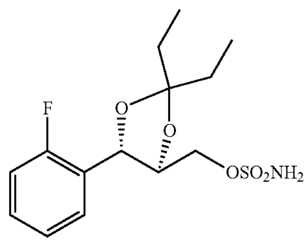 | ((4S,5S)-5-(2-fluorophenyl)-2,2-diethyl-1,3-dioxolan-4-yl)methyl sulfamate | Preparation example 90 | $^C$δ 1.59 (s, 10H), 4.14 (m, 3H), 4.98 (d, J = 8.4, 1H), 5.05 (s, 2H), 6.59 (t, J = 8.4, 1H), 6.65 (d, J = 8.4, 1H), 7.04~7.60 (m, 4H) |
| 21 | 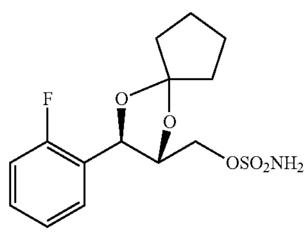 | ((2R,3R)-3-(2-fluorophenyl)-1,4-dioxaspiro[4,4]nonan-2-yl)methyl sulfamate | Preparation example 92 | $^D$δ 1.64~1.72 (m, 4H), 1.84~19.8 (m, 4H), 4.10~4.16 (m, 2H), 4.19~4.25 (m, 1H), 5.25 (d, J = 7.2, 1H), 7.34~7.62 (m, 6H) |
| 22 | 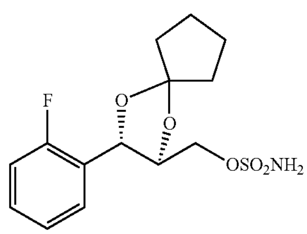 | ((2S,3S)-3-(2-fluorophenyl)-1,4-dioxaspiro[4,4]nonan-2-yl)methyl sulfamate | Preparation example 94 | Dδ 1.64~1.72 (m, 4H), 1.85~19.8 (m, 4H), 4.10~4.16 (m, 2H), 4.17~4.25 (m, 1H), 5.20 (d, J = 7.2, 1H), 7.34~7.62 (m, 6H) |
| 23 | 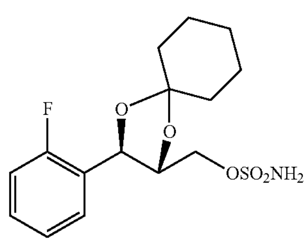 | ((2R,3R)-3-(2-fluorophenyl)-1,4-dioxaspiro[4,5]decan-2-yl)methyl sulfamate | Preparation example 96 | $^D$δ 1.51~1.67 (m, 10H), 4.11~4.23 (m, 3H), 4.98 (d, J = 8.0, 2H), 5.08 (s, 1H), 6.59 (t, J = 8.0, 1H), 6.68 (d, J = 8.0, 1H), 7.04~7.56 (m, 4H) |
| 24 | 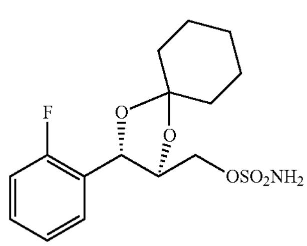 | ((2S,3S)-3-(2-fluorophenyl)-1,4-dioxaspiro[4,5]decan-2-yl)methyl sulfamate | Preparation example 98 | $^D$δ 1.51~1.67 (m, 10H), 4.11~4.23 (m, 3H), 4.98 (d, J = 8.0, 2H), 5.08 (s, 1H), 6.59 (t, J = 8.0, 1H), 6.68 (d, J = 8.0, 1H), 7.04~7.56 (m, 4H) |

TABLE 3-continued

Characterization of the examples of sulfamate compounds

| Example No. | Structure | Name | Starting material | $^1$H NMR (400 MHz) |
|---|---|---|---|---|
| 25 | 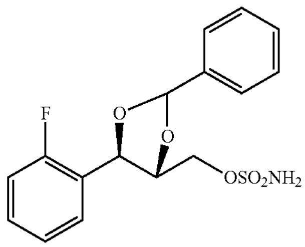 | ((4R,5R)-5-(2-fluorophenyl)-2-phenyl-1,3-dioxolan-4-yl)methyl sulfamate | Preparation example 100 | $^D$δ 4.25 (dt, J = 5.7, J = 3.3, 1H), 4.59 (d, J = 5.7, 1H), 4.75 (d, J = 3.3, 2H), 5.59 (m, 1H), 6.72~7.75 (m, 2H), 6.92~7.33 (m, 5H), 7.25 (m, 1H), 7.76 (m, 1H) |
| 26 | 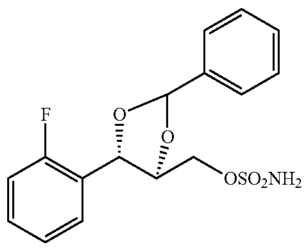 | ((4S,5S)-5-(2-fluorophenyl)-2-phenyl-1,3-dioxolan-4-yl)methyl sulfamate | Preparation example 102 | $^D$δ 4.25 (dt, J = 5.7, J = 3.3, 1H), 4.59 (d, J = 5.7, 1H), 4.75 (d, J = 3.3, 2H) 5.59 (m, 1H), 6.72~7.75 (m, 2H) 6.92~7.33 (m, 5H) 7.25 (m, 1H) 7.76 (m, 1H) |
| 27 | 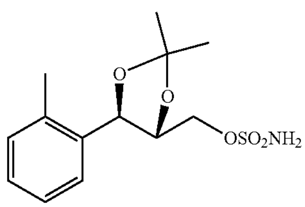 | ((4R,5R)-5-(2-iodophenyl)-2,2-dimethyl-1,3-dioxolan-4-yl)methyl sulfamate | Preparation example 21 | $^D$δ 1.55 (s, 3H), 1.47 (s, 3H) 4.21-4.11 (m, 3H), ), 5.10 (d, J = 7.6, 1H), 7.56~7.13 (m, 3H) 7.60 (s, 2H), 7.91 (d, J = 8.0, 1H) |
| 28 | 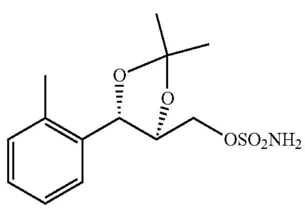 | ((4S,5S)-5-(2-iodophenyl)-2,2-dimethyl-1,3-dioxolan-4-yl)methyl sulfamate | Preparation example 23 | $^D$δ 1.55 (s, 3H), 1.47 (s, 3H) 4.21~4.11 (m, 3H), ), 5.10 (d, J = 7.6, 1H), 7.56~7.13 (m, 3H) 7.60 (s, 2H), 7.91 (d, J = 8.0, 1H) |
| 29 | 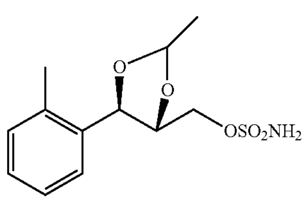 | ((4R,5R)-5-(2-iodophenyl)-2-methyl-1,3-dioxolan-4-yl)methyl sulfamate | Preparation example 107 | $^D$δ 1.40 (d, J = 6.4, 3H), 4.7 (d, J = 3.2, 2H), 5.46 (m, J = 6.4, 1H), 4.22 (dt, J = 3.3, J = 7.0, 1H), 5.10 (d, J = 7.0, 1H), 7.26-7.40 (m, 3H), 7.49 (s, 2H), 7.61 (dd, J = 1.2, J = 7.6, 1H). |
| 30 | 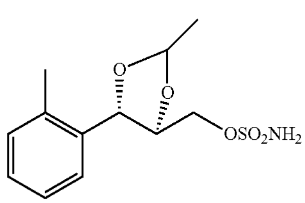 | ((4S,5S)-5-(2-iodophenyl)-2-methyl-1,3-dioxolan-4-yl)methyl sulfamate | Preparation example 109 | $^D$δ 1.40 (d, J = 6.4, 3H), 4.7 (d, J = 3.2, 2H), 5.46 (m, J = 6.4, 1H), 4.22 (dt, J = 3.3, J = 7.0, 1H), 5.08 (d, J = 7.0, 1H), 7.30-7.40 (m, 3H), 7.61 (s, 2H), 7.65 (dd, J = 1.2, J = 7.6, 1H). |

TABLE 3-continued

Characterization of the examples of sulfamate compounds

| Example No. | Structure | Name | Starting material | $^1$H NMR (400 MHz) |
|---|---|---|---|---|
| 31 | 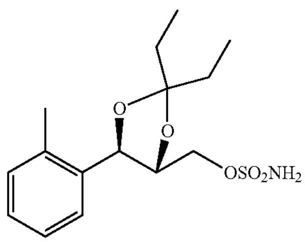 | ((4R,5R)-5-(2-iodophenyl)-2,2-diethyl-1,3-dioxolan-4-yl(methyl sulfamate | Preparation example 111 | $^C$δ 0.90 (t, J = 8.0, 6H), 1.59 (q, J = 8.0, 4H), 3.96-4.21 (m, 2H), 4.42 (q, J = 7.0, 1H), 4.88 (s, 2H), 5.17 (d, J = 7.0, 1H) 7.13~7.56 (m, 4H) |
| 32 | 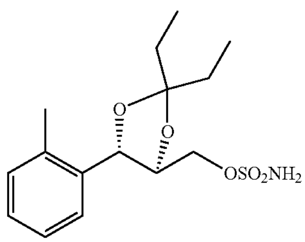 | ((4S,5S)-5-(2-iodophenyl)-2,2-diethyl-1,3-dioxolan-4-yl)methyl sulfamate | Preparation example 113 | $^C$δ 1.46-1.90 (m, 8H), 3.96-4.21(m, 2H), 4.42 (q, J = 7.0, 1H), 4.88 (s, 2H), 5.17 (d, J = 7.0, 1H), 7.13~7.56 (m, 4H) |
| 33 | 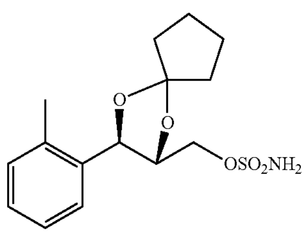 | ((2R,3R)-3-(2-iodophenyl)-1,4-dioxaspiro[4,4]nonan-2-yl)methyl sulfamate | Preparation example 115 | $^D$δ 1.46-1.90 (m, 8H), 3.96-4.21(m, 2H), 4.42 (q, J = 7.0, 1H), 4.88 (s, 2H), 5.17 (d, J = 7.0, 1H), 7.13~7.56 (m, 4H) |
| 34 | 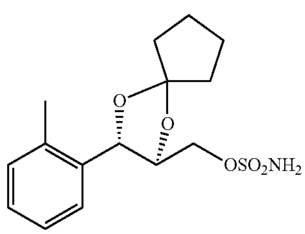 | ((2S,3S)-3-(2-iodophenyl)-1,4-dioxaspiro[4,4]nonan-2-yl)methyl sulfamate | Preparation example 117 | $^D$δ 1.46~1.92 (m, 8H), 3.96-4.21 (m, 2H), 4.42 (q, J = 7.0, 1H), 4.88 (s, 2H), 5.22 (d, J = 7.0, 1H), 7.13~7.59 (m, 4H) |
| 35 | 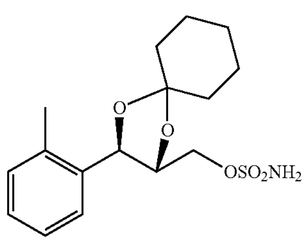 | ((2R,3R)-3-(2-iodophenyl)-1,4-dioxaspiro[4,5]decan-2-yl)methyl sulfamate | Preparation example 119 | $^D$δ 1.33~1.72 (m, 10H), 4.02-4.31 (m, 2H), 4.51(q, J = 7.0, 1H), 4.97 (s, 2H), 5.25 (d, J = 7.0, 1H), 7.19~7.65 (m, 4H) |
| 36 | 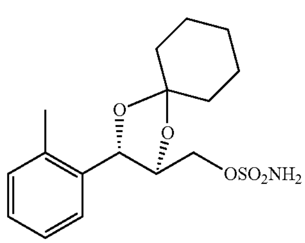 | ((2S,3S)-3-(2-iodophenyl)-1,4-dioxaspiro[4,5]decan-2-yl)methyl sulfamate | Preparation example 121 | $^D$δ 1.33~1.72 (m, 10H), 4.02-4.31 (m, 2H), 4.51 (q, J = 7.0, 1H), 4.97 (s, 2H), 5.25 (d, J = 7.0, 1H), 7.19~7.6 m, 4H) |

TABLE 3-continued

Characterization of the examples of sulfamate compounds

| Example No. | Structure | Name | Starting material | $^1$H NMR (400 MHz) |
|---|---|---|---|---|
| 37 | 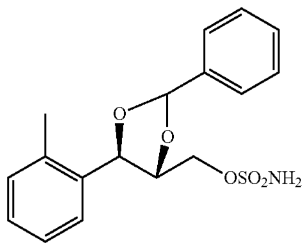 | ((4R,5R)-5-(2-iodophenyl)-2-phenyl-1,3-dioxolan-4-yl)methyl sulfamate | Preparation example 123 | $^D$δ 3.96-4.21 (m, 2H), 4.42 (q, J = 7.0, 1H), 4.92 (s, 2H), 5.20 (d, J = 7.0, 1H), 5.97 (s, 1H), 7.14~7.38 (m, 9H) |
| 38 | 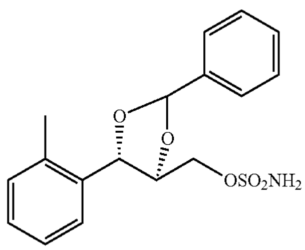 | ((4S,5S)-5-(2-iodophenyl)-2-phenyl-1,3-dioxolan-4-yl)methyl sulfamate | Preparation example 125 | $^D$δ 3.96-4.21 (m, 2H), 4.42 (q, J = 7.0, 1H), 4.92 (s, 2H), 5.20 (d, J = 7.0, 1H), 5.97 (s, 1H), 7.14~7.38 (m, 9H) |
| 39 | 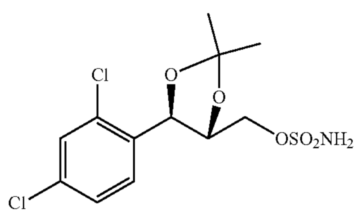 | ((4R,5R)-5-(2,4-dichlorophenyl)-2,2-dimethyl-1,3-dioxolan-4-yl)methyl sulfamate | Preparation example 38 | $^C$δ 1.27 (s, 6H), 3.90-4.15 (m, 2H), 4.37 (q, J = 7.0, 1H), 4.79 (s, 2H), 5.12 (d, J = 7.0, 1H), 7.29~7.42 (m, 2H), 7.79 (s, 1H). |
| 40 | 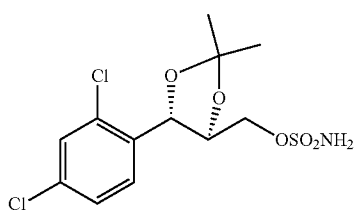 | ((4S,5S)-5-(2,4-dichlorophenyl)-2,2-dimethyl-1,3-dioxolan-4-yl)methyl sulfamate | Preparation example 31 | $^C$δ 1.27 (s, 6H), 3.90-4.15 (m, 2H), 4.37 (q, J = 7.0, 1H), 4.79 (s, 2H), 5.12 (d, J = 7.0, 1H), 7.29~7.42 (m, 2H), 7.79 (s, 1H). |
| 41 | 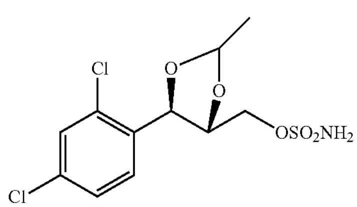 | ((4R,5R)-5-(2,4-dichlorophenyl)-2-methyl-1,3-dioxolan-4-yl)methyl sulfamate | Preparation example 127 | $^C$δ 1.40 (s, 3H), 3.81-4.08 (m, 2H), 4.25 (q, J = 7.0, 1H), 4.81 (s, 2H), 5.03 (q, J = 6.8, 1H), 5.12 (d, J = 7.0, 1H), 7.21~7.27 (m, 2H), 7.70 (s, 1H). |
| 42 | 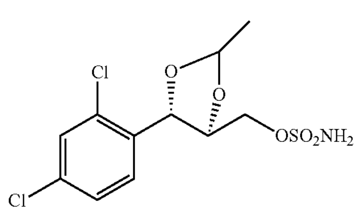 | ((4S,5S)-5-(2,4-dichlorophenyl)-2-methyl-1,3-dioxolan-4-yl)methyl sulfamate | Preparation example 129 | $^C$δ 1.40 (s, 3H), 3.81-4.08 (m, 2H), 4.25 (q, J = 7.0, 1H), 4.81 (s, 2H), 5.03 (q, J = 6.8, 1H), 5.12 (d, J = 7.0, 1H), 7.21~7.27 (m, 2H), 7.70 (s, 1H). |

TABLE 3-continued

Characterization of the examples of sulfamate compounds

| Example No. | Structure | Name | Starting material | $^1$H NMR (400 MHz) |
|---|---|---|---|---|
| 43 | 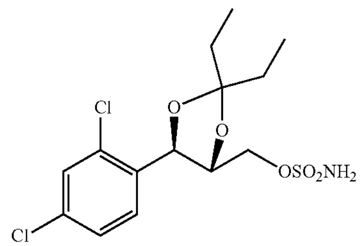 | ((4R,5R)-5-(2,4-dichlorophenyl)-2,2-diethyl-1,3-dioxolan-4-yl)methyl sulfamate | Preparation example 131 | $^C$δ 0.90 (t, J = 8.0, 6H), 1.59 (q, J = 8.0, 4H), 3.96-4.21 (m, 2H), 4.42 (q, J = 7.0, 1H), 4.88 (s, 2H), 5.17 (d, J = 7.0, 1H), 7.24~7.30 (m, 2H), 7.73 (s, 1H). |
| 44 | 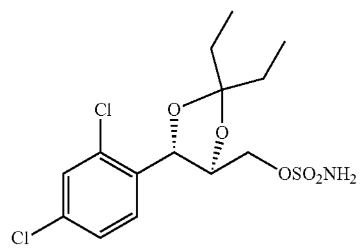 | ((4S,5S)-5-(2,4-dichlorophenyl)-2,2-diethyl-1,3-dioxolan-4-yl)methyl sulfamate | Preparation example 133 | $^C$δ 0.90 (t, J = 8.0, 6H), 1.59 (q, J = 8.0, 4H), 3.96-4.21 (m, 2H), 4.42 (q, J = 7.0, 1H), 4.88 (s, 2H), 5.17 (d, J = 7.0, 1H), 7.24~7.30 (m, 2H), 7.73 (s, 1H). |
| 45 | 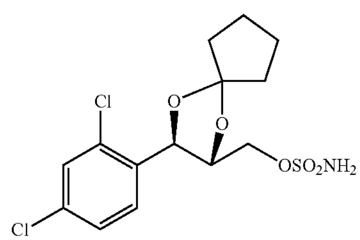 | ((2R,3R)-3-(2,4-dichlorophenyl)-1,4-dioxaspiro[4,4]nonan-2-yl)methyl sulfamate | Preparation example 135 | $^D$δ 1.46~1.90 (m, 8H), 3.79~4.05 (m, 2H), 4.25 (q, J = 7.0, 1H), 4.80 (s, 2H), 5.11 (d, J = 7.0, 1H), 7.28~7.34 (m, 2H), 7.76 (s, 1H). |
| 46 | 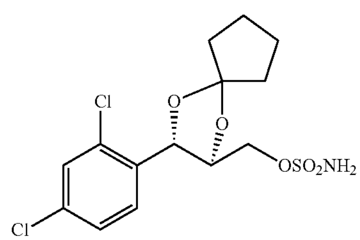 | ((2S,3S)-3-(2,4-dichlorophenyl)-1,4-dioxaspiro[4,4]nonan-2-yl)methyl sulfamate | Preparation example 137 | $^D$δ 1.46~1.90 (m, 8H), 3.79~4.05 (m, 2H), 4.25 (q, J = 7.0, 1H), 4.80 (s, 2H), 5.11 (d, J = 7.0, 1H), 7.28~7.34 (m, 2H), 7.76 (s, 1H). |
| 47 | 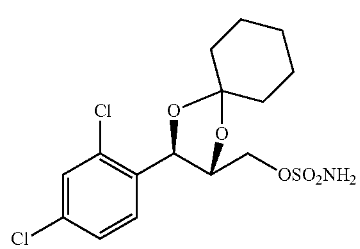 | ((2R,3R)-3-(2,4-dichlorophenyl)-1,4-dioxaspiro[4,5]decan-2-yl)methyl sulfamate | Preparation example 139 | $^D$δ 1.33~1.72 (m, 10H), 3.78-4.03 (m, 2H), 4.22 (q, J = 7.0, 1H), 4.78 (s, 2H), 5.07 (d, J = 7.0, 1H), 7.26~7.32 (m, 2H), 7.77 (s, 1H). |
| 48 | 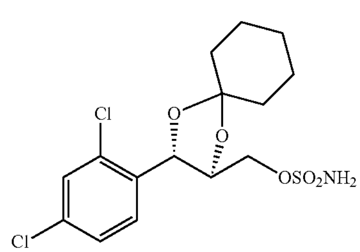 | (2S,3S)-3-(2,4-dichlorophenyl)-1,4-dioxaspiro[4,5]decan-2-yl)methyl sulfamate | Preparation example 141 | $^D$δ 1.33-1.72 (m, 10H), 3.78-4.03 (m, 2H), 4.22 (q, J = 7.0, 1H), 4.78 (s, 2H), 5.07 (d, J = 7.0, 1H), 7.26~7.32 (m, 2H), 7.77 (s, 1H). |

TABLE 3-continued

Characterization of the examples of sulfamate compounds

| Example No. | Structure | Name | Starting material | ¹H NMR (400 MHz) |
|---|---|---|---|---|
| 49 | 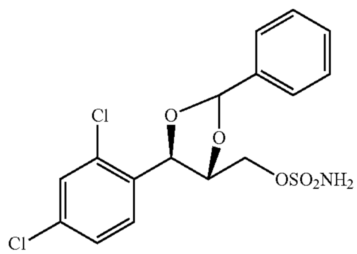 | (4R,5R)-5-(2,4-dichlorophenyl)-2-phenyl-1,3-dioxolan-4-yl)methyl sulfamate | Preparation example 143 | $^D$δ 3.96-4.21 (m, 2H), 4.42 (q, J = 7.0, 1H), 4.88 (s, 2H), 5.17 (d, J = 7.0, 1H), 5.97 (s, 1H), 7.14~7.39 (m, 8H) |
| 50 | 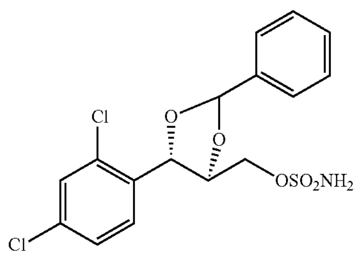 | ((4S,5S)-5-(2,4-dichlorophenyl)-2-phenyl-1,3-dioxolan-4-yl)methyl sulfamate | Preparation example 145 | $^D$δ 3.96-4.21(m, 2H), 4.42 (q, J = 7.0, 1H), 4.88 (s, 2H), 5.17 (d, J = 7.0, 1H), 5.97 (s, 1H), 7.14~7.39 (m, 8H) |
| 51 | 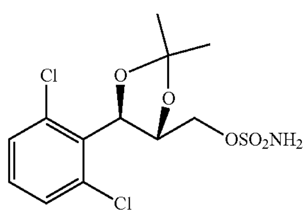 | ((4R,5R)-5-(2,6-dichlorophenyl)-2,2-dimethyl-1,3-dioxolan-4-yl)methyl sulfamate | Preparation example 41 | $^C$δ δ 1.27 (s, 6H), 3.96-4.21 (m, 2H), 4.42 (q, J = 7.0, 1H), 4.88 (s, 2H), 5.17 (d, J = 7.0, 1H), 7.45~7.58 (m, 3H). |
| 52 | 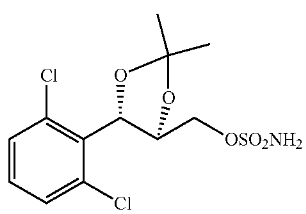 | ((4S,5S)-5-(2,6-dichlorophenyl)-2,2-dimethyl-1,3-dioxolan-4-yl)methyl sulfamate | Preparation example 35 | $^C$δ δ 1.27 (s, 6H), 3.96-4.21 (m, 2H), 4.42 (q, J = 7.0, 1H), 4.88 (s, 2H), 5.17 (d, J = 7.0, 1H), 7.45~7.58 (m, 3H). |
| 53 | 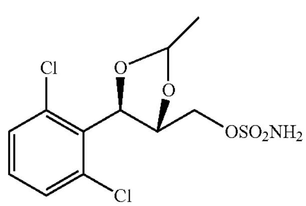 | ((4R,5R)-5-(2,6-dichlorophenyl)-2-methyl-1,3-dioxolan-4-yl)methyl sulfamate | Preparation example 147 | $^D$δ 1.40 (s, 3H), 3.88~4.13 (m, 2H), 4.42 (q, J = 7.0, 1H), 4.88 (s, 2H), 5.07 (q, J = 6.8, 1H), 5.21 (d, J = 7.0, 1H). 5.97 (s, 1H), 7.45~7.58 (m, 3H). |
| 54 | 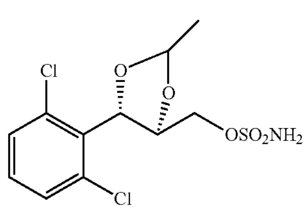 | ((4S,5S)-5-(2,6-dichlorophenyl)-2-methyl-1,3-dioxolan-4-yl)methyl sulfamate | Preparation example 149 | $^D$δ 1.40 (s, 3H), 3.88~4.13 (m, 2H), 4.42 (q, J = 7.0, 1H), 4.88 (s, 2H), 5.07 (q, J = 6.8, 1H), 5.21 (d, J = 7.0, 1H), 5.97 (s, 1H), 7.45~7.58 (m, 3H). |

TABLE 3-continued

Characterization of the examples of sulfamate compounds

| Example No. | Structure | Name | Starting material | $^1$H NMR (400 MHz) |
|---|---|---|---|---|
| 55 | 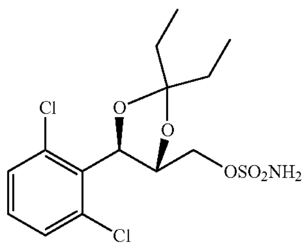 | ((4R,5R)-5-(2,6-dichlorophenyl)-2,2-diethyl-1,3-dioxolan-4-yl)methyl sulfamate | Preparation example 151 | $^C$δ 0.90 (t, J = 8.0, 6H), 1.59 (q, J = 8.0, 4H), 3.86~4.11 (m, 2H), 4.49 (q, J = 7.0, 1H), 4.88 (s, 2H), 5.15 (d, J = 7.0, 1H), 7.45~7.58 (m, 3H). |
| 56 | 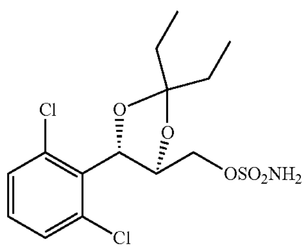 | (4S,5S)-5-(2,6-dichlorophenyl)-2,2-diethyl-1,3-dioxolan-4-yl)methyl sulfamate | Preparation example 153 | $^C$δ 0.90 (t, J = 8.0, 6H), 1.59 (q, J = 8.0, 4H), 3.86~4.11 (m, 2H), 4.49 (q, J = 7.0, 1H), 4.88 (s, 2H), 5.15 (d, J = 7.0, 1H), 7.45~7.58 (m, 3H). |
| 57 | 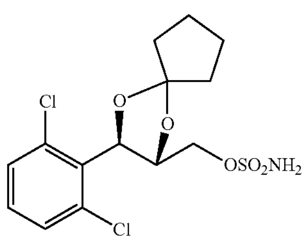 | ((2R,3R)-3-(2,6-dichlorophenyl)-1,4-dioxaspiro[4,4]nonan-2-yl)methyl sulfamate | Preparation example 155 | $^D$δ 1.46~1.90 (m, 8H), 3.98~4.24 (m, 2H), 4.45 (q, J = 7.0, 1H), 4.88 (s, 2H), 5.20 (d, J =7.0, 1H). 7.45~7.58 (m, 3H). |
| 58 | 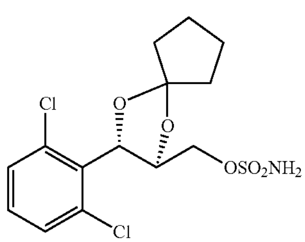 | ((2S,3S)-3-(2,6-dichlorophenyl)-1,4-dioxaspiro[4,4]nonan-2-yl)methyl sulfamate | Preparation example 157 | $^D$δ 1.46-1.90 (m, 8H), 3.98~4.24 (m, 2H), 4.45 (q, J = 7.0, 1H), 4.88 (s, 2H), 5.20 (d, J = 7.0, 1H), 7.45~7.58 (m, 3H). |
| 59 | 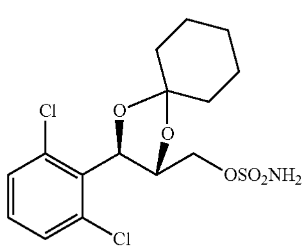 | (2R,3R)-3-(2,6-dichlorophenyl)-1,4-dioxaspiro[4,5]decan-2-yl)methyl sulfamate | Preparation example 159 | $^D$δ 1.33-1.72 (m, 10H), 3.96-4.21 (m, 2H), 4.42 (q, J = 7.0, 1H), 4.88 (s, 2H), 5.17 (d, J = 7.0, 1H), 7.45~7.58 (m, 3H). |
| 60 | 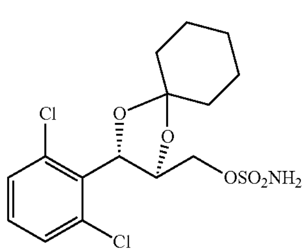 | ((2S,3S)-3-(2,6-dichlorophenyl)-1,4-dioxaspiro[4,5]decan-2-yl)methyl sulfamate | Preparation example 161 | $^D$δ 1.33~1.72 (m, 10H), 3.96-4.21 (m, 2H), 4.42 (q, J = 7.0, 1H), 4.88 (s, 2H), 5.17 (d, J = 7.0, 1H), 7.45~7.58 (m, 3H). |

TABLE 3-continued

Characterization of the examples of sulfamate compounds

| Example No. | Structure | Name | Starting material | $^1$H NMR (400 MHz) |
|---|---|---|---|---|
| 61 | 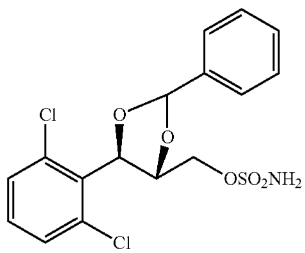 | ((4R,5R)-5-(2,6-dichlorophenyl)-2-phenyl-1,3-dioxolan-4-yl)methyl sulfamate | Preparation example 163 | $^D$δ 2.0 (s, 2H), 3.96~4.21 (m, 2H), 4.42 (dd, J = 7.0, J = 7.0, 1H), 5.17 (d, J = 7.0, 1H), 5.79 (s, 1H), 7.36~7.38 (m, 5H), 7.57~7.58 (m, 3H). |
| 62 | 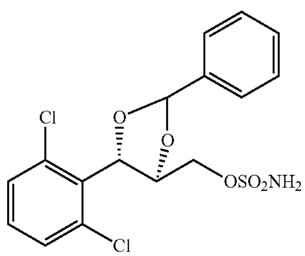 | ((4S,5S)-5-(2,6-dichlorophenyl)-2-phenyl-1,3-dioxolan-4-yl)methyl sulfamate | Preparation example 165 | $^D$δ 2.0 (s, 2H), 3.96~4.21 (m, 2H), 4.42 (dd, J = 7.0, J = 7.0, 1H), 5.17 (d, J = 7.0, 1H), 5.79 (s, 1H), 7.36~7.38 (m, 5H), 7.57~7.58 (m, 3H). |
| 63 | 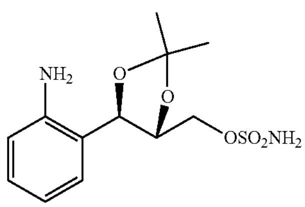 | ((4R,5R)-5-(2-aminophenyl)-2,2-dimethyl-1,3-dioxolan-4-yl)methyl sulfamate | Preparation example 47 | $^D$δ 1.27 (s, 6H), 2.0 (s, 2H), 3.96~4.21 (m, 2H), 4.42 (dt, J = 7.02, J = 3.27, 1H), 5.17 (d, J = 7.0, 1H), 6.27 (s, 2H), 6.73~7.13 (m, 4H). |
| 64 | 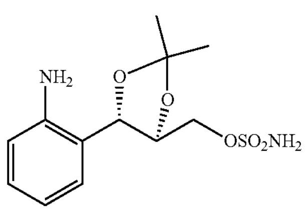 | ((4S,5S)-5-(2-aminophenyl)-2,2-dimethyl-1,3-dioxolan-4-yl)methyl sulfamate | Preparation example 51 | $^D$δ 1.27 (s, 6H), 2.0 (s, 2H), 3.96~4.21 (m, 2H), 4.42 (dt, J = 7.02, J = 3.27, 1H), 5.17 (d, J = 7.0, 1H), 6.27 (s, 2H), 6.73~7.13 (m, 4H). |
| 67 | 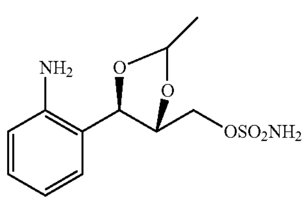 | ((4R,5R)-5-(2-aminophenyl)-2-methyl-1,3-dioxolan-4-yl)methyl sulfamate | Preparation example 206 | $^D$δ 1.40 (d, J = 6.8, 3H), 2.0 (s, 2H), 3.96~4.21 (m, 2H), 4.42 (q, J = 7.0, 1H), 5.07 (q, J = 7.0, 1H), 5.17 (d, J = 7.0, 1H), 6.27 (s, 2H), 6.73~7.13 (m, 4H). |
| 68 | 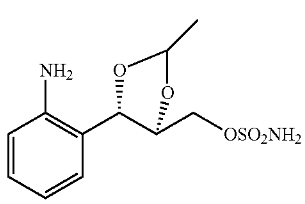 | ((4S,5S)-5-(2-aminophenyl)-2-methyl-1,3-dioxolan-4-yl)methyl sulfamate | Preparation example 207 | $^D$δ 1.40 (d, J = 6.8, 3H), 2.0 (s, 2H), 3.96~4.21 (m, 2H), 4.42 (q, J = 7.0, 1H), 5.07 (q, J = 7.0, 1H), 5.17 (d, J = 7.0, 1H), 6.27 (s, 2H), 6.73~7.13 (m, 4H) |

TABLE 3-continued

Characterization of the examples of sulfamate compounds

| Example No. | Structure | Name | Starting material | ¹H NMR (400 MHz) |
|---|---|---|---|---|
| 69 | 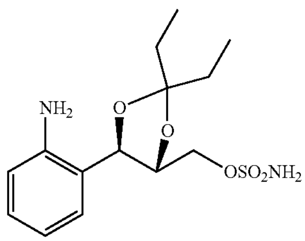 | ((4R,5R)-5-(2-aminophenyl)-2,2-diethyl-1,3-dioxolan-4-yl)methyl sulfamate | Preparation example 208 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 6.27 (s, 2H), 6.71~7.14 (m, 4H). |
| 70 | 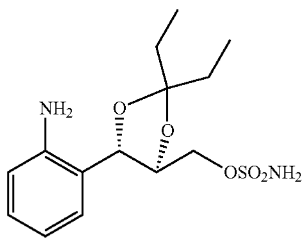 | ((4S,5S)-5-(2-aminophenyl)-2,2-diethyl-1,3-dioxolan-4-yl)methyl sulfamate | Preparation example 209 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 6.27 (s, 2H), 6.71~7.14 (m, 4H). |
| 71 | 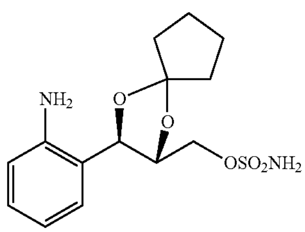 | ((2R,3R)-3-(2-aminophenyl)-1,4-dioxaspiro[4,4]nonan-2-yl)methyl sulfamate | Preparation example 210 | $^D$δ 1.46~1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 6.27 (s, 2H), 6.70~7.11 (m, 4H) |
| 72 | 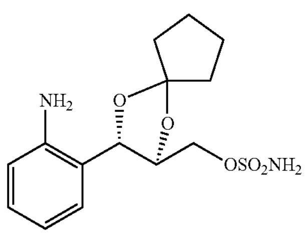 | ((2S,3S)-3-(2-aminophenyl)-1,4-dioxaspiro[4,4]nonan-2-yl)methyl sulfamate | Preparation example 211 | $^D$δ 1.46~1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 6.27 (s, 2H), 6.70~7.11 (m, 4H) |
| 73 | 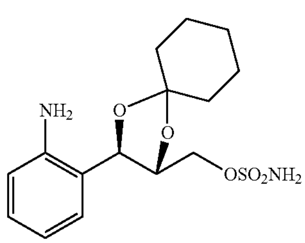 | ((2R,3R)-3-(2-aminophenyl)-1,4-dioxaspiro[4,5]decan-2-yl)methyl sulfamate | Preparation example 212 | $^D$δ 1.33~1.72 (m, 10H), 2.0 (s, 2H), 3.96~4.21 (m, 2H), 4.43 (dt, J = 7.02, J = 3.27, 1H), 5.17 (d, J = 7.0, 1H), 6.25 (s, 2H), 6.71~7.12 (m, 4H). |
| 74 | 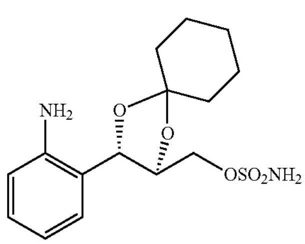 | ((2S,3S)-3-(2-aminophenyl)-1,4-dioxaspiro[4,5]decan-2-yl)methyl sulfamate | Preparation example 213 | $^D$δ 1.33-1.72 (m, 10H), 2.0 (s, 2H), 3.96~4.21 (m, 2H), 4.43 (dt, J = 7.02, J = 3.27, 1H), 5.17 (d, J = 7.0, 1H), 6.25 (s, 2H), 6.71~7.12 (m, 4H) |

TABLE 3-continued

Characterization of the examples of sulfamate compounds

| Example No. | Structure | Name | Starting material | $^1$H NMR (400 MHz) |
|---|---|---|---|---|
| 75 | (structure with NH₂, phenyl dioxolane, OSO₂NH₂) | ((4R,5R)-5-(2-aminophenyl)-2-phenyl-1,3-dioxolan-4-yl)methyl sulfamate | Preparation example 214 | $^D$δ 2.0 (s, 2H), 3.96~4.21 (m, 2H), 4.42 (dt, J = 7.02, J = 3.27, 1H), 5.17 (d, J = 7.0, 1H), 5.79 (s, 1H), 6.27 (s, 2H), 6.73~6.74 (m, 2H), 7.11~7.13 (m, 2H), 7.36~7.38 (m, 5H). |
| 76 | (structure with NH₂, phenyl dioxolane, OSO₂NH₂) | ((4S,5S)-5-(2-aminophenyl)-2-phenyl-1,3-dioxolan-4-yl)methyl sulfamate | Preparation example 215 | $^D$δ 2.0 (s, 2H), 3.96~4.21 (m, 2H), 4.42 (dt, J = 7.02, J = 3.27, 1H), 5.17 (d, J = 7.0, 1H), 5.79 (s, 1H), 6.27 (s, 2H), 6.73~6.74 (m, 2H), 7.11~7.13 (m, 2H), 7.36~7.38 (m, 5H). |
| 77 | (structure with NO₂, dimethyl dioxolane, OSO₂NH₂) | ((4R,5R)-5-(2-nitrophenyl)-2,2-dimethyl-1,3-dioxolan-4-yl)methyl sulfamate | Preparation example 46 | $^D$δ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |
| 78 | (structure with NO₂, dimethyl dioxolane, OSO₂NH₂) | ((4S,5S)-5-(2-nitrophenyl)-2,2-dimethyl-1,3-dioxolan-4-yl)methyl sulfamate | Preparation example 50 | $^D$δ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 79 | (structure with NO₂, methyl dioxolane, OSO₂NH₂) | ((4R,5R)-5-(2-nitrophenyl)-2-methyl-1,3-dioxolan-4-yl)methyl sulfamate | Preparation example 167 | $^D$δ 1.40 (d, J = 6.8, 3H), 2.0 (s, 2H), 3.96~4.21 (m, 2H), 4.42 (q, J = 7.0, 1H), 5.07 (q, J = 7.0, 1H), 5.17 (d, J = 7.0, 1H), 7.62~7.64 (m, 2H), 7.77~7.90 (m, 2H). |
| 80 | (structure with NO₂, methyl dioxolane, OSO₂NH₂) | ((4S,5S)-5-(2-nitrophenyl)-2-methyl-1,3-dioxolan-4-yl)methyl sulfamate | Preparation example 169 | $^D$δ 1.40 (d, J = 6.8, 3H), 2.0 (s, 2H), 3.96~4.21 (m, 2H), 4.42 (q, J = 7.0, 1H), 5.07 (q, J = 7.0, 1H), 5.17 (d, J = 7.0, 1H), 7.62~7.64 (m, 2H), 7.77~7.90 (m, 2H). |

TABLE 3-continued

Characterization of the examples of sulfamate compounds

| Example No. | Structure | Name | Starting material | ¹H NMR (400 MHz) |
|---|---|---|---|---|
| 81 | 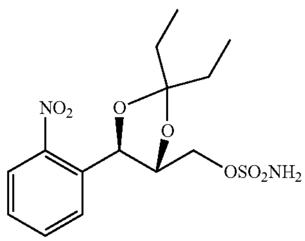 | ((4R,5R)-5-(2-nitrophenyl)-2,2-diethyl-1,3-dioxolan-4-yl)methyl sulfamate | Preparation example 171 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 82 | 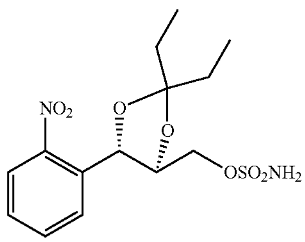 | ((4S,5S)-5-(2-nitrophenyl)-2,2-diethyl-1,3-dioxolan-4-yl)methyl sulfamate | Preparation example 173 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |
| 83 | 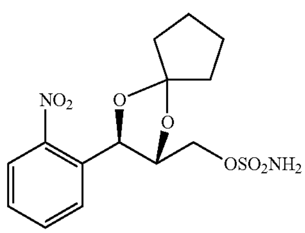 | ((2R,3R)-3-(2-nitrophenyl)-1,4-dioxaspiro[4,4]nonane-2-yl)methyl sulfamate | Preparation example 175 | $^D$δ 1.46~1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 84 | 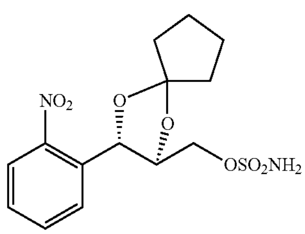 | ((2S,3S)-3-(2-nitrophenyl)-1,4-dioxaspiro[4,4]nonan-2-yl)methyl sulfamate | Preparation example 177 | $^D$δ 1.46~1.56 (m, 6H), 1.65~1.90 (m, 2H), 2.0 (s, 2H), 3.96~4.21 (m, 2H), 4.42 (dt, J = 7.02, J = 3.27, 1H). 5.17 (d, J = 7.0, 1H), 7.62~7.64 (m, 2H), 7.77~7.90 (m, 2H). |
| 85 | 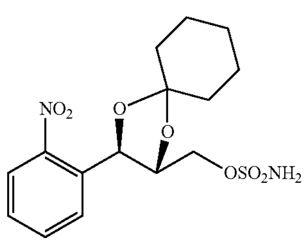 | ((2R,3R)-3-(2-nitrophenyl)-1,4-dioxaspiro[4,5]decan-2-yl)methyl sulfamate | Preparation example 179 | $^D$δ 1.33~1.72 (m, 10H), 2.0 (s, 2H), 3.96~4.21 (m, 2H), 4.42 (dt, J = 7.02, J = 3.27, 1H), 5.17 (d, J = 7.0. 1H), 7.62~7.64 (m, 2H), 7.77~7.90 (m, 2H). |
| 86 | 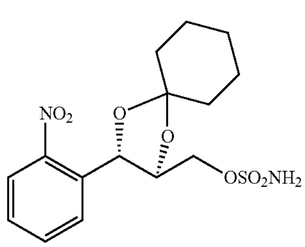 | ((2S,3S)-3-(2-nitrophenyl)-1,4-(dioxaspiro[4,5]decan-2-yl)methyl sulfamate | Preparation example 181 | $^D$δ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |

TABLE 3-continued

Characterization of the examples of sulfamate compounds

| Example No. | Structure | Name | Starting material | $^1$H NMR (400 MHz) |
|---|---|---|---|---|
| 87 | 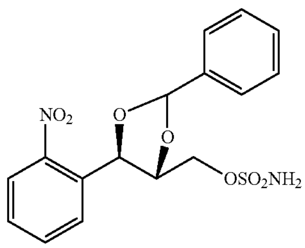 | ((4R,5R)-5-(2-nitrophenyl)-2-phenyl-1,3-dioxolan-4-yl)methyl sulfamate | Preparation example 183 | $^D\delta$ 2.0 (s, 2H), 3.96~4.21 (m, 2H), 4.42 (dt, J = 7.02, J = 3.27, 1H), 5.17 (d, J = 7.0, 1H), 5.79 (s, 1H), 6.73~6.74 (m, 2H), 7.11~7.13(m, 2H), 7.36~7.38(m, 5H). |
| 88 | 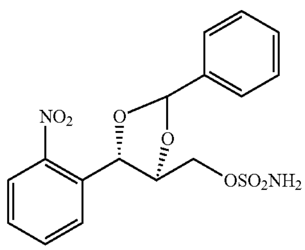 | ((4S,5S)-5-(2-nitrophenyl)-2-phenyl-1,3-dioxolan-4-yl)methyl sulfamate | Preparation example 185 | $^D\delta$ 2.0 (s, 2H), 3.96~4.21 (m, 2H), 4.42 (dt, J = 7.02, J = 3.27, 1H), 5.17 (d, J = 7.0, 1H), 5.79 (s, 1H), 6.73~6.74 (m, 2H), 7.11~7.13 (m, 2H). 7.36~7.38 (m, 5H). |
| 91 | 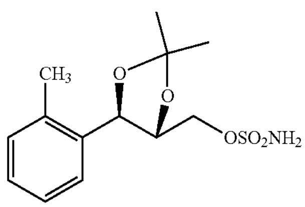 | (4R,5R)-5-(2-methylphenyl)-2,2-dimethyl-1,3-dioxolan-4-yl)methyl sulfamate | Preparation example 56 | $^C\delta$ 1.38 (s, 3H), 1.40 (s, 3H), 2.24 (s, 3H), 4.29 (d, J = 3.3, 2H), 4.74 (dt, J = 7.0, J = 3.3, 1H), 5.06 (d, J = 7.0, 1H), 5.52 (s, 2H), 7.13~7.29 (m, 4H) |
| 92 | 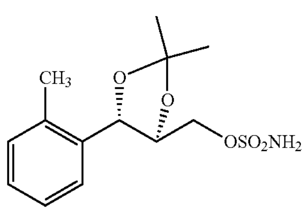 | ((4S,5S)-5-(2-methylphenyl)-2,2-dimethyl-1,3-dioxolan-4-yl)methyl sulfamate | Preparation example 59 | $^C\delta$ 1.38 (s, 3H), 1.40 (s, 3H), 2.24 (s, 3H), 2.24 (s, 3H), 4.29 (d, J = 3.3, 2H), 4.74 (dt, J = 7.0, J = 3.3, 1H), 5.06 (d, J = 7.0, 1H), 5.52 (s, 2H), 7.13~7.29 (m, 4H) |
| 93 | 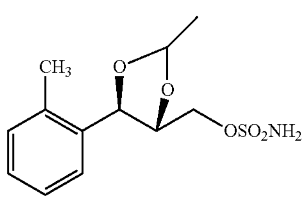 | ((4R,5R)-5-(2-methylphenyl)-2-methyl-1,3-dioxolan-4-yl)methyl sulfamate | Preparation example 187 | $^C\delta$ 1.40, J = 6.4, 3H), 2.24 (s, 3H), 4.27 (dt, J = 7.0, J = 3.3, 1H), 4.70 (d, J = 3.3, 2H), 5.13 (d, J = 7.0, 1H), 5.40 (q, J = 6.4, 1H), 5.52 (s, 2H), 7.13~7.29 (m, 4H) |
| 94 | 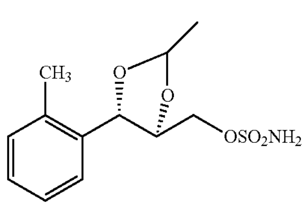 | ((4S,5S)-5-(2-methylphenyl)-2-methyl-1,3-dioxolan-4-yl)methyl sulfamate | Preparation example 189 | $^C\delta$ 1.40 (d, J = 6.4, 3H), 2.24 (s, 3H), 4.27 (dt, = 7.0, J = 3.3, 1H), 4.70 (d, J = 3.3, 2H), 5.13 (d, J = 7.0, 1H), 5.40 (q, J = 6.4, 1H), 5.52 (s, 2H), 7.13~7.29 (m, 4H) |

TABLE 3-continued

Characterization of the examples of sulfamate compounds

| Example No. | Structure | Name | Starting material | ¹H NMR (400 MHz) |
|---|---|---|---|---|
| 95 | 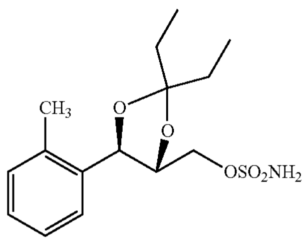 | ((4R,5R)-5-(2-methylphenyl)-2,2-diethyl-1,3-dioxolan-4-yl)methyl sulfamate | Preparation example 191 | $^c$δ 1.05 (t, J = 6.8, 3H), 1.15 (t, J = 6.8, 3H), 1.77~1.85 (m, 4H), 2.24 (s, 3H), 4.35 (d, J = 3.3, 2H), 4.75 (dt, J = 7.0, J = 3.3, 1H), 5.10 (d, J = 7.0, 1H), 5.52 (s, 2H), 7.18~7.30 (m, 4H) |
| 96 | 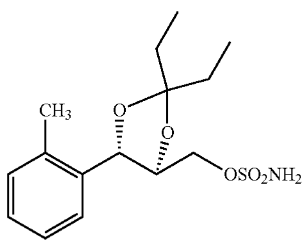 | ((4S,5S)-5-(2-methylphenyl)-2,2-diethyl-1,3-dioxolan-4-yl)methyl sulfamate | Preparation example 193 | $^c$δ 1.05 (t, J = 6.8, 3H), 1.15 (t, J = 6.8, 3H), 1.77~1.85 (m, 4H), 2.24 (s, 3H), 4.35 (d, J = 3.3, 2H), 4.75 (dt, J = 7.0, J = 3.3, 1H), 5.10 (d, J = 7.0, 1H), 5.52 (s, 2H), 7.18~7.30 (m, 4H) |
| 97 | 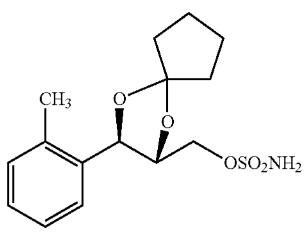 | ((2R,3R)-3-(2-methylphenyl)-1,4-dioxaspiro[4,4]nonane-2-yl)methyl sulfamate | Preparation example 195 | $^c$δ 1.60~1.70 (m, 4H), 1.74~1.99 (m, 4H), 2.24 (s, 3H), 4.75 (d, J = 3.267, 2H), 4.36 (dt, J = 7.1, J = 3.3, 1H), 5.13 (d, J = 7.0, 1H), 5.52 (s, 2H), 7.13~7.30 (m, 4H) |
| 98 | 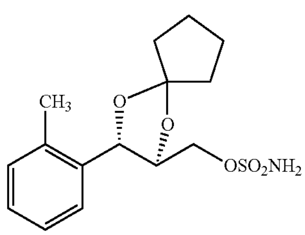 | ((2S,3S)-3-(2-methylphenyl)-1,4-dioxaspiro[4,4]nonane-2-yl)methyl sulfamate | Preparation example 197 | $^c$δ 1.60~1.70 (m, 4H), 1.74-1.99 (m, 4H), 2.24 (s, 3H), 4.75 (d, J = 3.267, 2H), 4.36 (dt, J = 7.1, J = 3.3, 1H), 5.13 (d, J = 7.0, 1H), 5.52 (s, 2H), 7.13~7.30 (m, 4H) |
| 99 | 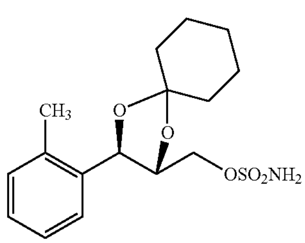 | ((2R,3R)-3-(2-methylphenyl)-1,4-dioxaspiro[4,5]decan-2-yl)methyl sulfamate | Preparation example 199 | $^c$δ 1.40-1.49 (m, 2H), 1.53~1.60 (m, 4H), 1.61~2.09 (m, 4H), 2.24 (s, 3H), 4.23 (d, J = 3.3, 2H), 4.75 (dt, J = 7.0, J = 3.3, 1H), 5.10 (d, J = 7.0, 1H), 5.62 (s, 2H), 7.13~7.30 (m, 4H) |
| 100 | 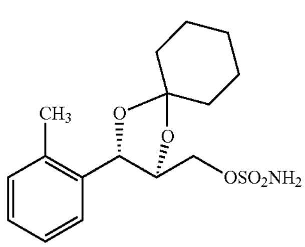 | ((2S,3S)-3-(2-methylphenyl)-1,4-dioxaspiro[4,5]decan-2-yl)methyl sulfamate | Preparation example 201 | $^c$δ 1.40-1.49 (m, 2H), 1.53~1.60 (m, 4H), 1.61~2.09 (m, 4H), 2.24 (s, 3H), 4.23 (d, J = 3.3, 2H), 4.75 (dt, J = 7.0, J =3.3, 1H), 5.10 (d, J = 7.0, 1H), 5.62 (s, 2H), 7.13~7.30 (m, 4H) |

TABLE 3-continued

Characterization of the examples of sulfamate compounds

| Example No. | Structure | Name | Starting material | $^1$H NMR (400 MHz) |
|---|---|---|---|---|
| 101 | 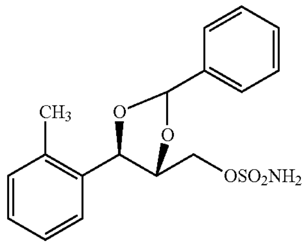 | ((4R,5R)-5-(2-methylphenyl)-2-phenyl-1,3-dioxolan-4-yl)methyl sulfamate | Preparation example 203 | $^C$δ 2.24 (s, 3H), 4.35 (d, J = 3.3, 2H), 4.64 (d, J = 5.7, 1H), 4.75 (dt, J = 5.7, J = 3.3, 1H), 5.59 (m, 1H), 5.78 (s, 2H), 7.13~7.29 (m, 4H), 7.33 (ddt, J = 7.7, J = 7.5, J = 1.5, 1H), 7.40~7.75 (m, 4H) |
| 102 | 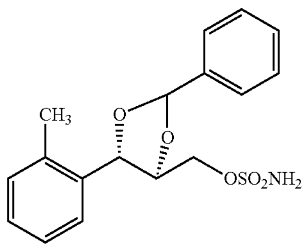 | ((4S,5S)-5-(2-methylphenyl)-2-phenyl-1,3-dioxolan-4-yl)methyl sulfamate | Preparation example 205 | $^C$δ 2.24 (s, 3H), 4.35 (d, J = 3.3, 2H), 4.64 (d, J = 5.7, 1H), 4.75 (dt, J = 5.7, J = 3.3, 1H), 5.59 (m, 1H), 5.78 (s, 2H), 7.13~7.29 (m, 4H), 7.33 (ddt, J = 7.7, J = 7.5, J = 1.5, 1H), 7.40~7.75 (m, 4H) |
| 105 | 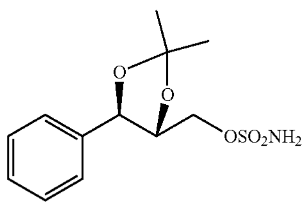 | ((4R,5R)-5-phenyl-2,2-dimethyl-1,3-dioxolan-4-yl)methyl sulfamate | Preparation example 219 | $^D$δ 1.27 (s, 6H), 1.40 (s, 3H), 2.0 (s, 2H), 3.96~4.21(m, 2H), 4.42 (dt, J = 7.02, J = 3.27, 1H), 5.17 (d, J = 7.0, 1H), 7.62~7.64 (m, 2H), 7.77~7.90 (m, 2H) |
| 106 | 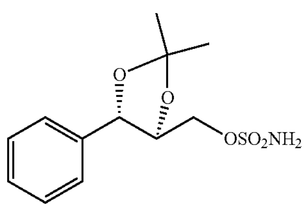 | ((4S,5S)-5-phenyl-2,2-dimethyl-1,3-dioxolan-4-yl)methyl sulfamate | Preparation example 222 | $^D$δ 1.27(s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |
| 107 | 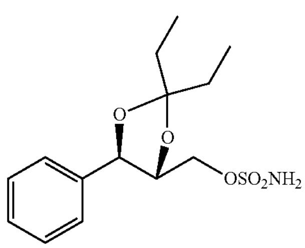 | ((4R,5R)-5-phenyl-2,2-diethyl-1,3-dioxolan-4-yl)methyl sulfamate | Preparation example 224 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |
| 108 | 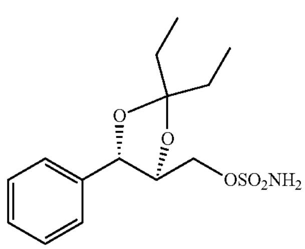 | ((4S,5S)-5-phenyl-2,2-diethyl-1,3-dioxolan-4-yl)methyl sulfamate | Preparation example 226 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |

TABLE 3-continued

Characterization of the examples of sulfamate compounds

| Example No. | Structure | Name | Starting material | $^1$H NMR (400 MHz) |
|---|---|---|---|---|
| 109 | 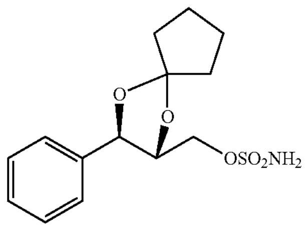 | ((2R,3R)-3-phenyl-1,4-dioxaspiro[4,4]nonan-2-yl)methyl sulfamate | Preparaion example 228 | $^D\delta$ 1.46~1.56 (m, 6H), 1.65-1.90 (m, 2H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 110 | 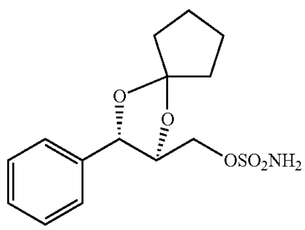 | ((2S,3S)-3-phenyl-1,4-dioxaspiro[4,4]nonan-2-yl)methyl sulfamate | Preparation example 230 | $^D\delta$ 1.46~1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 111 | 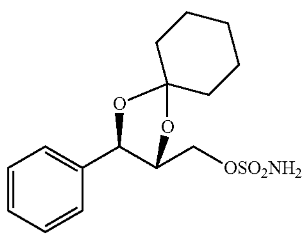 | ((2R,3R)-3-phenyl-1,4-dioxaspiro[4,5]decan-2-yl)methyl sulfamate | Preparation example 232 | $^D\delta$ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62-7.64 (m, 2H), 7.77~7.90 (m, 2H) |
| 112 | 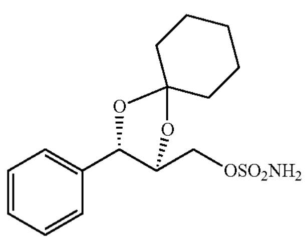 | ((2S,3S)-3-phenyl-1,4-dioxaspiro[4,5]decan-2-yl)methyl sulfamate | Preparation example 234 | $^D\delta$ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |
| 113 | 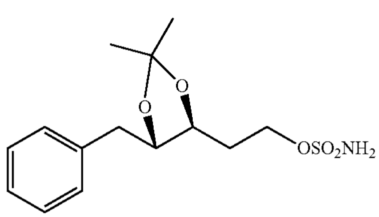 | 2-((4S,5S)-5-benzyl-2,2-dimethyl-1,3-dioxolan-4-yl)methyl sulfamate | Preparation example 241 | $^D\delta$ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 114 | 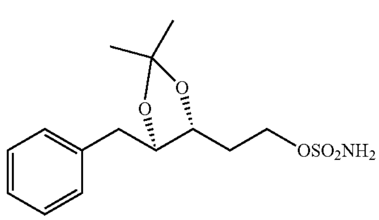 | 2-((4R,5R)-5-benzyl-2,2-dimethyl-1,3-dioxolan-4-yl)ethyl sulfamate | Preparation example 244 | $^D\delta$ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |

TABLE 3-continued

Characterization of the examples of sulfamate compounds

| Example No. | Structure | Name | Starting material | $^1$H NMR (400 MHz) |
|---|---|---|---|---|
| 115 | 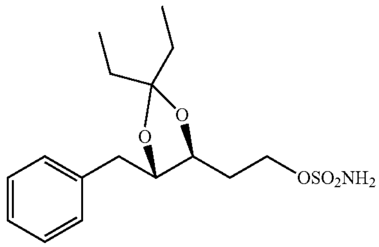 | 2-((4S,5S)-5-benzyl-2,2-diethyl-1,3-dioxolan-4-yl)ethyl sulfamate | Preparation example 247 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 116 | 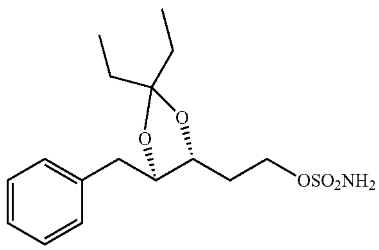 | 2-((4R,5R)-5-benzyl-2,2-diethyl-1,3-dioxolan-4-yl)ethyl sulfamate | Preparation example 250 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 117 | 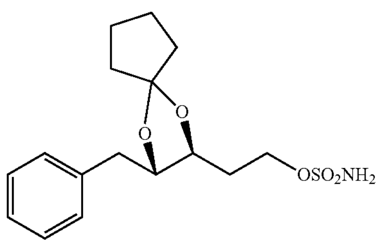 | 2-((2S,3S)-3-benzyl-1,4-dioxaspiro[4,4]nonan-2-yl)ethyl sulfamate | Preparation example 252 | $^D$δ 1.46-1.56 (m, 6H), 1.65-1.90 (m, 2H), 2.0 (s, 2H), 3.96~4.21(m, 2H), 4.42 (dt, J = 7.02, J = 3.27, 1H), 5.17 (d, J = 7.0, 1H), 7.62~7.64 (m, 2H), 7.77~7.90 (m, 2H). |
| 118 | 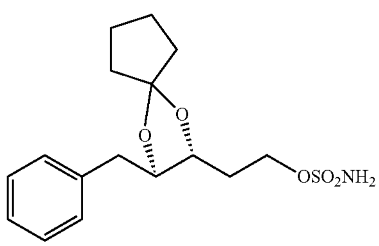 | 2-((2R,3R)-3-benzyl-1,4-dioxaspiro[4,4]nonan-2-yl)ethyl sulfamate | Preparation example 254 | $^D$δ 1.46~1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 119 | 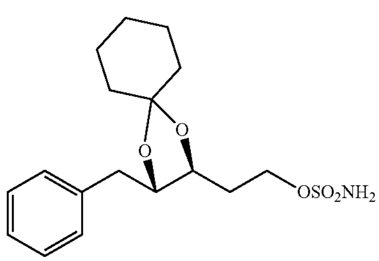 | 2-((2S,3S)-3-benzyl-1,4-dioxaspiro[4,5]decane-2-yl)ethyl sulfamate | Preparation example 256 | $^D$δ 1.33-1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 120 | 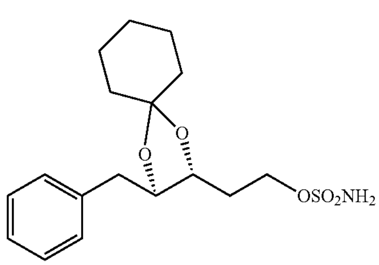 | 2-((2R,3R)-3-benzyl-1,4-dioxaspiro[4,5]decan-2-yl)ethyl sulfamate | Preparation example 258 | $^D$δ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |

TABLE 3-continued

Characterization of the examples of sulfamate compounds

| Example No. | Structure | Name | Starting material | ¹H NMR (400 MHz) |
|---|---|---|---|---|
| 121 | 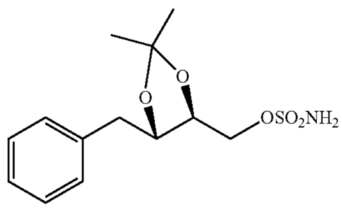 | ((4S,5S)-5-benzyl-2,2-dimethyl-1,3-dioxolan-4-yl)methyl sulfamate | Preparation example 262 | $^D$δ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |
| 122 | 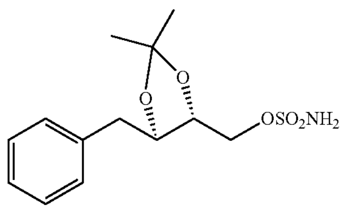 | ((4R,5R)-5-benzyl-2,2-dimethyl-1,3-dioxolan-4-yl)methyl sulfamate | Preparation example 271 | $^D$δ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 123 | 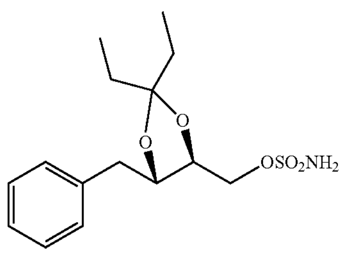 | ((4S,5S)-5-benzyl-2,2-diethyl-1,3-dioxolan-4-yl)methyl sulfamate | Preparation example 264 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |
| 124 | 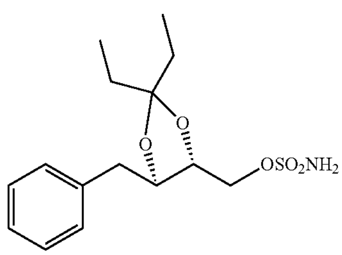 | ((4R,5R)-5-benzyl-2,2-diethyl-1,3-dioxolan-4-yl)methyl sulfamate | Preparation example 273 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |
| 125 | 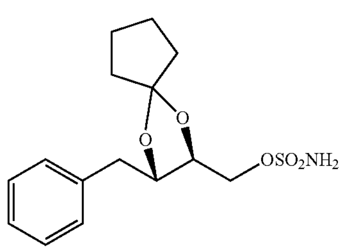 | ((2S,3S)-3-benzyl-1,4-dioxaspiro[4,4]nonan-2-yl)methyl sulfamate | Preparation example 266 | $^D$δ 1.46~1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 126 | 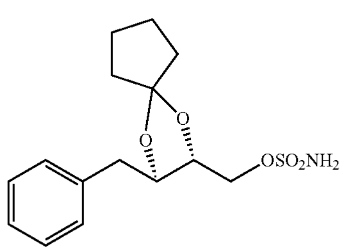 | ((2R,3R)-3-benzyl-1,4-dioxaspiro[4,4]nonan-2-yl)methyl sulfamate | Preparation example 275 | $^D$δ 1.46~1.56 (m, 6H), 1.65~1.90 (m, 2H), 2.0 (s, 2H), 3.96~4.21 (m, 2H), 4.42 (dt, J = 7.02, J = 3.27, 1H). 5.17 (d, J = 7.0, 1H), 7.62~7.64 (m, 2H), 7.77~7.90 (m, 2H). |

TABLE 3-continued

Characterization of the examples of sulfamate compounds

| Example No. | Structure | Name | Starting material | $^1$H NMR (400 MHz) |
|---|---|---|---|---|
| 127 | 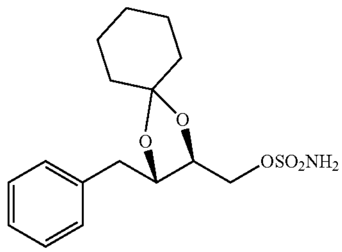 | ((2S,3S)-3-benzyl-1,4-dioxaspiro[4,5]decan-2-yl)methyl sulfamate | Preparation example 268 | $^D\delta$ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 128 | 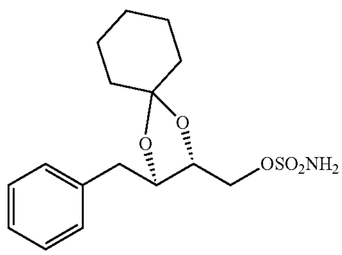 | ((2R,3R)-3-benzyl-1,4-dioxaspiro[4,5]decan-2-yl)methyl sulfamate | Preparation example 277 | $^D\delta$ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 129 | 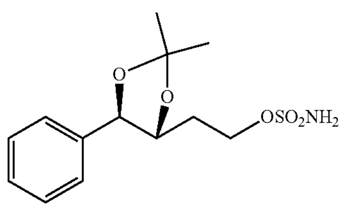 | 2-((4R,5R)-5-phenyl-2,2-dimethyl-1,3-dioxolan-4-yl)ethyl sulfamate | Preparaion example 285 | $^D\delta$ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |
| 130 | 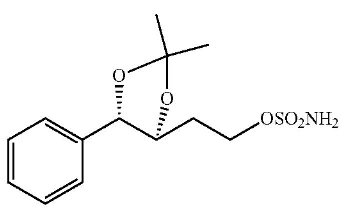 | 2-((4S,5S)-5-phenyl-2,2-dimethyl-1,3-dioxolan-4-yl)ethyl sulfamate | Preparaton example 289 | $^D\delta$ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 131 | 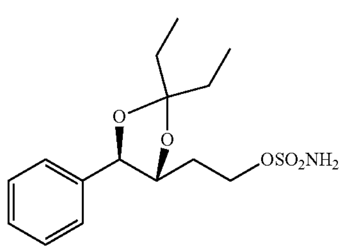 | 2-((4R,5R)-5-phenyl-2,2-diethyl-1,3-dioxolan-4-yl)ethyl sulfamate | Preparation example 291 | $^C\delta$ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |
| 132 | 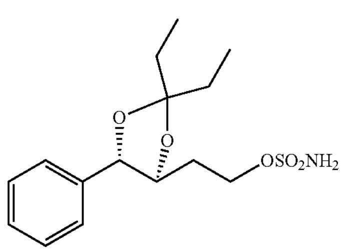 | 2-((4S,5S)-5-phenyl-2,2-diethyl-1,3-dioxolan-4-yl)ethyl sulfamate | Preparation example 297 | $^C\delta$ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |

TABLE 3-continued

Characterization of the examples of sulfamate compounds

| Example No. | Structure | Name | Starting material | $^1$H NMR (400 MHz) |
|---|---|---|---|---|
| 133 | 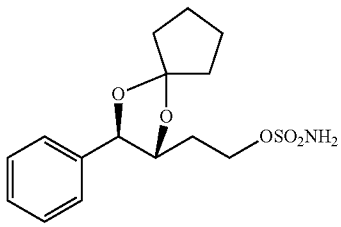 | 2-((2R,3R)-3-phenyl-1,4-dioxaspiro[4,4]nonan-2-yl)ethyl sulfamate | Preparation example 293 | $^D$δ 1.46~1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 134 | 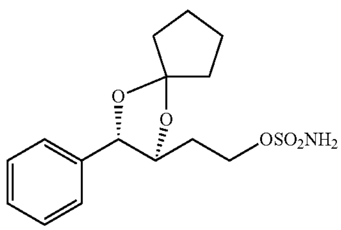 | 2-((2S,3S)-3-phenyl-1,4-dioxaspiro[4,4]nonan-2-yl)ethyl sulfamate | Preparation example 299 | $^D$δ 1.46-1.56 (m, 6H), 1.65~1.90 (m, 2H), 2.0 (s, 2H), 3.96-4.21 (m, 2H), 4.42 (dt, J = 7.02, J = 3.27, 1H), 5.17 (d, J = 7.0, 1H), 7.62~7.64 (m, 2H), 7.77~7.90 (m, 2H) |
| 135 | 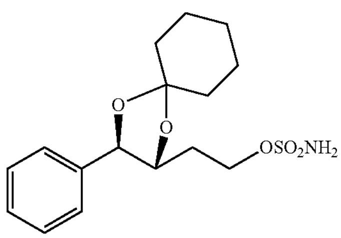 | 2-(2R,3R)-3-phenyl-1,4-dioxaspiro[4,5]decan-2-yl)ethyl sulfamate | Preparation example 295 | $^D$δ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 136 | 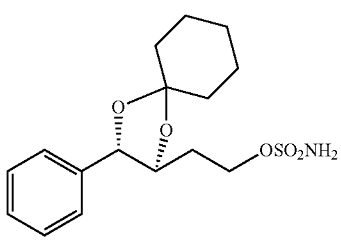 | 2-((2S,3S)-3-phenyl-1,4-dioxaspiro[4,5]decan-2-yl)ethyl sulfamate | Preparation example 301 | $^D$δ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 137 | 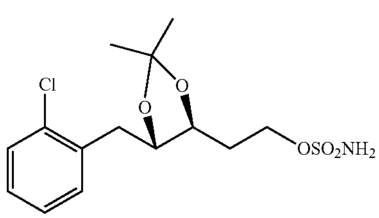 | 2-((4S,5S)-5-(2-chlorobenzyl)-2,2-dimethyl-1,3-dioxolan-4-yl)ethyl sulfamate | Preparation example 308 | $^D$δ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 138 | 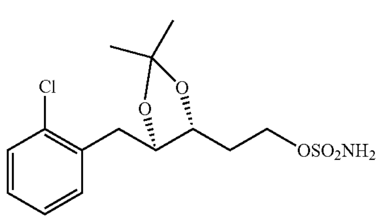 | 2-((4R,5R)-5-(2-chlorobenzyl)-2,2-dimethyl-1,3-dioxolan-4-yl)ethyl sulfamate | Preparation example 311 | $^D$δ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90(m, 2H). |

TABLE 3-continued

Characterization of the examples of sulfamate compounds

| Example No. | Structure | Name | Starting material | $^1$H NMR (400 MHz) |
|---|---|---|---|---|
| 139 | 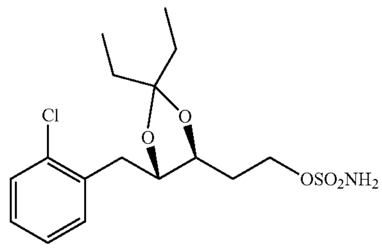 | 2-((4S,5S)-5-(2-chlorobenzyl)-2,2-diethyl-1,3-dioxolan-4-yl)ethyl sulfamate | Preparation example 314 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 140 | 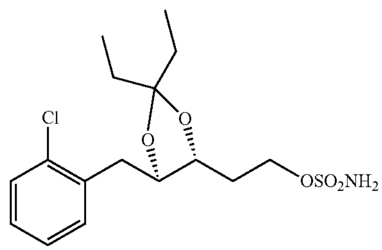 | 2-((4R,5R)-5-(2-chlorobenzyl)-2,2-diethyl-1,3-dioxolan-4-yl)ethyl sulfamate | Preparation example 317 | $^C$δ 0.90 (t, J = 8.0, 6H), 1.59 (q, J = 8.0, 4H), 2.0 (s, 2H), 3.96~4.21 (m, 2H), 4.42 (dt, J = 7.02. J = 3.27, 1H). 5.17 (d, J = 7.0, 1H), 7.62~7.64 (m, 2H), 7.77~7.90 (m, 2H). |
| 141 | 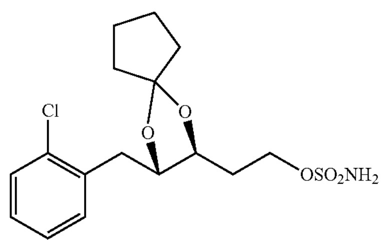 | 2-((2S,3S)-3-(2-chlorobenzyl)-1,4-dioxaspiro[4,4]nonan-2-yl)ethyl sulfamate | Preparation example 319 | $^D$δ 1.46~1.56 (m, 6H), 1.65-1.90 (m, 2H), 2.0 (s, 2H). 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 142 | 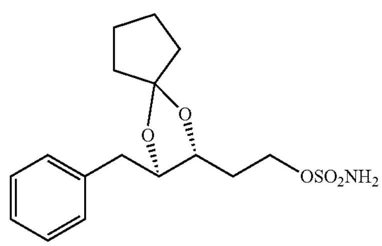 | 2-((2R,3R)-3-(2-chlorobenzyl)-1,4-dioxaspiro[4,4]nonan-2-yl)ethyl sulfamate | Preparation example 321 | $^D$δ 1.46~1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90(m, 2H) |
| 143 | 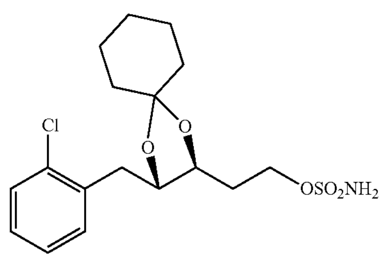 | 2-((2S,3S)-3-(2-chlorobenzyl)-1,4-dioxaspiro[4,5]decan-2-yl)ethyl sulfamate | Preparation example 323 | $^D$δ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 144 | 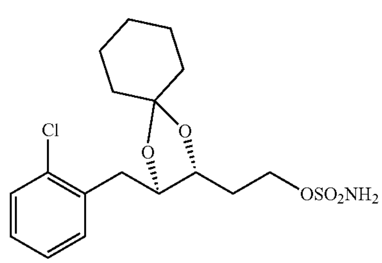 | 2-((2R,3R)-3-(2-chlorobenzyl)-1,4-dioxaspiro[4,5]decan-2-yl)ethyl sulfamate | Preparation example 325 | $^D$δ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |

TABLE 3-continued

Characterization of the examples of sulfamate compounds

| Example No. | Structure | Name | Starting material | ¹H NMR (400 MHz) |
|---|---|---|---|---|
| 145 | 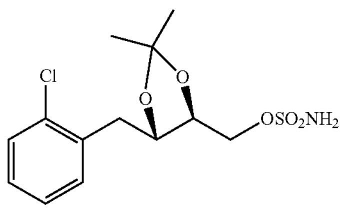 | ((4S,5S)-5-(2-chlorobenzyl)-2,2-dimethyl-1,3-dioxolan-4-yl)methyl sulfamate | Preparation example 329 | $^D$δ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 146 | 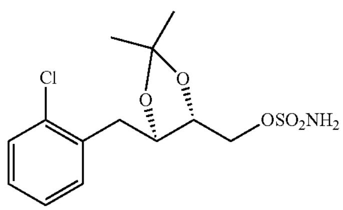 | ((4R,5R)-5-(2-chlorobenzyl)-2,2-dimethyl-1,3-dioxolan-4-yl)methyl sulfamate | Preparation example 338 | $^D$δ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 147 | 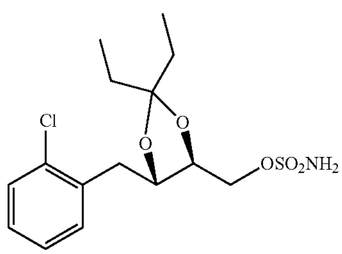 | ((4S,5S)-5-(2-chlorobenzyl)-2,2-diethyl-1,3-dioxolan-4-yl)methyl sulfamate | Preparation example 331 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H). 5.17 (d, J = 7.0, 1H), 7.62~7.64 (m, 2H), 7.77~7.90 (m, 2H). |
| 148 | 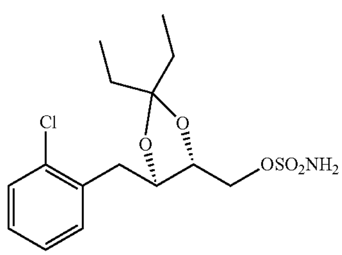 | ((4R,5R)-5-(2-chlorobenzyl)-2,2-diethyl-1,3-dioxolan-4-yl)methyl sulfamate | Preparation example 340 | $^C$δ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 149 | 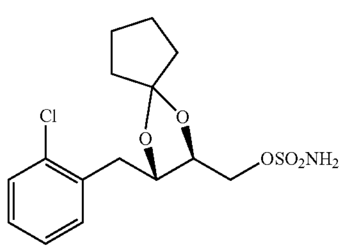 | ((2S,3S)-3-(2-chlorobenzyl)-1,4-dioxaspiro[4,4]nonan-2-yl)methyl sulfamate | Preparation example 333 | $^D$δ 1.46~1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 150 | 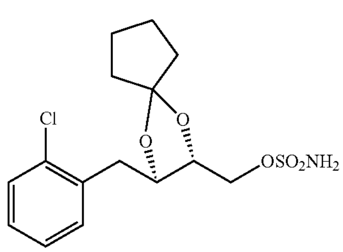 | ((2R,3R)-3-(2-chlorobenzyl)-1,4-dioxaspiro[4,4]nonan-2-yl)methyl sulfamate | Preparation example 342 | $^D$δ 1.46~1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 7.62-7.64 (m, 2H), 7.77~7.90 (m, 2H). |

TABLE 3-continued

Characterization of the examples of sulfamate compounds

| Example No. | Structure | Name | Starting material | $^1$H NMR (400 MHz) |
|---|---|---|---|---|
| 151 | 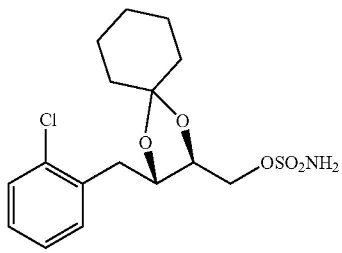 | ((2S,3S)-3-(2-chlorobenzyl)-1,4-dioxaspiro[4,5]decan-2-yl)methyl sulfamate | Preparation example 335 | $^D\delta$ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 152 | 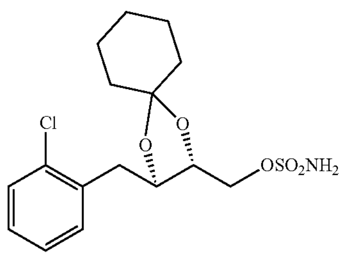 | ((2R,3R)-3-(2-chlorobenzyl)-1,4-dioxaspiro[4,5]decan-2-yl)methyl sulfamate | Preparation example 344 | $^D\delta$ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 153 | 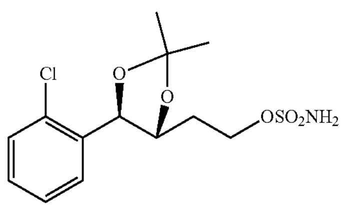 | 2-((4R,5R)-5-(2-chlorophenyl)-2,2-dimethyl-1,3-dioxolan-4-yl)ethyl sulfamate | Preparation example 352 | $^D\delta$ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 154 | 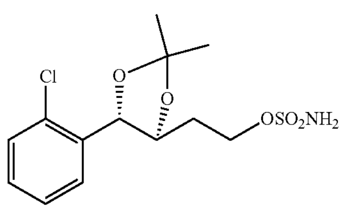 | 2-((4S,5S)-5-(2-chlorophenyl)-2,2-dimethyl-1,3-dioxolan-4-yl)ethyl sulfamate | Preparation example 356 | $^D\delta$ 1.27 (s, 6H), 1.40 (s, 3H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 155 | 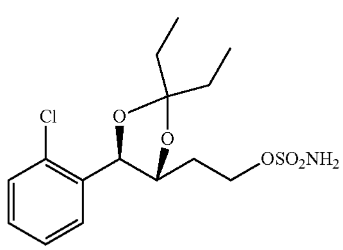 | 2-((4R,5R)-5-(2-chlorophenyl)-2,2-diethyl-1,3-dioxolan-4-yl)ethyl sulfamate | Preparation example 358 | $^C\delta$ 0.90 (t, J = 8.0, 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 156 | 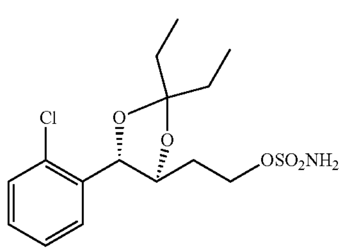 | 2-((4S,5S)-5-(2-chlorophenyl)-2,2-diethyl-1,3-dioxolan-4-yl)ethyl sulfamate | Preparation example 364 | $^C\delta$ 0.90 (t, J = 8.0 6H), 1.59 (q, J = 8.0, 4H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |

TABLE 3-continued

Characterization of the examples of sulfamate compounds

| Example No. | Structure | Name | Starting material | $^1$H NMR (400 MHz) |
|---|---|---|---|---|
| 157 | 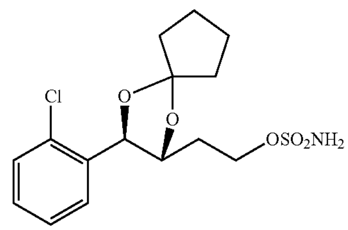 | 2-((2R,3R)-3-(2-chlorophenyl)-1,4-dioxaspiro[4,4]nonan-2-yl)ethyl sulfamate | Preparation example 360 | $^D\delta$ 1.46-1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 158 | 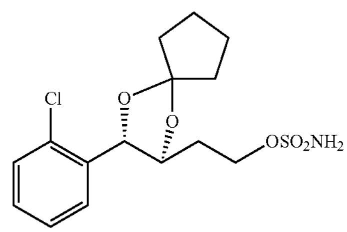 | 2-((2S,3S)-3-(2-chlorophenyl)-1,4-dioxaspiro[4,4]nonan-2-yl)ethyl sulfamate | Preparation example 366 | $^D\delta$ 1.46~1.56 (m, 6H), 1.65~1.90 (m, 2H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 159 | 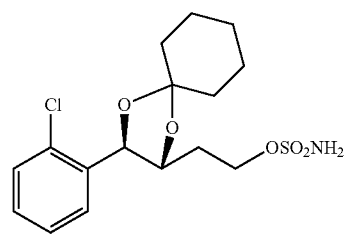 | 2-((2R,3R)-3-(2-chlorophenyl)-1,4-dioxaspiro[4,5]decan-2-yl)ethyl sulfamate | Preparation example 362 | $^D\delta$ 1.33~1.72 (m, 10H), 2.0 (s, 2H), 3.96~4.21 (m, 2H), 4.42 (dt, J = 7.02, J = 3.27, 1H), 5.17 (d, J = 7.0, 1H), 7.62~7.64 (m, 2H), 7.77~7.90 (m, 2H). |
| 160 | 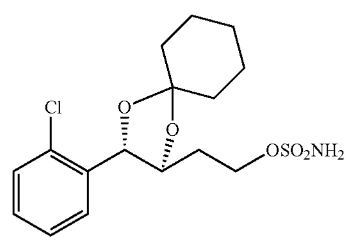 | 2-((2S,3S)-3-(2-chlorophenyl)-1,4-dioxaspiro[4,5]decan-2-yl)ethyl sulfamate | Prepration example 368 | $^D\delta$ 1.33-1.72 (m, 10H), 2.0 (s, 2H), 3.96~4.21 (m, 2H). 4.42 (dt, J = 7.02, J = 3.27, 1H), 5.17 (d, J = 7.0, 1H), 7.62~7.64 (m, 2H), 7.77~7.90 (m, 2H). |
| 161 | 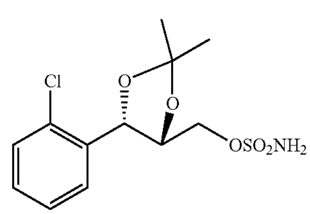 | ((4R,5S)-5-(2-chlorophenyl)-2,2-dimethyl-1,3-dioxoln-4-yl)methyl sulfamate | Preparation example 379 | $^C\delta$ 1.53 (s, 3H), 1.66 (s, 3H), 3.14~3.06 (m, 2H), 4.26 (d, J = 12, 2H), 4.83~4.78 (m, 1H), 5.63 (d, J = 6.8 Hz, 1H), 7.35-7.16 (m, 8H), 7.61 (dd, J = 7.4, 1.6, 1H). |
| 162 | 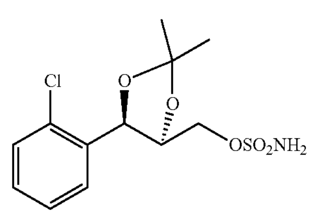 | ((4S,5R)-5-(2-chlorophenyl)-2,2-dimethyl-1,3-dioxolan-4-yl)methyl sulfamate | Preparation example 432 | $^C\delta$ 1.58 (s, 3H), 1.70 (s, 3H), 3.68~3.88 (m, 2H), 4.61 (s, 2H), 4.88~4.93 (m, 1H), 5.64 (d, J = 6.8 Hz, 1H), 7.29-7.66 (m, 4H) |

TABLE 3-continued

Characterization of the examples of sulfamate compounds

| Example No. | Structure | Name | Starting material | $^1$H NMR (400 MHz) |
|---|---|---|---|---|
| 163 | 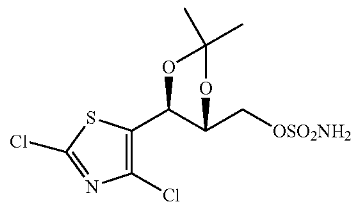 | ((4R,5S)-5-(2,4-dichlorothiazol-5-yl)-2,2-dimethyl-1,3-dioxolan-4-yl)methyl sulfamate | Preparation example 383 | $^D$δ 1.44 (s, 3H), 1.45 (s, 3H), 4.21~4.24 (m, 1H), 4.25~4.27 (m, 2H), 5.17 (d, J = 7.6, 1H), 7.64 (brs, 2H). |
| 164 | 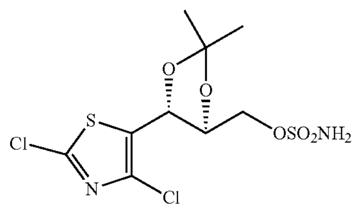 | ((4S,5R)-5-(2,4 dichlorothiazol-5-yl)-2,2-dimethyl-1,3-dioxolan-4-yl)methyl sulfamate | Preparation example 386 | $^D$δ 1.44 (s, 3H), 1.45 (s, 3H), 4.21~4.24 (m, 1H), 4.25-4.27 (m, 2H), 5.17 (d, J = 7.6, 1H), 7.64 (brs, 2H). |
| 165 | 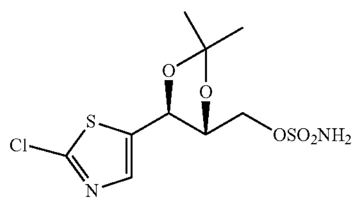 | ((4R,5S)-5-(2-chlorothiazol-5-yl)-2,2-dimethyl-1,3-dioxolan-4-yl)methyl sulfamate | Preparation example 390 | $^D$δ 1.42 (s, 3H), 1.43 (s, 3H), 4.16~4.19 (m, 1H), 4.20~4.22 (m, 2H), 5.20 (d, J = 8.4, 1H), 7.65 (brs, 2H), 7.74 (s, 1H). |
| 166 | 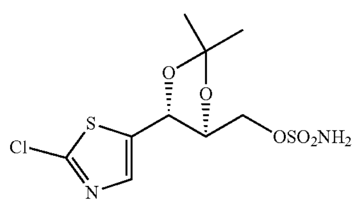 | ((4R,5S)-5-(2-chlorothiazol-5-yl)-2,2-dimethyl-1,3-dioxolan-4-yl)methyl sulfamate | Preparation example 393 | $^D$δ 1.42 (s, 3H), 1.43 (s, 3H), 4.16~4.19 (m, 1H) 4.20~4.22 (m, 2H) 5.20 (d, J = 8.4 1H), 7.65 (brs, 2H), 7.74 (s, 1H). |
| 167 | 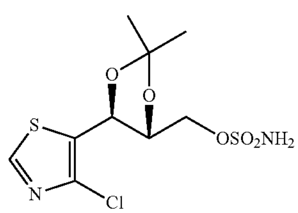 | ((4R,5S)-2,2-dimethyl-5-(4-methylthiazol-5-yl)-1,3-dioxolan-4-yl)methyl sulfamate | Preparation example 397 | $^D$δ 1.43 (s, 3H), 1.47 (s, 3H), 2.39 (s, 3H), 4.06~4.10 (m, 1H), 4.13 (d, J = 4.0, 2H), 5.27 (d, J = 8.0, 1H), 7.62 (brs, 2H), 9.04 (s, 1H) |
| 168 | 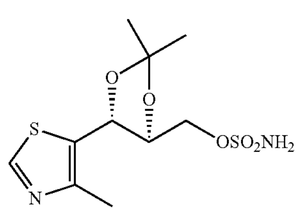 | ((4S,5R)-2,2-dimethyl-5-(4-methylthiazol-5-yl)-1,3-dioxolan-4-yl)methyl sulfamate | Preparation example 400 | $^D$δ 1.42 (s, 3H), 1.47 (s, 3H), 2.39 (s, 3H), 4.08~4.11 (m, 1H), 4.13 (d, J = 4.0, 2H), 5.27 (d, J = 8.0, 1H), 7.62 (brs, 2H), 9.04 (s, 1H). |
| 169 | 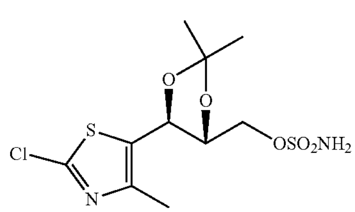 | ((4R,5S)-2,2-dimethyl-5-(2-chloro-4-methylthiazol-5-yl)-1,3-dioxolan-4-yl)methyl sulfamate | Preparation example 401 | $^D$δ 1.43(S, 3H), 1.44 (s, 3H), 2.33 (s, 3H), 4.11~4.25 (m, 1H), 4.15 (d, J = 4.4, 2H), 5.22 (d, J = 8.0. 1H), 7.62 (br s, 2H). |

TABLE 3-continued

Characterization of the examples of sulfamate compounds

| Example No. | Structure | Name | Starting material | $^1$H NMR (400 MHz) |
|---|---|---|---|---|
| 170 | 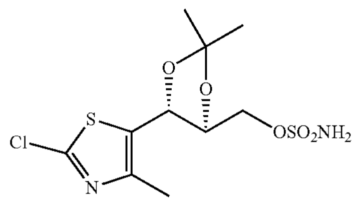 | ((4S,5R)-2,2-dimethyl-5-(2-chloro-4-methylthiazol-5-yl)-1,3-dioxolan-4-yl)methyl sulfamate | Preparation example 402 | $^D$δ 1.43 (S, 3H), 1.44 (s, 3H), 2.33 (s, 3H), 4.11~4.25 (m, 1H), 4.15 (d, J = 4.4, 2H), 5.22 (d, J = 8.0. 1H), 7.62 (br s, 2H). |
| 171 | 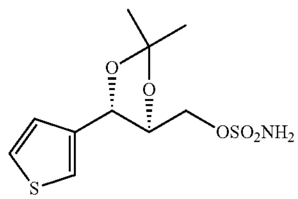 | ((4S,5S)-2,2-dimethyl-5-(thiophen-3-yl)-1,3-dioxolan-4-yl)methyl sulfamate | Preparation example 406 | $^D$δ 1.41 (s, 3H), 1.45 (s, 3H), 4.05~4.15 (m, 2H) 4.54~4.71 (m, 1H), 4.94 (d, J = 7.6, 1H), 7.03 (d, J = 3.6. 1H), 7.14 (s, 1H), 7.22 (brs, 2H), 7.42 (d, J = 3.6, 1H) |
| 172 | 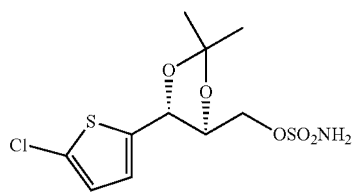 | ((4S,5R)-2,2-dimethyl-5-(5-chlorothiophen-2-yl)-1,3-dioxolan-4-yl)methyl sulfamate | Preparation example 410 | $^D$δ 1.51 (s, 3H), 1.54 (s, 3H), 4.11~4.14 (m, 2H), 4.16~4.18 (m, 1H), 5.10 (d, J = 7.6, 1H), 7.05 (dd, J = 3.6, J =10.0, 2H), 7.63 (brs, 2H) |
| 173 | 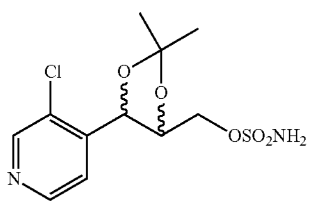 | (5-(3-chloropyridin-4-yl)-2,2-dimethyl-1,3-dioxolan-4-yl)methyl sulfamate | Preparation example 415 | $^D$δ 1.39 (s, 3H), 1.48 (s, 3H), 4.16~4.21 (m, 2H), 4.27~4.22 (m, 1H), 5.23 (d, J = 8.0, 1H), 7.37 (br s, 2H), 7.62 (d, J = 4.0, 1H), 8.59 (d, J = 4.0, 1H) 8.66 (s, 1H) |
| 174 | 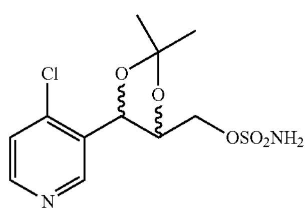 | (5-(4-chloropyridin-3-yl)-2,2-dimethyl-1,3-dioxolan-4-yl)methyl sulfamate | Preparation example 420 | $^D$δ 1.47(s, 3H), 1.54 (s, 3H), 4.23~4.30 (m, 2H), 4.40 (s, 1H), 5.25 (d, , J = 8.0, 1H), 7.58 (brs, 2H), 7.59 (s, 1H), 8.53 (d, J = 5.2, 1H), 8.75 (s, 1H) |
| 175 | 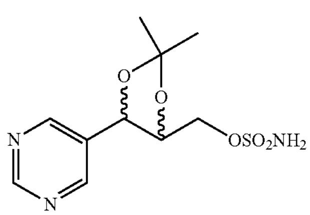 | 2,2-dimethyl-5-(pyrimidin-5-yl)-1,3-dioxolan-4-yl)methyl sulfamate | Preparation example 424 | $^C$δ 1.32 (s, 3H), 1.35 (s, 3H), 3.86-3.90 (m, 1H), 4.06-4.14 (m, 2H), 4.82 (d, J = 8.0, 2H), 6.92 (brs, 2H), 8.63 (s, 2H), 8.95 (s, 1H). |
| 176 | 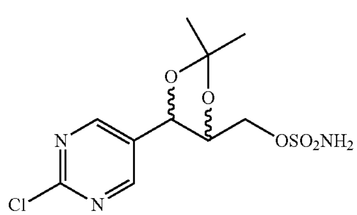 | (2,2-dimethyl-5-(2-chloropyrimidin-5-yl)-1,3-dioxolan-4-yl)methyl sulfamate | Preparation example 428 | $^C$δ 1.29 (s, 3H), 1.33 (s, 3H), 3.86-3.90 (m, 1H), 4.10-4.18 (m, 2H), 4.62 (d, J = 8.0, 2H), 6.92 (brs, 2H), 8.67 (s, 2H). |

$^C$CDCl$_3$, $^D$DMSO

Example 65: Sodium ((((4R, 5R)-5-(2-aminophenyl)-2,2-dimethyl-1,3-dioxolan-4-yl)methyl sulfonyl)amide

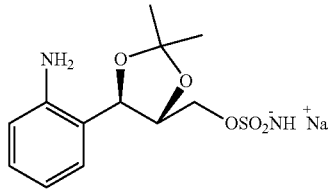

To stirred solution of ((4R,5R)-5-(2-aminophenyl)-2,2-dimethyl-1,3-dioxolan-4-yl)methyl sulfamate (Example 63, 5.5 g) in distilled water (55 ml) was added 1N NaOH (23 ml) then heated. After 30 min, the resulting mixture cooled to room temperature and concentrated under reduced pressure. The crude product in EA (ethyl acetate, 16.5 ml) was slowly added to Ether (200 ml) at low temperature. The precipitate was filtered off, washed with Hexane, and dried under vacuum to obtain the title compound (4.7 g, 65~85%)
$^1$H NMR (400 MHz, DMSO) δ 1.42 (s, 3H), 1.46 (s, 3H), 3.79~3.81 (m, 2H), 3.99~4.00 (m, 1H), 4.94 (d, 18.4, 1H), 6.59~7.16 (m, 4H).

Example 66: Sodium ((((4S, 5S)-5-(2-aminophenyl)-2,2-dimethyl-1,3-dioxolan-4-yl)methyl sulfonyl)amide

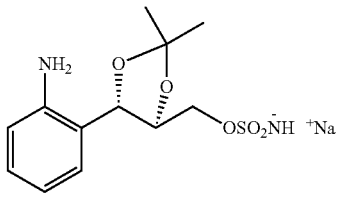

The substantially same method as described in Example 65 was conducted, except that ((4R,5R)-5-(2-aminophenyl)-2,2-dimethyl-1,3-dioxolan-4-yl)methyl sulfamate (Example 64) was used instead of ((4R,5R)-5-(2-aminophenyl)-2,2-dimethyl-1,3-dioxolan-4-yl)methyl sulfamate (Example 63), to obtain the title compound (4.23 g, 65~85%).
$^1$H NMR (400 MHz, DMSO) δ 1.42 (s, 3H), 1.46 (s, 3H), 3.79~3.81 (m, 2H), 3.99~4.00 (m, 1H), 4.94 (d, J=8.4, 1H), 6.59~7.16 (m, 4H).

Example 89: ((4R, 5R)-5-(2-nitrophenyl)-2-oxo-1,3-dioxolan-4-yl)methyl sulfamate

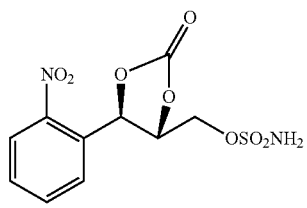

To a stirred solution of ((4R, 5R)-5-(2-nitrophenyl)-2,2-dimethyl-1,3-dioxolan-4-yl)methyl sulfamate (Example 77, 5.2 g, 16 mmol) in EtOAc (50 mL) was added 3N HCl (24.6 mL, 80.0 mmol) at room temperature. The mixture was stirred for 5 h. The resulting mixture was diluted with EtOAc, washed with sat. NaHCO$_3$, dried over MgSO$_4$, filtered, and concentrated under reduced pressure. The crude product stirred in THF (35 mL) was added CDI (2.91 g, 17.9 mmol) at room temperature. The mixture was stirred for 1 h. The resulting mixture was diluted with EtOAc, washed with water, dried over MgSO$_4$, filtered, and concentrated under reduced pressure. The crude product was purified by SiO$_2$ gel column chromatography to produce the title compound (2.6 g, 60~80%)
$^1$H NMR (400 MHz, CDCl$_3$) δ 2.0 (s, 2H), 4.08~4.33 (m, 2H), 4.72 (dt, J=7.02, J=3.27, 1H), 5.47 (d, J=7.0, 1H), 7.62~7.64 (m, 2H), 7.77~7.90 (m, 2H).

Example 90: ((4S, 5S)-5-(2-nitrophenyl)-2-oxo-1,3-dioxolan-4-yl)methyl sulfamate

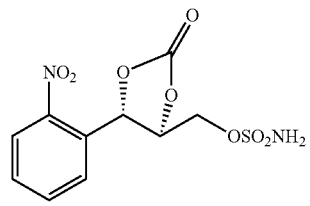

The substantially same method as described in Example 89 was conducted, except that ((4S, 5S)-5-(2-nitrophenyl)-2,2-dimethyl-1,3-dioxolan-4-yl)methyl sulfamate (Example 78) was used instead of ((4R, 5R)-5-(2-nitrophenyl)-2,2-dimethyl-1,3-dioxolan-4-yl)methyl sulfamate (Example 77), to obtain the title compound (0.9 g, 50~80%)
$^1$H NMR (400 MHz, CDCl$_3$) δ 2.0 (s, 2H), 4.08~4.33 (m, 2H), 4.72 (dt, J=7.02, J=3.27, 1H), 5.47 (d, J=7.0, 1H), 7.62~7.64 (m, 2H), 7.77~7.90 (m, 2H)

Example 103: ((4R, 5R)-5-(2-methylaminophenyl)-2,2-dimethyl-1,3-dioxolan-4-yl)methyl methylsulfamate

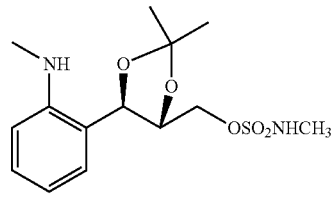

To a stirred solution of ((4R, 5R)-5-(2-aminophenyl)-2,2-dimethyl-1,3-dioxolan-4-yl)methyl sulfamate (Example 63, 0.68 g, 2.25 mmol) and benzotriazole (0.27 g, 2.25 mmol) in EtOH (10 mL) was slowly added formaldehyde (10 wt % in H$_2$O, 0.62 mL, 2.25 mmol) and NaBH$_4$ (0.085 g, 2.25 mmol) at 0° C. The resulting mixture was diluted with EtOAc, washed with water, dried over MgSO$_4$, filtered, and concentrated under reduced pressure. The crude product was purified by SiO$_2$ gel column chromatography to obtain the title compound (0.3 g, 30~50%)

$^1$H NMR (400 MHz, CDCl$_3$) δ 1.40 (s, 6H), 2.62 (s, 3H), 2.96 (s, 3H), 4.25 (dt, J=7.0, J=3.3, 1H), 4.75 (d, J=3.3, 2H), 4.84 (d, J=7.0, 1H), 6.99~7.20 (m, 4H)

Example 104: ((4S, 5S)-5-(2-methylaminophenyl)-2,2-dimethyl-1,3-dioxolan-4-yl)methyl methylsulfamate

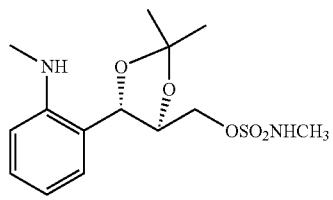

The substantially same method as described in Example 103 was conducted, except that ((4S, 5S)-5-(2-aminophenyl)-2,2-dimethyl-1,3-dioxolan-4-yl)methyl sulfamate (Example 64) was used instead of ((4R, 5R)-5-(2-aminophenyl)-2,2-dimethyl-1,3-dioxolan-4-yl)methyl sulfamate (Example 63), to obtain the title compound (0.5 g, 50~80%)
$^1$H NMR (400 MHz, CDCl$_3$) δ 1.40 (s, 6H), 2.62 (s, 3H), 2.96 (s, 3H), 4.25 (dt, J=7.0, J=3.3, 1H), 4.75 (d, J=3.3, 2H), 4.84 (d, J=7.0, 1H), 6.99~7.20 (m, 4H)

Example 177: sodium ((((4S,5S)-5-(2-chlorophenyl)-2,2-dimethyl-1,3-dioxolan-4-yl)methoxy)sulfonyl)amide

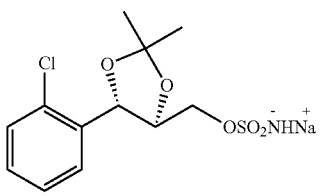

To a stirred solution of ((4S,5S)-5-(2-chlorophenyl)-2,2-dimethyl-1,3-dioxolan-4-yl)methyl sulfamate (Example 2, 5.0 g, 15.5 mmol) in a mixture of MTBE and IPA (50 mL, 3:1, v/v) was added 6 N NaOH aqueous solution (2.5 mL, 14.2 mmol) at room temperature then stirred for 1 hr at 0° C. The resulting mixture was removed solvent. The concentrated residue was added a mixture of H$_2$O and IPA (15 mL, 1:2, v/v) at room temperature then stirred for 30 min. The mixture was added MTBE (75 mL) then stirred for 1 hr at 0° C. Solid product was filtered and air-dried to give a title compound. (4.76 g, 70~90%).
Water content: 1.54%, MP: 1$^{st}$ 67.6~67.7° C., 2$^{nd}$ 126.9° C.
$^1$H NMR (400 MHz, DMSO-d$_6$) δ 1.43 (s, 3H), 1.50 (s, 3H), 3.77 (dd, J=7.2, 11.2, 1H), 3.87 (dd, J=2.8, 11.2, 1H), 3.99~4.03 (m, 1H), 5.09 (d, J=8.4, 1H), 7.35~7.47 (m, 3H), 7.61 (dd, J=1.8, 7.4, 1H)

Experimental Example 1: Evaluation of Antiallodynic Activity on Complete Freund's Adjuvant (CFA)-Induced Inflammatory Pain Model Male, Sprague-Dawley rats (200-220 g, Nara Bio, Korea) were habituated for 1 week before surgery and allowed free access to food and water throughout the experimentation. Room temperature and humidity were maintained at 24±2° C. and 50±10%, respectively.

CFA-induced inflammatory pain was induced by the procedure of Nagakura et al. (2003) and Gregory P. et al. (2010) with minor modifications. CFA (sigma, USA) was injected in the left plantar with a 100 ul volume under gaseous anesthesia with isoflurane a 4:4 flow ratio of NO$_2$ Sham controls were injected with 100 ul of saline and vehicle controls were identical to CFA infusion model, except for administration of vehicles.

Tactile sensitivity (Mechanical allodynia) was evaluated using von Frey monofilaments before and after treatment, and animals were used withdrawal threshold value was less than 4 g. One week after surgery, CFA-infused animals (n=4~6), sham-operated animals (n=12), and vehicle-operated animals (n=17) were tested for tactile sensitivity with von Frey monofilaments 3 trials in each animal. All Animals were placed in a stainless steel mashed chamber and habituated for 30 min in the test box. The tactile sensitivity for ipsilateral hind paw was measured using the up-and-down method (Dixon, 1980) with seven von Frey monofilaments (0.4, 1, 2, 4, 6, 8, and 15 g) to 3 trials. Tactile sensitivity test was followed by Dixon's method (Dixon, 1980). The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

The antiallodynic effect of compound of Examples was evaluated at the close of 10, 30 and 60 mg/kg (n=4~6), intraperitoneally administrated in a volume of 5 ul/g bw in a vehicle of 30% (v/v) PEG. The test was performed peak time of efficacy (0.5 hr) after compound administration.

The relative values compared to the sham (% control) were calculated and shown in Table 4, which show an antiallodynic effect of the compound of Examples on CFA-induced pain model in rats.

TABLE 4

Antiallodynic effect of the compound of Examples on CFA-induced pain model

| Example No | CFA model: ED50 mg/kg |
|---|---|
| 1 | #60 (21.1%, 0.5 h) |
| 2 | 5.9 (0.5 h) |
| 3 | #60 (24.0%, 0.5 h) |
| 4 | #60 (49.9%, 0.5 h) |
| 6 | #60 (22.4%, 0.5 h) |
| 8 | #40 (23.3%, 0.5 h) |
| 10 | #60 (20.7%, 0.5 h) |
| 12 | #18 (48.8%, 0.5 h) |
| 27 | #18 (20.2%, 0.5 h) |
| 28 | #40 (17.8%, 0.5 h) |
| 40 | #60 (22.5%, 0.5 h) |
| 52 | #60 (33.3%, 0.5 h) |
| 66 | #60 (16.5%, 1 h) |
| 70 | #40 (18.8%, 0.5 h) |
| 72 | #40 (22.6%, 0.5 h) |
| 74 | #60 (37.1%, 0.5 h) |
| 76 | #40 (25.7%, 0.5 h) |
| 90 | #60 (15.6%, 0.5 h) |
| 92 | #18 (22.3%, 0.5 h) |
| 104 | #40 (24.1%, 0.5 h) |
| 106 | #18 (23.2%, 0.5 h) |

TABLE 4-continued

Antiallodynic effect of the compound
of Examples on CFA-induced pain model

| Example No | CFA model: ED50 mg/kg |
|---|---|
| 108 | #40 (37.5%, 0.5 h) |
| 110 | #40 (42.7%, 0.5 h) |
| 112 | #40 (41.1%, 0.5 h) |
| 114 | #40 (29.8%, 0.5 h) |
| 116 | #40 (14.5%, 0.5 h) |
| 118 | #40 (25.0%, 0.5 h) |
| 120 | #40 (23.0%, 0.5 h) |
| 122 | #18 (22.3%, 0.5 h) |
| 124 | #40 (34.23%, 0.5 h) |
| 126 | #40 (43.47%, 0.5 h) |
| 128 | #18 (24.5%, 0.5 h) |
| 130 | #40 (19.4%, 0.5 h) |
| 132 | #40 (24.8%, 0.5 h) |
| 134 | #18 (71.1%, 0.5 h) |
| 136 | #18 (32.4%, 0.5 h) |
| 138 | #40 (32.7%, 0.5 h) |
| 140 | #40 (37.4%, 0.5 h) |
| 142 | #40 (24.9%, 0.5 h) |
| 144 | #40 (36.6%, 0.5 h) |
| 146 | #40 (16.5%, 0.5 h) |
| 148 | #40 (15.5%, 0.5 h) |
| 150 | #40 (17.6%, 0.5 h) |
| 152 | #40 (34.9%, 0.5 h) |
| 154 | #40 (32.1%, 0.5 h) |
| 156 | #40 (30.8%, 0.5 h) |
| 158 | #40 (29.8%, 0.5 h) |
| 160 | #40 (38.4%, 0.5 h) |
| 163 | #40 (23.1%, 0.5 h) |
| 164 | #60 (66.8%, 0.5 h) |
| 165 | >60 (Seizure) |
| 166 | #60 (30.4%, 0.5 h) |
| 167 | #60 (38.6%, 0.5 h) |
| 168 | #60 (77.2%, 0.5 h) |
| 170 | #60 (24.2%, 0.5 h) |
| 171 | #60 (29.8%, 0.5 h) |
| 172 | #60 (35.9%, 0.5 h) |
| 173 | #60 (33.9%, 0.5 h) |
| 174 | #60 (24.7%, 0.5 h) |
| 175 | #60 (44.4%, 0.5 h) |
| 176 | #60 (40.0%, 0.5 h) |
| 177 | #15 (67.2%, 0.5 h) | the concentration administered and effect (%) compared to that of control treated with vehicle only Experimental Example 2: Evaluation of Antiallodynic Activity on Chung Model Male. Sprague-Dawley rats (200-220 g, Orient Bio, Korea) were habituated for 1 week before the experiment and allowed free access to food and water throughout the experimentation. Room temperature and humidity were maintained at 24±2° C. and 50±10%, respectively. Neuropathic surgery (SNL, Spinal nerve ligation) model was clone as described in Kim and Chung (1992). Briefly, animal under gaseous anesthesia with isoflurane a 4:4 flow ratio of $NO_2$. The left lumber spinal nerve L5 and L6 were isolated and tightly ligated with 4-0 silk thread. The wound was treated with a gentamicin antibiotics solution (4 mg/kg, 4 ul/g, bw), and the wound muscle was closed with cat cut chrom 4/0 thread and skin was closed dafilon 4/0 tread. Sham controls were prepared in the same manner as the spinal nerves were exposed, but no ligated L5 and L6 nerves. But, vehicle controls were identical to SNL model, except for administration of vehicles.

Tactile sensitivity (Mechanical allodynia) was evaluated using von Frey monofilaments before and after treatment and animals were used withdrawal threshold value was less than 4 g. One week after surgery, SNL-operated animals (n=4~6), sham-operated animals (n=4~10) and vehicle-operated animals (n=4~13) were tested for tactile sensitivity with von Frey monofilaments 3 trials in each animal. All Animals were placed in a stainless steel mashed chamber and habituated for 30 min in the test box. The tactile sensitivity for ipsilateral hind paw was measured using the up-and-down method (Dixon, 1980) with seven von Frey monofilaments (0.4, 1, 2, 4, 6, 8, and 15 g) to 3 trials. Tactile sensitivity test was followed by Dixon's method (Dixon, 1980). The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

All animals were fasted 18 h before the administration of the compounds. The antiallodynic effect of the compounds were evaluated at the various dose (n=5~6), orally administrated in a volume of 5 ul/g, bw in a vehicle of 30% (v/v) PEG 400 or 20% (v/v) Tween 80 or Saline. The test was performed at the peak time of efficacy (1 hr) after compound administration.

The relative values compared to the sham group (% control) were calculated and shown in Table 5, which show an antiallodynic effect of the test compounds on SNL model in rats.

TABLE 5

Antiallodynic effect of the compound of examples on SNL model

| Example No | SNL model: ED50 mg/kg |
|---|---|
| 2 | 18.2 (1 h) |
| 15 | 69.8 (0.5 h) |
| 16 | 24.6 (0.5 h) |
| 27 | #50 (17.3%, 0.5 h) |
| 28 | #90 (72.6%, 0.5 h) |
| 72 | #50 (35.1%, 0.5 h) |
| 76 | #90 (22.9%, 0.5 h) |
| 92 | #50 (37.3%, 0.5 h) |
| 106 | #50 (25.4%, 0.5 h) |
| 118 | #90 (38.3%, 0.5 h) |
| 122 | #50 (64.1%, 0.5 h) |
| 138 | #90 (71.4%, 0.5 h) |
| 146 | #90 (45.8%, 0.5 h) | the concentration administered and effect (%) compared to that of control treated with vehicle only Experimental Example 3: Writhing Test To examine the pain relief effect of the sulfamate derivative compounds, a writhing test was conducted in general pain animal model referring to Fischer, L. G. et al. (2008). ICR mice (male, 24-28 g; Orient Bio, Korea) were habituated before test in test room for 1 hour. Animals were fasted 2 hr, before administration of compounds. Compounds was orally administered at the close of 20 mg/kg, 10 ul/g, bw (n=3~5/group). All compounds were dissolved in a vehicle of 30% (v/v) PEG 400 or 20% (v/v) Tween 80. The control group was treated the vehicle without compounds.

One hour after the administration of Compounds, 0.6% acetic acid at the close of 10 ul/g, bw was injected into the mice. Animals were habituated in the cage for 5 min. 5 min after habituation, the number of writhes (abdominal constriction) for 15 min was counted referring to Korzeniewska-Rybicka, I. et al. (1998) and compared with that of a control.

The relative values compared to the control (% control) were calculated and shown in Table 6

TABLE 6

Effect of the compound of examples in writhing test.

| Example No | Writ htest: ED50 mg/kg |
|---|---|
| 2 | 28.4 (0.5 h) |
| 12 | #50 (37.7%, 0.5 h) |
| 15 | #20 (74.4%, 0.5 h) |
| 27 | #50 (48.2%, 0.5 h) |
| 28 | #90 (66.0%, 0.5 h) |
| 72 | #50 (38.1%, 1 h) |
| 76 | #90 (40.5%, 0.5 h) |
| 106 | #50 (26.4%, 1 h) |
| 108 | #90 (23.9%, 1 h) |
| 112 | #90 (14.0%, 0.5 h) |
| 122 | #50 (48.8%, 1 h) |
| 128 | #50 (44.6%, 1 h) |
| 134 | #50 (9.6%, 0.5 h) |
| 136 | #50 (49.8%, 0.5 h) |
| 138 | #90 (35.8%, 0.5 h) |
| 140 | #90 (47.5%, 1 h) |
| 154 | #90 (73.8%, 0.5 h) |
| 156 | #90 (28.9%, 1 h) | the concentration administered and effect (%) compared to that of control treated with vehicle only Experimental Example 4: Evaluation of Antiallodynic Activity on Post Operative-Induced Pain Model Male Sprague-Dawley rats'(Orient Bio, Korea), 300~320 g, total of 201 rats were used (details in Table 7). Rats were habituated at least 3 clays before surgery and free access to food and water (room temperature and humidity were maintained at 24±2° C. and 50±10%, respectively). The process of performing the post-operation model's surgery was adapted from Brennan et al (1996). At first, rats with allodynia (threshold valueless than 8 g) were excluded in Pre-von Frey Test. During the post-operation surgery, rats were anesthetized under gaseous anesthesia with 2% isoflurane. Rats were laid face down on a plate fixed at 37° C. to prevent against hypothermia. The ipsilateral plantar aspect (left side) of the hind paw was prepared in a sterile manner with a 10% povidone-iodine solution. A longitudinal incision (1 cm) (FIG. 2-A) was made with a blade (number 11) through the skin and fascia of the ipsilateral plantar aspect of the foot, starting from 0.5 cm below the proximal edge of the heel and extending toward the toes. Rats' plantar muscles were elevated and incised longitudinally (FIG. 2-B). After hemostasis with gentle pressure, the skin was opposed with 2 mattress sutures (4-0 Dafilon) (FIG. 2-C). The wound site was covered with a 10% povidone-iodine solution gauze and injected with antibiotics (gentamicin, 8 mg/kg, ip). The sutures were removed under halothane anesthesia, approximately 30 hours later, at the end of post-operative day 1.

After 2-3 days of recovery, rats with a good response (threshold less than 4 g) in Pre-von Frey Test were selected. According to this response, we made three groups with each group having equal average responses: Group 1, post-operation and drug treated; Group 2, post-operation and vehicle treated; Group 3, no post-operation and vehicle treated. In this study, Group 3 was the sham control (positive) group. The group 2 was used to check for possible failures to generate post-operative pain.

For efficacy measure, the threshold value of group C was assigned 100% efficacy, and the percentage of the threshold values of group A compared to group C (for each different dose level) were calculated as the efficacies. Base on these efficacy values, ED50 was calculated using log fitting. If there was no clear ED50, then we marked the percent efficacy at the highest tested dose or larger than highest tested dose.

For pain threshold test, all animals were placed in a stainless steel meshed chamber and habituated for 30 min in the test box. The tactile sensitivity of the ipsilateral hind paw was measured using the up-and-down method (Dixon, 1980) with seven von Frey monofilaments (0.4, 1, 2, 4, 6, 8, and 15 g) using 3 trials. The 50% paw withdrawal threshold for each paw was calculated using the following formula: [Xth] log=[vFr] log+ky, where [vFr] is the force of the last von Frey filament used, k=0.2249 which is the average interval (in log units) between the von Frey monofilaments, y which is a value that depends upon the pattern of withdrawal responses, and Xth which is the threshold value (Dixon, 1980). If an animal did not respond to the highest von Frey hair (15 g), then the threshold value was assigned as 18.4.

Drugs were dissolved 30% PEG400 for example 2, 0.9% saline for Pregabalin, 20% Tween80 for Tylenol, 0.9% saline for Topiramate. These vehicles were selected depending on the compound's solubility. Intraperitoneal injection (5 μl/g) was clone for all drugs.

The relative values compared to the sham (% control) were calculated and shown in Table 8, which show an antiallodynic effect of the compound of examples on Post operation-induced pain model in rats.

TABLE 7

Number of animals used in this study

| Group | example 2 | Pregabalin | Tylenol | Topiramate |
|---|---|---|---|---|
| A Post-operative & Drug treated | 35 | 18 | 18 | 6 |
| B Post-operative & Vehicle treated | 36 | 18 | 18 | 6 |
| C Sham | 24 | 6 | 12 | 4 |

Overall experimental timeline is depicted in FIG. 1 and more detailed procedures are explained in the following sections.

TABLE 8

Antiallodynic effect of the compound of examples on Post operation-induced pain model

| Example No | Post Operation: ED50 mg/kg |
|---|---|
| 2 | 1.8 (0.5 h) |
| 177 | #2 (64.4%, 0.5 h) | the concentration administered and effect (%) compared to that of control treated with vehicle only Experimental Example 5: Evaluation of Antiallodynic Activity on Streptozotocin (STZ)-Induced Diabetic Pain Model Male, Sprague-Dawley rats (200-220 g, Nara Bio, Korea) were habituated for 1 week before surgery and allowed free access to food and water throughout the experimentation. Room temperature and humidity were maintained at 24±2° C. and 50±10%, respectively.

STZ-induced diabetic pain model was established with a modified method of Rakieten et al. (1963) and Bertrand Aubel et al. (2004). All animals were fasted 4 to 6 hr prior to STZ injection. STZ (sigma, USA) was dissolved in 20 mM sodium citrate buffer, pH 5.5 (sigma, USA) and intraperitoneally injected at 75 mg/kg, 4 ul/g, bw into the rats. Sham controls were injected with same volume of 20 mM sodium citrate buffer, pH 5.5 and vehicle controls were identical to STZ model, except for administration of vehicles. Rats were supplied with 10% sucrose water for 2 days against sudden hypoglycemia, 3 days later, the induction of diabetes was checked by measurement of tail vein blood glucose levels with a blood glucose meter. (Life Scan One Touch Ultra, USA). If blood glucose was not >300 mg/dl by 72 hr, the rat was excluded from the diabetic group.

Tactile sensitivity (Mechanical allodynia) was evaluated using von Frey monofilaments before and after treatment of the compound of Examples and animals were used withdrawal threshold value was less than 4 g. One week after surgery, diabetic animals (n=6), sham controls (n=12), and vehicle control (n=18) were tested for tactile sensitivity with von Frey monofilaments 3 trials in each animal. All Animals were placed in a stainless steel mashed chamber and habituated for 30 min in the test box. The tactile sensitivity for ipsilateral hind paw was measured using the up-and-down method (Dixon, 1980) with seven von Frey monofilaments (0.4, 1, 2, 4, 6, 8, and 15 g) to 3 trials. Tactile sensitivity test was followed by Dixon's method (Dixon, 1980). The 50% paw withdrawal threshold for each paw was calculated using the following formula: [Xth] log=[vFr] log+ky where [vFr] is the force of the last von Frey used k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

The antiallodynic effect of the compound of examples was evaluated at the dose of 10, 30 and 60 mg/kg (n=6), intraperitoneally administered in a volume of 5 ul/g, bw in a vehicle of 30% (v/v) PEG. The test was performed at the peak time of efficacy (0.5 hr) after compound administration.

The relative values compared to the sham (% control) were calculated and shown in Table 9, which show an antiallodynic effect of the compound of examples on STZ-induced pain model in rats.

TABLE 9

Antiallodynic effect of the compound of examples on STZ-induced pain model

| Example No | STZ model: ED50 mg/kg |
|---|---|
| 2 | 7.9 (0.5 h) |

Experimental Example 6: Hot-Plate Test

To examine the pain relief effect of the sulfamate derivative compounds, a hot-plate test was conducted in general pain animal model referring to Current Protocols in Neuroscience; Behavioral Neuroscience Unit 8.9.

ICR mice (male, 30-35 g: Orient Bio, Korea) were habituated before test in test room for 1 hour. Animals were fasted 2 hr before administration of compounds. Compounds were orally administered at the close of 150 mg/kg, 10 ul/g, bw (n=7~10/group). All compounds were dissolved in a vehicle of 30% (v/v) PEG 400 or 20% (v/v) Tween 80. The control group was treated the vehicle without compounds.

0.5 hr after the administration of compounds, the mice were put on a hot plate pre-heated to 55±1° C. (Hu, X. et al, 2008), and then, measured as the withdrawal latency (cut-off time: 30 sec) time until the point when each mouse was taking off a paw from the plate, shaking, licking a paw or hind leg, or jumping from the plate. The relative values compared to the control (% control) were calculated and shown in Table 10.

TABLE 10

Effect of the compound of examples in hot-plate test.

| Example No | Hot plate test: ED50 mg/kg |
|---|---|
| 2 | #200 (123.6%) |
| 15 | 112.6 (0.5 h) |
| 16 | 116.3 (1 h) |
| 28 | #100 (126.4%) | the concentration administered and effect (%) compared to that of control treated with vehicle only

Experimental Example 7: Evaluation of Antiallodynic Activity on Vincristine-Induced Pain Model Male, Sprague-Dawley rats (300-320 g, Nara Bio, Korea) were habituated for 1 week before surgery and allowed free access to food and water throughout the experimentation. Room temperature and humidity were maintained at 24±2° C. and 50±10%, respectively.

Vincristine was established by the procedure of Natsuko et al. (2001) with minor modifications. Vincristine was intravenously infused continuously for 14 clays using a mini-osmotic pump as follows. Vincristine sulfate solution (Hospira, Australia) was diluted with 0.9% saline to 30 ug/kg, final close. The pumps (Alzet Model 2002, USA) were filled with the vincristine solution and primed by incubation at 37° C. for 4 h before the infusion. Briefly, animal under gaseous anesthesia with isoflurane a 4:4 flow ratio of $NO_2$. Catheter made from PE-60 tube was inserted into an external jugular vein in rat. Sham controls were prepared in the same manner as expose of the external jugular vein, but, not cut down of external jugular vein and vehicle-control groups were identical to vincristine infusion model, except for administration of vehicles.

Tactile sensitivity (Mechanical allodynia) was evaluated using von Frey monofilaments before and after treatment, and animals were used withdrawal threshold value was less than 4 g. One week after surgery, vincristine-infused animals (n=6), sham-operated animals (n=12) and vehicle-operated (n=18) animals were tested for tactile sensitivity with von Frey monofilaments 3 trials in each animal. All Animals were placed in a stainless steel mashed chamber and habituated for 30 min in the test box. The tactile sensitivity for ipsilateral hind paw was measured using the up-and-down method (Dixon, 1980) with seven von Frey monofilaments (0.4, 1, 2, 4, 6, 8, and 15 g) to 3 trials. Tactile sensitivity test was followed by Dixon's method. The 50% paw withdrawal threshold for each paw was calculated using the following formula: [Xth] log=[vFr] log+ky where [vFr] is the force of the last von Frey used, k=0.2249 which is the average interval (in log units) between the von Frey monofilaments, and y is a value that depends upon the pattern of withdrawal responses (Dixon, 1980). If an animal did not respond to the highest von Frey hair (15 g), then the paw was assigned a value of 18.4 g.

The antiallodynic effect of the compound of the examples was evaluated at the close of 1, 5 and 10 mg/kg (n=6), intraperitoneally administrated in a volume of 5 ul/g, bw in a vehicle of 30% (v/v) PEG. The test was performed at the peak time of efficacy (0.5 hr) after compound administration.

The relative values compared to the sham (% control) were calculated and shown in Table 11, which show an antiallodynic effect of the compound of examples on vincristine-induced pain model in rats.

TABLE 11

Antiallodynic effect of the compound of examples on Vincristine-induced pain model

| Example No | Vincristine model: ED50 mg/kg |
|---|---|
| 2 | 1.0(0.5 h) |

Experimental Example 8: Tail-Flick Test

To examine the pain relief effect of the sulfamate compounds, a tail-flick test was conducted in general pain animal model referring to Current Protocols in Neuroscience; Behavioral Neuroscience Unit 8.9.

ICR mice (male, 25-30 g; Orient Bio, Korea) were habituated before test in test room for 1 hour. Animals were fasted 2 hr before administration of compounds. Each of Compound was orally administered at the close of 150 mg/kg, 10 ul/g, bw (n=7~10/group). All compounds were dissolved in a vehicle of 30% (v/v) PEG 400 or 20% (v/v) Tween 80. The control group was treated the vehicle without compounds.

After the administration of compounds, the mice tail were put on a tail-flick analgesia meter. To avoid tissue damage, maximal exposure time to pain stimuli was restricted to 15 s. The withdrawal latency was measured as the time to the point when each mouse response to the stimulus. The relative values compared to the control (% control) were calculated.

The relative values compared to the sham were calculated and shown in Table 12, which show effect of the compound of examples on tail-flick test in rats.

TABLE 12

Effect of the compound of examples in tail-flick test.

| Example No | tail-flick test: dose |
|---|---|
| 2 | >200 |
| 15 | >200 |
| 16 | >200 |
| 28 | >200 | the concentration administered and effect compared to that of control treated with vehicle only

[Statistical Analysis]

The obtained results are shown as mean±sem. The difference between the groups was statistically analyzed by ANOVA, and then, further examined by Dunnett's test or Bonferroni test. If p is less than 0.05, it was determined that the difference between the groups had statistical significance.

The invention claimed is:

1. A method of treating or alleviating pain in a subject in need thereof comprising administering a pharmaceutically effective amount of a pharmaceutical composition comprising a sulfamate derivative compound represented by the following Chemical Formula 1 or a pharmaceutically acceptable salt thereof as an active ingredient:

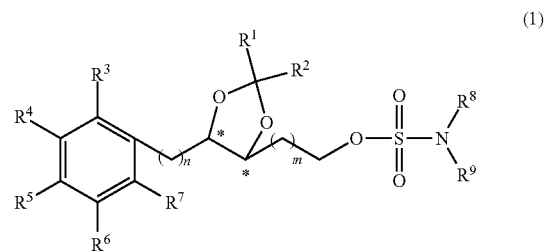

(1)

wherein $R^1$ and $R^2$ are each independently selected from the group consisting of hydrogen, $C_1$-$C_5$ alkyl group, $C_2$-$C_5$ alkenyl and $C_6$-$C_{10}$ aryl group, $R_1$ and $R_2$ together with the carbon atom to which they attach form a $C_3$-$C_{12}$ cycloalkyl group, or $R^1$ and $R^2$ are bond and they together with the oxygen atom to which they attach form a carbonyl group; $R^3$, $R^4$, $R^5$, $R^6$ and $R^7$ are each independently selected from the group consisting of hydrogen, hydroxyl, $C_1$-$C_5$ alkoxy, $C_1$-$C_5$ alkyl, $C_2$-$C_5$ alkenyl, $C_6$-$C_{10}$ aryl, $C_1$-$C_5$ alkoxycarbonyl, carboxyl, $C_2$-$C_5$ acyl, $C_1$-$C_5$ alkylthio, cyano, nitro, amine, $C_1$-$C_5$ alkylamine and halogen; $R^8$ and $R^9$ are each independently hydrogen or $C_1$-$C_3$ alkyl group; n and m are each independently an integer of 0-4.

2. The method according to claim 1, $R^8$ and $R^9$ are each independently hydrogen or methyl.

3. The method according to claim 1, m and n are each independently an integer of 0-2.

4. The method according to claim 1, wherein the compound is selected from the group consisting of:
(1) (5-(2-chlorophenyl)-2,2-dimethyl-1,3-dioxolan-4-yl) methylsulfamate;
(2) (5-(2-chlorophenyl)-2-methyl-1,3-dioxolan-4-yl) methyl sulfamate;
(3) (5-(2-chlorophenyl)-2,2-diethyl-1,3-dioxolan-4-yl) methyl sulfamate;
(4) (3-(2-chlorophenyl)-1,4-dioxaspiro[4,4]nonan-2-yl) methyl sulfamate;
(5) (3-(2-chlorophenyl)-1,4-dioxaspiro[4,5]decan-2-yl) methyl sulfamate;
(6) (5-(2-chlorophenyl)-2-phenyl-1,3-dioxolan-4-yl) methyl sulfamate;
(7) (5-(2-fluorophenyl)-2,2-dimethyl-1,3-dioxolan-4-yl) methyl sulfamate;
(8) (5-(2-fluorophenyl)-2-methyl-1,3-dioxolan-4-yl) methyl sulfamate;
(9) (5-(2-fluorophenyl)-2,2-diethyl-1,3-dioxolan-4-yl) methyl sulfamate;
(10) (3-(2-fluorophenyl)-1,4-dioxaspiro[4,4]nonan-2-yl) methyl sulfamate;
(11) (3-(2-fluorophenyl)-1,4-dioxaspiro[4,5]decan-2-yl) methyl sulfamate;
(12) (5-(2-fluorophenyl)-2-phenyl-1,3-dioxolan-4-yl) methyl sulfamate;
(13) (5-(2-iodophenyl)-2,2-dimethyl-1,3-dioxolan-4-yl) methyl sulfamate;
(14) (5-(2-iodophenyl)-2-methyl-1,3-dioxolan-4-yl) methyl sulfamate;

(15) (5-(2-iodophenyl)-2,2-diethyl-1,3-dioxolan-4-yl)methyl sulfamate;
(16) (3-(2-iodophenyl)-1,4-dioxaspiro[4,4]nonan-2-yl)methyl sulfamate;
(17) (3-(2-iodophenyl)-1,4-dioxaspiro[4,5]decan-2-yl)methyl sulfamate;
(18) (5-(2-iodophenyl)-2-phenyl-1,3-dioxolan-4-yl)methyl sulfamate;
(19) (5-(2,4-dichlorophenyl)-2,2-dimethyl-1,3-dioxolan-4-yl)methyl sulfamate;
(20) (5-(2,4-dichlorophenyl)-2-methyl-1,3-dioxolan-4-yl)methyl sulfamate;
(21) (5-(2,4-dichlorophenyl)-2,2-diethyl-1,3-dioxolan-4-yl)methyl sulfamate;
(22) (3-(2,4-dichlorophenyl)-1,4-dioxaspiro[4,4]nonan-2-yl)methyl sulfamate;
(23) (3-(2,4-dichlorophenyl)-1,4-dioxaspiro[4,5]decan-2-yl)methyl sulfamate;
(24) (5-(2,4-dichlorophenyl)-2-phenyl-1,3-dioxolan-4-yl)methyl sulfamate;
(25) (5-(2,6-dichlorophenyl)-2,2-dimethyl-1,3-dioxolan-4-yl)methylsulfamate;
(26) (5-(2,6-dichlorophenyl)-2-methyl-1,3-dioxolan-4-yl)methyl sulfamate;
(27) (5-(2,6-dichlorophenyl)-2,2-diethyl-1,3-dioxolan-4-yl)methyl sulfamate;
(28) (3-(2,6-dichlorophenyl)-1,4-dioxaspiro[4,4]nonan-2-yl)methyl sulfamate;
(29) (3-(2,6-dichlorophenyl)-1,4-dioxaspiro[4,5]decan-2-yl)methyl sulfamate;
(30) (5-(2,6-dichlorophenyl)-2-phenyl-1,3-dioxolan-4-yl)methyl sulfamate;
(31) (5-(2-aminophenyl)-2,2-dimethyl-1,3-dioxolan-4-yl)methyl sulfamate;
(32) (5-(2-aminophenyl)-2-methyl-1,3-dioxolan-4-yl)methyl sulfamate;
(33) (5-(2-aminophenyl)-2,2-diethyl-1,3-dioxolan-4-yl)methyl sulfamate;
(34) (3-(2-aminophenyl)-1,4-dioxaspiro[4,4]nonan-2-yl)methyl sulfamate;
(35) (3-(2-aminophenyl)-1,4-dioxaspiro[4,5]decan-2-yl)methyl sulfamate;
(36) (5-(2-aminophenyl)-2-phenyl-1,3-dioxolan-4-yl)methyl sulfamate;
(37) (5-(2-nitrophenyl)-2,2-dimethyl-1,3-dioxolan-4-yl)methyl sulfamate;
(38) (5-(2-nitrophenyl)-2-methyl-1,3-dioxolan-4-yl)methyl sulfamate;
(39) (5-(2-nitrophenyl)-2,2-diethyl-1,3-dioxolan-4-yl)methyl sulfamate;
(40) (3-(2-nitrophenyl)-1,4-dioxaspiro[4,4]nonan-2-yl)methyl sulfamate;
(41) (3-(2-nitrophenyl)-1,4-dioxaspiro[4,5]decan-2-yl)methyl sulfamate;
(42) (5-(2-nitrophenyl)-2-phenyl-1,3-dioxolan-4-yl)methyl sulfamate;
(43) (5-(2-nitrophenyl)-2-oxo-1,3-dioxolan-4-yl)methyl sulfamate;
(44) (5-(2-methylphenyl)-2,2-dimethyl-1,3-dioxolan-4-yl)methyl sulfamate;
(45) (5-(2-methylphenyl)-2-methyl-1,3-dioxolan-4-yl)methyl sulfamate;
(46) (5-(2-methylphenyl)-2,2-diethyl-1,3-dioxolan-4-yl)methyl sulfamate;
(47) (3-(2-methylphenyl)-1,4-dioxaspiro[4,4]nonan-2-yl)methyl sulfamate;
(48) (3-(2-methylphenyl)-1,4-dioxaspiro[4,5]decan-2-yl)methyl sulfamate;
(49) (5-(2-methylphenyl)-2-phenyl-1,3-dioxolan-4-yl)methyl sulfamate;
(50) (5-(2-methylaminophenyl)-2,2-dimethyl-1,3-dioxolan-4-yl)methyl methyl sulfamate;
(51) (5-phenyl-2,2-dimethyl-1,3-dioxolan-4-yl)methyl sulfamate;
(52) (5-phenyl-2,2-diethyl-1,3-dioxolan-4-yl)methyl sulfamate;
(53) (3-phenyl-1,4-dioxaspiro[4,4]nonan-2-yl)methyl sulfamate;
(54) (3-phenyl-1,4-dioxaspiro[4,5]decan-2-yl)methyl sulfamate;
(55) 2-(5-benzyl-2,2-dimethyl-1,3-dioxolan-4-yl)ethyl sulfamate;
(56) 2-(5-benzyl-2,2-diethyl-1,3-dioxolan-4-yl)ethyl sulfamate;
(57) 2-(3-benzyl-1,4-dioxaspiro[4,4]nonan-2-yl)ethyl sulfamate;
(58) 2-(3-benzyl-1,4-dioxaspiro[4,5]decane-2-yl)ethyl sulfamate;
(59) (5-benzyl-2,2-dimethyl-1,3-dioxolan-4-yl)methyl sulfamate;
(60) (5-benzyl-2,2-diethyl-1,3-dioxolan-4-yl)methyl sulfamate;
(61) (3-benzyl-1,4-dioxaspiro[4,4]nonan-2-yl)methyl sulfamate;
(62) (3-benzyl-1,4-dioxaspiro[4,5]decan-2-yl)methyl sulfamate;
(63) 2-(5-phenyl-2,2-dimethyl-1,3-dioxolan-4-yl)ethyl sulfamate;
(64) 2-(5-phenyl-2,2-diethyl-1,3-dioxolan-4-yl)ethyl sulfamate;
(65) 2-(3-phenyl-1,4-dioxaspiro[4,4]nonan-2-yl)ethyl sulfamate;
(66) 3-(3-phenyl-1,4-dioxaspiro[4,5]decan-2-yl)ethyl sulfamate;
(67) 2-(5-(2-chlorobenzyl)-2,2-dimethyl-1,3-dioxolan-4-yl)ethyl sulfamate;
(68) 2-(5-(2-chlorobenzyl)-2,2-diethyl-1,3-dioxolan-4-yl)ethyl sulfamate;
(69) 2-(3-(2-chlorobenzyl)-1,4-dioxaspiro[4,4]nonan-2-yl)ethyl sulfamate;
(70) 2-(3-(2-chlorobenzyl)-1,4-dioxaspiro[4,5]decan-2-yl)ethyl sulfamate;
(71) (5-(2-chlorobenzyl)-2,2-dimethyl-1,3-dioxolan-4-yl)methyl sulfamate;
(72) (5-(2-chlorobenzyl)-2,2-diethyl-1,3-dioxolan-4-yl)methyl sulfamate;
(73) (3-(2-chlorobenzyl)-1,4-dioxaspiro[4,4]nonan-2-yl)methyl sulfamate;
(74) (3-(2-chlorobenzyl)-1,4-dioxaspiro[4,5]decan-2-yl)methyl sulfamate;
(75) 2-(5-(2-chlorophenyl)-2,2-dimethyl-1,3-dioxolan-4-yl)ethyl sulfamate;
(76) 2-(5-(2-chlorophenyl)-2,2-diethyl-1,3-dioxolan-4-yl)ethyl sulfamate;
(77) 2-(3-(2-chlorophenyl)-1,4-dioxaspiro[4,4]nonan-2-yl)ethyl sulfamate; and
(78) 2-(3-(2-chlorophenyl)-1,4-dioxaspiro[4,5]decan-2-yl)ethyl sulfamate.

5. The method according to claim 1, wherein the compound is selected from the group consisting of:
((4R,5R)-5-(2-chlorophenyl)-2,2-dimethyl-1,3-dioxolan-4-yl)methyl sulfamate;

((4S,5S)-5-(2-chlorophenyl)-2,2-dimethyl-1,3-dioxolan-4-yl)methyl sulfamate;
(5-(2-chlorophenyl)-2,2-dimethyl-1,3-dioxolan-4-yl) methyl sulfamate (SS & RR mixture);
(5-(2-chlorophenyl)-2,2-dimethyl-1,3-dioxolan-4-yl) methyl sulfamate (SR & RS mixture);
((4R,5R)-5-(2-chlorophenyl)-2-methyl-1,3-dioxolan-4-yl)methyl sulfamate;
((4S, 5S)-5-(2-chlorophenyl)-2-methyl-1,3-dioxolan-4-yl)methyl sulfamate;
((4R, 5R)-5-(2-chlorophenyl)-2,2-diethyl-1,3-dioxolan-4-yl)methyl sulfamate;
((4S, 5S)-5-(2-chlorophenyl)-2,2-diethyl-1,3-dioxolan-4-yl)methyl sulfamate;
((2R, 3R)-3-(2-chlorophenyl)-1,4-dioxaspiro[4,4]nonan-2-yl)methyl sulfamate;
((2S, 3S)-3-(2-chlorophenyl)-1,4-dioxaspiro[4,4]nonan-2-yl)methyl sulfamate;
((2R, 3R)-3-(2-chlorophenyl)-1,4-dioxaspiro[4,5]decan-2-yl)methyl sulfamate;
((2S, 3S)-3-(2-chlorophenyl)-1,4-dioxaspiro[4,5]decan-2-yl)methyl sulfamate;
((4R,5R)-5-(2-chlorophenyl)-2-phenyl-1,3-dioxolan-4-yl)methyl sulfamate;
((4S,5S)-5-(2-chlorophenyl)-2-phenyl-1,3-dioxolan-4-yl) methyl sulfamate;
((4R,5R)-5-(2-fluorophenyl)-2,2-dimethyl-1,3-dioxolan-4-yl)methyl sulfamate;
((4S,5S)-5-(2-fluorophenyl)-2,2-dimethyl-1,3-dioxolan-4-yl)methyl sulfamate;
((4R,5R)-5-(2-fluorophenyl)-2-methyl-1,3-dioxolan-4-yl)methyl sulfamate;
((4S, 5S)-5-(2-fluorophenyl)-2-methyl-1,3-dioxolan-4-yl)methyl sulfamate;
((4R,5R)-5-(2-fluorophenyl)-2,2-diethyl-1,3-dioxolan-4-yl)methyl sulfamate;
((4S,5S)-5-(2-fluorophenyl)-2,2-diethyl-1,3-dioxolan-4-yl)methyl sulfamate;
((2R, 3R)-3-(2-fluorophenyl)-1,4-dioxaspiro[4,4]nonan-2-yl)methyl sulfamate;
((2S, 3S)-3-(2-fluorophenyl)-1,4-dioxaspiro[4,4]nonan-2-yl)methyl sulfamate;
((2R, 3R)-3-(2-fluorophenyl)-1,4-dioxaspiro[4,5]decan-2-yl)methyl sulfamate;
((2S, 3S)-3-(2-fluorophenyl)-1,4-dioxaspiro[4,5]decan-2-yl)methyl sulfamate;
((4R,5R)-5-(2-fluorophenyl)-2-phenyl-1,3-dioxolan-4-yl) methyl sulfamate;
((4S,5S)-5-(2-fluorophenyl)-2-phenyl-1,3-dioxolan-4-yl) methyl sulfamate;
((4R,5R)-5-(2-iodophenyl)-2,2-dimethyl-1,3-dioxolan-4-yl)methyl sulfamate;
((4S,5S)-5-(2-iodophenyl)-2,2-dimethyl-1,3-dioxolan-4-yl)methyl sulfamate;
((4R,5R)-5-(2-iodophenyl)-2-methyl-1,3-dioxolan-4-yl) methyl sulfamate;
((4S, 5S)-5-(2-iodophenyl)-2-methyl-1,3-dioxolan-4-yl) methyl sulfamate;
((4R,5R)-5-(2-iodophenyl)-2,2-diethyl-1,3-dioxolan-4-yl)methyl sulfamate;
((4S,5S)-5-(2-iodophenyl)-2,2-diethyl-1,3-dioxolan-4-yl) methyl sulfamate;
((2R, 3R)-3-(2-iodophenyl)-1,4-dioxaspiro[4,4]nonan-2-yl)methyl sulfamate;
((2S, 3S)-3-(2-iodophenyl)-1,4-dioxaspiro[4,4]nonan-2-yl)methyl sulfamate;
((2R, 3R)-3-(2-iodophenyl)-1,4-dioxaspiro[4,5]decan-2-yl)methyl sulfamate;
((2S, 3S)-3-(2-iodophenyl)-1,4-dioxaspiro[4,5]decan-2-yl)methyl sulfamate;
((4R,5R)-5-(2-iodophenyl)-2-phenyl-1,3-dioxolan-4-yl) methyl sulfamate;
((4S,5S)-5-(2-iodophenyl)-2-phenyl-1,3-dioxolan-4-yl) methyl sulfamate;
((4R,5R)-5-(2,4-dichlorophenyl)-2,2-dimethyl-1,3-dioxolan-4-yl)methyl sulfamate;
((4S,5S)-5-(2,4-dichlorophenyl)-2,2-dimethyl-1,3-dioxolan-4-yl)methyl sulfamate;
((4R,5R)-5-(2,4-dichlorophenyl)-2-methyl-1,3-dioxolan-4-yl)methyl sulfamate;
((4S, 5S)-5-(2,4-dichlorophenyl)-2-methyl-1,3-dioxolan-4-yl)methyl sulfamate;
((4R,5R)-5-(2,4-dichlorophenyl)-2,2-diethyl-1,3-dioxolan-4-yl)methyl sulfamate;
((4S,5S)-5-(2,4-dichlorophenyl)-2,2-diethyl-1,3-dioxolan-4-yl)methyl sulfamate;
((2R, 3R)-3-(2,4-dichlorophenyl)-1,4-dioxaspiro[4,4]nonan-2-yl)methyl sulfamate;
((2S, 3S)-3-(2,4-dichlorophenyl)-1,4-dioxaspiro[4,4]nonan-2-yl)methyl sulfamate;
((2R, 3R)-3-(2,4-dichlorophenyl)-1,4-dioxaspiro[4,5]decan-2-yl)methyl sulfamate;
((2S, 3S)-3-(2,4-dichlorophenyl)-1,4-dioxaspiro[4,5]decan-2-yl)methyl sulfamate;
((4R, 5R)-5-(2,4-dichlorophenyl)-2-phenyl-1,3-dioxolan-4-yl)methyl sulfamate;
((4S,5S)-5-(2,4-dichlorophenyl)-2-phenyl-1,3-dioxolan-4-yl)methyl sulfamate;
((4R, 5R)-5-(2,6-dichlorophenyl)-2,2-dimethyl-1,3-dioxolan-4-yl)methyl sulfamate;
((4S, 5S)-5-(2,6-dichlorophenyl)-2,2-dimethyl-1,3-dioxolan-4-yl)methyl sulfamate;
((4R, 5R)-5-(2,6-dichlorophenyl)-2-methyl-1,3-dioxolan-4-yl)methyl sulfamate;
((4S, 5S)-5-(2,6-dichlorophenyl)-2-methyl-1,3-dioxolan-4-yl)methyl sulfamate;
((4R, 5R)-5-(2,6-dichlorophenyl)-2,2-diethyl-1,3-dioxolan-4-yl)methyl sulfamate;
((4S, 5S)-5-(2,6-dichlorophenyl)-2,2-diethyl-1,3-dioxolan-4-yl)methyl sulfamate;
((2R, 3R)-3-(2,6-dichlorophenyl)-1,4-dioxaspiro[4,4]nonan-2-yl)methyl sulfamate;
((2S, 3S)-3-(2,6-dichlorophenyl)-1,4-dioxaspiro[4,4]nonan-2-yl)methyl sulfamate;
((2R, 3R)-3-(2,6-dichlorophenyl)-1,4-dioxaspiro[4,5]decan-2-yl)methyl sulfamate;
((2S, 3S)-3-(2,6-dichlorophenyl)-1,4-dioxaspiro[4,5]decan-2-yl)methyl sulfamate;
((4R, 5R)-5-(2,6-dichlorophenyl)-2-phenyl-1,3-dioxolan-4-yl)methyl sulfamate;
((4S,5 S)-5-(2,6-dichlorophenyl)-2-phenyl-1,3-dioxolan-4-yl)methyl sulfamate;
((4R, 5R)-5-(2-aminophenyl)-2,2-dimethyl-1,3-dioxolan-4-yl)methyl sulfamate;
((4S, 5S)-5-(2-aminophenyl)-2,2-dimethyl-1,3-dioxolan-4-yl)methyl sulfamate;
((4R, 5R)-5-(2-aminophenyl)-2-methyl-1,3-dioxolan-4-yl)methyl sulfamate;
((4S, 5S)-5-(2-aminophenyl)-2-methyl-1,3-dioxolan-4-yl)methyl sulfamate;
((4R, 5R)-5-(2-aminophenyl)-2,2-diethyl-1,3-dioxolan-4-yl)methyl sulfamate;

((4S, 5S)-5-(2-aminophenyl)-2,2-diethyl-1,3-dioxolan-4-yl)methyl sulfamate;
((2R, 3R)-3-(2-aminophenyl)-1,4-dioxaspiro[4,4]nonan-2-yl)methyl sulfamate;
((2S, 3S)-3-(2-aminophenyl)-1,4-dioxaspiro[4,4]nonan-2-yl)methyl sulfamate;
((2R, 3R)-3-(2-aminophenyl)-1,4-dioxaspiro[4,5]decan-2-yl)methyl sulfamate;
((2S, 3S)-3-(2-aminophenyl)-1,4-dioxaspiro[4,5]decan-2-yl)methyl sulfamate;
((4R, 5R)-5-(2-aminophenyl)-2-phenyl-1,3-dioxolan-4-yl)methyl sulfamate;
((4S, 5S)-5-(2-aminophenyl)-2-phenyl-1,3-dioxolan-4-yl)methyl sulfamate;
((4R, 5R)-5-(2-nitrophenyl)-2,2-dimethyl-1,3-dioxolan-4-yl)methyl sulfamate;
((4S, 5S)-5-(2-nitrophenyl)-2,2-dimethyl-1,3-dioxolan-4-yl)methyl sulfamate;
((4R, 5R)-5-(2-nitrophenyl)-2-methyl-1,3-dioxolan-4-yl)methyl sulfamate;
((4S, 5S)-5-(2-nitrophenyl)-2-methyl-1,3-dioxolan-4-yl)methyl sulfamate;
((4R,5R)-5-(2-nitrophenyl)-2,2-diethyl-1,3-dioxolan-4-yl)methyl sulfamate;
((4S,5S)-5-(2-nitrophenyl)-2,2-diethyl-1,3-dioxolan-4-yl)methyl sulfamate;
((2R, 3R)-3-(2-nitrophenyl)-1,4-dioxaspiro[4,4]nonane-2-yl)methyl sulfamate;
((2S, 3S)-3-(2-nitrophenyl)-1,4-dioxaspiro[4,4]nonan-2-yl)methyl sulfamate;
((2R, 3R)-3-(2-nitrophenyl)-1,4-dioxaspiro[4,5]decan-2-yl)methyl sulfamate;
((2S, 3S)-3-(2-nitrophenyl)-1,4-dioxaspiro[4,5]decan-2-yl)methyl sulfamate;
((4R, 5R)-5-(2-nitrophenyl)-2-phenyl-1,3-dioxolan-4-yl)methyl sulfamate;
((4S, 5S)-5-(2-nitrophenyl)-2-phenyl-1,3-dioxolan-4-yl)methyl sulfamate;
((4R, 5R)-5-(2-nitrophenyl)-2-oxo-1,3-dioxolan-4-yl)methyl sulfamate;
((4S, 5S)-5-(2-nitrophenyl)-2-oxo-1,3-dioxolan-4-yl)methyl sulfamate;
((4R, 5R)-5-(2-methylphenyl)-2,2-dimethyl-1,3-dioxolan-4-yl)methyl sulfamate;
((4S, 5S)-5-(2-methylphenyl)-2,2-dimethyl-1,3-dioxolan-4-yl)methyl sulfamate;
((4R, 5R)-5-(2-methylphenyl)-2-methyl-1,3-dioxolan-4-yl)methyl sulfamate;
((4S, 5S)-5-(2-methylphenyl)-2-methyl-1,3-dioxolan-4-yl)methyl sulfamate;
((4R, 5R)-5-(2-methylphenyl)-2,2-diethyl-1,3-dioxolan-4-yl)methyl sulfamate;
((4S, 5S)-5-(2-methylphenyl)-2,2-diethyl-1,3-dioxolan-4-yl)methyl sulfamate;
((2R, 3R)-3-(2-methylphenyl)-1,4-dioxaspiro[4,4]nonane-2-yl)methyl sulfamate;
((2S, 3S)-3-(2-methylphenyl)-1,4-dioxaspiro[4,4]nonane-2-yl)methyl sulfamate;
((2R, 3R)-3-(2-methylphenyl)-1,4-dioxaspiro[4,5]decan-2-yl)methyl sulfamate;
((2S, 3S)-3-(2-methylphenyl)-1,4-dioxaspiro[4,5]decan-2-yl)methyl sulfamate;
((4R, 5R)-5-(2-methylphenyl)-2-phenyl-1,3-dioxolan-4-yl)methyl sulfamate;
((4S, 5S)-5-(2-methylphenyl)-2-phenyl-1,3-dioxolan-4-yl)methyl sulfamate;
((4R, 5R)-5-(2-methylaminophenyl)-2,2-dimethyl-1,3-dioxolan-4-yl)methyl methylsulfamate;
((4S, 5S)-5-(2-methylaminophenyl)-2,2-dimethyl-1,3-dioxolan-4-yl)methyl methylsulfamate;
((4R, 5R)-5-phenyl-2,2-dimethyl-1,3-dioxolan-4-yl)methyl sulfamate;
((4S, 5S)-5-phenyl-2,2-dimethyl-1,3-dioxolan-4-yl)methyl sulfamate;
((4R, 5R)-5-phenyl-2,2-diethyl-1,3-dioxolan-4-yl)methyl sulfamate;
((4S, 5S)-5-phenyl-2,2-diethyl-1,3-dioxolan-4-yl)methyl sulfamate;
((2R 3R)-3-phenyl-1,4-dioxaspiro[4,4]nonan-2-yl)methyl sulfamate;
((2S, 3S)-3-phenyl-1,4-dioxaspiro[4,4]nonan-2-yl)methyl sulfamate;
((2R, 3R)-3-phenyl-1,4-dioxaspiro[4,5]decan-2-yl)methyl sulfamate;
((2S, 3S)-3-phenyl-1,4-dioxaspiro[4,5]decan-2-yl)methyl sulfamate;
2-((4S, 5S)-5-benzyl-2,2-dimethyl-1,3-dioxolan-4-yl)ethyl sulfamate;
2-((4R, 5R)-5-benzyl-2,2-dimethyl-1,3-dioxolan-4-yl)ethyl sulfamate;
2-((4S, 5S)-5-benzyl-2,2-diethyl-1,3-dioxolan-4-yl)ethyl sulfamate;
2-((4R, 5R)-5-benzyl-2,2-diethyl-1,3-dioxolan-4-yl)ethyl sulfamate;
2-((2S, 3S)-3-benzyl-1,4-dioxaspiro[4,4]nonan-2-yl)ethyl sulfamate;
2-((2R, 3R)-3-benzyl-1,4-dioxaspiro[4,4]nonan-2-yl)ethyl sulfamate;
2-((2S, 3S)-3-benzyl-1,4-dioxaspiro[4,5]decane-2-yl)ethyl sulfamate;
2-((2R, 3R)-3-benzyl-1,4-dioxaspiro[4,5]decan-2-yl)ethyl sulfamate;
((4S, 5S)-5-benzyl-2,2-dimethyl-1,3-dioxolan-4-yl)methyl sulfamate;
((4R, 5R)-5-benzyl-2,2-dimethyl-1,3-dioxolan-4-yl)methyl sulfamate;
((4S, 5S)-5-benzyl-2,2-diethyl-1,3-dioxolan-4-yl)methyl sulfamate;
((4R, 5R)-5-benzyl-2,2-diethyl-1,3-dioxolan-4-yl)methyl sulfamate;
((2S, 3S)-3-benzyl-1,4-dioxaspiro[4,4]nonan-2-yl)methyl sulfamate;
((2R, 3R)-3-benzyl-1,4-dioxaspiro[4,4]nonan-2-yl)methyl sulfamate;
((2S, 3S)-3-benzyl-1,4-dioxaspiro[4,5]decan-2-yl)methyl sulfamate;
((2R, 3R)-3-benzyl-1,4-dioxaspiro[4,5]decan-2-yl)methyl sulfamate;
2-((4R, 5R)-5-phenyl-2,2-dimethyl-1,3-dioxolan-4-yl)ethyl sulfamate;
2-((4S, 5S)-5-phenyl-2,2-dimethyl-1,3-dioxolan-4-yl)ethyl sulfamate;
2-((4R, 5R)-5-phenyl-2,2-diethyl-1,3-dioxolan-4-yl)ethyl sulfamate;
2-((4S, 5S)-5-phenyl-2,2-diethyl-1,3-dioxolan-4-yl)ethyl sulfamate;
2-((2R, 3R)-3-phenyl-1,4-dioxaspiro[4,4]nonan-2-yl)ethyl sulfamate;
2-((2S, 3S)-3-phenyl-1,4-dioxaspiro[4,4]nonan-2-yl)ethyl sulfamate;
2-(2R, 3R)-3-phenyl-1,4-dioxaspiro[4,5]decan-2-yl)ethyl sulfamate;

2-((2S, 3S)-3-phenyl-1,4-dioxaspiro[4,5]decan-2-yl)ethyl sulfamate;
2-((4S, 5S)-5-(2-chlorobenzyl)-2,2-dimethyl-1,3-dioxolan-4-yl)ethyl sulfamate;
2-((4R, 5R)-5-(2-chlorobenzyl)-2,2-dimethyl-1,3-dioxolan-4-yl)ethyl sulfamate;
2-((4S, 5S)-5-(2-chlorobenzyl)-2,2-diethyl-1,3-dioxolan-4-yl)ethyl sulfamate;
2-((4R, 5R)-5-(2-chlorobenzyl)-2,2-diethyl-1,3-dioxolan-4-yl)ethyl sulfamate;
2-((2S, 3S)-3-(2-chlorobenzyl)-1,4-dioxaspiro[4,4]nonan-2-yl)ethyl sulfamate;
2-((2R, 3R)-3-(2-chlorobenzyl)-1,4-dioxaspiro[4,4]nonan-2-yl)ethyl sulfamate;
2-((2S, 3S)-3-(2-chlorobenzyl)-1,4-dioxaspiro[4,5]decan-2-yl)ethyl sulfamate;
2-((2R, 3R)-3-(2-chlorobenzyl)-1,4-dioxaspiro[4,5]decan-2-yl)ethyl sulfamate;
((4S, 5S)-5-(2-chlorobenzyl)-2,2-dimethyl-1,3-dioxolan-4-yl)methyl sulfamate;
((4R, 5R)-5-(2-chlorobenzyl)-2,2-dimethyl-1,3-dioxolan-4-yl)methyl sulfamate;
((4S, 5S)-5-(2-chlorobenzyl)-2,2-diethyl-1,3-dioxolan-4-yl)methyl sulfamate;
((4R, 5R)-5-(2-chlorobenzyl)-2,2-diethyl-1,3-dioxolan-4-yl)methyl sulfamate;
((2S, 3S)-3-(2-chlorobenzyl)-1,4-dioxaspiro[4,4]nonan-2-yl)methyl sulfamate;
((2R, 3R)-3-(2-chlorobenzyl)-1,4-dioxaspiro[4,4]nonan-2-yl)methyl sulfamate;
((2S, 3S)-3-(2-chlorobenzyl)-1,4-dioxaspiro[4,5]decan-2-yl)methyl sulfamate;
((2R, 3R)-3-(2-chlorobenzyl)-1,4-dioxaspiro[4,5]decan-2-yl)methyl sulfamate;
2-((4R, 5R)-5-(2-chlorophenyl)-2,2-dimethyl-1,3-dioxolan-4-yl)ethyl sulfamate;
2-((4S, 5S)-5-(2-chlorophenyl)-2,2-dimethyl-1,3-dioxolan-4-yl)ethyl sulfamate;
2-((4R, 5R)-5-(2-chlorophenyl)-2,2-diethyl-1,3-dioxolan-4-yl)ethyl sulfamate;
2-((4S, 5S)-5-(2-chlorophenyl)-2,2-diethyl-1,3-dioxolan-4-yl)ethyl sulfamate;
2-((2R, 3R)-3-(2-chlorophenyl)-1,4-dioxaspiro[4,4]nonan-2-yl)ethyl sulfamate;
2-((2S, 3S)-3-(2-chlorophenyl)-1,4-dioxaspiro[4,4]nonan-2-yl)ethyl sulfamate;
2-((2R, 3R)-3-(2-chlorophenyl)-1,4-dioxaspiro[4,5]decan-2-yl)ethyl sulfamate;
2-((2S, 3S)-3-(2-chlorophenyl)-1,4-dioxaspiro[4,5]decan-2-yl)ethyl sulfamate;
((4S, 5R)-5-(2-chlorophenyl)-2,2-dimethyl-1,3-dioxolan-4-yl)methyl sulfamate;
((4R, 5S)-5-(2-chlorophenyl)-2,2-dimethyl-1,3-dioxolan-4-yl)methyl sulfamate;
Sodium ((((4R, 5R)-5-(2-aminophenyl)-2,2-dimethyl-1,3-dioxolan-4-yl)methyl sulfonyl)amide;
Sodium (((((4S, 5S)-5-(2-aminophenyl)-2,2-dimethyl-1,3-dioxolan-4-yl)methyl sulfonyl)amide; and
sodium ((((4S,5S)-5-(2-chlorophenyl)-2,2-dimethyl-1,3-dioxolan-4-yl)methoxy)sulfonyl)amide.

6. The method according to claim 1, wherein the pain is one or more selected from the group consisting of nociceptive pain, psychogenic pain, inflammatory pain, and pathological pain.

7. The method according to claim 1, wherein the pain is one or more selected from the group consisting of neuropathic pain, cancer pain, postoperative pain, trigeminal neuralgia pain, idiopathic pain, diabetic neuropathic pain, and migraine.

8. The method according to claim 1, wherein the compound is in the form of a racemate, an enantiomer, a diastereomer, a mixture of enantiomers, or a mixture of diastereomers.

9. The method according to claim 4, wherein the compound is in the form of a racemate, an enantiomer, a diastereomer, a mixture of enantiomers, or a mixture of diastereomers.

* * * * *